United States Patent
Cleary et al.

(10) Patent No.: US 12,165,743 B2
(45) Date of Patent: Dec. 10, 2024

(54) COMPRESSED SENSING FOR SCREENING AND TISSUE IMAGING

(71) Applicants: The Broad Institute, Inc., Cambridge, MA (US); Massachusetts Institute of Technology, Cambridge, MA (US)

(72) Inventors: Brian Cleary, Cambridge, MA (US); Aviv Regev, Cambridge, MA (US); Eric S. Lander, Cambridge, MA (US)

(73) Assignees: The Broad Institute, Inc.; Massachusetts Institute of Technology

( * ) Notice: Subject to any disclaimer, the term of this patent is extended or adjusted under 35 U.S.C. 154(b) by 1393 days.

(21) Appl. No.: 16/681,639

(22) Filed: Nov. 12, 2019

(65) Prior Publication Data

US 2020/0152289 A1   May 14, 2020

Related U.S. Application Data

(60) Provisional application No. 62/890,534, filed on Aug. 22, 2019, provisional application No. 62/820,165, filed on Mar. 18, 2019, provisional application No. 62/758,402, filed on Nov. 9, 2018.

(51) Int. Cl.
| | | |
|---|---|---|
| G16B 25/10 | (2019.01) | |
| C12Q 1/6806 | (2018.01) | |
| C12Q 1/6874 | (2018.01) | |
| G06T 5/50 | (2006.01) | |
| G16B 50/50 | (2019.01) | |

(52) U.S. Cl.
CPC ........... *G16B 25/10* (2019.02); *C12Q 1/6806* (2013.01); *C12Q 1/6874* (2013.01); *G06T 5/50* (2013.01); *G16B 50/50* (2019.02); *G06T 2207/20224* (2013.01)

(58) Field of Classification Search
CPC ...... G16B 25/10; G16B 50/50; C12Q 1/6806; C12Q 1/6874; C12Q 1/6841; C12Q 1/6869; G06T 5/50; G06T 2207/20224; G06T 2207/10056; G06T 2207/20084; G06T 2207/30024; G06T 7/0012
See application file for complete search history.

(56) References Cited

U.S. PATENT DOCUMENTS

| | | |
|---|---|---|
| 4,737,323 A | 4/1988 | Martin et al. |
| 4,837,028 A | 6/1989 | Allen |
| 4,897,355 A | 1/1990 | Eppstein et al. |
| 4,946,787 A | 8/1990 | Eppstein et al. |
| 5,049,386 A | 9/1991 | Eppstein et al. |
| 5,811,097 A | 9/1998 | Allison et al. |
| 5,869,326 A | 2/1999 | Hofmann |
| 6,479,626 B1 | 11/2002 | Kim et al. |
| 6,534,261 B1 | 3/2003 | Cox et al. |
| 6,607,882 B1 | 8/2003 | Cox et al. |
| 6,746,838 B1 | 6/2004 | Choo et al. |
| 6,794,136 B1 | 9/2004 | Eisenberg et al. |
| 6,824,978 B1 | 11/2004 | Cox et al. |
| 6,866,997 B1 | 3/2005 | Choo et al. |
| 6,903,185 B2 | 6/2005 | Kim et al. |
| 6,933,113 B2 | 8/2005 | Case et al. |
| 6,979,539 B2 | 12/2005 | Cox et al. |
| 7,013,219 B2 | 3/2006 | Case et al. |
| 7,030,215 B2 | 4/2006 | Liu et al. |
| 7,041,481 B2 | 5/2006 | Anderson et al. |
| 7,220,719 B2 | 5/2007 | Case et al. |
| 7,241,573 B2 | 7/2007 | Choo et al. |
| 7,241,574 B2 | 7/2007 | Choo et al. |
| 7,585,849 B2 | 9/2009 | Liu et al. |
| 7,595,376 B2 | 9/2009 | Kim et al. |
| 7,708,949 B2 | 5/2010 | Stone et al. |
| RE41,780 E | 9/2010 | Anderson et al. |
| 8,021,867 B2 | 9/2011 | Smith et al. |
| 8,119,361 B2 | 2/2012 | Smith et al. |
| 8,119,381 B2 | 2/2012 | Smith et al. |
| 8,124,369 B2 | 2/2012 | Smith et al. |
| 8,129,134 B2 | 3/2012 | Smith et al. |
| 8,133,697 B2 | 3/2012 | Smith et al. |
| 8,163,514 B2 | 4/2012 | Smith et al. |
| 8,440,431 B2 | 5/2013 | Voytas et al. |
| 8,440,432 B2 | 5/2013 | Voytas et al. |
| 8,450,471 B2 | 5/2013 | Voytas et al. |
| 8,697,359 B1 | 4/2014 | Zhang |
| 8,771,945 B1 | 7/2014 | Zhang |
| 8,795,965 B2 | 8/2014 | Zhang |

(Continued)

FOREIGN PATENT DOCUMENTS

| | | |
|---|---|---|
| EP | 2 047 910 B1 | 1/2012 |
| EP | 2 784 162 A1 | 10/2014 |

(Continued)

OTHER PUBLICATIONS

Cleary, Brian, Le Cong, Eric S. Lander, and Aviv Regev. "Composite measurements and molecular compressed sensing for highly efficient transcriptomics." bioRxiv (2017): 091926. (Year: 2017).*
Tasic, B., Menon, V., Nguyen, T. et al. Adult mouse cortical cell taxonomy revealed by single cell transcriptomics. Nat Neurosci 19, 18 pages (2016). https://doi.org/10.1038/nn.4216 (Year: 2016).*
Lonsdale, J., Thomas, J., Salvatore, M. et al. The Genotype-Tissue Expression (GTEx) project. Nat Genet 45, 580-585 (2013). https://doi.org/10.1038/ng.2653 (Year: 2013).*
Cleary, Brian, Le Cong, Anthea Cheung, Eric S. Lander, and Aviv Regev. "Efficient generation of transcriptomic profiles by random composite measurements." Cell 171, No. 6 (2017): 1424-1436. (Year: 2017).*
Kok Hao Chen et al. ,Spatially resolved, highly multiplexed RNA profiling in single cells.Science348,aaa6090(2015).DOI:10.1126/science.aaa6090 (Year: 2015).*

(Continued)

*Primary Examiner* — Larry D Riggs, II
*Assistant Examiner* — Nidhi Dharithreesan
(74) *Attorney, Agent, or Firm* — FIG. 1 Patents

(57) ABSTRACT

The present invention relates to tissue and cell imaging utilizing genomic informatics and gene-expression profiling. Gene-expression profiles utilized in methods to obtain in situ imaging of cells and tissues provide complex molecular fingerprints regarding the relative state of a cell or tissue.

19 Claims, 35 Drawing Sheets

Specification includes a Sequence Listing.

(56) References Cited

U.S. PATENT DOCUMENTS

| | | |
|---|---|---|
| 8,865,406 B2 | 10/2014 | Zhang et al. |
| 8,871,445 B2 | 10/2014 | Cong et al. |
| 8,889,356 B2 | 11/2014 | Zhang |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,932,814 B2 | 1/2015 | Cong et al. |
| 8,945,839 B2 | 2/2015 | Zhang |
| 8,993,233 B2 | 3/2015 | Zhang et al. |
| 8,999,641 B2 | 4/2015 | Zhang et al. |
| 9,790,490 B2 | 10/2017 | Zhang et al. |
| 10,815,730 B2 | 10/2020 | Liu et al. |
| 11,163,166 B1 | 11/2021 | Ebert |
| 2004/0171156 A1 | 9/2004 | Hartley et al. |
| 2005/0172476 A1 | 8/2005 | Stone et al. |
| 2006/0163385 A1 | 7/2006 | Link et al. |
| 2007/0003442 A1 | 1/2007 | Link et al. |
| 2007/0184489 A1 | 8/2007 | Griffiths et al. |
| 2007/0195127 A1 | 8/2007 | Ahn et al. |
| 2008/0003142 A1 | 1/2008 | Link et al. |
| 2008/0014589 A1 | 1/2008 | Link et al. |
| 2009/0005254 A1 | 1/2009 | Griffiths et al. |
| 2009/0131543 A1 | 5/2009 | Weitz et al. |
| 2010/0002241 A1 | 1/2010 | Hirose |
| 2010/0137163 A1 | 6/2010 | Link et al. |
| 2010/0172803 A1 | 7/2010 | Stone et al. |
| 2011/0265198 A1 | 10/2011 | Gregory et al. |
| 2012/0017290 A1 | 1/2012 | Cui et al. |
| 2012/0219947 A1 | 8/2012 | Yurkovetsky et al. |
| 2013/0236946 A1 | 9/2013 | Gouble |
| 2014/0170753 A1 | 6/2014 | Zhang |
| 2014/0179006 A1 | 6/2014 | Zhang |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0227787 A1 | 8/2014 | Zhang |
| 2014/0234972 A1 | 8/2014 | Zhang |
| 2014/0242664 A1 | 8/2014 | Zhang et al. |
| 2014/0242699 A1 | 8/2014 | Zhang |
| 2014/0242700 A1 | 8/2014 | Zhang et al. |
| 2014/0248702 A1 | 9/2014 | Zhang et al. |
| 2014/0256046 A1 | 9/2014 | Zhang et al. |
| 2014/0256595 A1 | 9/2014 | Link et al. |
| 2014/0273231 A1 | 9/2014 | Zhang et al. |
| 2014/0273232 A1 | 9/2014 | Zhang et al. |
| 2014/0273234 A1 | 9/2014 | Zhang et al. |
| 2014/0287938 A1 | 9/2014 | Zhang et al. |
| 2014/0310830 A1 | 10/2014 | Zhang et al. |
| 2015/0184139 A1 | 7/2015 | Zhang et al. |
| 2017/0052170 A1 | 2/2017 | Shekdar et al. |
| 2017/0211142 A1 | 7/2017 | Smargon et al. |
| 2017/0285009 A1 | 10/2017 | Rodriguez et al. |

FOREIGN PATENT DOCUMENTS

| | | |
|---|---|---|
| EP | 2 771 468 B1 | 2/2015 |
| EP | 2 764 103 B1 | 8/2015 |
| EP | 3 604 532 A1 | 2/2020 |
| WO | 91/16024 A1 | 10/1991 |
| WO | 91/17424 A1 | 11/1991 |
| WO | 96/40281 A2 | 12/1996 |
| WO | 97/49450 A1 | 12/1997 |
| WO | 98/52609 A1 | 11/1998 |
| WO | 01/89788 A2 | 11/2001 |
| WO | 2004/002627 A2 | 1/2004 |
| WO | 2004/091763 A2 | 10/2004 |
| WO | 2005/021151 A1 | 3/2005 |
| WO | 2006/040551 A2 | 4/2006 |
| WO | 2006/040554 A1 | 4/2006 |
| WO | 2006/096571 A2 | 9/2006 |
| WO | 2007/081385 A2 | 7/2007 |
| WO | 2007/089541 A2 | 8/2007 |
| WO | 2007/133710 A2 | 11/2007 |
| WO | 2008/063227 A2 | 5/2008 |
| WO | 2011/079176 A2 | 6/2011 |
| WO | 2014/018423 A2 | 1/2014 |
| WO | 2014/047561 A1 | 3/2014 |
| WO | 2014/085802 A1 | 6/2014 |
| WO | 2014/093595 A1 | 6/2014 |
| WO | 2014/093622 A2 | 6/2014 |
| WO | 2014/093635 A1 | 6/2014 |
| WO | 2014/093655 A2 | 6/2014 |
| WO | 2014/093661 A2 | 6/2014 |
| WO | 2014/093694 A1 | 6/2014 |
| WO | 2014/093701 A1 | 6/2014 |
| WO | 2014/093709 A1 | 6/2014 |
| WO | 2014/093712 A1 | 6/2014 |
| WO | 2014/093718 A1 | 6/2014 |
| WO | 2014/204723 A1 | 12/2014 |
| WO | 2014/204724 A1 | 12/2014 |
| WO | 2014/204725 A1 | 12/2014 |
| WO | 2014/204726 A1 | 12/2014 |
| WO | 2014/204727 A1 | 12/2014 |
| WO | 2014/204728 A1 | 12/2014 |
| WO | 2014/204729 A1 | 12/2014 |
| WO | 2014/210353 A2 | 12/2014 |
| WO | 2015/050998 A2 | 4/2015 |
| WO | 2015/058052 A1 | 4/2015 |
| WO | 2015/070083 A1 | 5/2015 |
| WO | 2015/089351 A1 | 6/2015 |
| WO | 2015/089354 A1 | 6/2015 |
| WO | 2015/089364 A1 | 6/2015 |
| WO | 2015/089419 A2 | 6/2015 |
| WO | 2015/089427 A1 | 6/2015 |
| WO | 2015/089462 A1 | 6/2015 |
| WO | 2015/089465 A1 | 6/2015 |
| WO | 2015/089473 A1 | 6/2015 |
| WO | 2015/089486 A2 | 6/2015 |
| WO | 2016/028682 A1 | 2/2016 |
| WO | 2016/040476 A1 | 3/2016 |
| WO | 2016/049258 A2 | 3/2016 |
| WO | 2016/094867 A1 | 6/2016 |
| WO | 2016/094872 A1 | 6/2016 |
| WO | 2016/094874 A1 | 6/2016 |
| WO | 2016/106236 A1 | 6/2016 |
| WO | 2016/106244 A1 | 6/2016 |
| WO | 2016/161516 A1 | 10/2016 |
| WO | 2016/168584 A1 | 10/2016 |
| WO | 2018/035250 A1 | 2/2018 |

OTHER PUBLICATIONS

Assarsson, et al., "Homogenous 96-plex PEA Immunoassay Exhibiting High Sensitivity, Specificity, and Excellent Scalability", PLoS One, vol. 9, Issue 4, Apr. 2014, 11 pages.

Cao, et al., "Comprehensive Single Cell Transcriptional Profiling of a Multicellular Organism by Combinatorial Indexing", Available at: BioRxiv https://doi.org/10.1101/104844, Feb. 2, 2017, 35 pages.

Choi, et al., "Third-Generation in Situ Hybridization Chain Reaction: Multiplexed, Quantitative, Sensitive, Versatile, Robust", Development, vol. 145, No. 12, 2018, 10 pages.

Chung, et al., "Structural and Molecular Interrogation of Intact Biological Systems", Nature, vol. 497, No. 7449, May 16, 2013, 23 pages.

Cleary, et al., "Efficient Generation of Transcriptomic Profiles by Random Composite Measurements", Cell, vol. 171, Issue 6, Nov. 2017, 1424-1436.

Codeluppi, et al., "Spatial Organization of the Somatosensory Cortex Revealed by osmFISH", bioRxiv, https://doi.org/10.1101/276097, Mar. 4, 2018, 8 pages.

Eng, et al., "Transcriptome-Scale Super-Resolved Imaging in Tissues by RNA seqFISH+", Nature, vol. 568, No. 7751. Apr. 2019, 235-239, 37 pages.

Fan, et al., "Combinatorial Labeling of Single Cells for Gene Expression Cytometry", Science, vol. 347, Issue 6222, Feb. 6, 2015, 10 pages.

Zilionis, et al., "Single-cell Barcoding and Sequencing Using Droplet Microfluidics", Nature Protocols, vol. 12, No. 1, Jan. 2017, 44-73.

(56) References Cited

OTHER PUBLICATIONS

Gazit, et al., "Super-Resolution and Reconstruction of Sparse Sub-Wavelength Images", Optical Society of America, vol. 17, No. 26, 2009, 23920-23946.

Habib, et al., "Div-Seq: Single-Nucleus RNA-Seq Reveals Dynamics of Rare Adult Newborn Neurons", Science, vol. 353, No. 6302, Aug. 26, 2016, 925-928.

Klein, et al., "Droplet Barcoding for Single-Cell Transcriptomics Applied to Embryonic Stem Cells", Cell, vol. 161, No. 6, May 21, 2015, 1187-1201.

Macosko, et al., "Highly Parallel Genome-Wide Expression Profiling of Individual Cells Using Nanoliter Droplets", Cell, vol. 161, No. 5, May 21, 2015, 1202-1214.

Zheng, et al., "Massively Parallel Digital Transcriptional Profiling of Single Cells", Nature Communications, vol. 8, No. 14049, Jan. 16, 2017, 12 pages.

Moffitt, et al., "High-Throughput Single-Cell Gene-Expression Profiling with Multiplexed Error-Robust Fluorescence In Situ Hybridization", Proceedings of the National Academy of Sciences, vol. 113, No. 39, Sep. 27, 2016, 11046-11051.

Rosenberg, et al., "Scaling Single Cell Transcriptomics Through Split Pool Barcoding", Available at:Bio Rxiv http://dx.doi.org/10.1101/105163, Feb. 2, 2017, 13 pages.

Shalek, et al., "Single-Cell RNA-Seq Reveals Dynamic Paracrine Control of Cellular Variation", Nature, vol. 510, Jun. 19, 2014, 363-369.

Sidorenko, et al., "Sparsity-Based Super-Resolved Coherent Diffraction Imaging of One-Dimensional Objects", Nature Communications, vol. 6, No. 1, 2015, 8 pages.

Solomon, et al., "Sparsity-Based Super-Resolution Microscopy from Correlation Information", Optics Express, vol. 26, Issue 14, 2018, 18238-18269.

Swiech, et al., "In Vivo Interrogation of Gene Function in the Mammalian Brain Using CRISPR-Cas9", Nature Biotechnology, vol. 33, No. 1, 2014, 102-106.

Tanay, et al., "Scaling Single-cell Genomics from Phenomenology to Mechanism", Nature, vol. 541, Jan. 19, 2017, 331-338.

Tsue, et al., "Articles Identification of Hair Cell Progenitors and Intermitotic Migration of Their Nuclei in the Normal and Regenerating Avian Inner Ear", Journal of Neuroscience, vol. 14, No. 1, 1994, 140-152.

Wang, et al., "Multiplexed Imaging of High-Density Libraries of RNAs with MERFISH and Expansion Microscopy", Scientific Reports, vol. 8, Article No. 4847, 2018, 13 pages.

Wang, et al., "Three-Dimensional Intact-Tissue Sequencing of Single-Cell Transcriptional States", Science, vol. 361, No. 6400, Jul. 27, 2018, 11 pages.

Zheng, et al., "Haplotyping Germline and Cancer Genomes with High-Throughput Linked-Read Sequencing", Nature Biotechnology, vol. 34, No. 3, Mar. 2016, 303-311.

* cited by examiner

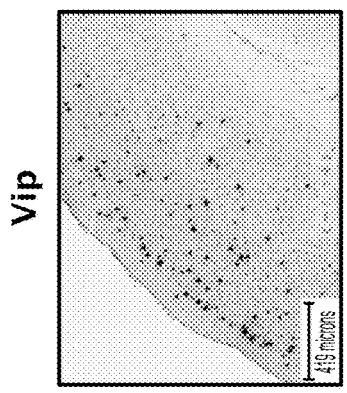
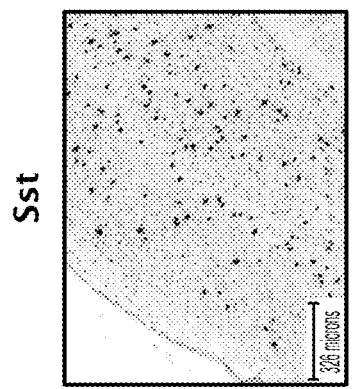
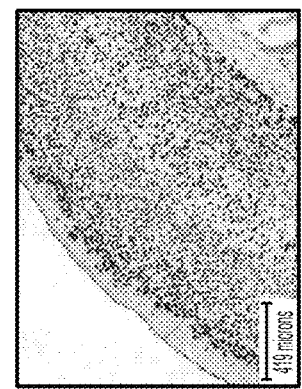
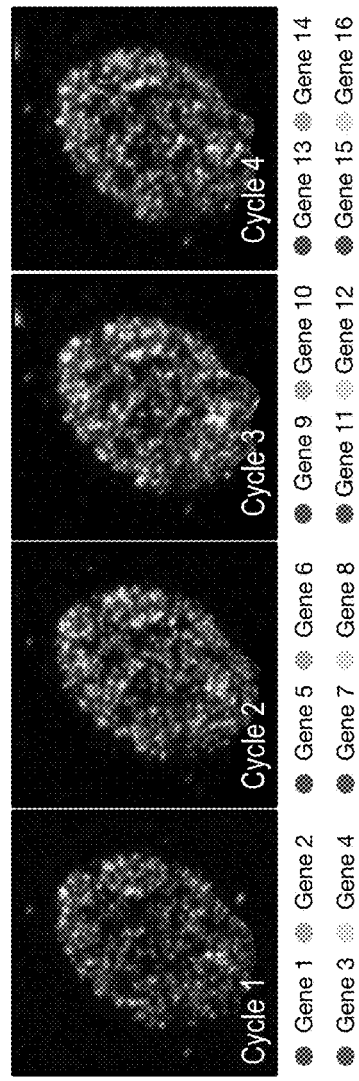
FIG. 2A
FIG. 2B

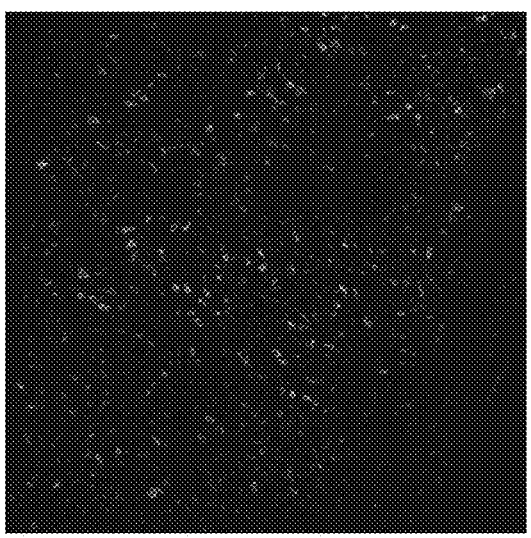
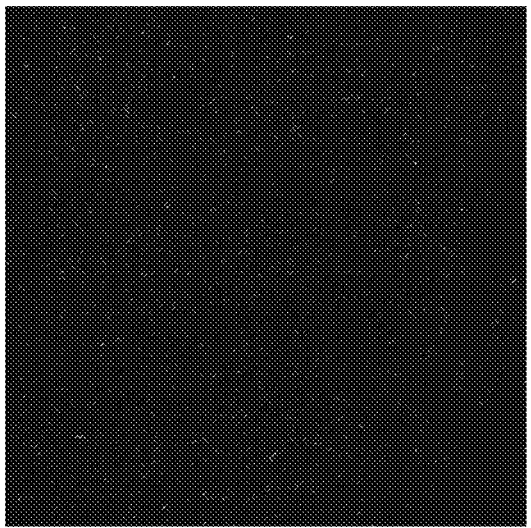
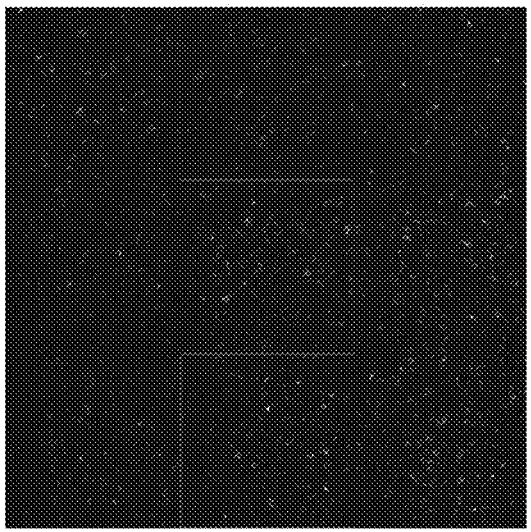
FIG. 11A
FIG. 11B
FIG. 11C olfactory sensory neuron
on olfactory receptor per cell non-olfactory cells
multiple receptor types expressed 710 unique receptors
2860 of 9904 total nuclei 277 unique receptors
409 of 9904 total nuclei

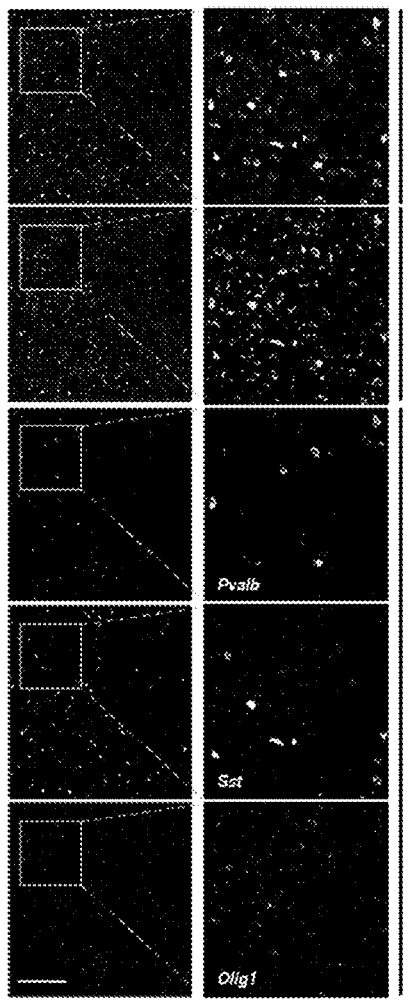
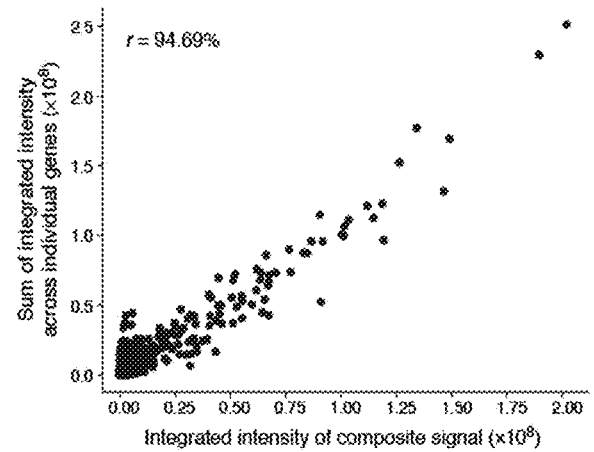
FIG. 24B
FIG. 24A
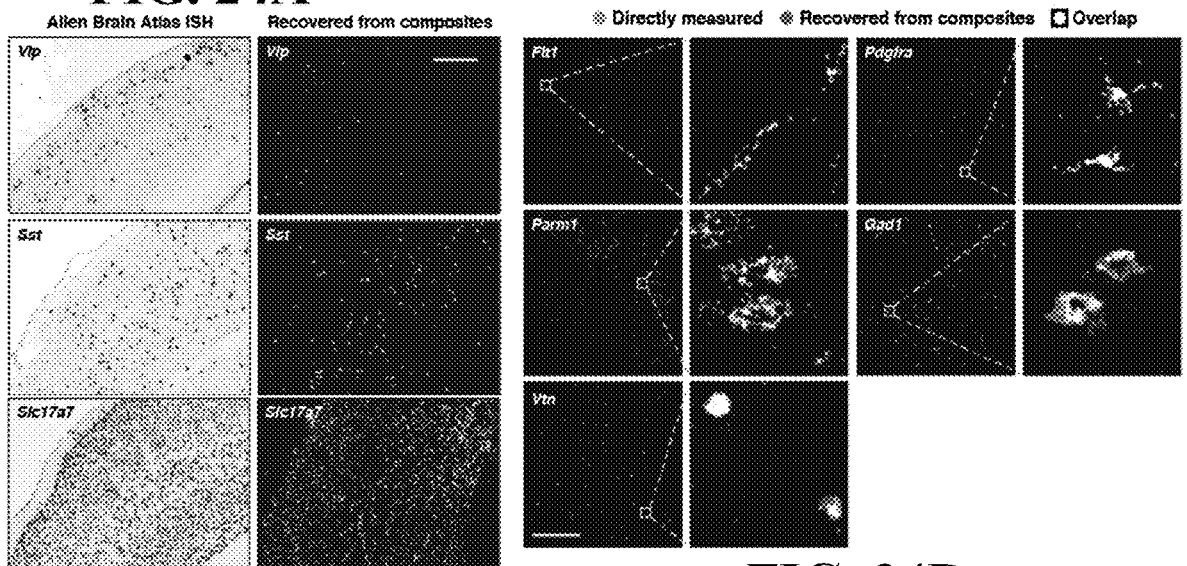
FIG. 24C
FIG. 24D

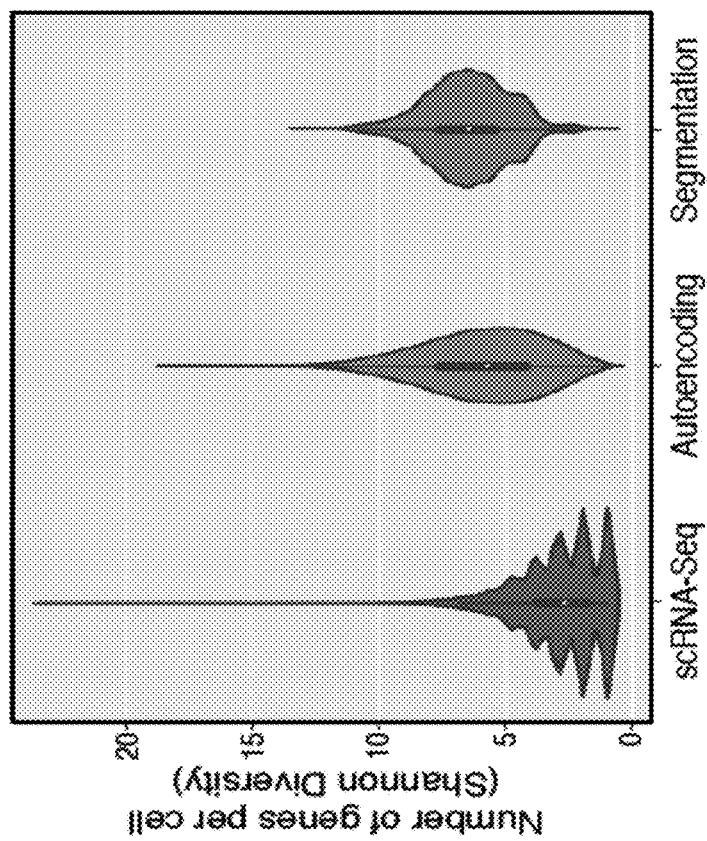
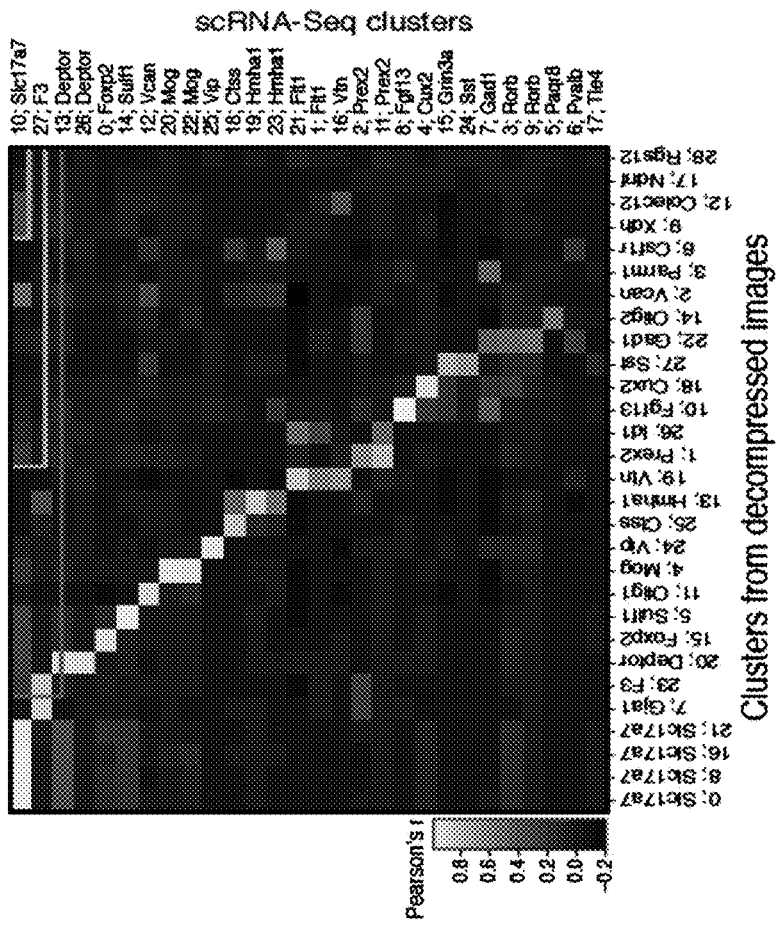
FIG. 31A
FIG. 31B

| | Initial throughput | Final throughput | Fold x |
|---|---|---|---|
| Aim 1 | 140 gene IDs | 10,000 gene IDs | 70 |
| Aim 2 | 1 color/image | 10 colors/image | 10 |
| Aim 3 | 0.1M cells/day | 3.6M cells/day | 36 |

COMPRESSED SENSING FOR SCREENING AND TISSUE IMAGING

CROSS-REFERENCE TO RELATED APPLICATIONS

This application claims the benefit of U.S. Provisional Application No. 62/758,402 filed Nov. 9, 2018, U.S. Provisional Application No. 62/820,165, filed Mar. 18, 2019, and U.S. Provisional Application No. 62/890,534, filed Aug. 22, 2019. The entire contents of the above-identified applications are hereby fully incorporated herein by reference.

STATEMENT REGARDING FEDERALLY SPONSORED RESEARCH

This invention was made with government support under Grant No. MH114821 awarded by the National Institutes of Health. The government has certain rights in the invention.

REFERENCE TO AN ELECTRONIC SEQUENCE LISTING

The contents of the electronic sequence listing (BROD_3960_ST25.txt"; size is 5,261 bytes and it was created on Sep. 20, 2019) is herein incorporated by reference in its entirety.

TECHNICAL FIELD

The subject matter disclosed herein is generally directed to methods of in situ imaging, particularly methods of imaging genes in situ.

BACKGROUND

Increasing understanding of underlying biology in cells and tissues is a continuing goal of researchers and practitioners. Human genomes contain massive amounts of variation (~4 million common variants/genome), with tumors containing a significantly number of additional mutations on top of that diversity. While it is possible to test a small number of genetic interactions in model systems, testing for all possible interaction effects has been out of reach. Understanding tissue ecosystems and tumor evolution is part of this goal, as tumor cells do not evolve in isolation, but within an ecosystem of cells.

Spatial profiling of protein/mRNA abundance could be very informative in aiding understanding of complex cell and tissue systems, but is currently limited to profiling a small number of genes, one per channel, limiting the use of the imaging of tissues. Clearly, additional modalities for imaging of cell and tissue physiology in complex disease are desirable, preferably without requiring acquisition, use, and manipulation of large collections of data.

Citation or identification of any document in this application is not an admission that such document is available as prior art to the present invention.

SUMMARY

In certain example embodiments, a method of imaging genes in situ is provided, comprising detecting one or more composite genes to identify gene modules from a tissue or cell from a region of interest in a subject by performing single cell sequencing of nucleic acid from the tissue or cell(s) from the region of interest, thereby collecting training data comprising gene modules; imaging the tissue or cell from the region of interest of the subject in situ; fitting the gene module activities spatially to form a composite image; and decompressing the composite image, thereby recording images for individual genes.

The one or more composite genes each comprises a linear weighted combination of abundances of two or more individual genes. In some embodiments, the one or more composite genes is comprised of between 2 and 2000 individual genes.

Detecting is performed in certain embodiments by scRNA-seq, in some instances the single cell sequencing comprises whole transcriptome amplification.

Detecting is in some instances across a library of cells. In some embodiments, the cell may comprise a eukaryotic cell. The eukaryotic cell may comprise a mammalian cell. The mammalian cell may comprise a human cell. In some embodiments, a tissue is imaged, and the tissue can comprise or is from a biopsy from a subject. In certain embodiments, the region of interest is in a mammalian subject. In some embodiments, the region of interest is the motor cortex. In embodiments, the one or more individual genes comprises one or more genes of Tables 1-4.

In some embodiments, identification of gene modules comprises determining gene modules based upon random sampling of the one or more composite genes.

In embodiments, the decompressing is by compressive sensing.

Methods of imaging gene expression in a cell or tissue are provided comprising collecting compressed data, the data comprising one or more composite genes, inferring module activity, and recovering images for individual genes by compressed sensing, thereby reconstructing gene expression.

In another aspect, the present disclosure provides a method of screening genes in response to a stimulus, the method comprising: isolating nuclei from a first and a second group of cells exposed to the stimulus, wherein the first group of cells are activated by the stimulus and the second group of cells are not activated by stimulus; sequencing one or more genes or portions thereof in the isolated nuclei; and comparing expression profiles of genes in the nuclei from the first and the second groups of cells, thereby identifying, based on the comparison, candidate genes that respond to the stimulus.

In some embodiments, the method further comprises separating the nuclei of the first group of cells from the nuclei of the second group of cells. In some embodiments, the method further comprises exposing the first and the second groups of cells to the stimulus. In some embodiments, the first and the second groups of cells are from a tissue exposed to the stimulus. In some embodiments, the tissue is from a subject exposed to the stimulus. In some embodiments, the first and the second group of cells are neurons. In some embodiments, the tissue is olfactory epithelium. In some embodiments, the one or more genes encode olfactory receptors.

In another aspect, the present disclosure provides a method of treating a disease, the method comprising administering an agent to a subject in need thereof, the agent modulating activity and/or expression of one or more genes responding to a stimulus related to the disease. In some embodiments, the method further comprises identifying the one or more genes according to the method disclosed herein.

These and other aspects, objects, features and advantages of the example embodiments will become apparent to those having ordinary skill in the art upon consideration of the following detailed description of illustrated example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which:

FIGS. 2A, 2B show the progression of multiplexed imaging. FIG. 2A shows images of tissue sections generated using the ISH approach, focusing on one gene per tissue section. FIG. 2B shows images showing compressed data using an exemplary multiplexing approach according to the methods disclosed herein.

FIG. 5A shows composites of 13 original images. FIG. 5B shows composites from 6 merged images. FIG. 5C shows composites of 13 recovered images.

FIG. 7A shows images of tissue sections generated using the Allen Atlas ISH approach. FIG. 7B shows individual and merged images of 3 of 37 total genes recovered from 9 composite images.

FIG. 11A-11C show a validation of experiments analyzing the (FIG. 11A) F3, (FIG. 111B) Pdgfra, and (FIG. 11C) Prex2 genes by making direct and composite measurements in the same tissue.

(FIG. 23B) Segmentation-free decompression. Top: An autoencoder is first trained on the composite images, with each composite measurement corresponding to one channel. Bottom: Once the autoencoder is trained, the composite images are encoded ("Encoding"), then decompressed to approximate the encoded representation for the unobserved image of each individual gene ("Decompression"), and the pre-trained decoder is used to recover individual images for each gene ("Decoding").

FIG. 24A-24B CISI recovers accurate spatial expression patterns from composite experiments. (FIGS. 24A, 24B) Quantitative accuracy of the composite imaging. (FIG. 24A) A composite image of 12 genes ("Composition 2") compared to a computational merge of 12 images for each individual gene ("Merged image"). 3 of the 12 individual gene images are shown for reference. Left: entire FOV; Right: zoomed in segment, as indicated. Scale bar: 500 um. (FIG. 24B) The integrated signal intensity in each segmented cell (individual dots) in the composite image (x axis) and the merged image (y axis). Pearson's r is noted in upper left corner. (FIGS. 24C, 24D) Autoencoder based decompression successfully recovers accurate spatial patterns of individual genes. (FIG. 24C) Agreement with canonical expression patterns. Spatial RNA expression for Vip (top), Sst (middle), Slc17a7 (bottom) by ISH (left; Allen Brain Atlas) and in the recovered images by the segmentation free algorithm (right). Scale bar: 500 um. (FIG. 24D) Agreement with individual gene measurements on the same section. RNA images recovered by decompression with the segmentation free algorithm and directly measured in the same tissue section. White: images overlap exactly. Scale bar 500 um. See also FIG. 28 for additional genes.

(FIGS. 30A, 30B) Adjustment improves recovered signals. Integrated signal intensity for each gene in each cell (individual dots) from direct measurements (x axis) and from estimates recovered by the autoencoder decompressed images (y axis) either before (FIG. 30A) and after (FIG. 30B) co-measurement correction. (FIG. 30C) Example correction. Segmented cell intensities before (left) and after (right) correction for two co-measured genes (Hmha1 and Slc17a7) that were not correlated in snRNA-Seq.

FIG. 31A-31B Evaluation based on genes per cell and cell clusters. (FIG. 31A) Distribution of expression diversity (effective number of genes per cell; y axis) in snRNA-Seq, or based on recovered expression levels using autoencoding or segmentation-based decompression (x axis). Mini boxplots depict median (dots), inner quartiles (box), and 1.5× quartile range (whiskers). (FIG. 31B) Correspondence (Pearson's correlation of mean gene expression; color bar) between cell clusters from snRNA-Seq (rows) and those found from post hoc segmentation of images recovered using the autoencoding algorithm (columns). One marker gene for each cluster is indicated.

FIG. 37B combinations of fluorophores.

Figure 1:
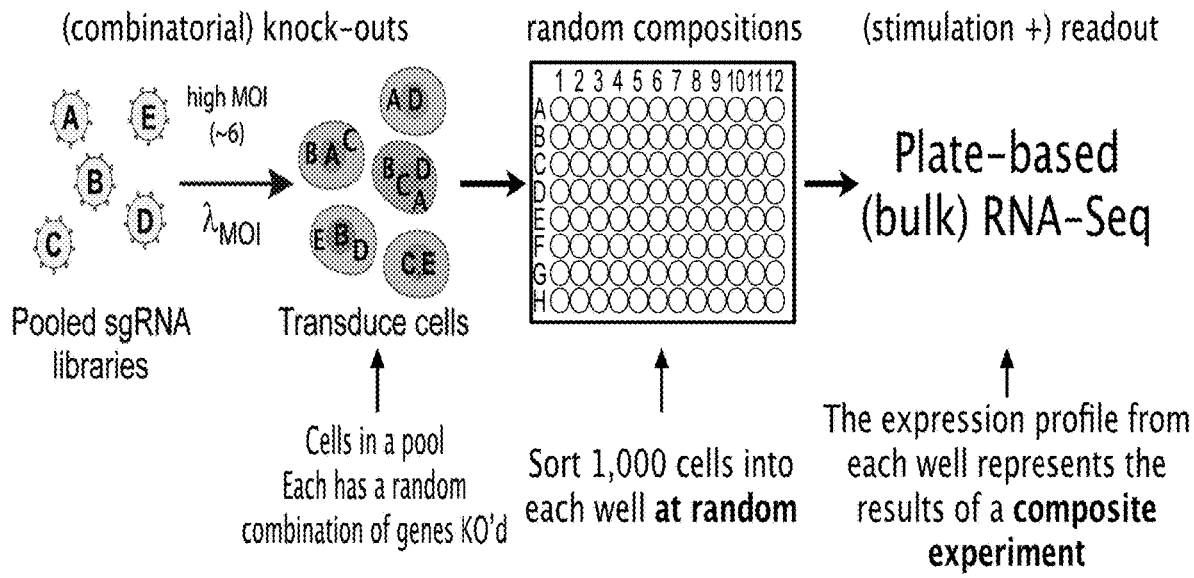
FIG. 1 shows a compressed experiment using composite perturbations using composite measurement approaches similar to the experiments used herein. The result of a composite experiment reflects the (weighted) average result of multiple independent experiments. Upper panel includes composite measurements for expression as disclosed in Cleary et al., Cell 2017.
Figure 1:
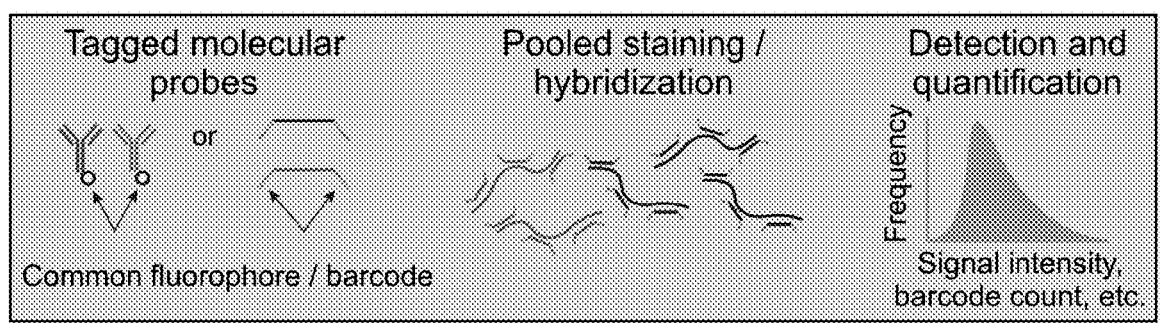
Figure 1:
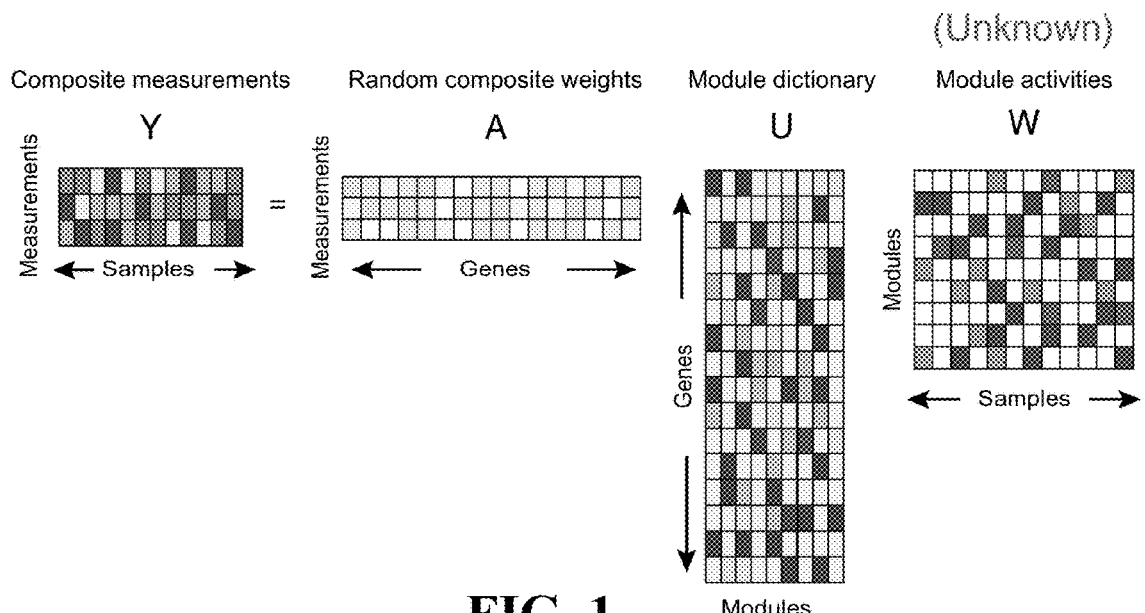
Figure 3:
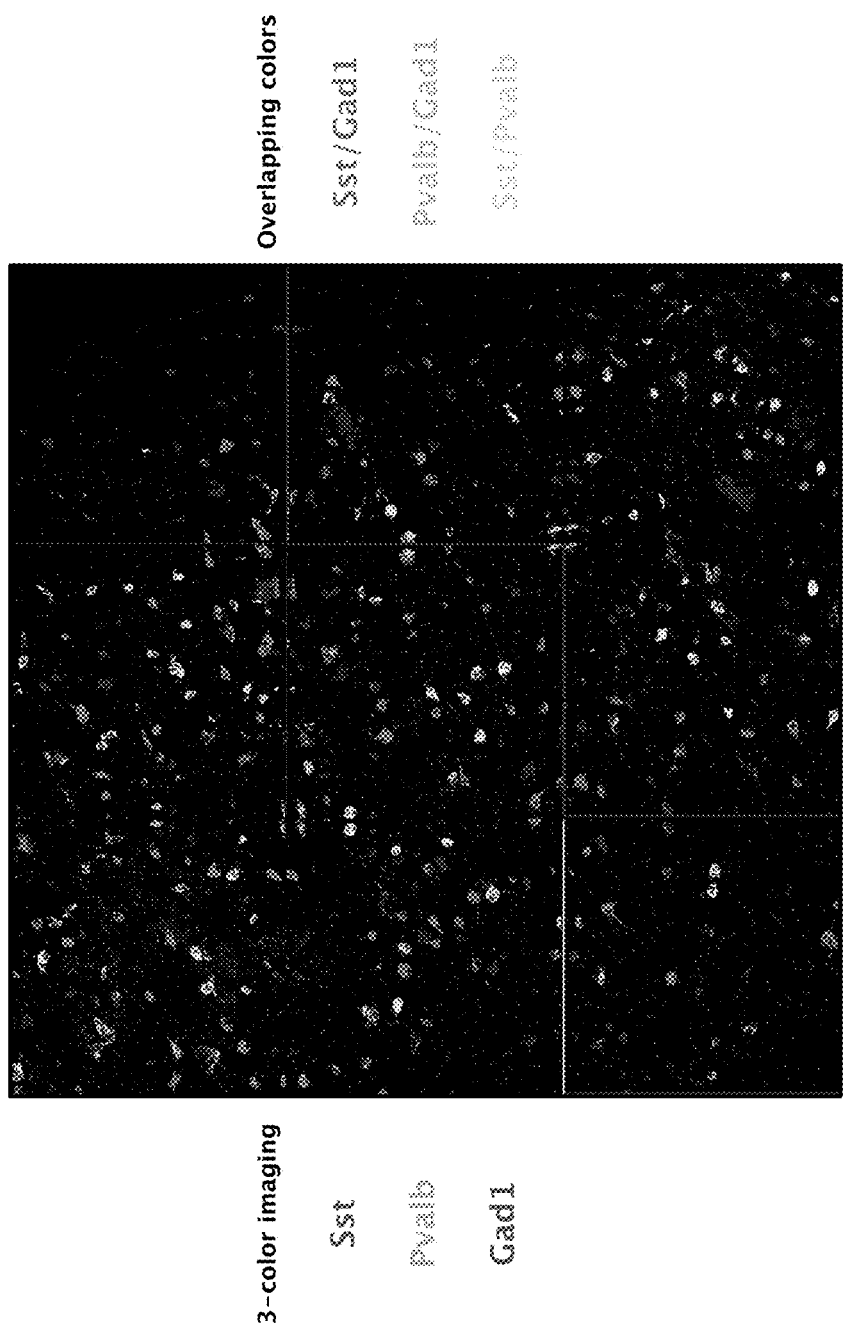
FIG. 3 shows multiplexed imaging mRNA abundance in mouse motor cortex, with nine fields of view stitched together.

The figures herein are for illustrative purposes only and are not necessarily drawn to scale.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, 2nd edition (1989) (Sambrook, Fritsch, and Maniatis); Molecular Cloning: A Laboratory Manual, 4th edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, 2nd edition 2013 (E. A. Greenfield ed.); Animal Cell Culture (1987) (R. I. Freshney, ed.); Benjamin Lewin, Genes IX, published by Jones and Bartlett, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, 2nd edition (2011).

As used herein, the singular forms "a" "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example, by puncture, or other collecting or sampling procedures.

The terms "subject," "individual," and "patient" are used interchangeably herein to refer to a vertebrate such as a mammal, e.g., a human. Examples of subjects include mammalian, human, chimpanzee, primates, such as monkeys, and mice, rat. Tissues, cells and their progeny of a biological entity obtained in vivo or cultured in vitro are also encompassed.

The term "exemplary" is used herein to mean serving as an example, instance, or illustration. Any aspect or design described herein as "exemplary" is not necessarily to be construed as preferred or advantageous over other aspects or designs. Rather, use of the word "exemplary" is intended to present concepts in a concrete fashion.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

All publications, published patent documents, and patent applications cited herein are hereby incorporated by reference to the same extent as though each individual publication, published patent document, or patent application was specifically and individually indicated as being incorporated by reference.

Overview

Embodiments disclosed herein provide methods of imaging a cell or tissue from a region of interest. The methods allow for the study of cell and tissue physiology in situ, thus providing insight into complex diseases. The spatial profiling of protein/mRNA abundance provided by the current methods can inform treatment, monitoring and diagnostics of disease states. Evaluation of tumor heterogeneity, cellular profiling, pathway identification, and gene co-regulations can be identified utilizing the approaches provided here.

Methods of in situ imaging are provided herein. The methods as described herein allow for the imaging of expressed genes in cells or tissue from a region of interest in situ. The methods disclosed herein can be used in a variety of applications, including the study of complex tissues, cells and systems. Accordingly, any tissue, cell, or population of cells can be used in the imaging methods disclosed herein, and may include multiple cell types, tissue types, or a library of cells.

Methods of Imaging

Methods of in situ imaging comprise steps of detecting one or more composite genes in a cell or tissue from a region of interest by performing single cell sequencing of nucleic acid sequencing and imaging the tissue or cell from the region of interest of the subject in situ, fitting the gene module activities spatially to form a composite image. In some embodiments, it is desired to decompress the composite image, thereby recording images for individual genes from the cell or tissue from the region of interest. Composite genes can each comprise a linear weighted combination of abundances of two or more individual genes. Composite genes can be detected by performing single cell sequencing of nucleic acid from the tissue or cell from the region of interest, as described herein, and as described in Cleary B, et al. Efficient generation of transcriptomic profiles by random composite measurements. Cell. Online Nov. 16, 2017. DOI: 10.1016/j.cell.2017.10.023, incorporated in its entirety herein.

Gene modules are identified from the tissue or cell from a region of interest. Because cells express genes in discrete programs, with only a limited number of such gene modules at a time (sparse), a gene module as provided herein can be a sum of multiple genes' weighted abundances that are actively expressed. Gene modules can be identified through methods known in the art from the training data collected from the region of interest, as described further herein. Gene modules can be found by applying algorithmic methods in some instances, for example, random forest assigning importance to features during training. Exemplary methods of identification of expressed genes is described in U.S. Provisional Application 62/698,778 entitled "High-Throughput Tests of Synergistic Gene Interactions" filed Jul. 16, 2018, at [0992]-[01014], and throughout, including discussion of unsupervised dimensionality reduction methods like Principal Component Analysis (PCA); and throughout International Patent Application PCT/US2016/059230, filed Oct. 27, 2016, in particular [0073]-[0155] for gene expression profiling and module identification, incorporated by reference in their entirety herein.

In some embodiments, the one or more composite genes are comprised of between 2 and 2000 individual genes. In some embodiments, the one or more composite genes are comprised of 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 135, 140, 145, 150 or more individual genes. In some embodiments, the region of interest is the motor cortex and one or more individual genes comprise one or more genes of Tables 1-4.

Single Cell Sequence Methods

Cells come in different types, sub-types and activity states, which are classify based on their shape, location, function, or molecular profiles, such as the set of RNAs that they express. RNA profiling is in principle particularly informative, as cells express thousands of different RNAs. Approaches that measure, for example, the level of every type of RNA have until recently been applied to "homogenized" samples—in which the contents of all the cells are mixed together. Methods to profile the RNA content of tens and hundreds of thousands of individual human cells have been recently developed, including from brain tissues, quickly and inexpensively. To do so, special microfluidic devices have been developed to encapsulate each cell in an individual drop, associate the RNA of each cell with a 'cell barcode' unique to that cell/drop, measure the expression level of each RNA with sequencing, and then use the cell barcodes to determine which cell each RNA molecule came from.

In certain embodiments, the invention involves high-throughput single-cell RNA-seq and/or targeted nucleic acid profiling (for example, sequencing, quantitative reverse transcription polymerase chain reaction, and the like). In certain embodiments, the nucleic acids (e.g., RNAs) from different cells are tagged individually, allowing a single library to be created while retaining the cell identity of each read. In this regard, reference is made to Macosko et al., 2015, "Highly Parallel Genome-wide Expression Profiling of Individual Cells Using Nanoliter Droplets" Cell 161, 1202-1214; International patent application number PCT/US2015/049178, published as WO2016/040476 on Mar. 17, 2016; Klein et al., 2015, "Droplet Barcoding for Single-Cell Transcriptomics Applied to Embryonic Stem Cells" Cell 161, 1187-1201; International patent application number PCT/US2016/027734, published as WO2016/168584A1 on Oct. 20, 2016; Zheng, et al., 2016, "Haplotyping germline and cancer genomes with high-throughput linked-read sequencing" Nature Biotechnology 34, 303-311; Zheng, et al., 2017, "Massively parallel digital transcriptional profiling of single cells" Nat. Commun. 8, 14049 doi: 10.1038/ncomms14049; International patent publication number WO 2014/210353 A2; Zilionis, et al., 2017, "Single-cell barcoding and sequencing using droplet microfluidics" Nat Protoc. January; 12(1):44-73; Cao et al., 2017, "Comprehensive single cell transcriptional profiling of a multicellular organism by combinatorial indexing", bioRxiv preprint first posted online Feb. 2, 2017, doi: dx.doi.org/10.1101/104844; and Rosenberg et al., 2017, "Scaling single cell transcriptomics through split pool barcoding", bioRxiv preprint first posted online Feb. 2, 2017, doi: dx.doi.org/10.1101/105163, all the contents and disclosure of each of which are herein incorporated by reference in their entirety.

In certain embodiments, the invention involves single nucleus RNA sequencing. In this regard, reference is made to Swiech et al., 2014, "In vivo interrogation of gene function in the mammalian brain using CRISPR-Cas9", Nature Biotechnology, Vol. 33, pp. 102-106; and Habib et al., 2016, "Div-Seq: Single-nucleus RNA-Seq reveals dynamics of rare adult newborn neurons" Science, Vol. 353, Issue 6302, pp. 925-928, both of which are herein incorporated by reference in their entirety.

Microfluidics involves micro-scale devices that handle small volumes of fluids. Because microfluidics may accurately and reproducibly control and dispense small fluid volumes, in particular volumes less than 1 µl, application of microfluidics provides significant cost-savings. The use of microfluidics technology reduces cycle times, shortens time-to-results, and increases throughput. Furthermore, incorporation of microfluidics technology enhances system integration and automation. Microfluidic reactions are generally conducted in microdroplets. The ability to conduct reactions in microdroplets depends on being able to merge different sample fluids and different microdroplets. See, e.g., US Patent Publication No. 20120219947. See also International Patent Application No. PCT/US2014/058637 for disclosure regarding a microfluidic laboratory on a chip.

Droplet microfluidics offers significant advantages for performing high-throughput screens and sensitive assays. Droplets allow sample volumes to be significantly reduced, leading to concomitant reductions in cost. Manipulation and measurement at kilohertz speeds enable up to 108 discrete biological entities (including, but not limited to, individual cells or organelles) to be screened in a single day. Compartmentalization in droplets increases assay sensitivity by increasing the effective concentration of rare species and decreasing the time required to reach detection thresholds. Droplet microfluidics combines these powerful features to enable currently inaccessible high-throughput screening applications, including single-cell and single-molecule assays. See, e.g., Guo et al., Lab Chip, 2012, 12, 2146-2155.

Drop-Sequence methods and apparatus provides a high-throughput single-cell RNA-Seq and/or targeted nucleic acid profiling (for example, sequencing, quantitative reverse transcription polymerase chain reaction, and the like) where the RNAs from different cells are tagged individually, allowing a single library to be created while retaining the cell identity of each read. A combination of molecular barcoding and emulsion-based microfluidics to isolate, lyse, barcode, and prepare nucleic acids from individual cells in high-throughput is used. Microfluidic devices (for example, fabricated in polydimethylsiloxane), can be utilized for sub-nanoliter reverse emulsion droplets. These droplets are used to co-encapsulate nucleic acids with a barcoded capture bead. Each bead, for example, is uniquely barcoded so that each drop, and its contents, are distinguishable. The nucleic acids may come from any source known in the art, such as for example, those which come from a single cell, a pair of cells, a cellular lysate, or a solution. The cell is lysed as it is encapsulated in the droplet. To load single cells and barcoded beads into these droplets with Poisson statistics, 100,000 to 10 million such beads are needed to barcode ~10,000-100,000 cells.

The invention provides a method for creating a single-cell sequencing library comprising: merging one uniquely barcoded mRNA capture microbead with a single-cell in an emulsion droplet having a diameter of 75-125 µm; lysing the cell to make its RNA accessible for capturing by hybridization onto RNA capture microbead; performing a reverse transcription either inside or outside the emulsion droplet to convert the cell's mRNA to a first strand cDNA that is covalently linked to the mRNA capture microbead; pooling the cDNA-attached microbeads from all cells; and preparing and sequencing a single composite RNA-Seq library.

The invention provides a method for preparing uniquely barcoded mRNA capture microbeads, which has a unique barcode and diameter suitable for microfluidic devices comprising: 1) performing reverse phosphoramidite synthesis on the surface of the bead in a pool-and-split fashion, such that in each cycle of synthesis the beads are split into four reactions with one of the four canonical nucleotides (T, C, G, or A) or unique oligonucleotides of length of two or more bases; 2) repeating this process a large number of times, at least two, and optimally more than twelve, such that, in the latter, there are more than 16 million unique barcodes on the surface of each bead in the pool (see www.ncbi.nlm.nih.gov/pmc/articles/PMC206447).

Generally, the invention provides a method for preparing a large number of beads, particles, microbeads, nanoparticles, or the like, with unique nucleic acid barcodes comprising performing polynucleotide synthesis on the surface of the beads in a pool-and-split fashion such that in each cycle of synthesis the beads are split into subsets that are subjected to different chemical reactions; and then repeating this split-pool process in two or more cycles, to produce a combinatorially large number of distinct nucleic acid barcodes. The invention further provides performing a polynucleotide synthesis wherein the synthesis may be any type of synthesis known to one of skill in the art for "building" polynucleotide sequences in a step-wise fashion. Examples include, but are not limited to, reverse direction synthesis with phosphoramidite chemistry or forward direction synthesis with phosphoramidite chemistry. Previous and well-known methods synthesize the oligonucleotides separately then "glue" the entire desired sequence onto the bead enzymatically. A complexed bead and a process for producing these beads where nucleotides are chemically built onto the bead material in a high-throughput manner may also be utilized. Moreover, delivering a "packet" of beads which allows one to deliver millions of sequences into separate compartments and then screen all at once can be used in accordance with the current methods.

The invention further provides an apparatus for creating a single-cell sequencing library via a microfluidic system, comprising: an oil-surfactant inlet comprising a filter and a carrier fluid channel, wherein said carrier fluid channel further comprises a resistor; an inlet for an analyte comprising a filter and a carrier fluid channel, wherein said carrier fluid channel further comprises a resistor; an inlet for mRNA capture microbeads and lysis reagent comprising a filter and a carrier fluid channel, wherein said carrier fluid channel further comprises a resistor; said carrier fluid channels have a carrier fluid flowing therein at an adjustable or predetermined flow rate; wherein each said carrier fluid channels merge at a junction; and said junction being connected to a mixer, which contains an outlet for drops.

A mixture comprising a plurality of microbeads adorned with combinations of the following elements: bead-specific oligonucleotide barcodes created by the described methods; additional oligonucleotide barcode sequences which vary among the oligonucleotides on an individual bead and can therefore be used to differentiate or help identify those individual oligonucleotide molecules; additional oligonucleotide sequences that create substrates for downstream molecular-biological reactions, such as oligo-dT (for reverse transcription of mature mRNAs), specific sequences (for capturing specific portions of the transcriptome, or priming for DNA polymerases and similar enzymes), or random sequences (for priming throughout the transcriptome or genome). In an embodiment, the individual oligonucleotide molecules on the surface of any individual microbead contain all three of these elements, and the third element includes both oligo-dT and a primer sequence.

Examples of the labeling substance which may be employed include labeling substances known to those skilled in the art, such as fluorescent dyes, enzymes, coenzymes, chemiluminescent substances, and radioactive substances. Specific examples include radioisotopes (e.g., 32P, 14C, 125I, 3H, and 131I), fluorescein, rhodamine, dansyl chloride, umbelliferone, luciferase, peroxidase, alkaline phosphatase, β-galactosidase, β-glucosidase, horseradish peroxidase, glucoamylase, lysozyme, saccharide oxidase, microperoxidase, biotin, and ruthenium. In the case where biotin is employed as a labeling substance, preferably, after addition of a biotin-labeled antibody, streptavidin bound to an enzyme (e.g., peroxidase) is further added.

Advantageously, the label is a fluorescent label. Examples of fluorescent labels include, but are not limited to, Atto dyes, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-(vinylsulfonyl)phenyl]naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcoumarin (Coumaran 151); cyanine dyes; cyanosine; 4', 6-diaminidino-2-phenylindole (DAPI); 5'5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosine and derivatives; erythrosine B, erythrosine, isothiocyanate; ethidium; fluorescein and derivatives; 5-carboxyfluorescein (FAM), 5-(4,6-dichlorotriazin-2-yl)aminofluorescein (DTAF), 2', 7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N' tetramethyl-6-carboxyrhodamine (TAMRA); tetramethyl rhodamine; tetramethyl rhodamine isothiocyanate (TRITC); riboflavin; rosolic acid; terbium chelate derivatives; Cy3; Cy5; Cy5.5; Cy7; IRD 700; IRD 800; La Jolla Blue; phthalo cyanine; and naphthalocyanine.

The fluorescent label may be a fluorescent protein, such as blue fluorescent protein, cyan fluorescent protein, green fluorescent protein, red fluorescent protein, yellow fluorescent protein or any photoconvertible protein. Colormetric labeling, bioluminescent labeling and/or chemiluminescent labeling may further accomplish labeling. Labeling further may include energy transfer between molecules in the hybridization complex by perturbation analysis, quenching, or electron transport between donor and acceptor molecules, the latter of which may be facilitated by double stranded match hybridization complexes. The fluorescent label may be a perylene or a terylene. In the alternative, the fluorescent label may be a fluorescent bar code.

In an advantageous embodiment, the label may be light sensitive, wherein the label is light-activated and/or light cleaves the one or more linkers to release the molecular cargo. The light-activated molecular cargo may be a major light-harvesting complex (LHCII). In another embodiment, the fluorescent label may induce free radical formation.

The invention described herein enables high throughput and high resolution delivery of reagents to individual emulsion droplets that may contain cells, organelles, nucleic acids, proteins, etc. through the use of monodisperse aqueous droplets that are generated by a microfluidic device as a water-in-oil emulsion. The droplets are carried in a flowing oil phase and stabilized by a surfactant. In one aspect, single cells or single organelles or single molecules (proteins, RNA, DNA) are encapsulated into uniform droplets from an aqueous solution/dispersion. In a related aspect, multiple cells or multiple molecules may take the place of single cells or single molecules. The aqueous droplets of volume ranging from 1 pL to 10 nL work as individual reactors. Disclosed embodiments provide 104 to 105 single cells in droplets which can be processed and analyzed in a single run.

To utilize microdroplets for rapid large-scale chemical screening or complex biological library identification, different species of microdroplets, each containing the specific chemical compounds or biological probes cells or molecular barcodes of interest, have to be generated and combined at the preferred conditions, e.g., mixing ratio, concentration, and order of combination.

Each species of droplet is introduced at a confluence point in a main microfluidic channel from separate inlet microfluidic channels. Preferably, droplet volumes are chosen by design such that one species is larger than others and moves at a different speed, usually slower than the other species, in the carrier fluid, as disclosed in U.S. Publication No. US 2007/0195127 and International Publication No. WO 2007/089541, each of which are incorporated herein by reference in their entirety. The channel width and length is selected such that faster species of droplets catch up to the slowest species. Size constraints of the channel prevent the faster moving droplets from passing the slower moving droplets resulting in a train of droplets entering a merge zone. Multi-step chemical reactions, biochemical reactions, or assay detection chemistries often require a fixed reaction time before species of different type are added to a reaction. Multi-step reactions are achieved by repeating the process multiple times with a second, third or more confluence points each with a separate merge point. Highly efficient and precise reactions and analysis of reactions are achieved when the frequencies of droplets from the inlet channels are matched to an optimized ratio and the volumes of the species are matched to provide optimized reaction conditions in the combined droplets.

Fluidic droplets may be screened or sorted within a fluidic system of the invention by altering the flow of the liquid containing the droplets. For instance, in one set of embodiments, a fluidic droplet may be steered or sorted by directing the liquid surrounding the fluidic droplet into a first channel, a second channel, etc. In another set of embodiments, pressure within a fluidic system, for example, within different channels or within different portions of a channel, can be controlled to direct the flow of fluidic droplets. For example, a droplet can be directed toward a channel junction including multiple options for further direction of flow (e.g., directed toward a branch, or fork, in a channel defining optional downstream flow channels). Pressure within one or more of the optional downstream flow channels can be controlled to direct the droplet selectively into one of the channels, and changes in pressure can be effected on the order of the time required for successive droplets to reach the junction, such that the downstream flow path of each successive droplet can be independently controlled. In one arrangement, the expansion and/or contraction of liquid reservoirs may be used to steer or sort a fluidic droplet into a channel, e.g., by causing directed movement of the liquid containing the fluidic droplet. In another embodiment, the expansion and/or contraction of the liquid reservoir may be combined with other flow-controlling devices and methods, e.g., as described herein. Non-limiting examples of devices able to cause the expansion and/or contraction of a liquid reservoir include pistons.

Key elements for using microfluidic channels to process droplets include: (1) producing droplets of the correct volume, (2) producing droplets at the correct frequency and (3) bringing together a first stream of sample droplets with a second stream of sample droplets in such a way that the frequency of the first stream of sample droplets matches the frequency of the second stream of sample droplets. Preferably, bringing together a stream of sample droplets with a stream of premade library droplets in such a way that the frequency of the library droplets matches the frequency of the sample droplets.

Methods for producing droplets of a uniform volume at a regular frequency are well known in the art. One method is to generate droplets using hydrodynamic focusing of a dispersed phase fluid and immiscible carrier fluid, such as disclosed in U.S. Publication No. US 2005/0172476 and International Publication No. WO 2004/002627. It is desirable for one of the species introduced at the confluence to be a pre-made library of droplets where the library contains a plurality of reaction conditions, e.g., a library may contain plurality of different compounds at a range of concentrations encapsulated as separate library elements for screening their effect on cells or enzymes. Alternatively, a library could be composed of a plurality of different primer pairs encapsulated as different library elements for targeted amplification of a collection of loci. Alternatively, a library could contain a plurality of different antibody species encapsulated as different library elements to perform a plurality of binding assays. The introduction of a library of reaction conditions onto a substrate is achieved by pushing a premade collection of library droplets out of a vial with a drive fluid. The drive fluid is a continuous fluid. The drive fluid may comprise the same substance as the carrier fluid (e.g., a fluorocarbon oil). For example, if a library consists of ten pico-liter droplets is driven into an inlet channel on a microfluidic substrate with a drive fluid at a rate of 10,000 pico-liters per second, then nominally the frequency at which the droplets are expected to enter the confluence point is 1000 per second. However, in practice droplets pack with oil between them that slowly drains. Over time the carrier fluid drains from the library droplets and the number density of the droplets (number/mL) increases. Hence, a simple fixed rate of infusion for the drive fluid does not provide a uniform rate of introduction of the droplets into the microfluidic channel in the substrate. Moreover, library-to-library variations in the mean library droplet volume result in a shift in the frequency of droplet introduction at the confluence point. Thus, the lack of uniformity of droplets that results from sample variation and oil drainage provides another problem to be solved. For example, if the nominal droplet volume is expected to be 10 pico-liters in the library, but varies from 9 to 11 pico-liters from library-to-library, then a 10,000 pico-liter/second infusion rate will nominally produce a range in frequencies from 900 to 1,100 droplet per second. In short, sample to sample variation in the composition of dispersed phase for droplets made on chip, a tendency for the number density of library droplets to increase over time and library-to-library variations in mean droplet volume severely limit the extent to which frequencies of droplets may be reliably matched at a confluence by simply using fixed infusion rates. In addition, these limitations also have an impact on the extent to which volumes may be reproducibly combined. Combined with typical variations in pump flow rate precision and variations in channel dimensions, systems are severely limited without a means to compensate on a run-to-run basis. The foregoing facts not only illustrate a problem to be solved, but also demonstrate a need for a method of instantaneous regulation of microfluidic control over microdroplets within a microfluidic channel.

Combinations of surfactant(s) and oils must be developed to facilitate generation, storage, and manipulation of droplets to maintain the unique chemical/biochemical/biological environment within each droplet of a diverse library. Therefore, the surfactant and oil combination must (1) stabilize droplets against uncontrolled coalescence during the drop forming process and subsequent collection and storage, (2) minimize transport of any droplet contents to the oil phase and/or between droplets, and (3) maintain chemical and biological inertness with contents of each droplet (e.g., no adsorption or reaction of encapsulated contents at the oil-water interface, and no adverse effects on biological or chemical constituents in the droplets). In addition to the requirements on the droplet library function and stability, the surfactant-in-oil solution must be coupled with the fluid physics and materials associated with the platform. Specifically, the oil solution must not swell, dissolve, or degrade the materials used to construct the microfluidic chip, and the physical properties of the oil (e.g., viscosity, boiling point, etc.) must be suited for the flow and operating conditions of the platform.

Droplets formed in oil without surfactant are not stable to permit coalescence, so surfactants must be dissolved in the oil that is used as the continuous phase for the emulsion library. Surfactant molecules are amphiphilic—part of the molecule is oil soluble, and part of the molecule is water soluble. When a water-oil interface is formed at the nozzle of a microfluidic chip, for example, in the inlet module described herein, surfactant molecules that are dissolved in the oil phase adsorb to the interface. The hydrophilic portion of the molecule resides inside the droplet and the fluorophilic portion of the molecule decorates the exterior of the droplet. The surface tension of a droplet is reduced when the interface is populated with surfactant, so the stability of an emulsion is improved. In addition to stabilizing the droplets against coalescence, the surfactant should be inert to the contents of each droplet and the surfactant should not promote transport of encapsulated components to the oil or other droplets.

A droplet library may be made up of a number of library elements that are pooled together in a single collection (see, e.g., US Patent Publication No. 2010002241). Libraries may vary in complexity from a single library element to 1015 library elements or more. Each library element may be one or more given components at a fixed concentration. The element may be, but is not limited to, cells, organelles, virus, bacteria, yeast, beads, amino acids, proteins, polypeptides, nucleic acids, polynucleotides or small molecule chemical compounds. The element may contain an identifier such as a label. The terms "droplet library" or "droplet libraries" are also referred to herein as an "emulsion library" or "emulsion libraries." These terms are used interchangeably throughout the specification.

A cell library element may include, but is not limited to, hybridomas, B-cells, primary cells, cultured cell lines, cancer cells, stem cells, cells obtained from tissue, or any other cell type. Cellular library elements are prepared by encapsulating a number of cells from one to hundreds of thousands in individual droplets. The number of cells encapsulated is usually given by Poisson statistics from the number density of cells and volume of the droplet. However, in some cases the number deviates from Poisson statistics as described in Edd et al., "Controlled encapsulation of single-cells into monodisperse picolitre drops." Lab Chip, 8(8): 1262-1264, 2008. The discrete nature of cells allows for libraries to be prepared in mass with a plurality of cellular variants all present in a single starting media and then that media is broken up into individual droplet capsules that contain at most one cell. These individual droplets capsules are then combined or pooled to form a library consisting of unique library elements. Cell division subsequent to, or in some embodiments following, encapsulation produces a clonal library element.

A bead based library element may contain one or more beads, of a given type and may also contain other reagents, such as antibodies, enzymes or other proteins. In the case where all library elements contain different types of beads, but the same surrounding media, the library elements may all be prepared from a single starting fluid or have a variety of starting fluids. In the case of cellular libraries prepared in mass from a collection of variants, such as genomically modified, yeast or bacteria cells, the library elements will be prepared from a variety of starting fluids.

Often it is desirable to have exactly one cell per droplet with only a few droplets containing more than one cell when starting with a plurality of cells or yeast or bacteria, engineered to produce variants on a protein. In some cases, variations from Poisson statistics may be achieved to provide an enhanced loading of droplets such that there are more droplets with exactly one cell per droplet and few exceptions of empty droplets or droplets containing more than one cell.

Examples of droplet libraries are collections of droplets that have different contents, ranging from beads, cells, small molecules, DNA, primers, antibodies. Smaller droplets may be in the order of femtoliter (fL) volume drops, which are especially contemplated with the droplet dispensers. The volume may range from about 5 to about 600 fL. The larger droplets range in size from roughly 0.5 micron to 500 micron in diameter, which corresponds to about 1 pico liter to 1 nano liter. However, droplets may be as small as 5 microns and as large as 500 microns. Preferably, the droplets are at less than 100 microns, about 1 micron to about 100 microns in diameter. The most preferred size is about 20 to 40 microns in diameter (10 to 100 picoliters). The preferred properties examined of droplet libraries include osmotic pressure balance, uniform size, and size ranges.

The droplets comprised within the emulsion libraries of the present invention may be contained within an immiscible oil which may comprise at least one fluorosurfactant. In some embodiments, the fluorosurfactant comprised within immiscible fluorocarbon oil is a block copolymer consisting of one or more perfluorinated polyether (PFPE) blocks and one or more polyethylene glycol (PEG) blocks. In other embodiments, the fluorosurfactant is a triblock copolymer consisting of a PEG center block covalently bound to two PFPE blocks by amide linking groups. The presence of the fluorosurfactant (similar to uniform size of the droplets in the library) is critical to maintain the stability and integrity of the droplets and is also essential for the subsequent use of the droplets within the library for the various biological and chemical assays described herein. Fluids (e.g., aqueous fluids, immiscible oils, etc.) and other surfactants that may be utilized in the droplet libraries of the present invention are described in greater detail herein.

The present invention provides an emulsion library which may comprise a plurality of aqueous droplets within an immiscible oil (e.g., fluorocarbon oil) which may comprise at least one fluorosurfactant, wherein each droplet is uniform in size and may comprise the same aqueous fluid and may comprise a different library element. The present invention also provides a method for forming the emulsion library which may comprise providing a single aqueous fluid which may comprise different library elements, encapsulating each library element into an aqueous droplet within an immiscible fluorocarbon oil which may comprise at least one fluorosurfactant, wherein each droplet is uniform in size and may comprise the same aqueous fluid and may comprise a different library element, and pooling the aqueous droplets within an immiscible fluorocarbon oil which may comprise at least one fluorosurfactant, thereby forming an emulsion library.

For example, in one type of emulsion library, all different types of elements (e.g., cells or beads), may be pooled in a single source contained in the same medium. After the initial pooling, the cells or beads are then encapsulated in droplets to generate a library of droplets wherein each droplet with a different type of bead or cell is a different library element. The dilution of the initial solution enables the encapsulation process. In some embodiments, the droplets formed will either contain a single cell or bead or will not contain anything, i.e., be empty. In other embodiments, the droplets formed will contain multiple copies of a library element. The cells or beads being encapsulated are generally variants on the same type of cell or bead. In one example, the cells may comprise cancer cells of a tissue biopsy, and each cell type is encapsulated to be screened for genomic data or against different drug therapies. Another example is that 1011 or 1015 different type of bacteria, each having a different plasmid spliced therein, are encapsulated. One example is a bacterial library where each library element grows into a clonal population that secretes a variant on an enzyme.

In another example, the emulsion library may comprise a plurality of aqueous droplets within an immiscible fluorocarbon oil, wherein a single molecule may be encapsulated, such that there is a single molecule contained within a droplet for every 20-60 droplets produced (e.g., 20, 25, 30, 35, 40, 45, 50, 55, 60 droplets, or any integer in between). Single molecules may be encapsulated by diluting the solution containing the molecules to such a low concentration that the encapsulation of single molecules is enabled. In one specific example, a LacZ plasmid DNA was encapsulated at a concentration of 20 fM after two hours of incubation such that there was about one gene in 40 droplets, where 10 µm droplets were made at 10 kHz per second. Formation of these libraries rely on limiting dilutions.

Methods of the invention involve forming sample droplets. The droplets are aqueous droplets that are surrounded by an immiscible carrier fluid. Methods of forming such droplets are shown for example in Link et al. (U.S. Patent Application Publication Nos. 2008/0014589, 2008/0003142, and 2010/0137163), Stone et al. (U.S. Pat. No. 7,708,949 and U.S. Patent Application Publication No. 2010/0172803), Anderson et al. (U.S. Pat. No. 7,041,481 and which reissued as RE 41,780) and European Publication No. EP2047910 to Raindance Technologies Inc, the content of each of which is incorporated by reference herein in its entirety.

In certain embodiments, the carrier fluid may contain one or more additives, such as agents which reduce surface tensions (surfactants). Surfactants can include Tween, Span, fluorosurfactants, and other agents that are soluble in oil relative to water. In some applications, performance is improved by adding a second surfactant to the sample fluid. Surfactants can aid in controlling or optimizing droplet size, flow and uniformity, for example by reducing the shear force needed to extrude or inject droplets into an intersecting channel. This can affect droplet volume and periodicity, or the rate or frequency at which droplets break off into an intersecting channel. Furthermore, the surfactant can serve to stabilize aqueous emulsions in fluorinated oils from coalescing.

In certain embodiments, the droplets may be surrounded by a surfactant which stabilizes the droplets by reducing the surface tension at the aqueous oil interface. Preferred surfactants that may be added to the carrier fluid include, but are not limited to, surfactants such as sorbitan-based carboxylic acid esters (e.g., the "Span" surfactants, Fluka Chemika), including sorbitan monolaurate (Span 20), sorbitan monopalmitate (Span 40), sorbitan monostearate (Span 60) and sorbitan monooleate (Span 80), and perfluorinated polyethers (e.g., DuPont Krytox 157 FSL, FSM, and/or FSH). Other non-limiting examples of non-ionic surfactants which may be used include polyoxyethylenated alkylphenols (for example, nonyl-, p-dodecyl-, and dinonylphenols), polyoxyethylenated straight chain alcohols, polyoxyethylenated polyoxypropylene glycols, polyoxyethylenated mercaptans, long chain carboxylic acid esters (for example, glyceryl and polyglyceryl esters of natural fatty acids, propylene glycol, sorbitol, polyoxyethylenated sorbitol esters, polyoxyethylene glycol esters, etc.) and alkanolamines (e.g., diethanolamine-fatty acid condensates and isopropanolamine-fatty acid condensates).

By incorporating a plurality of unique tags into the additional droplets and joining the tags to a solid support designed to be specific to the primary droplet, the conditions that the primary droplet is exposed to may be encoded and recorded. For example, nucleic acid tags can be sequentially ligated to create a sequence reflecting conditions and order of same. Alternatively, the tags can be added independently appended to solid support. Non-limiting examples of a dynamic labeling system that may be used to bioninformatically record information can be found at US Provisional Patent Applications entitled "Compositions and Methods for Unique Labeling of Agents" filed Sep. 21, 2012 and Nov. 29, 2012. In this way, two or more droplets may be exposed to a variety of different conditions, where each time a droplet is exposed to a condition, a nucleic acid encoding the condition is added to the droplet, each ligated together or to a unique solid support associated with the droplet such that, even if the droplets with different histories are later combined, the conditions of each of the droplets are remain available through the different nucleic acids. Non-limiting examples of methods to evaluate response to exposure to a plurality of conditions can be found at US Provisional Patent Application entitled "Systems and Methods for Droplet Tagging" filed Sep. 21, 2012.

Applications of the disclosed device may include use for the dynamic generation of molecular barcodes (e.g., DNA oligonucleotides, fluorophores, etc.) either independent from or in concert with the controlled delivery of various compounds of interest (drugs, small molecules, siRNA, CRISPR guide RNAs, reagents, etc.). For example, unique molecular barcodes can be created in one array of nozzles while individual compounds or combinations of compounds can be generated by another nozzle array. Barcodes/compounds of interest can then be merged with cell-containing droplets. An electronic record in the form of a computer log file is kept to associate the barcode delivered with the downstream reagent(s) delivered. This methodology makes it possible to efficiently screen a large population of cells for applications such as single-cell drug screening, controlled perturbation of regulatory pathways, etc. The device and techniques of the disclosed invention facilitate efforts to perform studies that require data resolution at the single cell (or single molecule) level and in a cost effective manner. Disclosed embodiments provide a high throughput and high resolution delivery of reagents to individual emulsion droplets that may contain cells, nucleic acids, proteins, etc. through the use of monodisperse aqueous droplets that are generated one by one in a microfluidic chip as a water-in-oil emulsion. Hence, the invention proves advantageous over prior art systems by being able to dynamically track individual cells and droplet treatments/combinations during life cycle experiments. Additional advantages of the disclosed invention provides an ability to create a library of emulsion droplets on demand with the further capability of manipulating the droplets through the disclosed process(es). Disclosed embodiments may, thereby, provide dynamic tracking of the droplets and create a history of droplet deployment and application in a single cell based environment.

Droplet generation and deployment is produced via a dynamic indexing strategy and in a controlled fashion in accordance with disclosed embodiments of the present invention. Disclosed embodiments of the microfluidic device described herein provides the capability of microdroplets to be processed, analyzed and sorted at a highly efficient rate of several thousand droplets per second, providing a powerful platform which allows rapid screening of millions of distinct compounds, biological probes, proteins or cells either in cellular models of biological mechanisms of disease, or in biochemical, or pharmacological assays.

Single cell RNA may also be analyzed as described in Klein, A. M., Mazutis, L., Akartuna, I., Tallapragada, N., Veres, A., Li, V., Peshkin, L., Weitz, D. A., Kirschner, M. W. Droplet barcoding for single-cell transcriptomics applied to embryonic stem cells. Cell 2015 May 21; 161(5):1187-201. doi: 10.1016/j.cell.2015.04.044. PMCID: 4441768.

The method of the invention may include determining RNA transcription and degradation rates. One may use RNA metabolically labeled with 4-thiouridine to measure RNA transcription and degradation rates (Rabani, M., Raychowdhury, R., Jovanovic, M., Rooney, M., Stumpo, D. J., Pauli, A., Hacohen, N., Schier, A. F., Blackshear, P. J., Friedman, N., Amit, I. & Regev, A. High-resolution sequencing and modeling identifies distinct dynamic RNA regulatory strategies. Cell 159, 1698-1710, doi:10.1016/j.cell.2014.11.015 (2014). PMCID:4272607; Rabani, M., Levin, J. Z., Fan, L., Adiconis, X., Raychowdhury, R., Garber, M., Gnirke, A., Nusbaum, C., Hacohen, N., Friedman, N., Amit, I. & Regev, A. Metabolic labeling of RNA uncovers principles of RNA production and degradation dynamics in mammalian cells. Nature Biotechnology 29, 436-442, doi:10.1038/nbt.1861 (2011). PMCID:3114636).

The method of the invention may include a step of determining DNA methylation. One may apply methods for reduced representation (RRBS), targeted capture, and whole genome bisulfite sequencing of DNA methylation from bulk to ultra-low inputs (Chan, M. M., Smith, Z. D., Egli, D., Regev, A. & Meissner, A. Mouse ooplasm confers context-specific reprogramming capacity. Nature Genetics 44, 978-980, doi:10.1038/ng.2382 (2012). PMCID:3432711; Smith, Z. D., Chan, M. M., Humm, K. C., Karnik, R., Mekhoubad, S., Regev, A., Eggan, K. & Meissner, A. DNA methylation dynamics of the human preimplantation embryo. Nature. 511, 611-615, doi:10.1038/nature13581 (2014). PMCID: 4178976; Smith, Z. D., Chan, M. M., Mikkelsen, T. S., Gu, H., Gnirke, A., Regev, A. & Meissner, A. A unique regulatory phase of DNA methylation in the early mammalian embryo. Nature 484, 339-344, doi:10.1038/nature10960 (2012). PMCID:3331945) to single cells.

The method of the invention may include a step determining chromatin accessibility. This may be performed by ATAC-Seq. For massively parallel single cell ATAC-Seq one may implement a droplet-based assay. First, in-tube, one may use Tn5 transposase to fragment chromatin inside isolated intact nuclei and add universal primers at cutting sites. Next, in-drop, one may use a high diversity library of barcoded primers to uniquely tag all DNA that originated from the same single cell. Alternatively, one may perform all steps in-drop. One may also use a strategy that relies on split pooled nuclei barcoding in plates (Cusanovich, D. A., Daza, R., Adey, A., Pliner, H., Christiansen, L., Gunderson, K. L., Steemers, F. J., Trapnell, C. & Shendure, J. Multiplex single-cell profiling of chromatin accessibility by combinatorial cellular indexing. Science. 2015 May 22; 348(6237): 910-4. doi: 10.1126/science.aab1601. Epub 2015 May 7). Key steps have been optimized in a mixture of human and mouse cells, with specificity that exceeds the initial performance of mRNA Drop-Seq. A Fluidigm C1 protocol (see www.fluidigm.com/products/cl-system) has also been used to analyze ~100 single DCs, closely reproducing ensemble measures, high enrichment in TSSs, and nucleosome-like periodicity.

ATAC-seq (assay for transposase-accessible chromatin) identifies regions of open chromatin using a hyperactive prokaryotic Tn5-transposase, which preferentially inserts into accessible chromatin and tags the sites with sequencing adaptors (Pott and Lieb, Genome Biology (2015) 16:172 DOI 10.1186/s13059-015-0737-7 and Buenrostro J D, Giresi P G, Zaba L C, Chang H Y, Greenleaf W J. Transposition of native chromatin for fast and sensitive epigenomic profiling of open chromatin, DNA-binding proteins and nucleosome position. Nat Methods. 2013; 10:1213-128). Two very different approaches were used: one relied on physical isolation of single cells (Buenrostro J D, Wu B, Litzenburger U M, Ruff D, Gonzales M L, Snyder M P, et al. Single-cell chromatin accessibility reveals principles of regulatory variation. Nature. 2015; 523:486-90), and the other avoided single-cell reaction volumes by using a two-step combinatorial indexing strategy (Cusanovich D A, Daza R, Adey A, Pliner H A, Christiansen L, Gunderson K L, et al. Epigenetics. Multiplex single-cell profiling of chromatin accessibility by combinatorial cellular indexing. Science. 2015; 348:910-4).

In the indexing scheme, Cusanovich et al. (Cusanovich D A, Daza R, Adey A, Pliner H A, Christiansen L, Gunderson K L, et al. Epigenetics. Multiplex single-cell profiling of chromatin accessibility by combinatorial cellular indexing. Science. 2015; 348:910-4) lysed cells, and 2500 nuclei were placed into each well of a 96-well plate. Transposases loaded with unique adaptors were added to each well, creating 96 pools of approximately 2500 nuclei, each pool with distinct barcodes. Nuclei from all of the transposition reactions were mixed, and using a fluorescence-activated cell sorter (FACS) 15-25 nuclei were deposited into each well of a second 96-well plate. Nuclei in each well of this second plate were lysed, and the DNA was amplified using a primer containing a second barcode. The low number of nuclei per well ensured that about 90% of the resulting barcode combinations were unique to a single cell. This combinatorial indexing strategy enabled the recovery of 500-1500 cells with unique tags per experiment. Overall Cusanovich et al. obtained scATAC-seq data from over 15,000 individual cells from mixtures of GM12878 lymphoblastoid cells with HEK293, HL-60, or mouse Patski cells. The number of reads associated with any single cell was very low, varying from 500 to about 70,000 with a median of fewer than 3000 reads per cell.

Buenrostro et al. (Buenrostro J D, Wu B, Litzenburger U M, Ruff D, Gonzales M L, Snyder M P, et al. Single-cell chromatin accessibility reveals principles of regulatory variation. Nature. 2015; 523:486-90) used a programmable microfluidic device (Cl, Fluidigm) to isolate single cells and perform ATAC-seq on them in nanoliter reaction chambers. Each nanochamber was analyzed under a microscope to ensure that a single viable cell had been captured. This approach is simple and has the significant advantage of a carefully monitored reaction environment for each individual cell, although the throughput was limited to processing 96 cells in parallel. Buenrostro et al. sampled 1632 cells from eight different cell lines, including GM12878, K562, and H1 cells, and obtained an average of 73,000 reads per cell, about 20 times the number of reads per cell obtained using the barcoding strategy.

The method of the invention may include a step of determining histone modifications and protein-DNA interactions. One may apply tools that use genomic barcoding to index chromatin prior to immunoprecipitation to enable multiplexed analysis of limited samples and individual cells in a single reaction. For single-cell chromatin profiling, one may use Drop-ChTP where the chromatin of individual cells is barcoded in droplets. Based on the Drop-Seq technique, one may encapsulate single cells, lyse and MNase-digest chromatin, then fuse a second droplet with barcoded oligos, ligate them to the fragmented chromatin, break the emulsion, add carrier chromatin, and carry out ChIP-Seq. This may be performed using a protocol with split-pool barcoding to collect 104-105 single cells/assay.

ChIP-sequencing, also known as ChIP-seq, combines chromatin immunoprecipitation (ChIP) with massively parallel DNA sequencing to identify the binding sites of DNA-associated proteins. It can be used to map global binding sites precisely for any protein of interest. ChIP-seq is used primarily to determine how transcription factors and other chromatin-associated proteins influence phenotype-affecting mechanisms. Determining how proteins interact with DNA to regulate gene expression is for understanding many biological processes and disease states. This epigenetic information is complementary to genotype and expression analysis. ChIP-seq technology is as an alternative to ChIP-chip which requires a hybridization array. Specific DNA sites in direct physical interaction with transcription factors and other proteins can be isolated by chromatin immunoprecipitation. ChIP produces a library of target DNA sites bound to a protein of interest in vivo. Massively parallel sequence analyses are used in conjunction with whole-genome sequence databases to analyze the interaction pattern of any protein with DNA, see, e.g., Johnson D S, Mortazavi A et al. (2007) Genome-wide mapping of in vivo protein-DNA interactions. Science 316: 1497-1502, or the pattern of any epigenetic chromatin modifications. This can be applied to the set of ChIP-able proteins and modifications, such as transcription factors, polymerases and transcriptional machinery, structural proteins, protein modifications, and DNA modifications. See, e.g., "Whole Genome Chromatin I P Sequencing," Illumina, Inc. (2010), available at www.illumina.com/Documents/products/datasheets/datasheet chip_sequence.pdf (Chromatin Immunoprecipitation with massively parallel sequencing).

For multiplex analysis of (limited) bulk samples, one may rely on chromatin indexing (MINT-ChIP; iChIP), where MNase-fragmented chromatin is indexed by ligation to a uniquely barcoded adaptor and then pooled and processed in multiplex through all subsequent phases, either with (MINT-ChIP) or without (iChIP: Lara-Astiaso, D., Weiner, A., Lorenzo-Vivas, E., Zaretsky, I., Jaitin, D. A., David, E., Keren-Shaul, H., Mildner, A., Winter, D., Jung, S., Friedman, N. & Amit, I. Immunogenetics. Chromatin state dynamics during blood formation. Science. 345, 943-949, doi:10.1126/science.1256271 (2014). PMCID:4412442) carrier chromatin (without adaptors).

The method of the invention may include a step of determining proteins. Recently developed assays (e.g., CyTOF: Bendall, S. C., Simonds, E. F., Qiu, P., Amir el, A. D., Krutzik, P. O., Finck, R., Bruggner, R. V., Melamed, R., Trejo, A., Ornatsky, O. I., Balderas, R. S., Plevritis, S. K., Sachs, K., Pe'er, D., Tanner, S. D. & Nolan, G. P. Single-cell mass cytometry of differential immune and drug responses across a human hematopoietic continuum. Science. 332, 687-696, doi:10.1126/science.1198704 (2011). PMCID: 3273988), allow multiplexed, single cell detection of dozens of proteins in millions of cells, but rely on antibodies and cannot yet be combined with DNA readout. Conversely, mass spectrometry (LC-MS/MS) allows quantitative analysis of entire proteomes, but deep analysis requires large amounts of protein/cells. To measure single cell protein levels and post-translational modifications (PTMs), one may use one of three complementary antibody-based assays: (1) standard flow cytometry with a few proteins/PTMs, >106 single cells; (2) CyTOF (Bendall, S. C., Simonds, E. F., Qiu, P., Amir el, A. D., Krutzik, P. O., Finck, R., Bruggner, R. V., Melamed, R., Trejo, A., Ornatsky, O. I., Balderas, R. S., Plevritis, S. K., Sachs, K., Pe'er, D., Tanner, S. D. & Nolan, G. P. Single-cell mass cytometry of differential immune and drug responses across a human hematopoietic continuum. Science. 332, 687-696, doi:10.1126/science.1198704 (2011). PMCID:3273988) (heavy metal labeling with multiplex barcoding; ~30-50 proteins/PTMs, 105-106 single cells); and (3) novel, highly multiplexed, DNA sequencing-based readouts of protein levels (100s proteins/PTMs; 106 cells). For sequencing based readouts, one may use one of two approaches, geared at detecting hundreds of proteins in single cells: Immuno-Seq (when antibodies can be washed out: Niemeyer, C. M., Adler, M. & Wacker, R. Detecting antigens by quantitative immuno-PCR. Nat Protoc. 2, 1918-1930, doi:10.1038/nprot.2007.267 (2007)) and proximity extension assays (PEA, when antibodies cannot be washed away: Hammond, M., Nong, R. Y., Ericsson, O., Pardali, K. & Landegren, U. Profiling cellular protein complexes by proximity ligation with dual tag microarray readout. PLoS One. 7, e40405, doi:10.1371/journal.pone.0040405 (2012). PMCID:3393744; Nong, R. Y., Wu, D., Yan, J., Hammond, M., Gu, G. J., Kamali-Moghaddam, M., Landegren, U. & Darmanis, S. Solid-phase proximity ligation assays for individual or parallel protein analyses with readout via real-time PCR or sequencing. Nat Protoc. 8, 1234-1248, doi:10.1038/nprot.2013.070 (2013); Stahlberg, A., Thomsen, C., Ruff, D.

& Aman, P. Quantitative PCR analysis of DNA, RNAs, and proteins in the same single cell. Clin Chem. 58, 1682-1691, doi:10.1373/clinchem.2012.191445 (2012)). These use DNA-sequence based encoding, and are compatible with other genomic readouts (e.g., sgRNA barcodes). DNA-sequence tags can be conjugated to antibodies (Janssen, K. P., Knez, K., Spasic, D. & Lammertyn, J. Nucleic acids for ultra-sensitive protein detection. Sensors (Basel). 13, 1353-1384, doi:10.3390/s130101353 (2013). PMCID:3574740), nanobodies (Pardon, E., Laeremans, T., Triest, S., Rasmussen, S. G., Wohlkonig, A., Ruf, A., Muyldermans, S., Hol, W. G., Kobilka, B. K. & Steyaert, J. A general protocol for the generation of Nanobodies for structural biology. Nat Protoc. 9, 674-693, doi:10.1038/nprot.2014.039 (2014). PMCID:4297639; Theile, C. S., Witte, M. D., Blom, A. E., Kundrat, L., Ploegh, H. L. & Guimaraes, C. P. Site-specific N-terminal labeling of proteins using sortase-mediated reactions. Nat Protoc. 8, 1800-1807, doi:10.1038/nprot.2013.102 (2013). PMCID:3941705) or aptamers (Janssen, K. P., Knez, K., Spasic, D. & Lammertyn, J. Nucleic acids for ultra-sensitive protein detection. Sensors (Basel). 13, 1353-1384, doi:10.3390/s130101353 (2013). PMCID:3574740). Detection of specific transcripts and proteins in single cells may be performed as well (Frei et al., Highly multiplexed simultaneous detection of RNAs and proteins in single cells. Nat Methods. 2016 March; 13(3): 269-75).

In certain embodiments of the present invention, quantitative measurements of both the copy number and spatial distribution of large fractions of the transcriptome in single cells is measured by multiplexed error-robust fluorescence in situ hybridization (MERFISH) (Moffitt and Zhuang, Chapter One—RNA Imaging with Multiplexed Error-Robust Fluorescence In situ Hybridization (MERFISH), *Methods in Enzymology*. Volume 572, 2016, Pages 1-49).

Multiplex Analysis of Single Cell Constituents

It is an object of the present invention to provide a method for the high multiplex analysis of cellular constituents by linking nucleic acids tags to existing ligand binding and/or antibody technologies to enable proteomic or cellular constituent detection and relative quantification by next-generation sequencing (NGS) in single cells or isolated aggregations of cellular constituents. The present invention may combine perturbation of single cells followed by protein analysis in the single cells. Thus, protein expression may be linked to a perturbation.

It is a further object of the present invention to provide for comparing high multiplex protein data variation between single cells or isolated aggregation of cellular constituents and between different biological conditions (e.g. healthy vs. diseased states; one genetic perturbation vs. another, different genetic backgrounds).

It is a further object of the present invention to provide massively parallel profiling of all circuit aspects in single cells or isolated aggregations of cellular constituents: from RNA to chromatin organization to protein levels.

In a first aspect, the present invention provides a method of assaying segregated cellular constituents, comprising: admixing at least one isolated aggregation of cellular constituents with monomers of a polymerizable gel; polymerizing the gel, to embed the cellular constituents in discrete polymer matrices; incubating the cellular constituents embedded in the polymer matrices with one or more labeling ligands with specific binding affinity for one or more target cellular constituents to produce one or more labeled cellular constituents in the polymer matrices, wherein each of the one or more labeling ligand comprises a bound oligonucleotide label comprising a unique constituent identifier (UCI) sequence, and wherein the incubation comprises binding conditions under which the labeling ligand will bind to the cellular constituent within the polymer matrix, and the incubation further comprises washing conditions under which unbound labeling ligands will be washed out of the polymer matrix; and sequencing the oligonucleotide label, whereby detecting the UCI by sequencing indicates the presence of the target cellular constituent.

Cellular constituents may include any molecule within a cell; i.e. proteins, nucleic acids, or post translational modifications (PTM). The cellular constituent may be a protein, RNA transcript, metabolite, or a DNA molecule. Specific cellular constituents may be proteins, modified proteins, hormones, cytokines, cellular metabolites, or carbohydrates. The isolated aggregation of cellular constituents may be a cell, an extracellular vesicle, an organelle, or an organized subcomponent thereof, including molecular complexes. Isolated aggregations of cellular constituents may include separate organelles of a single cell or separate organelles isolated from a population of cells. Organelles may be, for example, mitochondria, nuclei, or cellular vesicles. In one embodiment, a specific type of single cells may be isolated. In one embodiment, immune cells are isolated from a population of cells. Not being bound by a theory, single mitochondria can be purified from a population of cells and the relative amounts of constituents present in each individual mitochondrion may be analyzed. Not being bound by a theory, immune cells may be isolated by a method such as cell sorting and the relative representation of cellular constituents may be determined for each individual cell.

The step of admixing the isolated aggregation of cellular constituents with monomers may be carried out in an aqueous solution, or in an aqueous aliquot or droplet present in an oil emulsion. The polymer matrix may be a hydrogel. The polymer matrix may be any hydrogel capable of polymerization to create a solid matrix that fixes the cellular constituents and provides a porosity capable of allowing labeling ligands to freely diffuse through the network of pores. The cellular constituents may be further fixed by treating with an aldehyde. The aldehyde may be formaldehyde, paraformaldehyde, or glutaraldehyde. Not being bound by a theory, the fixation in a solid matrix prevents the mixing of the cellular constituents between the isolated aggregations of cellular constituents. Not being bound by a theory, capturing cellular constituents in a solid polymer mesh insures that they are physical units that can be ligand and/or antibody stained as a pool and isolated as single cells or isolated aggregates of cellular constituents subsequently. Not being bound by a theory, the fixing of cellular constituents in the polymer matrix allows access to the labeling ligands to intracellular constituents.

The physical units formed by the polymer matrix may be particles, droplets, or a continuous polymer matrix with discrete regions comprising the isolated aggregates of cellular constituents. Therefore, the polymer matrix may include more than one isolated aggregate of cellular constituents. The polymer matrix may be divided such that isolated aggregates of cellular constituents are separable. The polymer matrix may be separable in that individual particles, droplets, or sections can be isolated. They may be isolated by physical manipulation using a sorting device. The sorting device may use microfluidics. They may be separated by use of dilution or manual manipulation by a user. They may be separated by use of any kind of (micro) dissection. The cellular constituents within the polymer matrix may be stained with a dye, or a dye-conjugated ligand indicating the location of individual cellular constituents or cells. The polymer matrix may be punched to isolate a core, wherein each core from the polymer matrix contains a single isolated aggregate of cellular constituents. Not being bound by a theory, the fixation of isolated aggregates of cellular constituents in a matrix allows each isolated aggregate of cellular constituents to be compartmentalized wherein the separate compartments can be treated in a single experimental vessel or container and separated subsequently.

The labeling ligands are linked with an oligonucleotide label that can be used to determine the identity of the ligand. Each oligonucleotide label may comprise a unique constituent identifier (UCI) that can be used to determine the presence of a cellular constituent. Not being bound by a theory, the availability of unique sequences allows the labeling and detection of a plurality of ligands each for a specific constituent. Not being bound by a theory, the UCI allows a DNA readout for detection of a cellular constituent. The DNA readout may be by any sequencing method or method of amplification, such as by PCR or next generation sequencing. The oligonucleotide label may additionally include a promoter for amplification by an RNA polymerase, such as T7 polymerase. Not being bound by a theory, amplification by T7 polymerase allows amplification of low represented sequences, whereas such sequences may be diluted out by domination of a higher represented sequence during PCR. Not being bound by a theory, the labeling of each labeling ligand with a unique UCI allows the identification of more than ten, or hundred, or thousands of cellular constituents in an isolated aggregation of cellular constituents.

The method may further comprise segregating the discrete polymer matrices comprising the labeled constituents before the step of sequencing. Segregating the discrete polymer matrices may be by sorting single discrete matrices into separate reaction vessels. Segregating the discrete polymer matrices may be by forming discrete unique-identifier-transfer compositions, each comprising the cellular constituents embedded in a discrete polymer matrix and a transfer particle, wherein: the ligand oligonucleotide label further comprises a capture sequence, and the UCI and capture sequence are together releasably attached to the labeling ligand; the labelling ligand is bound to the target cellular constituent; and, the transfer particle comprises: a capture-binding-sequence having specific binding affinity for the capture sequence attached to the UCI, and, a unique source identifier (USI) sequence that is unique to each transfer particle. The USI of each transfer particle preferably comprises 4-15 nucleotides. The method may further comprise releasing the UCI from the labeled ligand, under conditions within the unique-identifier-transfer composition so that the released capture sequence binds to the capture-binding-sequence on the transfer particle, thereby transferring the UCI to the transfer particle. The transfer particle may be a solid bead. The transfer particle may be a hydrogel bead. The transfer particle may also be used to capture nucleic acids present in a discrete polymer matrix. The nucleic acids may be RNA and/or DNA. Not being bound by a theory, the transfer particle may be used to capture both the UCI and the nucleic acids, whereby the source of the bound cellular constituents and nucleic acids can be determined after sequencing.

The method may further comprise, before the sequencing step, generating a USI for each discrete polymer matrix by a split pool ligation method, wherein the oligonucleotide label further comprises a universal ligation handle (ULH) sequence configured to produce a DNA overhang capable of hybridization to a complementary overhang on a first index nucleotide sequence, wherein the first index nucleotide sequence comprises an overhang complementary to a final index sequence or optionally a middle index sequence, wherein the middle index sequence comprises overhangs complementary to the first index sequence and to the final index sequence or optionally to another middle index sequence and final index sequence, wherein the final index sequence has a single overhang complementary to the preceding index sequence, and wherein the first, middle, and final index sequences are selected from a plurality of unique sequences comprising compatible DNA overhangs and 10 to 30 base pairs of unique sequence.

The split pool ligation method may comprise: splitting the pool of discrete polymer matrices into separate pools of polymer matrices, each containing a unique first index sequence; ligating the first index sequence to the ligation handle; pooling the discrete polymer matrices; optionally, splitting the pool of discrete polymer matrices into separate pools each containing a unique middle index sequence; ligating the middle index sequence to the first index sequence; and pooling the discrete polymer matrices; optionally, repeating the steps with another middle index sequence; splitting the pool of discrete polymer matrices into pools containing a unique final index sequence; and ligating the final index sequence to the preceding index sequence, whereby each discrete polymer matrix comprises a USI. The USI may have no middle index sequence, one middle index sequence, two middle index sequences, preferably the USI has a first, middle, and final index sequence. Not being bound by a theory, the size of the unique sequences in each index determines the amount included. Not being bound by a theory, the number of indices selected is the amount necessary such that the probability of having identical USI sequences on spate polymer matrices is approaching zero. In an exemplary embodiment, each index includes 192 unique sequences.

The ligation handle may comprise a restriction site for producing an overhang complementary with a first index sequence overhang, and wherein the method further comprises digestion with a restriction enzyme. The ligation handle may comprise a nucleotide sequence complementary with a ligation primer sequence and wherein the overhang complementary with a first index sequence overhang is produced by hybridization of the ligation primer to the ligation handle. Additionally, the ULH may comprise a dsDNA part that already includes the overhang needed for index ligation.

The UCI may comprise 4 to 30 nucleotides or 7 to 30 nucleotides, preferably about 21 nucleotides. The oligonucleotide label may further comprise a unique molecular identifier (UMI) sequence. The first, middle, or final index sequence may further comprises a unique molecular identifier (UMI) sequence. The UMI may comprise 4 to 20 nucleotides. The UMI may comprise 8 to 16 nucleotides.

The isolated aggregation of cellular constituents may be a cell, an extracellular vesicle, an organelle, or an organized subcomponent thereof.

The sequencing may comprise combining a primer having a unique source identifier (USI) sequence with UCI, so that the USI and UCI sequences are sequenced together, and the USI preferably comprises 20 to 120 nucleotides.

The step of admixing the isolated aggregation of cellular constituents with monomers may be carried out in an aqueous aliquot or in a droplet formed by an aqueous solution in oil emulsion. The aqueous aliquot may be a separate reaction vessel such as a well in a plate. The droplet may be formed by a microfluidic device. The polymer matrix may be a hydrogel. The method may be a multiplex assay with a plurality of labeling ligands, and each labeling ligand have a distinct UCI. The labeling ligand may be non-covalently bound to the target cellular constituent.

The method may further comprise pooling the oligonucleotide labels comprising a USI from a plurality of polymer matrices and sequencing the pooled UCI sequences and USI sequences. The method may further comprise pooling the oligonucleotide labels comprising a USI and UMI from a plurality of polymer matrices and sequencing the pooled UCI sequences, USI sequences, and UMI sequences.

The method may further comprise washing the cellular constituents embedded in the polymer matrices to remove selected cellular components from the polymer matrices before incubating the cellular constituents with the labeling ligand. The washing may comprise treating the cellular constituents embedded in the polymer matrices with a detergent so as to remove lipids from the polymer matrices before incubating the cellular constituents with the labeling ligand. The detergent may be an anionic detergent or non-ionic detergent. The detergent may be SDS, NP-40, triton X-100, or any other detergent known in the art capable of removing lipids.

The method may further comprise quantitating the relative amount of the UCI sequence associated with a first aggregation of cellular constituents to the amount of the same UCI sequence associated with a second aggregation of cellular constituents, whereby the relative differences of a cellular constituent between aggregations of cellular constituents are determined. The relative amount may be compared to a control sample. The control sample may have predetermined amounts of cellular constituents. There may be more than one control sample. There may be at least three control samples. The at least three control samples can be used to generate a standard curve upon which all of the other cellular constituents within discrete polymer matrices are compared. The control sample may comprise isolated aggregations of cellular constituents that were untreated as compared relative to isolated aggregations of cellular constituents that were treated with a different condition. Cells may be treated with drugs, small molecules, pathogens, hormones, cytokines, proteins, nucleic acids, virus particles, or grown in different cellular environments. Cells may be isolated from a diseased tissue. The cells from the diseased tissue may be compared to cells from non-diseased tissue. Cells may be treated with systems that knockout, decrease or increase expression of a gene. Cells may be treated with systems that knockout functional elements of a genome. Functional elements include, but are not limited to, promoters, enhancers, repressors, centromeres, or telomeres. CRISPR systems may be used.

The labeling ligand may be an antibody or an antibody fragment. The antibody fragment may be a nanobody, Fab, Fab', F(ab')$_2$, Fv, ScFv, diabody, triabody, tetrabody, Bis-scFv, minibody, Fab2, or Fab3 fragment. The labeling ligand may be an aptamer. The labeling ligand may be a nucleotide sequence complementary to a target sequence.

The method may comprise multiplex binding of two or more labeling ligands to each aggregation of cellular constituents. The two or more distinct labeling ligands may comprise complementary oligonucleotide sequences, so that binding of the labeling ligands to respective target cellular constituents that are in proximity permits the complementary sequences of the distinct ligands to hybridize, forming an amplifiable polynucleotide duplex. The method may further comprise amplifying the polynucleotide duplex to provide an amplified sequence that is a detectable signal that target cellular constituents that are in proximity. The complementary oligonucleotide sequences, which serve as a start site for polymerase extension, can either be designed to query proximity of two specific cellular constituents, or it can be designed to be universal, thereby querying interactions between all members of the labeling ligand panel.

In one embodiment, at least two distinct labeling ligands comprise oligonucleotide sequences configured to be ligated, so that binding of the labeling ligands to respective target cellular constituents that are in proximity permits the oligonucleotide sequences of the distinct ligands to ligate, forming an amplifiable polynucleotide duplex. The method may further comprise amplifying the polynucleotide duplex to provide an amplified sequence that is a detectable signal that target cellular constituents that are in proximity.

One of the labeling ligands may comprise an oligonucleotide label with a restriction enzyme site between the labeling ligand and the UCI, and wherein the method may further comprise treating with a restriction enzyme, whereby the UCI from the labeling ligand is transferred to the oligonucleotide label of the labeling ligand in proximity.

The method may further comprise labeling the aggregation of cellular constituents by fluorescent in situ hybridization.

The aggregation of cellular constituents may be a cell that is a member of a cell population. The cell may be transformed or transduced with one or more genomic sequence-perturbation constructs that perturb a genomic sequence in the cells, wherein each distinct genomic sequence-perturbation construct comprises a unique-perturbation-identifier (UPI) sequence unique to that construct. The genomic sequence-perturbation construct may comprise a sequence encoding a guide RNA sequence of a CRISPR-Cas targeting system. The method may further comprise multiplex transformation of the population of cells with a plurality of genomic sequence-perturbation constructs. The UPI sequence may be attached to a perturbation-sequence-capture sequence, and the microbeads may comprise a perturbation-sequence-capture-binding-sequence having specific binding affinity for the perturbation-sequence-capture sequence attached to the UPI sequence. The UPI sequence may be attached to a universal ligation handle sequence, whereby a USI may be generated by split-pool ligation. The method may further comprise multiplex sequencing of the pooled UCI sequences, USI sequences, and UPI sequences.

The oligonucleotide label may comprise a regulatory sequence configured for amplification by an RNA polymerase, such as T7 polymerase. The labeling ligands may comprise oligonucleotide sequences configured to hybridize to a transcript specific region. The oligonucleotide label may further comprise attachment chemistry, such as an acrylic phosphoramidite modification, whereby the modification allows for incorporation into the polymer matrices upon polymerization. The acrylic phosphoramidite may be Acrydite™ (Eurofins Scientific, Luxembourg). The method may further comprise amplification of the oligonucleotide label and USI by PCR or T7 amplification before sequencing. T7 amplification may be followed by cDNA generation and optionally amplification by PCR. The oligonucleotide label may further comprise at least one spacer sequence, preferably two spacer sequences. The oligonucleotide label may further comprise a photocleavable linker. The oligonucleotide label may further comprise a restriction enzyme site between the labeling ligand and UCI.

The discrete polymer matrices may be labeled and washed more than once. Discrete polymer matrices may be labeled with a marker specific for a cell type or cell cycle marker or developmental marker, or differentiation marker, or disease marker. The label may be a fluorescent label. The fluorescent label may be used to separate the discrete polymer matrices into distinct groups. The label may be used to identify a certain cell type prior to embedding it into a discrete polymer matrix. The discrete polymer matrices of a distinct group may then be labeled again with labeling ligands that contain an oligonucleotide label of the present invention. After novel information is obtained from the multiplex assay of the present invention, a 'banked' population of polymer matrices can be stained for newly identified markers and the population of interest can be sorted (enriched) for, and investigated more deeply.

In another aspect, the present invention provides a method of determining open chromatin in individual cells comprising: isolating single cells into droplets formed by an aqueous solution in oil emulsions, wherein the droplets further comprise Tn5-transposase loaded with two tagmentation adapters, wherein one adapter is configured for incorporation into a polymer matrix and the second adapter is configured with a ligation handle for generating a USI; incubating the droplets to allow cell lysis and tagmentation of open chromatin; infusing monomers of a polymerizable gel into the droplets; polymerizing the gel, to embed the cellular constituents in discrete polymer matrices; optionally incubating the polymer matrices with one or more labeling ligands with specific binding affinity for one or more target cellular constituents to produce one or more labeled cellular constituents in the polymer matrices, wherein each of the one or more labeling ligand(s) comprises a bound oligonucleotide label comprising a unique constituent identifier (UCI) sequence and a sequence capable of hybridization to the tagmentation adapter configured for incorporation into a polymer matrix, and wherein the incubation comprises binding conditions under which the labeling ligand will bind to the cellular constituent within the polymer matrix and the oligonucleotide label will hybridize to said tagmentation adapter, and wherein the incubation further comprises washing conditions under which unbound labeling ligands will be washed out of the polymer matrix; and extending the genomic DNA and adapter DNA, whereby a continuous DNA strand is generated comprising the adapters, genomic DNA, and DNA overhang; optionally the oligonucleotide label is bound to a labeling ligand; generating a USI at the DNA overhang by split-pool ligation; sequencing the continuous DNA strand, whereby open chromatin is determined and optionally the presence of a cellular constituent at a site of open chromatin is determined.

In another aspect, the present invention provides a method of measuring RNA levels in individual cells comprising: isolating single cells into droplets formed by an aqueous solution in oil emulsions, wherein the droplets comprise at least one labeling ligands specific for binding at one or more target RNA transcripts, wherein the labeling ligands are configured for incorporation into a polymer matrix and comprise a ligation handle for generating a USI; lysing the cells in the droplets under conditions wherein the labeling ligands will bind to the target RNA transcripts; injecting monomers of a polymerizable gel into the droplets; polymerizing the gel, to embed the labeling ligands in discrete polymer matrices; optionally, staining the discrete polymer matrices with at least one additional labeling ligand; generating a USI by split-pool ligation; and sequencing the resulting DNA, whereby RNA levels and optionally protein levels are determined in single cells. The droplets may comprise at least one pair of labeling ligands specific for binding at adjacent sites of one or more target RNA transcripts, wherein each pair of labeling ligands comprises one labeling ligand configured for incorporation into a polymer matrix and one labeling ligand comprising a ligation handle for generating a USI, and wherein the method may further comprise injecting a ligation reaction buffer comprising a ligase that is configured to allow ligation of the pair of labeling ligands if they are hybridized adjacently with single nucleotide resolution on the target RNA transcript, such that off target binding of labeling ligand does not get ligated, and will not be amplified in subsequent steps.

In another aspect, the present invention provides a method of assaying segregated cellular constituents, comprising: fixing and permeabilizing at least one cell; incubating the fixed and permeabilized cell(s) with one or more labeling ligands with specific binding affinity for one or more target cellular constituents to produce one or more labeled cell(s), wherein each of the one or more labeling ligands comprise a bound oligonucleotide label comprising a unique constituent identifier (UCI) sequence, and wherein the incubation comprises binding conditions under which the labeling ligand will bind to the cellular constituent within the cell(s), and the incubation further comprises washing conditions under which unbound labeling ligands will be washed from the cell(s); admixing the cell(s) with monomers of a polymerizable gel; isolating single cells into droplets formed by an aqueous solution in oil emulsions; polymerizing the gel, to embed the labeling ligands and other cellular constituents in discrete polymer matrices; optionally, staining the discrete polymer matrices with at least one additional labeling ligand; generating a USI by split-pool ligation; and sequencing the oligonucleotide label, whereby detecting the UCI by sequencing indicates the presence of the target cellular constituent. The labeling of ligands may comprise at least one pair of labeling ligands specific for binding at adjacent sites of one or more target RNA transcripts, wherein each pair of labeling ligands comprises one labeling ligand configured for incorporation into a polymer matrix and one labeling ligand comprising a ligation handle for generating a USI, and wherein the method further comprises ligating the pair of labeling ligands if they are within proximity after binding to the target RNA transcripts. Any of the preceding methods may comprise polymer matrices wherein they further comprise magnetic particles. In one embodiment, any hydrogel droplet encapsulated aggregations of cellular constituents may further comprise magnetic particles embedded into the droplets. Not being bound by a theory, magnetic particles enable magnetic separation, aiding in clean up and washing steps in multiple reactions. Not being bound by a theory, the use of magnetic particles greatly enhances automation and therefore throughput.

In another aspect, the present invention provides a method of assaying segregated cellular constituents, comprising: fixing and permeabilizing at least one cell; incubating the fixed and permeabilized cell(s) with one or more labeling ligands with specific binding affinity for one or more target cellular constituents to produce one or more labeled cell(s), wherein each of the one or more labeling ligands comprise a bound oligonucleotide label comprising a unique constituent identifier (UCI) sequence, and wherein the incubation comprises binding conditions under which the labeling ligand will bind to the cellular constituent within the cell(s), and the incubation further comprises washing conditions under which unbound labeling ligands will be washed from the cell(s); and sequencing the oligonucleotide label, whereby detecting the UCI by sequencing indicates the presence of the target cellular constituent. The cellular constituent may comprise a protein, RNA transcript, or a DNA molecule. The method may further comprise segregating the cell(s) before sequencing. The segregating the cell(s) may comprise sorting the single cell(s) into a separate reaction vessel(s). The segregating the cell(s) may comprise forming discrete unique-identifier-transfer compositions, each comprising a cell and a transfer particle, wherein: the oligonucleotide label further comprises a capture sequence, and the UCI and capture sequence are together releasably attached to the labeling ligand; the labeling ligand is bound to the target cellular constituent; and, the transfer particle comprises: a capture-binding-sequence having specific binding affinity for the capture sequence attached to the UCI, and, a unique source identifier (USI) sequence that is unique to each transfer particle, and the USI preferably comprises 4- to 15 nucleotides. The method may further comprise releasing the UCI from the labeled ligand, under conditions within the unique-identifier-transfer composition so that the released capture sequence binds to the capture-binding-sequence on the transfer particle, thereby transferring the UCI to the transfer particle. The method may further comprise, before sequencing in step, generating a USI for each cell(s) by a split pool ligation method, wherein the oligonucleotide label further comprises a universal ligation handle (ULH) sequence configured to produce a DNA overhang capable of hybridization to a complementary overhang on a first index nucleotide sequence, wherein the first index nucleotide sequence comprises an overhang complementary to a final index sequence or optionally a middle index sequence, wherein the middle index sequence comprises overhangs complementary to the first index sequence and to the final index sequence or optionally to another middle index sequence and final index sequence, wherein the final index sequence has a single overhang complementary to the preceding index sequence, and wherein the first, middle, and final index sequences are selected from a plurality of unique sequences comprising compatible DNA overhangs and 10 to 30 base pairs of unique sequence. The split pool ligation method may comprise: splitting the pool of cell(s) into separate pools of cell(s), each containing a unique first index sequence; ligating the first index sequence to the ligation handle; pooling the cell(s); optionally, splitting the pool of cell(s) into separate pools each containing a unique middle index sequence; ligating the middle index sequence to the first index sequence; and pooling the cell(s); optionally, repeating with another middle index sequence; splitting the pool of cell(s) into pools containing a unique final index sequence; and ligating the final index sequence to the preceding index sequence, whereby each cell comprises a USI.

The ligation handle may comprise a restriction site for producing an overhang complementary with a first index sequence overhang, and wherein the method further comprises digestion with a restriction enzyme. The ligation handle may comprise a nucleotide sequence complementary with a ligation primer sequence and wherein the overhang complementary with a first index sequence overhang is produced by hybridization of the ligation primer to the ligation handle.

The UCI may comprise 4 to 30 nucleotides, or 7 to 30 nucleotides, or about 21 nucleotides. The oligonucleotide label may further comprise a unique molecular identifier (UMI) sequence. The first, middle, or final index sequence may further comprise a unique molecular identifier (UMI) sequence. The UMI may be 4 to 20 nucleotides. The UMI may be 8 to 16 nucleotides.

The sequencing may comprise combining a primer having a unique source identifier (USI) sequence with UCI, so that the USI and UCI sequences are sequenced together, and the USI preferably comprises 20 to 120 nucleotides.

The method may comprise a multiplex assay with a plurality of labeling ligands, each labeling ligand have a distinct UCI. The labeling ligand may be non-covalently bound to the target cellular constituent. The method may further comprise pooling the oligonucleotide labels comprising a USI from a plurality of cells and sequencing the pooled UCI sequences and USI sequences. The method may further comprise pooling the oligonucleotide labels comprising a USI and UMI from a plurality of cells and sequencing the pooled UCI sequences, USI sequences, and UMI sequences. The method may further comprise quantitating the relative amount of the UCI sequence associated with a first cell to the amount of the same UCI sequence associated with a second cell, whereby the relative differences of a cellular constituent between cell(s) are determined.

The labeling ligand may be an antibody or an antibody fragment. The antibody fragment may be a nanobody, Fab, Fab', F(ab')$_2$, Fv, ScFv, diabody, triabody, tetrabody, BisscFv, minibody, Fab2, or Fab3 fragment. The labeling ligand may be an aptamer. The labeling ligand may be a nucleotide sequence complementary to a target sequence.

The method may comprise multiplex binding of two or more labeling ligands to the cellular constituents. At least two distinct labeling ligands may comprise complementary oligonucleotide sequences, so that binding of the labeling ligands to respective target cellular constituents that are in proximity permits the complementary sequences of the distinct ligands to hybridize, forming an amplifiable polynucleotide duplex. The method may further comprise amplifying the polynucleotide duplex to provide an amplified sequence that is a detectable signal that target cellular constituents are in proximity. At least two distinct labeling ligands may comprise oligonucleotide sequences configured to be ligated, so that binding of the labeling ligands to respective target cellular constituents that are in proximity permits the oligonucleotide sequences of the distinct ligands to ligate, forming an amplifiable polynucleotide duplex. The method may further comprise amplifying the polynucleotide duplex to provide an amplified sequence that is a detectable signal that target cellular constituents are in proximity. One of the labeling ligands may comprise a restriction enzyme site between the labeling ligand and the oligonucleotide label, and wherein the method further comprises treating with a restriction enzyme, whereby the UCI from said labeling ligand is transferred to the oligonucleotide label of the labeling ligand in proximity.

The method may further comprise labeling the cell(s) by fluorescent in situ hybridization.

The cell(s) may be a member of a cell population, further comprising transforming or transducing the cell population with one or more genomic sequence-perturbation constructs that perturb a genomic sequence in the cells, wherein each distinct genomic sequence-perturbation construct comprises a unique-perturbation-identified (UPI) sequence unique to that construct. The genomic sequence-perturbation construct may comprise a sequence encoding a guide RNA sequence of a CRISPR-Cas targeting system. The method may further comprise multiplex transformation of the population of cells with a plurality of genomic sequence-perturbation constructs. The UPI sequence may be attached to a perturbation-sequence-capture sequence, and the transfer particle may comprise a perturbation-sequence-capture-binding-sequence having specific binding affinity for the perturbation-sequence-capture sequence attached to the UPI sequence. The UPI sequence may be attached to a universal ligation handle sequence, whereby a USI may be generated by split-pool ligation. The method may further comprise multiplex sequencing of the pooled UCI sequences, USI sequences, and UPI sequences.

In another aspect, the present invention provides a method of determining interactions between 2 or more cellular constituents, comprising: admixing at least one isolated aggregation of cellular constituents with monomers of a polymerizable gel; polymerizing the gel, to embed the cellular constituents in discrete polymer matrices; incubating the cellular constituents embedded in the polymer matrices with one or more labeling ligands with specific binding affinity for one or more target cellular constituents to produce one or more labeled cellular constituents in the polymer matrices, wherein each of the one or more labeling ligands comprise a bound oligonucleotide label comprising a unique constituent identifier (UCI) sequence and a universal hybridization nucleotide sequence, and wherein the incubation comprises binding conditions under which the labeling ligand will bind to the cellular constituent within the polymer matrix, and the incubation further comprises washing conditions under which unbound labeling ligands will be washed out of the polymer matrix; incubating the polymer matrices with at least one Unique Location Index probe, wherein the probe comprises at least two repeating nucleotide sequences, each repeat comprising a restriction enzyme site, a Unique Location Index (ULI) sequence, and a complementary universal hybridization nucleotide sequence, and wherein the incubation comprises binding conditions under which the universal hybridization sequence will hybridize the complementary universal hybridization sequence; extending the oligonucleotide label hybridized to the probe such that the oligo bound to the affinity ligand incorporates the ULI sequence that is unique to that Unique Location Index probe; digestion with a restriction enzyme specific for the site on the probe, sequencing the oligonucleotide label, whereby detecting the same ULI with two or more UCIs indicates that the cellular constituents were interacting. The ULI sequence may be randomly generated, such that no two ULI sequences are the same. Methods of generating a barcode sequence described herein may be used to generate a ULI. The ULI will be detected with the UCI, such that when multiple cellular constituents are in proximity oligonucleotide labels comprising each UCI and the ULI from a single probe will be generated. Not being bound by a theory, using a plurality of labeling ligands with specificity for a plurality of cellular constituents will allow novel interactions to be determined. The use of polymer matrices allows a stable platform for washing out the unbound labeling ligands before staining with the ULI probes. The cellular constituent may comprise a protein, RNA transcript, or a DNA molecule. The ULI may be 4 to 30 nucleotides. The ULI may be 8 to 20 nucleotides.

The method may further comprise segregating the discrete polymer matrices comprising the labeled constituents before sequencing. The segregating of the discrete polymer matrices may comprise sorting single discrete matrices into separate reaction vessels.

The method may further comprise, before sequencing, generating a USI for each discrete polymer matrix by a split pool ligation method, wherein the restriction site on the ULI probe is a universal ligation handle (ULH) sequence configured to produce a DNA overhang capable of hybridization to a complementary overhang on a first index nucleotide sequence, wherein the first index nucleotide sequence comprises an overhang complementary to a final index sequence or optionally a middle index sequence, wherein the middle index sequence comprises overhangs complementary to the first index sequence and to the final index sequence or optionally to another middle index sequence and final index sequence, wherein the final index sequence has a single overhang complementary to the preceding index sequence, and wherein the first, middle, and final index sequences are selected from a plurality of unique sequences comprising compatible DNA overhangs and 10 to 30 base pairs of unique sequence. The split pool ligation method may comprise: splitting the pool of discrete polymer matrices into separate pools of polymer matrices, each containing a unique first index sequence; ligating the first index sequence to the ligation handle; pooling the discrete polymer matrices; optionally, splitting the pool of discrete polymer matrices into separate pools each containing a unique middle index sequence; ligating the middle index sequence to the first index sequence; and pooling the discrete polymer matrices; optionally, repeating with another middle index sequence; splitting the pool of discrete polymer matrices into pools containing a unique final index sequence; and ligating the final index sequence to the preceding index sequence, whereby each discrete polymer matrix comprises a USI.

The oligonucleotide label may further comprise a unique molecular identifier (UMI) sequence. The first, middle, or final index sequence may further comprise a unique molecular identifier (UMI) sequence. The method may further comprise pooling the oligonucleotide labels comprising a USI, ULI and UMI from a plurality of polymer matrices and sequencing the pooled UCI sequences, USI sequences, ULI sequences, and UMI sequences.

The aggregation of cellular constituents may be a cell that is a member of a cell population, further comprising transforming or transducing the cell population with one or more genomic sequence-perturbation constructs that perturb a genomic sequence in the cells, wherein each distinct genomic sequence-perturbation construct comprises a unique-perturbation-identified (UPI) sequence unique to that construct.

In another aspect, the present invention provides a method of determining interactions between 2 or more cellular constituents, comprising: fixing and permeabilizing at least one cell; incubating the fixed and permeabilized cell(s) with one or more labeling ligands with specific binding affinity for one or more target cellular constituents to produce one or more labeled cell(s), wherein each of the one or more labeling ligands comprise a bound oligonucleotide label comprising a unique constituent identifier (UCI) sequence and a universal hybridization nucleotide sequence, and wherein the incubation comprises binding conditions under which the labeling ligand will bind to the cellular constituent within the cell(s), and the incubation further comprises washing conditions under which unbound labeling ligands will be washed from the polymer cell(s); incubating the cell(s) with at least one Unique Location Index probe, wherein the probe comprises at least two repeating nucleotide sequences, each repeat comprising a restriction enzyme site, a Unique Location Index (ULI) sequence, and a complementary universal hybridization nucleotide sequence, and wherein the incubation comprises binding conditions under which the universal hybridization sequence will hybridize to the complementary universal hybridization sequence; extending the oligonucleotide label hybridized to the probe; digesting with a restriction enzyme specific for the site on the probe; and sequencing the oligonucleotide label, whereby detecting the same ULI with two or more UCIs indicates that the cellular constituents were interacting. The cellular constituent may comprise a protein, RNA transcript, or a DNA molecule. The ULI may be 4 to 30 nucleotides. The ULI may be 8 to 20 nucleotides.

The method may further comprise segregating the cell(s) comprising the labeled constituents before sequencing. The segregating of the cell(s) may comprise sorting single discrete matrices into separate reaction vessels. The method may further comprise, before sequencing, generating a USI for each cell by a split pool ligation method, wherein the restriction site on the ULI probe is a universal ligation handle (ULH) sequence configured to produce a DNA overhang capable of hybridization to a complementary overhang on a first index nucleotide sequence, wherein the first index nucleotide sequence comprises an overhang complementary to a final index sequence or optionally a middle index sequence, wherein the middle index sequence comprises overhangs complementary to the first index sequence and to the final index sequence or optionally to another middle index sequence and final index sequence, wherein the final index sequence has a single overhang complementary to the preceding index sequence, and wherein the first, middle, and final index sequences are selected from a plurality of unique sequences comprising compatible DNA overhangs and 10 to 30 base pairs of unique sequence. The split pool ligation method may comprise: splitting the pool of cells into separate pools of cells, each containing a unique first index sequence; ligating the first index sequence to the ligation handle; pooling the cells; optionally, splitting the pool of cells into separate pools each containing a unique middle index sequence; ligating the middle index sequence to the first index sequence; and pooling the cells; optionally, repeating with another middle index sequence; splitting the pool of cells into pools containing a unique final index sequence; and ligating the final index sequence to the preceding index sequence, whereby each cell comprises a USI.

The oligonucleotide label may further comprise a unique molecular identifier (UMI) sequence. The first, middle, or final index sequence may further comprise a unique molecular identifier (UMI) sequence. The method may further comprise pooling the oligonucleotide labels comprising a USI, ULI and UMI from a plurality of polymer matrices and sequencing the pooled UCI sequences, USI sequences, ULI sequences, and UMI sequences.

The cells may be a member of a cell population, further comprising transforming or transducing the cell population with one or more genomic sequence-perturbation constructs that perturb a genomic sequence in the cells, wherein each distinct genomic sequence-perturbation construct comprises a unique-perturbation-identified (UPI) sequence unique to that construct. The perturbation constructs may be any as described herein.

The oligonucleotide label may comprise a regulatory sequence configured for amplification by T7 polymerase.

The labeling ligands may comprise oligonucleotide sequences configured to hybridize to a transcript specific region.

Before sequencing, the method may further comprise: amplification of the oligonucleotide label by PCR; or T7 amplification of the oligonucleotide label followed by subsequent cDNA generation, and optionally amplification by PCR.

The oligonucleotide label may further comprise at least one spacer sequence. The oligonucleotide label may further comprise a photocleavable linker. The oligonucleotide label may further comprise a restriction enzyme site between the labeling ligand and UCI.

The oligonucleotide label may comprise one or more iso-dG and/or iso-dC nucleotides. The oligonucleotide labels for hybridization in a proximity assay may comprise one or more iso-dG and/or iso-dC nucleotides. The universal hybridization sequences may comprise one or more iso-dG and/or iso-dC nucleotides. Not being bound by a theory, the one or more iso-dG and/or iso-dC nucleotides will increase specificity of hybridization.

In one embodiment, the oligonucleotide label of any of the methods described herein may comprise one or more iso-dG and/or iso-dC nucleotides. Two complementary sequences may comprise one sequence with iso-dG and the other complementary sequence with iso-dC, whereby the two sequences are capable of hybridizing with each other, but not with sequences containing only dG, dC, dA, and/or dT. The sequence of the oligonucleotide labels for hybridization in a proximity assay may advantageously comprise one or more iso-dG and/or iso-dC nucleotides.

Any of the methods of the present invention may advantageously be combined for determining any combination of protein detection, RNA detection, open chromatin detection, protein-protein interactions, protein-RNA interactions, or protein-DNA interactions.

The terms "isolated aggregation of cellular constituents" or "single aggregations of cellular constituents" or "aggregations of cellular constituents" or "aggregations of biologically connected cellular constituents" are used interchangeably and refer to any group of cellular constituents that originate from the same source, that are functionally connected biologically, and that can be isolated individually. Examples may be a cell, an extracellular vesicle, an organelle, or an organized subcomponent thereof. Specific examples may be a nucleus or a mitochondria.

The term "cellular constituent" refers to any cellular molecule including, but not limited to, a protein, nucleic acid, RNA molecule, DNA molecule, or carbohydrate.

The term "unique molecular identifiers" (UMI) refers to a sequencing linker used in a method that uses molecular tags to detect and quantify unique amplified products. A UMI is used to distinguish effects through a single clone from multiple clones. In preferred embodiments, the amplification is by PCR. A sequencer linker with a random sequence of between 4 and 20 basepairs and an index sequence is added to the 5' end of the template, which is amplified and sequenced. Sequencing allows for high resolution reads, enabling accurate detection of true variants. As used herein, a "true variant" will be present in every amplified product originating from the original clone as identified by aligning all products with a UMI. Each clone amplified will have a different random UMI that will indicate that the amplified product originated from that clone. Background caused by the fidelity of the amplification process can be eliminated because true variants will be present in all amplified products and background representing random error will only be present in single amplification products (see e.g., Islam S. et al., 2014. Nature Methods No:11, 163-166). Not being bound by a theory, the UMIs and UCIs are designed such that assignment to the original can take place despite up to 4-7 errors during amplification or sequencing.

The term "unique constituent identifier" (UCI) refers to any unique nucleotide sequence linked to a labeling ligand, such that the presence of the sequence indicates the presence of the cellular constituent that the labeling ligand specifically binds. In an exemplary embodiment, the UCI is linked to an antibody for a specific cellular constituent. If the cellular constituent is present in a sample, the antibody will bind and the UCI can be detected. If the cellular constituent is not present in a sample, the antibody will not bind and the UCI will not be detected above background. In another exemplary embodiment, the labeling ligand is an oligonucleotide probe and the cellular constituent is an RNA transcript molecule complementary to the sequence of the oligonucleotide probe. The sequence of the oligonucleotide probe may be the UCI or may comprise an additional UCI sequence to identify the RNA transcript.

The term "unique source identifier" (USI) refers to a unique nucleotide sequence that is associated with the nucleic acids from a single cell or single isolated aggregation of cellular constituents (source), such that upon sequencing, a pool of nucleic acid sequences from more than one cell or isolated aggregation of cellular constituents, the presence of a USI in the sequenced product indicates that a product originated from a single source. USI may be used interchangeably with the term "barcode."

The term "unique-amplification-identifier" (UAI) refers to a nucleotide sequence that is formed only when two or more nucleotide sequences are in close proximity to each other such that they can be ligated. The UAI can be generated using methods described for the proximity ligation assay (PLA) or proximity extension assay (PEA) (Fredriksson S, et al. (2002) Protein detection using proximity-dependent DNA ligation assays. Nature Biotechnology 20: 473-477; Gullberg M, et al. (2004) Cytokine detection by antibody-based proximity ligation. Proceedings of the National Academy of Sciences of the United States of America 101: 8420-8424; and Lundberg M, et al. (2011) Homogeneous antibody-based proximity extension assays provide sensitive and specific detection of low-abundant proteins in human blood. Nucleic Acids Research 39(15): e102). PEA is based on pairs of antibodies that are linked to oligonucleotides having slight affinity to one another (PEA probes). Upon target binding the probes are brought in proximity, and the two oligonucleotides are extended by a DNA polymerase forming the UAI that now acts as a unique surrogate marker for the specific antigen.

The terms "sticky end," "overhang" and "DNA overhang" refer to a double stranded DNA having either a 3' or 5' single stranded DNA overhang capable of hybridization to another complementary sticky end or DNA overhang.

The term "hydrogel" refers to any network of polymer chains that are hydrophilic, and sometimes found as a colloidal gel, in which water is the dispersion medium. Hydrogels are highly absorbent (they can contain over 90% water) natural or synthetic polymeric networks. Hydrogels also possess a degree of flexibility very similar to natural tissue, due to their significant water content. Hydrogel may include polyvinyl alcohol, sodium polyacrylate, acrylate polymers, copolymers with an abundance of hydrophilic groups, agarose, methylcellulose, hyaluronan, and other naturally derived polymers.

The term "tagmentation" refers to a step in the Assay for Transposase Accessible Chromatin using sequencing (ATAC-seq) as described. (See, Buenrostro, J. D., Giresi, P. G., Zaba, L. C., Chang, H. Y., Greenleaf, W. J., Transposition of native chromatin for fast and sensitive epigenomic profiling of open chromatin, DNA-binding proteins and nucleosome position. Nature Methods 2013; 10 (12): 1213-1218). Specifically, a hyperactive Tn5 transposase loaded in vitro with adapters for high-throughput DNA sequencing, can simultaneously fragment and tag a genome with sequencing adapters. In one embodiment, the adapters are compatible with the methods described herein.

The present invention may also include barcoding. Barcoding may be performed based on any of the compositions or methods disclosed in International Publication No. WO 2014/047561 A1, Compositions and methods for labeling of agents, incorporated herein in its entirety. In one embodiment, each labeling ligand has a barcode (UCI). In one embodiment, a sgRNA has a barcode. In one embodiment, the UCI is captured on a bead that includes a barcode sequence (USI). Not being bound by a theory, amplified sequences from single cells or isolated aggregations of cellular constituents can be sequenced together and resolved based on the barcode associated with each USI. Not being bound by a theory, the presence of a labeling ligand can be determined by sequencing of the UCI.

In certain embodiments, barcoding uses an error correcting scheme (T. K. Moon, Error Correction Coding: Mathematical Methods and Algorithms (Wiley, New York, ed. 1, 2005)). Not being bound by a theory, amplified sequences from single cells can be sequenced together and resolved based on the barcode associated with each cell.

The term "barcode" as used herein, refers to any unique, non-naturally occurring, nucleic acid sequence that may be used to identify the originating source of a nucleic acid fragment. Such barcodes may be sequences including, but not limited to, about 20 base pair sequences. Although it is not necessary to understand the mechanism of an invention, it is believed that the barcode sequence provides a high-quality individual read of a barcode associated with a viral vector, labeling ligand, shRNA, sgRNA or cDNA such that multiple species can be sequenced together.

DNA barcoding is also a taxonomic method that uses a short genetic marker in an organism's DNA to identify it as belonging to a particular species. It differs from molecular phylogeny in that the main goal is not to determine classification but to identify an unknown sample in terms of a known classification. Kress et al., "Use of DNA barcodes to identify flowering plants" Proc. Natl. Acad. Sci. U.S.A. 102(23):8369-8374 (2005). Barcodes are sometimes used in an effort to identify unknown species or assess whether species should be combined or separated. Koch H., "Combining morphology and DNA barcoding resolves the taxonomy of Western Malagasy Liotrigona Moure, 1961" African Invertebrates 51(2): 413-421 (2010); and Seberg et al., "How many loci does it take to DNA barcode a *crocus*?" PLoS One 4(2):e4598 (2009). Barcoding has been used, for example, for identifying plant leaves even when flowers or fruit are not available, identifying the diet of an animal based on stomach contents or feces, and/or identifying products in commerce (for example, herbal supplements or wood). Soininen et al., "Analysing diet of small herbivores: the efficiency of DNA barcoding coupled with high-throughput pyrosequencing for deciphering the composition of complex plant mixtures" Frontiers in Zoology 6:16 (2009).

It has been suggested that a desirable locus for DNA barcoding should be standardized so that large databases of sequences for that locus can be developed. Most of the taxa of interest have loci that are sequencable without species-specific PCR primers. CBOL Plant Working Group, "A DNA barcode for land plants" PNAS 106(31):12794-12797 (2009). Further, these putative barcode loci are believed short enough to be easily sequenced with current technology. Kress et al., "DNA barcodes: Genes, genomics, and bioinformatics" PNAS 105(8):2761-2762 (2008). Consequently, these loci would provide a large variation between species in combination with a relatively small amount of variation within a species. Lahaye et al., "DNA barcoding the floras of biodiversity hotspots" Proc Natl Acad Sci USA 105(8): 2923-2928 (2008).

DNA barcoding is based on a relatively simple concept. For example, most eukaryote cells contain mitochondria, and mitochondrial DNA (mtDNA) has a relatively fast mutation rate, which results in significant variation in mtDNA sequences between species and, in principle, a comparatively small variance within species. A 648-bp region of the mitochondrial cytochrome c oxidase subunit 1 (CO1) gene was proposed as a potential 'barcode'. As of 2009, databases of CO1 sequences included at least 620,000 specimens from over 58,000 species of animals, larger than databases available for any other gene. Ausubel, J., "A botanical macroscope" Proc. Natl Acad. Sci. 106(31):12569 (2009).

Software for DNA barcoding requires integration of a field information management system (FIMS), laboratory information management system (LIMS), sequence analysis tools, workflow tracking to connect field data and laboratory data, database submission tools and pipeline automation for scaling up to eco-system scale projects. Geneious Pro can be used for the sequence analysis components, and the two plugins made freely available through the Moorea Biocode Project, the Biocode LIMS and Genbank Submission plugins handle integration with the FIMS, the LIMS, workflow tracking and database submission.

Additionally, other barcoding designs and tools have been described (see e.g., Birrell et al., (2001) Proc. Natl Acad. Sci. USA 98, 12608-12613; Giaever, et al., (2002) Nature 418, 387-391; Winzeler et al., (1999) Science 285, 901-906; and Xu et al., (2009) Proc Natl Acad Sci USA. February 17; 106(7):2289-94).

In certain embodiments, sequencing is performed using unique molecular identifiers (UMI). The term "unique molecular identifiers" (UMI) refers to a sequencing linker used in a method that uses molecular tags to detect and quantify unique amplified products. A UMI is used to distinguish effects through a single clone from multiple clones. In preferred embodiments, the amplification is by PCR. A sequencer linker with a random sequence of between 4 and 20 base pairs is added to the 5' end of the template, which is amplified and sequenced. Sequencing allows for high resolution reads, enabling accurate detection of true variants. As used herein, a "true variant" will be present in every amplified product originating from the original clone as identified by aligning all products with a UMI. Each clone amplified will have a different random UMI that will indicate that the amplified product originated from that clone. Background caused by the fidelity of the amplification process can be eliminated because true variants will be present in all amplified products and background representing random error will only be present in single amplification products (see e.g., Islam S. et al., 2014. Nature Methods No:11, 163-166). Not being bound by a theory, the UMI's are designed such that assignment to the original can take place despite up to 4-7 errors during amplification or sequencing.

Unique molecular identifiers are a subtype of nucleic acid barcode that can be used, for example, to normalize samples for variable amplification efficiency. For example, in various embodiments, featuring a solid or semisolid support (for example a hydrogel bead), to which nucleic acid barcodes (for example a plurality of barcode sharing the same sequence) are attached, each of the barcodes may be further coupled to a unique molecular identifier, such that every barcode on the particular solid or semisolid support receives a distinct unique molecule identifier. A unique molecular identifier can then be, for example, transferred to a target molecule with the associated barcode, such that the target molecule receives not only a nucleic acid barcode, but also an identifier unique among the identifiers originating from that solid or semisolid support.

In certain embodiments, multiple displacement amplification (MDA) is used. Multiple displacement amplification (MDA), is a non-PCR-based isothermal method based on the annealing of random hexamers to denatured DNA, followed by strand-displacement synthesis at constant temperature (Blanco et al. J. Biol. Chem. 1989, 264, 8935-8940). It has been applied to samples with small quantities of genomic DNA, leading to the synthesis of high molecular weight DNA with limited sequence representation bias (Lizardi et al. Nature Genetics 1998, 19, 225-232; Dean et al., Proc. Natl. Acad. Sci. USA 2002, 99, 5261-5266). As DNA is synthesized by strand displacement, a gradually increasing number of priming events occur, forming a network of hyper-branched DNA structures. The reaction can be catalyzed by enzymes such as the Phi29 DNA polymerase or the large fragment of the Bst DNA polymerase. The Phi29 DNA polymerase possesses a proofreading activity resulting in error rates 100 times lower than Taq polymerase (Lasken et al. Trends Biotech. 2003, 21, 531-535).

The invention provides a method for preparing uniquely barcoded particles. Unique barcode sequences may be generated by a split pool method. The split pool method may include sticky end ligation. Sticky end ligation may include a sticky end ligation handle and separate indexes containing unique sequences capable of hybridizing to a sticky end (see examples). The sticky end may comprise a ssDNA overhang. The overhang may have 2, 3, 4, 5, 6, 7, 8, preferably 4 bases. The overhang may be generated by a restriction enzyme. Each index may contain a plurality of unique sequences. Each index may contain 10, 20, 30, 40, 50, 60, 70, 80, 90, 100, 200, preferably 192 sequences. In one embodiment there are 2, 3, 4, preferably 3 indexes. A unique barcode sequence is generated by ligation of the first index to the ligation handle, splitting and pooling of the ligated samples, and then addition of the next index also containing sticky ends. The last index preferably has a sticky end for ligation to the previous index. The last index may advantageously include a primer sequence for priming of PCR. Methods of split pooling have been described. In one embodiment, the ligation handle is digested with a restriction enzyme to produce a four base overhang. In another embodiment, a ligation primer is hybridized to the ligation handle to generate an at least 4 base overhang that is complementary to an index in the split pool method.

In one exemplary embodiment, the hydrogel particles or polymer matrices are split into pools, each pool containing a unique index A and each ligation handle is ligated to a sequence in index A. All particles are then pooled and re-split into new pools containing a unique index B. After ligation, all of the particles are pooled again and re-split into new pools containing a unique index C. If each index has 100 unique sequences and for each cycle the particles are split into 100 pools each containing a unique sequence, then after 3 cycles of split and pool ligation, the barcode on any given particle possess the same one of $100^1=1,000,000$ possible barcodes, but different particles have different sequences.

In another embodiment, single cell or single isolated aggregation of cellular constituent analysis is performed by digital polymerase chain reactions (PCR), e.g., Fluidigm C. Digital polymerase chain reaction (digital PCR, DigitalPCR, dPCR, or dePCR) is a refinement of conventional polymerase chain reaction methods that can be used to directly quantify and clonally amplify nucleic acids including DNA, cDNA or RNA. The key difference between dPCR and traditional PCR lies in that PCR carries out one reaction per single sample and dPCR carries out a single reaction within samples separated into a large number of partitions wherein the reactions are carried out in each partition individually. A sample is partitioned so that individual nucleic acid molecules within the sample are localized and concentrated within many separate regions. The capture or isolation of individual nucleic acid molecules may be effected in micro well plates, capillaries, the dispersed phase of an emulsion, and arrays of miniaturized chambers, as well as on nucleic acid binding surfaces.

In a preferred embodiment, single cell or single aggregation of cellular constituent analysis is performed using microfluidics. Microfluidics involves micro-scale devices that handle small volumes of fluids. Because microfluidics may accurately and reproducibly control and dispense small fluid volumes, in particular volumes less than 1 µl, application of microfluidics provides significant cost-savings. The use of microfluidics technology reduces cycle times, shortens time-to-results, and increases throughput. Furthermore, incorporation of microfluidics technology enhances system integration and automation. Microfluidic reactions are generally conducted in microdroplets. The ability to conduct reactions in microdroplets depends on being able to merge different sample fluids and different microdroplets. See, e.g., US Patent Application Publication No. 20120219947 and International Publication No. WO 2014/085802 A1.

Droplet microfluidics offers significant advantages for performing high-throughput screens and sensitive assays. Droplets allow sample volumes to be significantly reduced, leading to concomitant reductions in cost. Manipulation and measurement at kilohertz speeds enable up to $10^8$ samples to be screened in a single day. Compartmentalization in droplets increases assay sensitivity by increasing the effective concentration of rare species and decreasing the time required to reach detection thresholds. Droplet microfluidics combines these powerful features to enable currently inaccessible high-throughput screening applications, including single-cell and single-molecule assays. See, e.g., Guo et al., Lab Chip, 2012, 12, 2146-2155.

The manipulation of fluids to form fluid streams of desired configuration, discontinuous fluid streams, droplets, particles, dispersions, etc., for purposes of fluid delivery, product manufacture, analysis, and the like, is a relatively well-studied art. Microfluidic systems have been described in a variety of contexts, typically in the context of miniaturized laboratory (e.g., clinical) analysis. Other uses have been described as well. For example, WO 2001/89788; WO 2006/040551; U.S. Patent Application Publication No. 2009/0005254; WO 2006/040554; U.S. Patent Application Publication No. 2007/0184489; WO 2004/002627; U.S. Pat. No. 7,708,949; WO 2008/063227; U.S. Patent Application Publication No. 2008/0003142; WO 2004/091763; U.S. Patent Application Publication No. 2006/0163385; WO 2005/021151; U.S. Patent Application Publication No. 2007/0003442; WO 2006/096571; U.S. Patent Application Publication No. 2009/0131543; WO 2007/089541; U.S. Patent Application Publication No. 2007/0195127; WO 2007/081385; U.S. Patent Application Publication No. 2010/0137163; WO 2007/133710; U.S. Patent Application Publication No. 2008/0014589; U.S. Patent Application Publication No. 2014/0256595; and WO 2011/079176. In a preferred embodiment, single cell analysis is performed in droplets using methods according to WO 2014/085802. Each of these patents and publications is herein incorporated by reference in their entireties for all purposes.

Single cells or isolated aggregations of cellular constituents may be sorted into separate vessels by dilution of the sample and physical movement, such as pipetting. A machine can control the pipetting and separation. The machine may be a computer-controlled robot.

Microfluidics may also be used to separate the single cells and/or isolated aggregations of cellular constituents. Single cells and/or isolated aggregations of cellular constituents can be separated using microfluidic devices. Microfluidics involves micro-scale devices that handle small volumes of fluids. Because microfluidics may accurately and reproducibly control and dispense small fluid volumes, in particular volumes less than 1 µl, application of microfluidics provides significant cost-savings. The use of microfluidics technology reduces cycle times, shortens time-to-results, and increases throughput. The small volume of microfluidics technology improves amplification and construction of DNA libraries made from single cells and single isolated aggregations of cellular constituents. Furthermore, incorporation of microfluidics technology enhances system integration and automation.

Single cells and/or single isolated aggregations of cellular constituents of the present invention may be divided into single droplets using a microfluidic device. The single cells and/or single isolated aggregations of cellular constituents in such droplets may be further labeled with a barcode. In this regard, reference is made to Macosko et al., 2015, "Highly Parallel Genome-wide Expression Profiling of Individual Cells Using Nanoliter Droplets" Cell 161, 1202-1214 and Klein et al., 2015, "Droplet Barcoding for Single-Cell Transcriptomics Applied to Embryonic Stem Cells" Cell 161, 1187-1201, all the contents and disclosure of each of which are herein incorporated by reference in their entirety. Not being bound by a theory, the volume size of an aliquot within a droplet may be as small as 1 fL.

Single cells and/or single aggregations of cellular constituents may be diluted into a physical multi-well plate or a plate free environment. The multi-well assay modules (e.g., plates) may have any number of wells and/or chambers of any size or shape, arranged in any pattern or configuration, and be composed of a variety of different materials. Preferred embodiments of the invention are multi-well assay plates that use industry standard multi-well plate formats for the number, size, shape and configuration of the plate and wells. Examples of standard formats include 96-, 384-, 1536- and 9600-well plates, with the wells configured in two-dimensional arrays. Other formats include single well, two well, six well and twenty-four well and 6144-well plates. Plate free environments of the present invention utilize a single polymerizable gel containing compartmentalized cells and/or isolated aggregations of cellular constituents. In one embodiment, extraction of single cells and/or single isolated aggregations of cellular constituents may be by a mechanical punch. Single cells and/or single isolated aggregations of cellular constituents may be visualized in the gel before a punch.

In one embodiment, a DNA tag including a protein specific barcode (UCI) is conjugated to detection biomolecules or labeling ligands with high target affinity and low unspecific binding, such as antibodies (Janssen et al., 2013) or nanobodies (Pardon et al., 2014; Theile et al., 2013) or aptamers (Janssen et al., 2013).

In one embodiment, to ensure proper staining of intracellular and cell surface proteins with, for instance, DNA-tagged antibodies, single cells are embedded in hydrogel droplets. Not being bound by a theory, the hydrogel mesh provides a physical framework, chemically incorporates biomolecules and is permeable to macromolecules such as antibodies (Chung et al., 2013). In one embodiment, to further improve permeability and staining efficiency, lipids are cleared (Chung et al., 2013). Not being bound by a theory, the clearance of the lipids and the porosity of the hydrogel allow for more efficient washing and removal of unspecific antibodies. This higher accuracy of measurement is important for the high multiplex measurements and computational inference of regulatory mechanisms.

In one embodiment, cells embedded in a hydrogel mesh can be stained with the DNA-tagged antibodies and washed in bulk before isolating the single cells. Once isolated, a cell specific oligonucleotide barcode (USI) can be introduced before subsequent DNA amplification and library preparation steps. Isolating single cells into individual reaction chambers to perform PCR amplification or a proximity ligation/extension assay (Assarsson et al., 2014) can be achieved at modest throughput either by FACS sorting into multi-well plates or microfluidic capture using the Fluidigm C1 (Shalek et al., 2014).

In one embodiment, for more high-throughput processing, a microfluidic chip can be used to capture the hydrogel embedded cells or cellular constituents in nanoliter-sized aqueous droplets (Macosko et al., 2015, "Highly Parallel Genome-wide Expression Profiling of Individual Cells Using Nanoliter Droplets" Cell 161, 1202-1214). In one embodiment, the hydrogel embedded cells or cellular constituents are poisson loaded into microwells (Fan et al., 2015). The aqueous droplets or microwells may be simultaneously loaded with barcoded beads, each of which has oligonucleotides including; a "cell barcode" that is the same across all the primers on the surface of any one bead, but different from the cell barcodes on all other beads; a Unique Molecular Identifier (UMI), different on each primer, that enables sequence reads derived from the same original DNA tag (amplification and PCR duplicates) to be identified computationally (Kivioja et al., 2012); and a capture sequence to bind the oligos (either amplified PCR products or original DNA tags released by proteinase K treatment, or enzymatic/photonic oligo cleavage). Once the beads are loaded, they can be pooled for amplification and library preparation, and sequencing. These beads can take multiple forms, the preferred drop-seq beads are polystyrene, oligo functionalized beads, but alternative beads are possible, such as soft beads (polymer gel based beads), that allow for one on one pairing with cells, as to avoid the poisson loading needed in the described drop-seq scheme. This reduces the amount of cells one needs, and makes it possible to analyze rare cell types or clinical samples only available in low amounts of cells.

In one embodiment, the present invention provides for the simultaneous detection of proteins and nucleic acids. Nucleic acids can be reverse cross-linked after separation of discrete polymer matrices into separate wells or droplets. The contents of individual wells or droplets may then be sequenced. In one embodiment, crosslinking is reversed by incubating the cross-linked sample in high salt (approximately 200 mM NaCl) at 65° C. for at least 4 hours.

In one embodiment, Drop-Seq (Macosko et al., 2015) is used to analyze RNA or DNA in single cells in parallel to the detection of cellular constituents. Drop-Seq is a reverse emulsion, early barcoding method for analyzing $10^4$-$10^6$ cells/experiment at very low cost ($0.06/cell). The Drop-seq method may be used to encapsulate discrete hydrogel matrices in a droplet. The RNA and/or DNA can be reverse cross-linked and the oligonucleotide labels can be removed from the labeling ligand. Capture of RNA, DNA, and oligonucleotide labels on barcoded beads, library preparation, and sequencing is performed as described previously.

In one embodiment, the detection of proteins or post translational modifications (PTM) is determined by sequencing based readouts. In some embodiments, Immuno-Seq is used when antibodies can be washed out (Niemeyer, C. M., et al., Nat Protoc. 2, 1918-1930 (2007)) and proximity extension assays (PEA) are used when antibodies cannot be washed away (Hammond, M., et al. PLoS One. 7, e40405, (2012); and Stahlberg, A., et al. Clin Chem. 58, 1682-1691 (2012)). These methods use DNA-sequence based encoding, and are compatible with other genomic readouts (e.g., sgRNA barcodes).

In another embodiment, the detection of proteins embedded in a hydrogel matrix is determined by FACS. Not being bound by a theory, the encapsulation of cellular constituents in a hydrogel matrix and removing lipids provides for improved binding of antibodies to intracellular targets as compared to regular fixation and permeabilization protocols for FACS alone.

Undersampling—a Sampling Based Framework for Genetic Interactions

According to the invention, random sampling may comprise matrix completion, tensor completion, compressed sensing, or kernel learning.

In some aspects, where random sampling comprises matrix completion, tensor completion, or compressed sensing, $\pi$ may be of the order of log P.

The invention relies on a random sampling assumption, e.g. that the combinatorial space is sparse and/or of low rank. This assumption is generic and advantageously does not rely on the pre-determination of a (known) set of genetic interactions. This assumption constrains the range or complexity of models, and thus can be used to restrict sampling size (undersampling). The sample may be a biological sample, for example a blood, buccal, cell, cerebrospinal fluid, mucus, saliva, semen, tissue, tumor, feces, urine, or vaginal sample. It may be obtained from an animal, a plant or a fungus. The animal may be a mammal. The mammal may be a primate. The primate may be a human. In other embodiments, the sample may be an environmental sample, such as water or soil.

As used herein, the term "sample template" refers to nucleic acid originating from a sample which is analyzed for the presence of a target sequence of interest. In contrast, "background template" is used in reference to nucleic acid other than sample template which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

"Target sequence" is intended to designate either one target sequence or more than one target sequence, i.e. any sequence of interest at which the analysis is aimed. Thus, the sample may comprise more than one target sequence and preferably a plurality of target sequences, the number of which may be 2, 3, 4, 5, 6, 7, 8, 9, 10, 11, 12, 13, 14, 15, 16, 17, 18, 19, 20 and above. A target sequence may be comprised in a gene or gene transcript, such as gene mRNA.

The present invention is related to the field of genomic informatics and gene-expression profiling. Gene-expression profiles provide complex molecular fingerprints regarding the relative state of a cell or tissue. Similarities in gene-expression profiles between organic states (i.e., for example, normal and diseased cells and/or tissues) provide molecular taxonomies, classification, and diagnostics. Similarities in gene-expression profiles between organic (e.g. disease) and induced (e.g. by small molecule) states may identify clinically-effective therapies.

Some embodiments of the present invention contemplate measuring relative gene abundances of transcripts in a pool of samples to allow genome-wide transcriptional profiling for applications including, but not limited to, disease classification and diagnosis without resort to expensive and laborious microarray technology (i.e., for example, Affymetrix GeneChip microarrays). Other uses include, but are not limited to, generating gene-expression data for use in and with information databases (i.e., for example, connectivity maps). A connectivity map typically may comprise a collection of a large number of gene-expression profiles together with allied pattern-matching software. The collection of profiles is searched with the pattern-matching algorithm for profiles that are similar to gene-expression data derived from a biological state of interest. The utility of this searching and pattern-matching exercise resides in the belief that similar biological states may be identified through the transitory feature of common gene-expression changes. The gene-expression profiles in a connectivity map may be derived from known cellular states, or cells or tissues treated with known chemical or genetic perturbagens. In this mode, the connectivity map is a tool for the functional annotation of the biological state of interest. Alternatively, the connectivity map is populated with gene-expression profiles from cells or tissues treated with previously uncharacterized or novel perturbagens. In this mode, the connectivity map functions as a screening tool. Most often, a connectivity map is populated with profiles of both types. Connectivity maps, in general, establish biologically-relevant connections between disease states, gene-product function, and small-molecule action. In particular, connectivity maps have wide-ranging applications including, but not limited to, functional annotation of unknown genes and biological states, identification of the mode of action or functional class of a small molecule, and the identification of perturbagens that modulate or reverse a disease state towards therapeutic advantage as potential drugs. See Lamb et al, "The Connectivity Map: using gene-expression signatures to connect small molecules, genes and disease" Science 313: 1929-1935 (2006), and Lamb, "The Connectivity Map: a new tool for biomedical research" Nature Reviews Cancer 7: 54-60 (2007). However, the high cost of generating gene-expression profiles severely limits the size and scope of connectivity maps. A connectivity map populated with gene-expression profiles derived from every member of an industrial small-molecule drug-screening library, a saturated combinatorial or diversity-orientated chemical library, a comprehensive collection of crude or purified plant or animal extracts, or from the genetic ablation or forced expression of every gene in a mammalian genome, for example, would be expected to facilitate more, and more profound, biological discoveries than those of existing connectivity maps.

The present invention contemplates compositions and methods for making and using a transcriptome-wide gene-expression profiling platform that "under samples" the total number of transcripts. Because gene expression is believed to be highly correlated, direct measurement of a small number allows the expression levels of the remainder to be inferred. The present invention, therefore, has the potential to reduce the cost and increase the throughput of full-transcriptome gene-expression profiling relative to the well-known conventional approaches that require all transcripts to be measured.

Gene expression data are highly structured, such that the expression level of some genes is predictive of the expression level of others. Knowledge that gene expression data are highly structured allows for the assumption that the number of degrees of freedom in the system are small, which allows for assuming that the basis for computation of the relative gene abundances is sparse.

In the framework of matrix completion, or more generally tensor completion, the goal is to fill in. As may be appreciated by one of skill in the art, the "sparsity" of a matrix is a measure of the non-zero elements of a matrix relative to the total number of elements of a matrix. A sparse matrix is a matrix in which most of the elements are zero, which is indicative of loose correlation between systems.

Matrix (Tensor) Completion

All the values of a matrix (tensor) are filled in using a small collection of sampled entries. It is hypothesized that the rank of a tensor of higher-order interactions is a fraction of the number of tested genes which is tested by calculating the rank from a dense sampling of second or third order knockouts from a small collection of genes. If the rank of interactions is limited, then randomly sets of genes to knockout from a larger collection can be sampled, and the remaining values filled in via nuclear norm regularized least-squares optimization (Candes, E. J. & Plan, Y. Matrix Completion With Noise. Proceedings of the IEEE. 98, 925-936, doi:Doi 10.1109/Jproc.2009.2035722 (2010)). Provable guarantees suggest that if the rank, r, is small relative to the number of genes, n, then $m \geq O(n^{6/5} r \log n)$ sampled entries are sufficient. However, since these guarantees assume rough uniformity in the loadings of interaction singular vectors, this assumption is unlikely to hold if the interaction matrix is very sparse. In this case, one performs the same random sampling, and simultaneously regularize over both the nuclear norm and the L1 norm of the matrix (Richard, E., Savalle, P. & Vayatis, N. Estimation of Simultaneously Sparse and Low Rank Matrices. arXiv. doi:arXiv:1206.6474).

Compressed Sensing

Here, instead of working with a tensor of interaction terms, one works with a basis that spans all higher order interactions. Each single quantitative phenotype is a real-valued function $f(g)$ on possible genotypes g (the 2' possible allelic or knockout states), represented as binary strings of length m. Then, analyzing such Boolean functions using *Fourier decomposition* (O'Donnell, R. *Analysis of boolean functions*. (Cambridge University Press, 2014))

$$f(g) = \sum_{b \in \{0,1\}^m} \hat{f}_b (-1)^{b \cdot g}, \hat{f}_b = \frac{1}{2^m} \sum_{g \in \{0,1\}^m} f(g)(-1)^{g \cdot b},$$

where $f$ is an orthogonal basis indexed by binary strings b, and each Fourier coefficient $\hat{f}_b$ precisely quantifies the effect of one possible multi-gene interaction. For example, with m=2, $\hat{f}_{00}$ is the average phenotype; $\hat{f}_{10}$ is the effect of the first gene knockout, marginalized over the genetic background of the second; similarly for $\hat{f}_{01}$; and $\hat{f}_{11}$ quantifies the two-way interaction (the extent to which the double knockout phenotype differs from that predicted by the sum of the effects of the single knockouts). It is hypothesized that such genotype-phenotype maps are approximately sparse in the Fourier basis, such that there is a small number, s, of nonzero Fourier coefficients (not known apriori). With perturbations generated only up to a limited order, one can obtained a truncated Fourier model, which is a general linear model: the genetic interactions are in the basis functions (encoded into a design matrix), and the response is linear in the unknown Fourier coefficients. It is assumed most truncated coefficients are negligible. Assuming that the genotype-phenotype maps are approximately sparse in the Fourier basis, L1-penalized regression is used to learn the coefficients of the map from paired genotype-phenotype observations $g_i$, $f(g_i)$ (with uncertainty or noise in both).

An Observed Measurement Matrix may thus be constructed using the measurement results for each cell/sample to populate the elements/entries of the Observed Measurement Matrix. Construction of the Observed Measurement Matrix can include tag quantification, and tag quantification can include sequencing. For example, a relative count is conducted of the tags such that the relative number of times a certain tag is counted per cell is entered into an appropriate element of the Observed Measurement Matrix M. A sparse coding solving process may then be applied to the Observed Measurement Matrix M to learn system matrix S as indicative of relative abundance of the transcripts in each of the samples.

An example of a sparse coding process can be exemplified by $$\underset{m \times c}{M} = \underset{m \times n}{DM} \cdot \underset{n \times c}{S}$$

where m is the number of measurement vectors, c is the number of cell vectors, and n is the number of gene vectors. S is a System Matrix, which can be determined once M and DM are populated (M with actual measurements/counts and DM with random measurement values). S is thus indicative of the relative gene abundances.

Moreover, once S is known, a Basis Matrix B, can be determined based on knowledge of X, a matrix populated by known contributions of genes n and cells c to the sample.

$$\underset{n \times c}{S} = \underset{n \times n}{B} \cdot \underset{n \times c}{X}$$

Knowledge of the Basis can then be used to generate new measurement values of the Design Matrix to refine calculation of a new System Matrix S'.

In one embodiment of the present invention, the sparse coding solving process comprises the use of noisy compositional observations. In order to simulate m noisy compositional observations of each of n samples, the following matrix product may be used:

$$M=DM(S+\text{noise})$$

In one particular embodiment, the System Matrix S may represent the original gene expression profiles (g genes×n samples) and the Design Matrix DM has each of its m rows representing one of the random linear combinations of the n genes, with m<<n. When noise is taken into consideration, the Observed Measurement Matrix M gives the m noisy linear combinations for each sample (m rows×c samples), according to the weights given in a row of the Design Matrix DM.

In some variants taking noise into consideration, the noise process for each gene in each sample is identically and independently distributed (i.i.d.), for example as a Gaussian. In some embodiments, the magnitude of the noisy components may be set by a signal-to-noise ratio, for example a signal-to-noise ratio of 2.

Due to sparsity of the system, the different interactions between genes may be treated as modules, wherein a module may be seen as a biological process in which each gene may or may not take part in a coordinated manner under a subset of conditions.

Sparsity of the system makes it possible to treat the different interactions between genes as modules. In this theoretical example, gene expression can be decomposed into the activity of three modules. If all three modules could be active, then a minimum of three measurements (corresponding to each module) would be required to infer gene abundance levels. However, because of sparsity, if each sample has only one active module, i.e. it is 1-sparse, then only two measurements per sample are needed:

a first measurement composed of modules A and B; and
a second measurement composed of modules B and C.

If module A is active, then only the first measurement will exhibit a high level of activity. If module B is active, then both the first and second measurements will exhibit a high level of activity. Finally, if module C is active, then only the second measurement will exhibit a high level of activity.

In one embodiment, the matrix factorization step comprises at least one, preferably all, of the following:

setting the number of modules active in any sample at a relatively small number;

setting the number of genes in any module at relatively small number and the number of modules in which each gene participates to a relatively small number;

taking the assumption according to which different modules represent distinct pathways or programs and do not overlap too much with one another as a condition of the sparse coding solving process; and/or setting the total number of modules at a not too large number.

In one sub-embodiment, the total number of genes being n, the number of active modules in any sample is set to be lower than 500, lower than 400, lower than 300, lower than 200, lower than 100, lower than 90, lower than 80, lower than 70, lower than 60, lower than 50, lower than 40, lower than 30, lower than 20, or lower than 10. In one sub-embodiment, the total number of genes being n, the number of active modules in any sample is set to be greater than 1, greater than 2, greater than 5, or greater than 10. In certain embodiments, the total number of genes being n, the number of active modules is between 1 and 500, or any possible sub-range within the stated range of 1 to 500, for example between 1 and 400, between 1 and 300, between 1 and 200, between 2 and 100, between 2 and 90, between 2 and 80, between 5 and 70, between 5 and 60, between 5 and 50, between 10 and 40, between 10 and 30, for example about 20.

In one sub-embodiment, the total number of genes being n, the number of genes in any module is set to be lower than 25,000, lower than 20,000, lower than 15,000, lower than 10,000, lower than 9,000, lower than 8,000, lower than 7,000, lower than 6,000, lower than 5,000, lower than 4,000, lower than 3,000, lower than 2,000, lower than 1,000, lower than 900, lower than 800, lower than 700, lower than 600, lower than 500, lower than 400, lower than 300, lower than 200, or lower than 100. In one sub-embodiment, the total number of genes being n, the number of genes in any module is set to be greater than 5, greater than 10, greater than 20, greater than 50, greater than 100, greater than 200, greater than 500, or greater than 1,000. In certain embodiments, the total number of genes being n, the number of genes in any module is between 5 and 1,000, 10 and 5,000, 20 and 5,000, 50 and 5,000, 100 and 5,000, 200 and 5,000, 500 and 5,000, 1,000 and 5,000, 1,000 and 10,000, 1,000 and 15,000, 1,000 and 20,000, 1,000 and 25,000, 5,000 and 10,000, 5,000 and 15,000, 5,000 and 20,000, 5,000 and 25,000, 10,000 and 15,000, 10,000 and 20,000, 10,000 and 25,000, 15,000 and 20,000, 15,000 and 25,000, 20,000 and 25,000. In certain embodiments, the total number of genes being n, the number of genes in any module is between 1,000 and 2,000.

In some embodiments, the total number of genes being n, each gene is present in at least one module.

In one embodiment, the total number of modules is between one tenth the number of samples to be analyzed and five times the number of samples to be analyzed. For example, if the total number of samples is 1,000, the number of modules may be at least 100 and at most 5,000.

The System Matrix S of observed expression levels may be expressed as the product of the X matrix, which can also be considered as a dictionary of expression modules wherein each column is a vector of length n (one entry per gene) and is one element of the dictionary, and a Basis matrix B of module activity levels wherein each column describes a linear combination of columns of X. In other words, X reflects the possible modules and B the level of expression of each module. Abundance levels may be approximated as a linear combination of gene modules. In a very general sense, any decomposition of multiple expression profiles in the following form fits with this interpretation. Posed in this way, this becomes a problem of matrix factorization: S=BX. In order to solve the equation, the sparse coding solving process thus may comprise a matrix factorization step. In one embodiment, the matrix factorization step comprises non-negative matrix factorization (NMF). In Nonnegative Matrix Factorization (NMF), all the entries of the module dictionary matrix and the basis matrix are nonnegative. NMF has the advantage that, like gene expression values themselves, the coefficients in the module dictionary and the module activity levels are not allowed to take on negative values. In some embodiments, a specific version of this algorithm (Sparse NMF) also constrains the number of active modules in each sample to be small: additional sparsity constraints are enforced on the activity levels, such that there are relatively few nonzero entries in B. Nonnegativity is sensible for expression analysis, since negative expression levels do not exist, but one might expect that some modules are actively repressed, and that this might be best represented with negative activity coefficients. Moreover, typically in Sparse NMF, there are no sparsity constraints on the module dictionary, and so one might find that most genes participate in most modules.

Alternatively, the matrix factorization step comprises Sparse Module Activity Factorization (SMAF). As used herein, SMAF is defined as having two important properties. First, both the module dictionary and the module activity levels are required to be sparse. Second, the entries of the dictionary matrix X is required to be nonnegative (because these values are meant to be interpreted as "membership" in a module), but the entry of the basis matrix B may be either positive or negative (because modules can either be activated or repressed).

SMAF makes it possible to improve ability to recover representations that are not just reduced in dimensions and sparse but also yield modules with relatively few genes and distinct biological features.

Like some algorithms for sparse NMF, SMAF optimization may proceed through alternating updates to X and B:

$$\text{initialize a random } X, B; \quad (1)$$

$$\text{update } X: \min_X \|X\|_1 \text{ such that } \|S - BX\|_2^2 < \lambda_X, \quad (2)$$

$$u_{i,j} \geq 0, \text{ and } \|x_i\|_2 = 1 \text{ for all } i \text{ and } j;$$

$$\text{update } B: \min_B \|B\|_1 \text{ such that } \|S - BX\|_2^2 < \lambda_B. \quad (3)$$

Steps 2 and 3 may be iterated until convergence, or until a desired sparsity level is reached. In some embodiments, the algorithm is initialized with the output of another matrix factorization method, such as sparse NMF. In some embodiments, a random initialization is used. In practice, the best results were found with a random initialization, although this may take more iterations to converge. The parameters $\lambda_X$ and $\lambda_B$ can be used to set a desired level of accuracy.

With each matrix factorization algorithm, preferably sparse NMF or SMAF as discussed above, the number of dictionary elements may be specified. For sparse NMF, a truncated decomposition is preferably used, keeping the vectors corresponding to the largest singular values. In some embodiments, a minimally sized dictionary with at least a 99% fit to the original data is used:

$$fit = 1 - \frac{\|S - BX\|_2^2}{\|S\|_2^2}$$

With SMAF, the desired fit according to constraints may be set in steps 2 and 3, as discussed above. In some embodiments, the SMAF dictionary size is set to be 4 times the size of the sparse NMF dictionary, without being larger than min(500,1.5·c).

In an aspect of the present invention, the sparse coding solving process comprises compressed sensing (CS) using training data to learn the system matrix S. For example, using training sets, $S_{training}$, a module dictionary weight may be calculated via matrix factorization:

$$S_{training} \approx BX$$

In some embodiments, the training set consist of a fraction, preferably at least 1% and at most 10%, of the samples in a given dataset, for example the training set may consist of about 5% of the samples in a given dataset. Preferably, the matrix factorization is performed using sparse NMF or SMAF, as described above.

In a following step, simulated compositional measurements may be performed on the testing samples (for example 95%):

$$M = DM(S_{testing} + \text{noise})$$

where the Design Matrix DM defines the random composition of n genes in each of m measurements (as before, with m<<g). For a given module dictionary ($X_{NMF}$, or $X_{SMAF}$), the module activities, that best fits the observations is preferably sought, so that:

$$S \approx DM\hat{B}X$$

The optimization may be performed while enforcing sparsity in $\hat{B}$, for example so that there are no more than 5 active modules per sample, for example so that there are no more than 10 active modules per sample, for example so that there are no more than 15 active modules per sample. The module activity coefficients in each testing sample may then be used to compute predicted gene expression values, $\hat{S}=\hat{B}X$.

In some embodiments, the problem is written as:

$$M \approx DB$$

and the spark of D is bound. For example, by choosing random Gaussian entries in the measurement matrix, the spark condition is satisfied with high probability.

In another aspect of the present invention, the sparse coding solving process comprises Blind Compressed Sensing (BCS) to learn the System Matrix S. This presents the advantage, which has been unheard of until this day, that the BCS approach is not limited by training data, particularly by the nature of the training data and model used for imputation. Indeed, training data necessarily introduces biases in learning a model. In some embodiments, the dictionary is learned from low-dimensional composite measurements. In some embodiments, the module activity levels and the gene abundances may be inferred, without ever observing high dimensional gene expression patterns.

Blind Compressed Sensing may be reduced to the problem of learning a good (i.e. sparsely activated) dictionary. Once the dictionary is fixed, the previously discussed matrix factorization methods may be used to recover the activity coefficients. To get the dictionary, a dictionary learning algorithm with high dimensional input is preferably used. Initially, the high dimensional input may consist of (possibly very poor) approximations to gene abundances, based on low dimensional observations and the composition of each measurement. A small number of composite measurements may generate a good first approximation of a sparsely activated module dictionary.

In an aspect of the present invention, the sparse coding solving process comprises sparse module activity factorization (SMAF) for the matrix factorization step and blind compressed sensing (BCS) to learn the System Matrix S. SMAF may be used to find the initial sample clusters and modules for BCS. Given the SMAF approximation, the dictionary may be updated using standard algorithms, then the module activity levels may be updated, and then all three steps may be iterated. For example, noisy composite measurements may be simulated across a randomly selected subset of genes.

Variable Gaussian measurements are preferably used; for each sample, m compositional observations may be generated using different measurement matrices, $DM_i$. The BCS-SMAF algorithm preferably proceeds as follows:
1. Get initial estimates of each sample as: $\hat{s}_i = DM_i^T (DM_i^T DM_i)^{-1} m_i$.
2. Based on current estimates, calculate SMAF($\hat{S}$): $\hat{S} \approx \hat{B}\hat{X}$.
3. Update estimate of the dictionary with a standard dictionary learning (DL) algorithm, using $\hat{X}$ for initialization: $\hat{X}=DL(\hat{S}, \hat{X})$.
4. Estimate module activities using Orthogonal Matching Pursuit: for each column $\hat{b}_i = OMP(m_i, DM_i\hat{X}, k)$.
5. Iterate steps 2-4.
6. Return the estimated signals: $\hat{S}=\hat{B}\hat{X}$.

The present invention enables both to design new ways to compress biological systems and to better understand the organization and regulation of gene expression and biological processes. First, it is possible to recover the high-dimensional representation of n abundance levels (e.g. 20,000, which correspond roughly to the number of genes in a mammalian genome) from a collection of many fewer measurements. Indeed, from the fewer measurements, it is possible to recover the active module(s) and thus the full expression profile for any sample/cell.

Further, the knowledge of a dictionary of universal programs (modules), and the activation of these programs across cell types could teach us a great deal about biological systems and gene regulation, e.g. it makes it possible to identify the key functional modules active in a biological sample and help infer the regulatory mechanisms that control them.

SVD, Singular Value Decomposition, is one of the best known algorithms for matrix factorization in gene expression analysis: Alter et al. Proc. Natl. Acad. Sci. U.S.A. 97:10101-106 (2000) and can be utilized herein. Each algorithm produces a module dictionary and module activity levels in each sample that are consistent with observed expression levels. Gene set enrichment analysis can be performed on the set of genes in each module, preferably by comparing genes in a module to genes in known databases. In some previous instances of evaluating gene expression analysis, SVD did not generally recover a sparse representation: samples were frequently represented by a linear combination of hundreds of modules, whereas sparse NMF could generally fit the data well (88.6% fit on average across all datasets) while also producing sparse solutions, as could SMAF (93% fit on average); while producing sparse dictionaries and sparse activity levels; average of 1.45 uniquely enriched gene set per module, without truncation. In an approach, using only the top genes for each module (genes found to be most active in the module) may be utilized to improve enrichments. In this way, the modules produced by SMAF were found to be readily interpretable. As an example, the SMAF algorithm constrained by assumptions of sparsity and modularity can explain most of the information in gene expression and that the discovered dictionary of gene modules appears to be biologically meaningful.

Analyzing a Cell Population at the Single Cell Level

The method according to the invention may comprise a step for single-cell molecular profiling. In some embodiments, the step may comprise processing said cell population in order to physically separate cells. In some embodiments, the step may comprise single-cell manipulation, e.g. using microfluidics-based techniques. In some embodiments, the step may comprise reverse emulsion droplet-based single-cell analysis or hydrogel droplet-based single-cell analysis.

The method of the invention may use microfluidics, e.g. to culture cells in specific combinations, control the spatiotemporal signals they receive, and/or trace and sample them as desired.

Molecular Profiling at the Single Cell Level

The method according to the invention may comprise a step for single-cell molecular profiling. This step may involve analyzing biomolecules quantitatively or semi-quantitatively. The biomolecules may include RNA, mRNA, pre-mRNA, proteins, chromatin or DNA. Said analysis may be performed genome-wide. Said analysis may be coupled (dual or sequential analysis of two or more types of biomolecules).

In some embodiments, the step may comprise single-cell genomic profiling, single-cell RNA profiling, single-cell DNA profiling, single-cell epigenomic profiling, single-cell protein profiling, or single-cell reporter gene expression profiling. Proteins that may be used to alter genomic and epigenomic state are described in Shmakov et al., 2015, Molecular Cell 60, 1-13 and Zetsche et al., 2015, Cell 163, 759-771.

In some embodiments, the step may comprise single-cell RNA abundance analysis, single-cell transcriptome analysis, single-cell exome analysis, single-cell transcription rate analysis, or single-cell RNA degradation rate analysis.

In some embodiments, the step may comprise single-cell DNA abundance analysis, single-cell DNA methylation profiling, single-cell chromatin profiling, single-cell chromatin accessibility profiling, single-cell histone modification profiling, or single-cell chromatin indexing.

In some embodiments, the step may comprise single-cell protein abundance analysis, single-cell post-translational protein modification analysis, or single-cell proteome analysis.

In some embodiments, the step may comprise single-cell mRNA reporter analysis, detection or quantification.

In some embodiments, the step may comprise single-cell dual molecular profiling, such as combination of two amongst single-cell RNA profiling, single-cell DNA profiling, single-cell protein profiling, and mRNA reporter analysis.

The method of the invention may include the step of determining single cell RNA levels. For single cell RNA-Seq (scRNA-Seq), one may use Drop-Seq (Macosko, E. Z., Basu, A., Satija, R., Nemesh, J., Goldman, M., Tirosh, I., Bialas, A. R., Kamitaki, N., Sanes, J. R., Weitz, D. A., Shalek, A. K., Regev, A. & McCarroll, S. A. Highly Parallel Genome-wide Expression Profiling of Individual Cells Using Nanoliter Droplets. Cell. 2015 May 21; 161(5):1202-14. doi: 10.1016/j.cell.2015.05.002. PMCID:4481139) and variants thereof. This technique relies on reverse-emulsion, early barcoding for analyzing $10^4$-$10^6$ cells/experiment at very low cost. Drop-Seq enables co-encapsulation of individual cells with uniquely barcoded mRNA capture beads in reverse emulsion droplets. After lysis and mRNA capture, the emulsion is broken and all beads/cells are processed (RT, library prep) together, deconvolving each cell's profile from bead barcodes. In some embodiments, droplets can compartmentalize hundreds of cells/sec, are stable over time and stable to heat, and can serve as micro-vessels to add reagents; after RT, barcoded beads are stable and can be sorted or subselected. The invention involves high-throughput single-cell RNA-seq and/or targeted nucleic acid profiling (for example, sequencing, quantitative reverse transcription polymerase chain reaction, and the like). In certain embodiments, the nucleic acids (e.g., RNAs) from different cells are tagged individually, allowing a single library to be created while retaining the cell identity of each read. In this regard, reference is further made to International patent application number PCT/US2015/049178, published as WO2016/040476 on Mar. 17, 2016; Klein et al., 2015, "Droplet Barcoding for Single-Cell Transcriptomics Applied to Embryonic Stem Cells" Cell 161, 1187-1201; International patent application number PCT/US2016/027734, published as WO2016/168584A1 on Oct. 20, 2016; Zheng, et al., 2016, "Haplotyping germline and cancer genomes with high-throughput linked-read sequencing" Nature Biotechnology 34, 303-311; Zheng, et al., 2017, "Massively parallel digital transcriptional profiling of single cells" Nat. Commun. 8, 14049 doi: 10.1038/ncomms14049; International patent publication number WO 2014/210353 A2; Zilionis, et al., 2017, "Single-cell barcoding and sequencing using droplet microfluidics" Nat Protoc. January; 12(1):44-73; Cao et al., 2017, "Comprehensive single cell transcriptional profiling of a multicellular organism by combinatorial indexing", bioRxiv preprint first posted online Feb. 2, 2017, doi: dx.doi.org/10.1101/104844; and Rosenberg et al., 2017, "Scaling single cell transcriptomics through split pool barcoding", bioRxiv preprint first posted online Feb. 2, 2017, doi: dx.doi.org/10.1101/105163, all the contents and disclosure of each of which are herein incorporated by reference in their entirety. The methods can be further used with approaches and methods disclosed and described in International Patent Application Number PCT/US2019/30194, entitled "High-Resolution Spatial Macromolecule Abundance Assessment" filed May 1, 2019, and with methods as described in U.S. Provisional Applications 62/797, 831 filed Jan. 28, 2019 and 62/811,528 filed Feb. 27, 2019, both entitled In-Situ Spatial Transcriptomics, and incorporated herein by reference in their entirety.

Sampling noise from shallow read depth is substantially lower than the technical variability between cells (Shalek, A. K., Satija, R., Shuga, J., Trombetta, J. J., Gennert, D., Lu, D., Chen, P., Gertner, R. S., Gaublomme, J. T., Yosef, N., Schwartz, S., Fowler, B., Weaver, S., Wang, J., Wang, X., Ding, R., Raychowdhury, R., Friedman, N., Hacohen, N., Park, H., May, A. P. & Regev, A. Single-cell RNA-seq reveals dynamic paracrine control of cellular variation. Nature. 510, 363-369, doi:10.1038/nature13437 (2014). PMCID:4193940.), so one may sufficiently estimate expression with ~100,000 reads per cell for many applications (especially with a 5' or 3'-end protocol, Satija, R., Farrell, J. A., Gennert, D., Schier, A. F. & Regev, A. Spatial reconstruction of single-cell gene expression data. Nature Biotechnology. 33, 495-502, doi:10.1038/nbt.3192 (2015)).

In one embodiment, hybrid measurements or alternative readouts are measured. The alternative readouts may either be stand alone, or hybrid measurements. One alternative readout may be epigenetic measurements. Not being bound by a theory, when biomolecules with functional groups are formaldehyde fixed and bound to the polymer mesh, and membrane and nuclear lipids are cleared, chromosomal DNA is preserved and is accessible for further interrogation. Not being bound by a theory, the new layers of information aid in understanding of the regulatory mechanisms underpinning cellular behavior. Histone modifications have been measured at specific gene loci at the single cell level (Gomez et al., 2013). Gomez et al. uses ISH-PLA (in situ hybridization (ISH), proximity ligation assay (PLA))., using a biotin modified ISH probe, by binding with streptavidin and an oligo bound anti-streptavidin antibody. As antibodies against multiple histone modifications are readily available, the PLA scheme is applicable to the present invention. Not being bound by a theory, a histone code based on the combination of a plurality of histone modifications determines gene expression at a given locus. Many histone modifications at many genetic loci can be determined simultaneously by replacing the biotin-streptavidin construct by an ISH probe conjugated to a linker (peptide, DNA or nanoparticles, . . . ), followed by another DNA barcode reporting on the genetic locus, and including a binding sequence to the oligo conjugated to the histone modification antibody.

In one embodiment, chromatin accessibility is determined using a single cell ATAC-seq assay. ATAC-seq offers genome-wide chromatin accessibility of regulatory elements, transcription factor binding and nucleosome positioning.

In one embodiment, DNA methylation analysis is determined. Cytosine methylation analysis has been analyzed at the single cell level (Kantlehner et al., 2011), as has adenine methylation (Lorthongpanich et al., 2013).

In one embodiment, the spatial organization of chromosomes is determined. The spatial organization of chromosomes has been found to have fundamental effects on gene expression and cellular function. Single cell measurements (Hi-C) have revealed extensive cell-to-cell heterogeneity in chromosome structure (Nagano et al., 2013). This method can be incorporated into the present invention.

In one embodiment, protein-protein interactions are measured. In addition to assessing presence and abundance of individual proteins, assays such as Proximity Extension Assay (PEA) allow for assaying the proximity of two proteins. In particular, the present invention allows for probing protein-protein interactions by designing pairs of antibodies for the interacting proteins of interest, such that the oligos conjugated to these antibodies have a binding region, which only bind when the two proteins are in near proximity, and therefore only PCR amplify in this case.

In one embodiment, protein-DNA interaction measurements are determined. Similar to the modified ISH-PLA described herein, instead of probing histone modifications, one could probe protein (transcription factor) proximity to many specific genetic loci, in a multiplex fashion.

In one embodiment, fluorescent in situ hybridization methods are used in the present invention. The present invention allows a combined approach where cells can be fluorescently labeled by methods known in the art, and cells of interest can be selected for downstream profiling of cellular constituents. In addition, the assays of the present invention can be combined with in situ hybridization methods such as RNA and DNA FISH.

In another embodiment, the gelled and cleared cells offer a platform in which any biological agent that is able to be detected by a high affinity and specific counterpart or ligand that can directly or indirectly be conjugated to a DNA molecule could be detected and quantified using the methods of the present invention.

Releasing the oligos to be sequenced from their antibody can take a multitude of forms; i.e. in one embodiment, oligos could be released from their antibodies by digesting all proteins (for instance proteinase K). Alternatively, photocleavable linkers could be used, or restriction sites could be included in the oligo sequence to allow for enzymatic restriction and release. In another embodiment, the oligo can stay bound to the antibody, and in situ amplified (i.e. either by PCR, rolling circle amplification or T7 polymerase amplification) and the products of this reaction could be captured and sequenced.

Similarly, capturing the released oligos could take a number of forms: in a drop based approach, beads can be loaded with capture oligos as described herein. Microwells could either be loaded with beads, or their surface could be functionalized with capture oligos from which further amplification could take place. Alternatively, in the scenario where drops are sorted into multiwell plates, or microfluidic reaction chambers such as the Fluidigm C1 system, oligos can be amplified linearly or exponentially, and cellular barcodes and library adapters can be added on during these amplification steps.

Many different assays have been developed for oligo-barcode based detection of proteins (Janssen et al., 2013) and may be used in the present invention.

In one embodiment, cells are fixed and monomer infused before capturing them in a droplet. Alternatively, cells or aggregations of constituents are co-flowed with a lysis/monomer solution into a larger diameter drop. In this embodiment, biomolecules from a single cell or isolated aggregation of constituents are spread over a larger volume, which with similar polymer density could increase accessibility for staining.

The present invention also provides for cell handling before hydrogel polymerization. In one embodiment, cells are fixed and infused with polymer monomers in bulk. Cells may then be segregated and polymerization initiated. Segregation can be by any means described herein. In preferred embodiments, segregation is performed by making single cell drops.

In another embodiment, biochemical, thermal, or optical treatment on chip of individual cells in reverse emulsion droplets is performed. In this embodiment, polymer monomers may be spiked in microfluidically and optionally fixation reagents. Polymerization of the monomers may then be performed. This allows biochemical, thermal, or optical treatments at the single-cell level. Examples include, but are not limited to, lysis, DNA/RNA fragmentation/tagmentation, dosing with drugs, enzymatic reactions, or any perturbation of the sample before fixation and/or anchoring biomolecules to the polymer mesh upon polymerization.

In one embodiment, the oligonucleotide label may comprise iso-deoxyguanosine (iso-dG) and 5-methyl iso-dC (iso-dC). Iso-deoxyguanosine forms a Watson-Crick base pair with 5-methyl iso-dC, but has a different type of hydrogen bonding pattern than those observed for the natural base pairs A:T and C:G. Substitution of a iso-dG:5-Me-iso-dC base pair for a C:G pair increases the Tm of the resulting duplex by ~2 deg C. per base pair substitution (Switzer, C., et al., Enzymatic incorporation of a new base pair into DNA and RNA. J. Am Chem. Soc. (1989), 111: 8322-8323; and Horn, T., et al., Hybridization properties of the 5-methyl-isocytidine/isoguanosine base pair in synthetic oligodeoxynucleotides. Tetrahedron Lett. (1995), 36: 2033-2036). Furthermore, since iso-dG does not pair with dC, iso-dG:5-Me-iso-dC can function as a stable unnatural base pair that can be used to expand the genetic code. The combination of iso-dGs high selectivity for 5-Me-iso-dC, and the resulting base pair's high thermodynamic stability, makes this modified base particular attractive in embodiments of the present invention.

In one embodiment, iso-dG:5-Me-iso-dC base pairing is used for molecular recognition. The 5-Me-iso-dC:iso-dG base pair may be incorporated into hybridization assays to enhance probe-target specificity and reduce spurious hybridization to non-target sequences. For example, Collins and co-workers significantly improved the sensitivity of a branched DNA quantitative hybridization assay for detecting the HIV POL sequence by incorporating ~30% 5-Me-iso-dC and iso-dG into the pre-amplifier, branched DNA (bDNA) amplifier and alkaline phosphate probe sequences used in the assay (Collins, M. L, et al. A branched DNA signal amplification assay for quantification of nucleic acid targets below 100 molecules/ml. Nucleic Acids Res. (1997), 25: 2979-2984). Use of this strategy resulted in a significant reduction in non-specific hybridization of the above three sequence types to non-target nucleic acid sequences, and thus less amplification of background. The limits of detection of the assay were improved 10-fold, from <500 HIV molecules/mL to <50 molecules/mL. In preferred embodiments, the present invention utilizes the 5-Me-iso-dC:iso-dG base pair to ensure the correct sequences base pair during hybridization of ligation handle primers and during hybridization of two oligonucleotide labels in proximity assays.

In another embodiment, iso-dG:5-Me-iso-dC base pairing is used for qPCR and artificially expanded genetic systems. A number of research groups have been working on optimizing PCR amplification on templates containing 5-Me-iso-dC. Such optimization is necessary to enable the full development of artificially expanded genetic systems utilizing an expanded genetic code, thereby allowing for the site-specific incorporation of novel functional components (such as unnatural amino acids) into proteins. In 2004, Johnson and co-workers observed that, by using the Klenow fragment of Taq polymerase (KF-Taq) in PCR, the fidelity of the 5-Me-iso-dC:iso-dG base pair was about 96% per amplification cycle (Johnson, S. C., et al., A third base pair for the polymerase chain reaction: inserting isoC and isoG. Nucleic Acids Resl. (2004), 32: 1937-1941). The limit in fidelity is chiefly due to the ability of iso-dG's 1,2 tautomer to mis-pair with dT. More recently, Sismour and Benner solved this problem by using 2-thio-dT (dT*) in place of dT. dT*pairs with dA, but not with iso-dG (Sismour, A. M.; Benner, S. A. The use of thymidine analogs to improve the replication of an extra DNA base pair: a synthetic biological system. Nucleic Acids Resl. (2005), 33: 5640-5646). Using this artificial base pair system (5-Me-iso-dC:iso-dG, dA:dT*, dC:dG) with KF-Taq, the fidelity in PCR was increased to about 98% per amplification cycle.

The present invention also provides methods applicable to the study of bulk cells and is not limited to single cells. Moreover, the assays described herein are also amenable to regularly fixed and permeabilized cells (i.e. not using polymerization). The proximity assays described herein may be performed on cells without generating discrete polymer matrices. Additionally, detection of cellular constituents utilizing labeling ligands and a sequencing readout may be used to detect low abundant cellular constituents. Not being bound by a theory, the oligonucleotide label may be amplified and increase the signal as compared to antibody readouts known in the art. Moreover, determination of proteins in relation to open chromatin need not be performed in a polymer matrix.

The present invention provides advantages over prior assays for detecting proteins and post translation modifications (PTM) in single cells or isolated aggregations of cellular constituents. Standard flow cytometry can be used to detect a few proteins/PTMs in greater than 106 single cells; and CyTOF (heavy metal labeling with multiplex barcoding) can be used to detect ~30-50 proteins/PTMs in 105-106 single cells. The present invention provides highly multiplexed, DNA sequencing-based readouts of protein/PTM levels of greater than 100's of proteins/PTMs in greater than $10^6$ cells.

Undersampling—a Sampling Based Framework for Genetic Interactions

Random sampling may comprise matrix completion, tensor completion, compressed sensing, or kernel learning. Approaches utilized herein rely on a random sampling assumption, e.g. that the combinatorial space is sparse and/or of low rank. This assumption is generic and advantageously does not rely on the pre-determination of a (known) set of genetic interactions. This assumption constrains the range or complexity of models, and thus can be used to restrict sampling size (undersampling).

Random matrix theory and compressive sensing may be used to re-formulate this as a random sampling problem, developing a new framework from experimental design to model inference, testing and refinement.

The advantage of compressive sensing is that it can obtain highly-resolved signals from a smaller number of measurements. RNA profiling, while providing a phenotype of cellular responses and tissue states, can be costly to generate at the massive scale required for spatial imaging. Latent, sparse representations of gene expression data enables decompression of a small number of random composite measurements and recover high-dimensional gene expression levels that were not measured (unobserved).

Compressed Sensing

Applicants work with a basis that spans all higher order interactions. In the instant case, instead of real genes, quantifying an abundance of composite genes is performed. A composite gene represents a linear combination of abundances:

$$cg_1 = \sum_{i=1}^{20000} w_{1,i} \quad x_i \leftarrow \text{abundance of gene}_i. \quad \text{Formula I}$$
$$\uparrow \qquad\qquad \uparrow$$
$$\text{composite gene}_1 \qquad \text{weight of gene}_i \text{ in } cg_1$$

The number of composite genes (m) is much smaller than the number of genes (g). In this manner, latent structure in high-dimensional data can be used to understand underlying biology in a scalable method. In particular embodiments, a gene module can be identified that includes two or more genes in a target. Gene modules can be identified utilizing the composite gene Formula I. An abundance of composite genes may be calculated, with gene modules identified based on training data collected from a cell or tissue from a region of interest. Once composite measurements are made from samples, random composite weights can be calculated. Finally, modules can be identified for the genes, which are utilized for imaging the region of interest in situ to create a composite image. The gene module activities can be fitted spatially to allow final recovery of images for individual genes contained in the gene modules of the composite image.

It is anticipated that probe libraries may be constructed and provided and present methods applied to provide cost-effective gene-expression profiling. Accordingly, a product comprising completed probe libraries, or a kit for making the libraries according to principles of the present invention are possible. For some applications it may make sense to focus on a subset of genes, in which case the kit would be particularly appropriate and would include instructions for implementing the steps to obtain in situ imaging of tissues and cells.

In addition, random probes and sparse coding could be applied as a service. That is, a customer may provide a sample or sample pools to an entity for constructing a probe library according to customer objectives and sample, applying the steps of the methods according to principles of the present invention and providing as its result a tissue or cell imaging of gene-expression profile or the like. This could be particularly useful for applications that require the analysis of tens to hundreds of thousands of transcriptional profiles, and utilizing methods according to principles of the present invention reduce enhanced imaging techniques multi-fold.

Methods of Screening Genes and Proteins Responding to Stimuli

The present disclosure further includes methods for screening genes and proteins in response to stimuli. In general, the methods include determining expression profiles of one or more genes in nuclei from cells treated with a stimulus. Among these cells, a first group of cells are, while a second group of cells are not, activated by the stimulus. Expression profiles of the genes in nuclei from the two groups of cells are compared to determine the candidate genes in response to the stimulus. In some examples, the methods include isolating nuclei from a first and a second group of cells exposed to the stimulus, wherein the first group of cells are activated by the stimulus and the second group of cells are not activated by stimulus; sequencing one or more genes or portions thereof in the isolated nuclei; and comparing expression profiles of genes in the nuclei from the first and the second groups of cells, thereby identifying candidate genes that respond to the stimulus based on the comparison.

Treating Cells with Stimuli

The methods may include treating cells (e.g., by exposing the cells to) one or more stimuli. The cells may be of a tissue or organ. In some cases, the treatment may be ex vivo. For example, the tissue or organ may be separated from a subject when treated with the stimuli. In certain cases, the treatment may be in vivo. For example, a subject may be treated and the cells, then the tissue, or organ may be harvest from the subject for further analysis.

The treatment may be performed by exposing the cells to the one or more stimuli. For example, the cells may be exposed to air or solution containing the stimuli. In cases where the cells are in a subject, the subject may be exposed to air, water, and/or food containing the stimuli.

The cells herein may be from a tissue or organ of interest. As used herein, "organ" means a collection of tissues joined into structural unit to serve a common function. Examples of organs include skin, sweat glands, sebaceous glands, mammary glands, bone, brain, hypothalamus, pituitary gland, pineal body, heart, blood vessels, larynx, trachea, bronchus, lung, lymphatic vessel, salivary glands, mucous glands, esophagus, stomach, gallbladder, liver, pancreas, small intestine, large intestine, colon, urethra, kidney, adrenal gland, conduit, ureter, bladder, fallopian tube, uterus, ovaries, testes, prostate, thyroid, parathyroid, meibomian gland, parotid gland, tonsil, adenoid, thymus, and spleen. In one example, the organ is liver. In certain examples, the organ is liver, spleen, intestine, colon, bone marrow, an immune tissue or organ, or a tissue or organ of the gastrointestinal track. In certain cases, the organ or tissue is an organ or tissue of the immune system, e.g., lymphoid organs such as bone marrow, thymus, lymph nodes, spleen, tonsils, other specialized tissues in the mucous membranes of the body, e.g., the bowel. In certain cases, the organ or tissue is a part of the gastrointestinal track, e.g., pharynx, esophagus, stomach, duodenum, small intestine, large intestine. As used herein, "tissue" means an aggregate of cells. Examples of tissues include, but are not limited to, connective tissue (e.g., areolar connective tissue, dense connective tissue, elastic tissue, reticular connective tissue, and adipose tissue), muscle tissue (e.g., skeletal muscle, smooth muscle and cardiac muscle), genitourinary tissue, gastrointestinal tissue, pulmonary tissue, bone tissue, nervous tissue, and epithelial tissue (e.g., simple epithelium and stratified epithelium), endoderm-derived tissue, mesoderm-derived tissue, and ectoderm-derived tissue.

In some cases, the cells herein may be sensory cells, e.g., cells from a sensory organ such as eyes, ears, nose, skin, and tongue. Examples of sensory cells include taste cells, olfactory epithelial cell, rod and cone photoreceptors, Meisner corpuscle, Ruffini corpuscle, Merkel receptor, Pacinian corpuscle, muscle spindle cell, cochleovestibular hair cells and joint mechanoreceptor cells. A more complete definition of sensory organ cells and their progenitors can be found in, Wheater, et al., Functional Histology (1987), Churchill Livingstone, New York, N.Y.; Mahanthappa and Schwarting, Neuron (1993) 10:293-305; Forge, Li, Corwin and Nevill, Science (1993) 259:1616-1622; Tsue, Watling, Weisleder, Coltrera and Rubel, J. Neurosci (1994) 14:140-152, which are incorporated by reference in their entireties.

In certain examples, the sensory cells are those in olfactory epithelium. In some examples, the sensory cells may be neuron cells. In some examples, the sensory cells may be neurons in olfactory epithelium.

The stimuli may be chemicals, lights, mechanical forces, and change of temperature (e.g., heating or cooling).

Isolating Nuclei

The methods may include isolating nuclei from the cells. The nuclei may be isolated by lysing the cells. After lysis, molecules, organelles and/or nuclei may be released from the cells for further analysis. In some embodiments, cells may be lysed under conditions that preserve the molecules, organelles, and/or nuclei in other lysis may be performed. In some embodiments, the cell lysis is performed to release nuclei from cells. In certain embodiments, the cell lysis is performed to release molecules, e.g., RNA or DNA from cells, organelles, and/or nuclei. In certain embodiments, the cells lysis is performed to separate RNA molecules from DNA molecules.

Cells may be lysed using a lysis agent. Examples of lysis agents include a detergent, a salt, and a combination thereof. Examples of salts include NaCl, KCl, ammonium sulfate [$(NH_4)_2SO_4$], and others. Examples of detergents include Triton X-100, sodium dodecyl sulfate (SDS), CHAPS (3-[(3-cholamidopropyl)dimethylammonio]-1-propanesulfonate), ethyl trimethyl ammonium bromide, nonyl phenoxypolyethoxylethanol (NP-40), digitonin and any combination thereof. In some cases, the detergent may be SDS.

Concentrations of detergents may depend on the particular application, and may be specific to the reaction in some cases. For example, the concentration of detergent (e.g., SDS) used herein may be from 0.005% to 1%, from 0.01% to 0.8%, from 0.01% to 0.6%, from 0.01% to 0.4%, from 0.01% to 0.2%, from 0.01% to 0.1%, from 0.005% to 0.05%, from 0.01% to 0.03%, from 0.015% to 0.025%, from 0.018% to 0.022%, from 0.015% to 0.017%, from 0.016% to 0.018%, from 0.017% to 0.019%, from 0.018% to 0.02%, from 0.019% to 0.021%, from 0.02% to 0.022%, or from 0.021% to 0.023%. In some cases, the concentration of the detergent may be about 0.01%, about 0.015%, about 0.02%, about 0.025%, or about 0.03%. For example, the concentration of the detergent may be about 0.02%.

For lysis, the cells may be incubated with the detergent for from 0.5 hours to 20 hours, e.g., from 0.5 hour to 2 hours, from 1 hour to 3 hours, from 2 hours to 4 hours, from 3 hours to 5 hours, from 4 hours to 6 hours, from 5 hours to 7 hours, from 6 hours to 8 hours, from 7 hours to 9 hours, from 8 hours to 10 hours, from 9 hours to 11 hours, from 10 hours to 12 hours, from 11 hours to 13 hours, from 12 hours to 14 hours, from 13 hours to 15 hours, from 14 hours to 16 hours, from 15 hours to 17 hours, or from 16 hours to 18 hours. In some cases, the cells may be incubated with the detergent for about 1, about 2, about 3, about 4, about 5, about 6, about 7, about 8, about 9, about 10, about 11, about 12, about 13, about 14, about 15, about 16, about 17, or about 18 hours.

For lysis, the cells may be incubated with the detergent at a temperature ranging from 50° C. to 80° C., from 50° C. to 70° C., from 50° C. to 60° C., from 52° C. to 58° C., or from 54° C. to 56° C. In some examples, the temperature may be about 50° C., about 51° C., about 52° C., about 53° C., about 54° C., about 55° C., about 56° C., about 57° C., about 58° C., about 59° C., or about 60° C. For example, the temperature may be from 54° C. to 56° C. In one example, the temperature may be about 55° C.

In some embodiments, the cells are lysed in the presence of one or more inhibitors, which preserve molecules from the cells from degradation by enzymes. Such inhibitors may be protease inhibitors and nuclease inhibitors, e.g., RNase inhibitors and DNase inhibitors.

In certain cases, the cells are lysed in the presence of one or more RNase inhibitors. The RNase inhibitors may be compatible with enzymes used for further analysis. For example, the RNase inhibitors do not alter (e.g., reduce) the activity of other enzymes. In some cases, the RNase may be compatible with insertional enzymes such as transposases (e.g., Tn5).

In some examples, the RNase inhibitors may be RNAse inhibitor (Cat No. Y9240L, Enzymatics) or SUPERase® In™ RNase Inhibitor (Cat No. AM2694, Invitrogen). Other RNase inhibitors, such as RNaseOUT (Thermo Fisher) and Recombinant RNase Inhibitor (Takara), may also be used.

Cell lysis may also be performed in the presence of one or more protease inhibitors. Examples of protease inhibitors include Protease Inhibitor Cocktail (P8340, Sigma), complete ULTRA and PhosSTOP (Roche Applied Science), Protease Inhibitor Set (EMD Chemicals); and Phosphatase Inhibitor Cocktail Set I-IV (EMD Chemicals).

The methods may further include fixing the nuclei. Fixation may be carried out to preserve the intactness of the cells, organelles, and/or nuclei in the cells. In some cases, once fixed, the cells, organelles, and/or nuclei in the cells remain intact during reactions and handling. Fixation may involve the use of cross-linking agents, such as formaldehyde, paraformaldehyde, alcohol (e.g., methanol), and may involve embedding cells or tissue in a paraffin wax or polyacrylamide support matrix.

Nuclei Separation and Sorting

The methods may further include separating the nuclei from cells activated by the stimuli and the nuclei from cells not activated by the stimuli. The separation may be performed using a sorting technology. Such separation may be based on one or more markers of the activated cells.

In some embodiments, markers used for separating the nuclei include immediate early genes or product encoded thereby. Immediate early genes (IEGs) include genes activated transiently and rapidly in response to a wide variety of cellular stimuli. They may represent a standing response mechanism that is activated at the transcription level in the first round of response to stimuli, before any new proteins are synthesized. Thus, IEGs may be distinct from "late response" genes, which can only be activated later, following the synthesis of early response gene products. In some examples, the term can describe viral regulatory proteins that are synthesized following viral infection of a host cell, or cellular proteins that are made immediately following stimulation of a resting cell by extracellular signals.

In some cases, the marker may be nuclei-specific. For example, the marker may be nuclei-specific immediate early genes. In a particular example, the marker is Snap25. Such nuclei-specific markers may be identified using sequencing, e.g., 10× sequencing.

In certain embodiments, examples of sorting technologies used for separating nuclei include flow cytometry, fluorescence activated cell sorting, mass cytometry, fluorescence microscopy, affinity separation, magnetic cell separation, microfluidic separation, and combinations thereof.

Flow cytometry encompasses methods by which individual cells of a cell population are analyzed by their optical properties (e.g., light absorbance, light scattering and fluorescence properties, etc.) as they pass in a narrow stream in single file through a laser beam. Flow cytometry methods include fluorescence activated cell sorting (FACS) methods by which a population of cells having particular optical properties are separated from other cells.

Elemental mass spectrometry-based flow cytometry, or mass cytometry, offers an approach to analyze cells by replacing fluorochrome-labelled binding reagents with mass tagged binding reagents, i.e., tagged with an element or isotope having a defined mass. In these methods, labeled particles are introduced into a mass cytometer, where they are individually atomized and ionized. The individual particles are then subjected to elemental analysis, which identifies and measures the abundance of the mass tags used. The identities and the amounts of the isotopic elements associated with each particle are then stored and analyzed. Due to the resolution of elemental analysis and the number of elemental isotopes that can be used, it is possible to simultaneously measure up to 100 or more parameters on a single particle.

Fluorescence microscopy broadly encompasses methods by which individual cells of a cell population are microscopically analyzed by their fluorescence properties. Fluorescence microscopy approaches may be manual or preferably automated.

Affinity separation, also referred to as affinity chromatography, broadly encompasses techniques involving specific interactions of cells present in a mobile phase, such as a suitable liquid phase (e.g., cell population in an aqueous suspension) with, and thereby adsorption of the cells to, a stationary phase, such as a suitable solid phase; followed by separation of the stationary phase from the remainder of the mobile phase; and recovery (e.g., elution) of the adsorbed cells from the stationary phase. Affinity separation may be columnar, or alternatively, may entail batch treatment, wherein the stationary phase is collected/separated from the liquid phases by suitable techniques, such as centrifugation or application of magnetic field (e.g., where the stationary phase comprises magnetic substrate, such as magnetic particles or beads). Accordingly, magnetic cell separation is also envisaged herein.

Microfluidic systems allow for accurate and high-throughput cell detection, quantification and/or sorting, exploiting a variety of physical principles. Cell sorting on microchips provides numerous advantages by reducing the size of necessary equipment, eliminating potentially biohazardous aerosols, and simplifying the complex protocols commonly associated with cell sorting. The term "microfluidic system" as used throughout this specification broadly refers to systems having one or more fluid microchannels. Microchannels denote fluid channels having cross-sectional dimensions the largest of which are typically less than 1 mm, preferably less than 500 m, more preferably less than 400 m, more preferably less than 300 m, more preferably less than 200 m, e.g., 100 µm or smaller. Such microfluidic systems can be used for manipulating fluid and/or objects such as droplets, bubbles, capsules, particles, cells and the like. Microfluidic systems may allow, for example, for fluorescent label-based (e.g., employing fluorophore-conjugated binding agent(s), such as fluorophore-conjugated antibody(ies)), bead-based (e.g., bead-conjugated binding agent(s), such as bead-conjugated antibody(ies)), or label-free cell sorting (reviewed in Shields et al., Lab Chip. 2015, vol. 15: 1230-1249).

The nuclei may be separated using any of a variety of commercially available cell sorters, including, but not limited to, MoFlo sorter (DakoCytomation, Fort Collins, Colo.), FACSAria™, FACSArray™, FACSVantage™, BD™ LSR II, and FACSCalibur™ (BD Biosciences, San Jose, Calif).

Sequencing

The methods may further include determining expression profiles of one or more genes in the nuclei. The expression profiles may be determined using sequencing. For examples, mRNA or molecules derived therefrom (e.g., cDNA molecules) may be sequenced to determine the expression profiles. The sequencing may be performed using any methods discussed herein.

In some cases, the sequencing may be next generation sequencing. The terms "next-generation sequencing" or "high-throughput sequencing" refer to the so-called parallelized sequencing-by-synthesis or sequencing-by-ligation platforms currently employed by Illumina, Life Technologies, and Roche, etc. Next-generation sequencing methods may also include nanopore sequencing methods or electronic-detection based methods such as Ion Torrent technology commercialized by Life Technologies or single-molecule fluorescence-based method commercialized by Pacific Biosciences. Any method of sequencing known in the art can be used before and after isolation. In certain embodiments, a sequencing library is generated and sequenced.

At least a part of the processed nucleic acids and/or barcodes attached thereto may be sequenced to produce a plurality of sequence reads. The fragments may be sequenced using any convenient method. For example, the fragments may be sequenced using Illumina's reversible terminator method, Roche's pyrosequencing method (454), Life Technologies' sequencing by ligation (the SOLiD platform) or Life Technologies' Ion Torrent platform. Examples of such methods are described in the following references: Margulies et al. (Nature 2005 437: 376-80); Ronaghi et al. (Analytical Biochemistry 1996 242: 84-9); Shendure et al. (Science 2005 309: 1728-32); Imelfort et al. (Brief Bioinform. 2009 10:609-18); Fox et al. (Methods Mol Biol. 2009; 553:79-108); Appleby et al. (Methods Mol Biol. 2009; 513:19-39) and Morozova et al. (Genomics. 2008 92:255-64), which are incorporated by reference for the general descriptions of the methods and the particular steps of the methods, including all starting products, methods for library preparation, reagents, and final products for each of the steps. As would be apparent, forward and reverse sequencing primer sites that are compatible with a selected next generation sequencing platform can be added to the ends of the fragments during the amplification step. In certain embodiments, the fragments may be amplified using PCR primers that hybridize to the tags that have been added to the fragments, where the primer used for PCR have 5' tails that are compatible with a particular sequencing platform. In certain cases, the primers used may contain a molecular barcode (an "index") so that different pools can be pooled together before sequencing, and the sequence reads can be traced to a particular sample using the barcode sequence.

In some cases, the sequencing may be performed at certain "depth." The terms "depth" or "coverage" as used herein refers to the number of times a nucleotide is read during the sequencing process. In regard to single cell RNA sequencing, "depth" or "coverage" as used herein refers to the number of mapped reads per cell. Depth in regard to genome sequencing may be calculated from the length of the original genome (G), the number of reads (N), and the average read length (L) as N×L/G. For example, a hypothetical genome with 2,000 base pairs reconstructed from 8 reads with an average length of 500 nucleotides will have 2× redundancy.

In some cases, the sequencing herein may be low-pass sequencing. The terms "low-pass sequencing" or "shallow sequencing" as used herein refers to a wide range of depths greater than or equal to 0.1× up to 1×. Shallow sequencing may also refer to about 5,000 reads per cell (e.g., 1,000 to 10,000 reads per cell).

In some cases, the sequencing herein may deep sequencing or ultra-deep sequencing. The term "deep sequencing" as used herein indicates that the total number of reads is many times larger than the length of the sequence under study. The term "deep" as used herein refers to a wide range of depths greater than 1× up to 100×. Deep sequencing may also refer to 100× coverage as compared to shallow sequencing (e.g., 100,000 to 1,000,000 reads per cell). The term "ultra-deep" as used herein refers to higher coverage (>100-fold), which allows for detection of sequence variants in mixed populations.

Genes and Proteins Identified from the Screening

The genes and proteins may be identified and analyzed using the methods described herein. In general, the activities, concentrations, epigenetic features, chromatin architectures, and/or other features of the genes and proteins may change in response to one or more stimuli.

In some embodiments, such genes or proteins may be those of sensory receptors. The sensory receptors may be chemoreceptors (including those responding to chemicals and other molecules, e.g., those for sensing tastes, smell, blood pH, etc.), photoreceptors (including those responding to light energy, e.g., those for vision), mechanoreceptors (including those stimulated by mechanical forces, e.g., those for hearing, sensing gravity, motion, and body position), thermoreceptors (including those stimulated by changes in temperatures, e.g., those located in the hypothalamus and skin), pressure receptors, and pain receptors.

In some examples, the genes and proteins include those of olfactory receptors. Olfactory receptors include the receptors expressed in the cell membranes of olfactory sensory neurons responsible for the detection of chemical cues. Activated olfactory receptors are the initial player in a signal transduction cascade which ultimately produces a nerve impulse which is transmitted to the brain. Most of these receptors are members of the GPCR superfamily. The olfactory receptors form a multigene family consisting of about 400 potentially functional genes in humans and about 1,250 genes in mice. Olfactory receptors are generally categorized, in mammals, into several receptor families including odorant receptors (ORs), vomeronasal receptors (V1Rs and V2Rs), trace amine-associated receptors (TAARs), formyl peptide receptors (FPRs), and the membrane guanyl cyclase GC-D. The genes and proteins herein may be those of odorant receptor. The term "odorant receptor" refers to odorant receptors generated from olfactory sensory neurons. Examples of odorant receptors include, but are not limited to, OR-S6, 01fr62, S6/79, S18, S46, S50, MOR23-1, MOR31-4, MOR31-6, MOR32-5 and MOR32-11. Additional examples of odorant or olfactory receptors include OR10A1, OR10A3, OR10A4, OR10A5, OR10A6, OR10A7, OR10C1, OR10C2, OR10D4, OR10G2, OR10G3, OR10G4, OR10G7, OR10G8, OR10G9, OR10H1, OR10H2, OR10H3, OR10H4, OR10H5, OR10J1, OR10J3, OR10J5, OR10J6, OR10K1, OR10K2, OR10Q1, OR10R2, OR10S1, OR10T2, OR10V1, OR10Z1, OR11A1, OR11G2, OR11H1, OR11H4, OR11H6, OR11H7P, OR11L1, OR12D3, OR13A1, OR13C2, OR13C3, OR13C4, OR13C5, OR13C7, OR13C8, OR13C9, OR13D1, OR13E2, OR13F1, OR13G1, OR13H1, OR13J1, OR14A16, OR14A2, OR14C36, OR14J1, OR1A1, OR1A2, OR1A2, OR1B1, OR1C1, OR1D2, OR1D4, OR1D5, OR1E1, OR1E2, OR1E2, OR1E5, OR1E5, OR1E6, OR1E7, OR1F1, OR1F10, OR1F11, OR1F12, OR1F2, OR1G1, OR1I1, OR1J1, OR1J2, OR1J2, OR1J4, OR1J5, OR1K1, OR1L1, OR1L3, OR1L4, OR1L6, OR1L8, OR1M1, OR1M1, OR1N1, OR1N2, OR1N3, OR1Q1, OR1S1, OR1S2, OR2A1, OR2A10, OR2A19, OR2A20, OR2A21, OR2A4, OR2A42, OR2A5, OR2A6, OR2A7, OR2AE1, OR2AJ1, OR2AK2, OR2B1, OR2B2, OR2B3, OR2B6, OR2B9, OR2C1, OR2D1, OR2D2, OR2D3, OR2F1, OR2F2, OR2F3, OR2G2, OR2G3, OR2H1, OR2H2, OR2H3, OR2J2, OR2J3, OR2K1, OR2K2, OR2L1, OR2L2, OR2L3, OR2L5, OR2L8, OR2M1, OR2M2, OR2M4, OR2S2, OR2T1, OR2T3, OR2T4, OR2T5, OR2T6, OR2T7, OR2T8, OR2V1, OR2V2, OR2V3, OR2W1, OR2W3, OR2Y1, OR2Z1, OR3A1, OR3A2, OR3A3, OR3A4, OR4A15, OR4A16, OR4A4, OR4A5, OR4B1, OR4C12, OR4C13, OR4C15, OR4C16, OR4C3, OR4C6, OR4D1, OR4D2, OR4D5, OR4D6, OR4D9, OR4E2, OR4F10, OR4F15, OR4F16, OR4F16, OR4F17, OR4F18, OR4F19, OR4F3, OR4F6, OR4K1, OR4K13, OR4K14, OR4K15, OR4K17, OR4K2, OR4K3, OR4K5, OR4L1, OR4M1, OR4M2, OR4N2, OR4N4, OR4N5, OR4P4, OR4Q3, OR4S1, OR4X1, OR4X2, OR51A2, OR51A4, OR51A7, OR51B2, OR51B4, OR51D1, OR51E1, OR51E2, OR51F2, OR51G1, OR51G2, OR51H1, OR51I1, OR51I2, OR51L1, OR51M1, OR51Q1, OR51S1, OR51T1, OR52A1, OR52A2, OR52B2, OR52B4, OR52B4, OR52B4, OR52B6, OR52D1, OR52E2, OR52E4, OR52E5, OR52E6, OR52E8, OR52H1, OR52I1, OR52I2, OR52J3, OR52K1, OR52K2, OR52L1, OR52L2, OR52N1, OR52N2, OR52N4, OR52N5, OR52P1, OR52R1, OR56A4, OR56A6, OR56B2, OR56B4, OR5A1, OR5A2, OR5AC2, OR5AK2, OR5AK3, OR5AN1, OR5AP2, OR5AR1, OR5AS1, OR5AU1, OR5AU1, OR5B13, OR5B16, OR5B17, OR5B2, OR5B3, OR5C1, OR5D13, OR5D14, OR5D16, OR5D18, OR5F1, OR5G3, OR5H1, OR5H2, OR5H6, OR5I1, OR5K1, OR5K2, OR5L1, OR5L2, OR5M1, OR5M10, OR5M11, OR5M11, OR5M3, OR5M3, OR5M8, OR5M9, OR5P2, OR5P3, OR5T2, OR5T3, OR5V1, OR6A1, OR6B1, OR6B2, OR6C1, OR6C2, OR6C3, OR6F1, OR6J2, OR6K3, OR6K6, OR6M1, OR6N1, OR6N2, OR6P1, OR6Q1, OR6S1, OR6T1, OR6V1, OR6X1, OR6Y1, OR7A10, OR7A17, OR7A2, OR7A5, OR7C1, OR7C2, OR7D2, OR7D2, OR7D4P, OR7E102, OR7E120, OR7G1, OR7G2, OR7G3, OR8A1, OR8B12, OR8B2, OR8B3, OR8B4, OR8B8, OR8D1, OR8D2, OR8D4, OR8G1, OR8G2, OR8H1, OR8H2, OR8H3, OR812, OR8J1, OR8J3, OR8K1, OR8K3, OR8K5, OR9A2, OR9A4, OR9G1, OR9G4, OR9G5, OR911, OR9K2, and OR9Q1 (as described in U.S. Patent Application Publication No. 2017/0052170) (e.g., Tables 9 and 10 of U.S. Patent Application Publication No. 2017/0052170) e.g., OR10A2, OR13C8, OR2AG2, OR2T8, OR4M2, OR52L1, OR5M3, OR7G2, OR10A3, OR13C9, OR2AJ1, OR2V1, OR4N2, OR52M1, OR5M8, OR7G3, OR10A4, OR13D1, OR2AK2, OR2V2, OR4N4, OR52N1, OR5M9, OR8A1, OR10A5, OR13F1, OR2AP1, OR2W1, OR4N5, OR52N2, OR5P2, OR8B12, OR10A6, OR13G1, OR2AT4, OR2W3, OR4P4, OR52N4, OR5P3, OR8B2, OR10A7, OR13H1, OR2B11, OR2Y1, OR4Q3, OR52N5, OR5R1, OR8B3, OR10AD1, OR13J1, OR2B2, OR2Z1, OR4S1, OR52R1, OR5T1, OR8B4, OR10AG1, OR14A16, OR2B3, OR3A1, OR4S2, OR52W1, OR5T2, OR8B8, OR10C1, OR14A2, OR2B6, OR3A2, OR4X1, OR56A1, OR5T3, OR8D1, OR10D3, OR14C36, OR2C1, OR3A3, OR4X2, OR56A3, OR5V1, OR8D2, OR10G2, OR14I1, OR2C3, OR4A15, OR51A2, OR56A4, OR5W2, OR8D4, OR10G3, OR14J1, OR2D2, OR4A16, OR51A4, OR56B1, OR6A2, OR8G1, OR10G4, OR14K1, OR2D3, OR4A47, OR51A7, OR56B3P, OR6B1, OR8G5, OR10G6, OR1A1, OR2F1, OR4A5, OR51B2, OR56B4, OR6B2, OR8H1, OR10G7, OR1A2, OR2F2, OR4B1, OR51B4, OR5A1, OR6B3, OR8H2, OR10G8, OR1B1, OR2G2, OR4C11, OR51B5, OR5A2, OR6C1, OR8H3, OR10G9, OR1C1, OR2G3, OR4C12, OR51B6, OR5AC2, OR6C2, OR812, OR10H1, OR1D2, OR2G6, OR4C13, OR51D1, OR5AK2, OR6C3, OR8J1, OR10H2, OR1D5, OR2H1, OR4C15, OR51E1, OR5AN1, OR6C4, OR8J3, OR10H3, OR1E1, OR2H2, OR4C16, OR51E2, OR5AP2, OR6C6, OR8K1, OR10H4, OR1E2, OR2J1, OR4C3, OR51F1, OR5AR1, OR6C65, OR8K3, OR10H5, OR1F1, OR2J2, OR4C46, OR51F2, OR5AS1, OR6C68, OR8K5, OR10J1, OR1G1, OR2J3, OR4C5, OR51G1, OR5AU1, OR6C70, OR8S1, OR10J3, OR1I, OR2K2, OR4C6, OR51G2, OR5B12, OR6C74, OR8U1, OR10J5, OR1J, OR2L13, OR4D1, OR51H1P, OR5B17, OR6C75, OR8U9, OR10K1, OR1J2, OR2L2, OR4D10, OR51I1, OR5B2, OR6C76, OR9A2, OR10K2, OR1J4, OR2L3, OR4D11, OR51I2, OR5B21, OR6F1, OR9A4, OR10P1, OR1K1, OR2L5, OR4D2, OR51L1, OR5B3, OR6J1, OR9G1, OR10Q1, OR1L1, OR2L8, OR4D5, OR51M1, GR5C1, OR6K2, OR9G4, OR10R2, OR1L3, OR2M2, OR4D6, OR51Q1, OR5D13, OR6K3, OR9G9, OR10S1, OR1L4, OR2M3, OR4D9, OR51S1, OR5D14, OR6K6, OR9I1, OR10T2, OR1L6, OR2M4, OR4E2, OR51T1, OR5D16, OR6M1, OR9K2, OR10V1, OR1L8, OR2M5, OR4F15, OR51V1, OR5D18, OR6N1, OR9Q1, OR10W1, OR1M1, OR2M7, OR4F16, OR52A1, GR5F1, OR6N2, OR9Q2, OR10X1, OR1N1, OR2S2, OR4F17, OR52A5, OR5H1, OR6P1, OR10Z1, OR1N2, OR2T1, OR4F21, OR52B1P, OR5H14, OR6Q1, OR11A1, OR1Q1, OR2T10, OR4F29, OR52B2, OR5H15, OR6S1, OR11G2, OR1S1, OR2T11, OR4F3, OR52B4, OR5H2, OR6T1, OR11H1, OR1S2, OR2T12, OR4F4, OR52B6, OR5H6, OR6V1, OR11H12, OR2A1, OR2T2, OR4F5, OR52D1, OR5I1, OR6X1, OR11H4, OR2A12, OR2T27, OR4F6, OR52E2, OR5J2, OR6Y1, OR11H6, OR2A14, OR2T29, OR4K1, OR52E4, OR5K1, OR7A10, OR11L1, OR2A2, OR2T3, OR4K13, OR52E6, OR5K2, OR7A17, OR12D2, OR2A25, OR2T33, OR4K14, OR52E8, OR5K3, OR7A5, OR12D3, OR2A4, OR2T34, OR4K15, OR52H1, OR5K4, OR7C1, OR13A1, OR2A42, OR2T35, OR4K17, OR52I1, OR5L1, OR7C2, OR13C2, OR2A5, OR2T4, OR4K2, OR52I2, OR5L2, OR7D2, OR13C3, OR2A7, OR2T5, OR4K5, OR52J3, OR5M1, OR7D4, OR13C4, OR2AE1, OR2T6, OR4L1, OR52K1, OR5M10, OR7E24, OR13C5, OR2AG1, OR2T7, OR4M1, OR52K2, OR5M11, OR7G1 (as described in U.S. Patent Application Publication No. 2017/0285009), 17, M71, MOR23, mOR-EG, mOR-EV, U131, I-C6, I-D3, I-G7, mOR912-93, OR17-40, and OR174.

In some examples, the genes and proteins are those of G protein-coupled receptor proteins. As used herewith, "G protein-coupled receptor proteins (GPCRs)", also known as "seven-transmembrane domain receptors", "7TM receptors", "heptahelical receptors", "serpentine receptors", and "G protein-linked receptors (GPLR)", designate a large protein family of receptors that sense molecules outside the cell and activate, inside the cell, signal transductions pathways and, ultimately, cellular responses. GPCRs are found in eukaryotes, including yeast and animals. The ligands that bind and activate these receptors include light-sensitive compounds, odors, pheromones, hormones, and neurotransmitters, and vary in size from small molecules to peptides to large proteins.

Method of Treatment

In one aspect, the present disclosure provides methods for treating a disease or condition. In general, the methods include modulating the expression and/or activity of one or more genes or proteins, e.g., those identified or identifiable by the methods herein.

As used herein, the terms "treat", "treating" and "treatment" refer to the alleviation or measurable lessening of one or more symptoms or measurable markers of an injury, disease or disorder. Measurable lessening includes any statistically significant decline in a measurable marker or symptom. In some embodiments, treatment is prophylactic treatment.

The treatment method may include administering a therapeutically effective amount of agent. The term "therapeutically effective amount" refers to an amount effective, at dosages and for periods of time necessary, to achieve the desired therapeutic result, e.g., a diminishment or prevention of effects associated with various disease states or conditions. The term "therapeutically effective amount" refers to an amount of a target gene or gene product modulator effective to treat or prevent a disease or disorder in a mammal. A therapeutically effective amount of a target gene or gene product modulator can vary according to factors such as the disease state, age, sex, and weight of the subject, and the ability of the therapeutic compound to elicit a desired response in the subject. A therapeutically effective amount is also one in which any toxic or detrimental effects of the therapeutic agent are outweighed by the therapeutically beneficial effects. In some embodiments, a therapeutically effective amount is an "effective amount" which, as used herein, refers to the amount of therapeutic agent or pharmaceutical composition to alleviate at least one or some of the symptoms of the disease or disorder. An "effective amount" for purposes herein is thus determined by such considerations as are known in the art and is the amount to achieve improvement including, but not limited to, improved survival rate or more rapid recovery, or improvement or elimination of at least one symptom and other indicator of an immune or autoimmune disease which are appropriate measures by those skilled in the art. It should be noted that a target gene or gene product modulator as disclosed herein can be administered as a pharmaceutically acceptable salt and can be administered alone or as an active ingredient in combination with pharmaceutically acceptable carriers, diluents, adjuvants and vehicles.

The treatment method may include administering a prophylactically effective amount of agent. The term "prophylactically effective amount" refers to an amount of a target gene or gene product modulator which is effective, at dosages and for periods of time necessary, to achieve the desired prophylactic result, e.g., the amount of a target gene or gene product modulator. Typically, since a prophylactic dose of a target gene or gene product modulator is administered to a subject prior to or at an earlier stage of a disease, and in some embodiments, a prophylactically effective amount is less than the therapeutically effective amount. A prophylactically effective amount of a target gene or gene product modulator is also one in which any toxic or detrimental effects of the compound are outweighed by the beneficial effects.

As used herein, the terms "prevent", "preventing" and "prevention" refer to the avoidance or delay in manifestation of one or more symptoms or measurable markers of a disease or disorder. A delay in the manifestation of a symptom or marker is a delay relative to the time at which such symptom or marker manifests in a control or untreated subject with a similar likelihood or susceptibility of developing the disease or disorder. The terms "prevent" "preventing" and "prevention" include not only the avoidance or prevention of a symptom or marker of the disease, but also a reduced severity or degree of any one of the symptoms or markers of the disease, relative to those symptoms or markers in a control or non-treated individual with a similar likelihood or susceptibility of developing the disease or disorder, or relative to symptoms or markers likely to arise based on historical or statistical measures of populations affected by the disease or disorder. By "reduced severity" is meant at least a 10% reduction in the severity or degree of a symptom or measurable disease marker, relative to a control or reference, e.g., at least 15%, 20%, 30%, 40%, 50%, 60%, 70%, 80%, 90%, 95%, 99% or even 100% (i.e., no symptoms or measurable markers).

As used herein, the terms "administering" and "introducing" are used interchangeably herein and refer to the placement of the agents or metabolic regulators of the present invention into a subject by a method or route which results in at least partial localization of a target gene or gene product modulator at a desired site. The compounds of the present invention can be administered by any appropriate route which results in an effective treatment in the subject. In some embodiments, administering is not systemic administration.

The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, subcapsular, subarachnoid, intraspinal, intracerebrospinal, and intrasternal injection and infusion. The phrases "systemic administration", "administered systemically", "peripheral administration" and "administered peripherally" as used herein mean the administration of a modulator such that it enters the animal's system and, thus, is subject to metabolism and other like processes, for example, subcutaneous administration.

Modulating Agents

In some embodiments, the methods herein include administering one or more agents that modulate the expression and/or activity of gene(s).

For example, the methods may include administering at least 1, at least 2, at least 3, at least 4, at least 5, at least 6, at least 7, at least 8, at least 9, at least 10, at least 15, at least 20, at least 30, at least 40, at least 50, at least 60, at least 70, at least 80, at least 90, at least 100 modulating agents.

As will be clear to the skilled person, "modulating" can also involve affecting a change (which can either be an increase or a decrease) in affinity, avidity, specificity and/or selectivity of a target or antigen, for one or more of its targets compared to the same conditions but without the presence of a modulating agent. Again, this can be determined in any suitable manner and/or using any suitable assay known per se, depending on the target. In particular, an action as an inhibitor/antagonist or activator/agonist can be such that an intended biological or physiological activity is increased or decreased, respectively, by at least 5%, at least 10%, at least 25%, at least 50%, at least 60%, at least 70%, at least 80%, or 90% or more, compared to the biological or physiological activity in the same assay under the same conditions but without the presence of the inhibitor/antagonist agent or activator/agonist agent. Modulating can also involve activating the target or antigen or the mechanism or pathway in which it is involved.

"Altered expression" as intended herein may encompass modulating the activity of one or more endogenous gene products. Accordingly, "altered expression", "altering expression", "modulating expression", or "detecting expression" or similar may be used interchangeably with respectively "altered expression or activity", "altering expression or activity", "modulating expression or activity", or "detecting expression or activity" or similar. As used herein the term "altered expression" may particularly denote altered production of the recited gene products by a cell. As used herein, the term "gene product(s)" includes RNA transcribed from a gene (e.g., mRNA), or a polypeptide encoded by a gene or translated from RNA.

Modulation herein may include increasing, decreasing, abolishing, expression and/or activity of the one or more genes. The terms "increased" or "increase" or "upregulated" or "upregulate" as used herein generally mean an increase by a statistically significant amount. For avoidance of doubt, "increased" means a statistically significant increase of at least 10% as compared to a reference level, including an increase of at least 20%, at least 30%, at least 40%, at least 50%, at least 60%, at least 70%, at least 80%, at least 90%, at least 100% or more, including, for example at least 2-fold, at least 3-fold, at least 4-fold, at least 5-fold, at least 10-fold increase or greater as compared to a reference level, as that term is defined herein.

The term "reduced" or "reduce" or "decrease" or "decreased" or "downregulate" or "downregulated" as used herein generally means a decrease by a statistically significant amount relative to a reference. For avoidance of doubt, "reduced" means statistically significant decrease of at least 10% as compared to a reference level, for example a decrease by at least 20%, at least 30%, at least 40%, at least 50%, at least 60%, at least 70%, at least 80%, at least 90% or more, up to and including a 100% decrease (i.e., absent level as compared to a reference sample), or any decrease between 10-100% as compared to a reference level, as that term is defined herein. The term "abolish" or "abolished" may in particular refer to a decrease by 100%, i.e., absent level as compared to a reference sample.

The term "agent" as used herein generally refers to any substance or composition, such as a chemical entity or biological product, or combination of chemical entities or biological products, capable of achieving a desired effect in a system, more particularly in a biological system, e.g., in a cell, tissue, organ, or an organism. In the present context, an agent may be exposed to, contacted with or introduced into an immune cell to modify at least one characteristic of the immune cell, such as to (inducibly) alter the expression or activity of the one or more genes or gene products as taught herein by the immune cell. Further in the present context, an agent may be administered to a subject to treat or prevent or control a disease or condition, for example by (inducibly) altering the expression or activity of the one or more genes or gene products as taught herein by immune cells of the subject.

In alternative embodiments, agents useful in the methods as disclosed herein are proteins and/or peptides or fragment thereof, which inhibit the gene expression of a target gene or gene product, or the function of a target protein. Such agents include, for example but are not limited to protein variants, mutated proteins, therapeutic proteins, truncated proteins and protein fragments. Protein agents can also be selected from a group comprising mutated proteins, genetically engineered proteins, peptides, synthetic peptides, recombinant proteins, chimeric proteins, antibodies, midibodies, minibodies, triabodies, humanized proteins, humanized antibodies, chimeric antibodies, modified proteins and fragments thereof. As disclosed herein, a protein which inhibits the function of a target protein may be a soluble dominant negative form of the target protein or a functional fragment or variant thereof which inhibits wild-type full length target protein function.

In certain embodiments, the agents may be small molecules, antibodies, therapeutic antibody, antibody fragment, antibody-like protein scaffold, aptamer, protein, genetic modifying agent or small molecule. The chemical entity or biological product is preferably, but not necessarily, a low molecular weight compound, but may also be a larger compound, or any organic or inorganic molecule effective in the given situation, including modified and unmodified nucleic acids such as antisense nucleic acids, RNAi, such as siRNA or shRNA, CRISPR-Cas systems, peptides, peptidomimetics, receptors, ligands, and antibodies, aptamers, polypeptides, nucleic acid analogues or variants thereof. Examples include an oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof. Agents can be selected from a group comprising chemicals, small molecules, nucleic acid sequences, nucleic acid analogues, proteins, peptides, aptamers, antibodies, or fragments thereof. A nucleic acid sequence can be RNA or DNA, and can be single or double stranded, and can be selected from a group comprising nucleic acid encoding a protein of interest, oligonucleotides, nucleic acid analogues, for example, peptide—nucleic acid (PNA), pseudo-complementary PNA (pc-PNA), locked nucleic acid (LNA), modified RNA (mod-RNA), single guide RNA etc. Such nucleic acid sequences include, for example, but are not limited to, nucleic acid sequence encoding proteins, for example, that act as transcriptional repressors, antisense molecules, ribozymes, small inhibitory nucleic acid sequences, for example, but are not limited to, RNAi, shRNAi, siRNA, micro RNAi (mRNAi), antisense oligonucleotides, CRISPR guide RNA, for example, that target a CRISPR enzyme to a specific DNA target sequence etc. A protein and/or peptide or fragment thereof can be any protein of interest, for example, but are not limited to, mutated proteins, therapeutic proteins and truncated proteins, wherein the protein is normally absent or expressed at lower levels in the cell. Proteins can also be selected from a group comprising; mutated proteins, genetically engineered proteins, peptides, synthetic peptides, recombinant proteins, chimeric proteins, antibodies, minibodies, humanized proteins, humanized antibodies, chimeric antibodies, modified proteins and fragments thereof. Alternatively, the agent can be intracellular within the cell as a result of introduction of a nucleic acid sequence into the cell and its transcription resulting in the production of the nucleic acid and/or protein modulator of a gene within the cell. In some embodiments, the agent is any chemical entity or moiety including, without limitation, synthetic and naturally-occurring non-proteinaceous entities. In certain embodiments, the agent is a small molecule having a chemical moiety. Agents can be known to have a desired activity and/or property, or can be selected from a library of diverse compounds.

In some embodiments, the one or more agents may be small molecules. The term "small molecule" refers to compounds, preferably organic compounds, with a size comparable to those organic molecules generally used in pharmaceuticals. The term excludes biological macromolecules (e.g., proteins, peptides, nucleic acids, etc.). Preferred small organic molecules range in size up to about 5,000 Da, e.g., up to about 4,000 Da, preferably up to 3.000 Da, more preferably up to 2,000 Da, even more preferably up to about 1,000 Da, e.g., up to about 900, 800, 700, 600 or up to about 500 Da.

In certain embodiments, the modulating agent can refer to a protein-binding agent that permits modulation or activity of proteins or disrupts interactions of proteins and other biomolecules such as but not limited to, disrupting protein-protein interaction, ligand-receptor interaction, or protein-nucleic acid interaction. Agents can also refer to DNA targeting or RNA targeting agents. Agents may include a fragment, derivative and analog of an active agent. The terms "fragment," "derivative" and "analog" when referring to polypeptides as used herein refers to polypeptides which either retain substantially the same biological function or activity as such polypeptides. An analog includes a proprotein which can be activated by cleavage of the proprotein portion to produce an active mature polypeptide. Such agents include, but are not limited to, antibodies ("antibodies" includes antigen-binding portions of antibodies such as epitope- or antigen-binding peptides, paratopes, functional CDRs, recombinant antibodies, chimeric antibodies, humanized antibodies, nanobodies, tribodies, midibodies, or antigen-binding derivatives, analogs, variants, portions, or fragments thereof), protein-binding agents, nucleic acid molecules, small molecules, recombinant protein, peptides, aptamers, avimers and protein-binding derivatives, portions or fragments thereof.

As used herein, a "blocking" antibody or an antibody "antagonist" is one which inhibits or reduces biological activity of the antigen(s) it binds. For example, an antagonist antibody may bind a surface receptor or ligand and inhibit the ability of the receptor and ligand to induce an ILC class 2 inflammatory response. In certain embodiments, the blocking antibodies or antagonist antibodies or portions thereof described herein completely inhibit the biological activity of the antigen(s).

Antibodies may act as agonists or antagonists of the recognized polypeptides. For example, the present invention includes antibodies which disrupt receptor/ligand interactions either partially or fully. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or of one of its down-stream substrates by immunoprecipitation followed by western blot analysis. In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex. Likewise, encompassed by the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides disclosed herein. The antibody agonists and antagonists can be made using methods known in the art. See, e.g., PCT publication WO 96/40281; U.S. Pat. No. 5,811,097; Deng et al., Blood 92(6):1981-1988 (1998); Chen et al., Cancer Res. 58(16): 3668-3678 (1998); Harrop et al., J. Immunol. 161(4):1786-1794 (1998); Zhu et al., Cancer Res. 58(15):3209-3214 (1998); Yoon et al., J. Immunol. 160(7):3170-3179 (1998); Prat et al., J. Cell. Sci. III (Pt2):237-247 (1998); Pitard et al., J. Immunol. Methods 205(2):177-190 (1997); Liautard et al., Cytokine 9(4):233-241 (1997); Carlson et al., J. Biol. Chem. 272(17):11295-11301 (1997); Taryman et al., Neuron 14(4): 755-762 (1995); Muller et al., Structure 6(9):1153-1167 (1998); Bartunek et al., Cytokine 8(1):14-20 (1996).

The antibodies as defined for the present invention include derivatives that are modified, i.e., by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques including, but not limited to, specific chemical cleavage, acetylation, formylation, metabolic synthesis of tunicamycin, etc. Additionally, the derivative may contain one or more non-classical amino acids.

Methods for administering antibodies for therapeutic use is well known to one skilled in the art. In certain embodiments, small particle aerosols of antibodies or fragments thereof may be administered, preferably for treating a respiratory inflammatory disease (see e.g., Piazza et al., J. Infect. Dis., Vol. 166, pp. 1422-1424, 1992; and Brown, Aerosol Science and Technology, Vol. 24, pp. 45-56, 1996). In certain embodiments, antibodies are administered in metered-dose propellant driven aerosols. In preferred embodiments, antibodies are used as inhibitors or antagonists to depress inflammatory diseases or allergen-induced asthmatic responses. In certain embodiments, antibodies may be administered in liposomes, i.e., immunoliposomes (see, e.g., Maruyama et al., Biochim. Biophys. Acta, Vol. 1234, pp. 74-80, 1995). In certain embodiments, immunoconjugates, immunoliposomes or immunomicrospheres containing an agent of the present invention is administered by inhalation.

In some embodiments, the agents may be nucleic acid molecules. Exemplary nucleic acid molecules include aptamers, siRNA, artificial microRNA, interfering RNA or RNAi, dsRNA, ribozymes, antisense oligonucleotides, and DNA expression cassettes encoding said nucleic acid molecules. Preferably, the nucleic acid molecule is an antisense oligonucleotide. Antisense oligonucleotides (ASO) generally inhibit their target by binding target mRNA and sterically blocking expression by obstructing the ribosome. ASOs can also inhibit their target by binding target mRNA thus forming a DNA-RNA hybrid that can be a substance for RNase H. Preferred ASOs include Locked Nucleic Acid (LNA), Peptide Nucleic Acid (PNA), and morpholinos. Preferably, the nucleic acid molecule is an RNAi molecule, i.e., RNA interference molecule. Preferred RNAi molecules include siRNA, shRNA, and artificial miRNA. The design and production of siRNA molecules is well known to one of skill in the art (e.g., Hajeri P B, Singh S K. Drug Discov Today. 2009 14(17-18):851-8). The nucleic acid molecule inhibitors may be chemically synthesized and provided directly to cells of interest. The nucleic acid compound may be provided to a cell as part of a gene delivery vehicle. Such a vehicle is preferably a liposome or a viral gene delivery vehicle.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection.

In certain embodiments, an agent may be a hormone, a cytokine, a lymphokine, a growth factor, a chemokine, a cell surface receptor ligand such as a cell surface receptor agonist or antagonist, or a mitogen.

Non-limiting examples of hormones include growth hormone (GH), adrenocorticotropic hormone (ACTH), dehydroepiandrosterone (DHEA), cortisol, epinephrine, thyroid hormone, estrogen, progesterone, testosterone, or combinations thereof.

Non-limiting examples of cytokines include lymphokines (e.g., interferon-γ, IL-2, IL-3, IL-4, IL-6, granulocyte-macrophage colony-stimulating factor (GM-CSF), interferon-γ, leukocyte migration inhibitory factors (T-LIF, B-LIF), lymphotoxin-alpha, macrophage-activating factor (MAF), macrophage migration-inhibitory factor (MIF), neuroleukin, immunologic suppressor factors, transfer factors, or combinations thereof), monokines (e.g., IL-1, TNF-alpha, interferon-α, interferon-β, colony stimulating factors, e.g., CSF2, CSF3, macrophage CSF or GM-CSF, or combinations thereof), chemokines (e.g., beta-thromboglobulin, C chemokines, CC chemokines, CXC chemokines, CX3C chemokines, macrophage inflammatory protein (MIP), or combinations thereof), interleukins (e.g., IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, IL-36, or combinations thereof), and several related signaling molecules, such as tumor necrosis factor (TNF) and interferons (e.g., interferon-α, interferon-β, interferon-γ, interferon-λ, or combinations thereof).

Non-limiting examples of growth factors include those of fibroblast growth factor (FGF) family, bone morphogenic protein (BMP) family, platelet derived growth factor (PDGF) family, transforming growth factor beta (TGFbeta) family, nerve growth factor (NGF) family, epidermal growth factor (EGF) family, insulin related growth factor (IGF) family, hepatocyte growth factor (HGF) family, hematopoietic growth factors (HeGFs), platelet-derived endothelial cell growth factor (PD-ECGF), angiopoietin, vascular endothelial growth factor (VEGF) family, glucocorticoids, or combinations thereof.

Non-limiting examples of mitogens include phytohaemagglutinin (PHA), concanavalin A (conA), lipopolysaccharide (LPS), pokeweed mitogen (PWM), phorbol ester such as phorbol myristate acetate (PMA) with or without ionomycin, or combinations thereof.

Non-limiting examples of cell surface receptors, the ligands of which may act as agents, include Toll-like receptors (TLRs) (e.g., TLR1, TLR2, TLR3, TLR4, TLR5, TLR6, TLR7, TLR8, TLR9, TLR10, TLR11, TLR12 or TLR13), CD80, CD86, CD40, CCR7, or C-type lectin receptors.

Genetic Modifying Agents

In certain embodiments, the one or more modulating agents may be a genetic modifying agent. The genetic modifying agent may comprise a CRISPR-Cas system, a zinc finger nuclease system, a TALEN, or a meganuclease.

CRISPR-Cas System

The one or more modulating agents may be one or more components in a CRISPR-Cas system, or nucleic acids encoding thereof. In general, a CRISPR-Cas or CRISPR system as used in herein and in documents, such as WO 2014/093622 (PCT/US2013/074667), refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas, such as Cas9, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). See, e.g. Shmakov et al. (2015) "Discovery and Functional Characterization of Diverse Class 2 CRISPR-Cas Systems", Molecular Cell, DOI: dx.doi.org/10.1016/j.molcel.2015.10.008.

In certain embodiments, a protospacer adjacent motif (PAM) or PAM-like motif directs binding of the effector protein complex as disclosed herein to the target locus of interest. In some embodiments, the PAM may be a 5' PAM (i.e., located upstream of the 5' end of the protospacer). In other embodiments, the PAM may be a 3' PAM (i.e., located downstream of the 5' end of the protospacer). The term "PAM" may be used interchangeably with the term "PFS" or "protospacer flanking site" or "protospacer flanking sequence".

In a preferred embodiment, the CRISPR effector protein may recognize a 3' PAM. In certain embodiments, the CRISPR effector protein may recognize a 3' PAM which is 5'H, wherein HisA, C or U.

In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise RNA polynucleotides. The term "target RNA" refers to a RNA polynucleotide being or comprising the target sequence. In other words, the target RNA may be a RNA polynucleotide or a part of a RNA polynucleotide to which a part of the gRNA, i.e. the guide sequence, is designed to have complementarity and to which the effector function mediated by the complex comprising CRISPR effector protein and a gRNA is to be directed. In some embodiments, a target sequence is located in the nucleus or cytoplasm of a cell.

In certain example embodiments, the CRISPR effector protein may be delivered using a nucleic acid molecule encoding the CRISPR effector protein. The nucleic acid molecule encoding a CRISPR effector protein, may advantageously be a codon optimized CRISPR effector protein. An example of a codon optimized sequence is in this instance a sequence optimized for expression in eukaryote, e.g., humans (i.e. being optimized for expression in humans), or for another eukaryote, animal or mammal as herein discussed; see, e.g., SaCas9 human codon optimized sequence in WO 2014/093622 (PCT/US2013/074667). While this is preferred, it will be appreciated that other examples are possible and codon optimization for a host species other than human or for codon optimization for specific organs is known. In some embodiments, an enzyme coding sequence encoding a CRISPR effector protein is a codon optimized for expression in particular cells, such as eukaryotic cells. The eukaryotic cells may be those of or derived from a particular organism, such as a plant or a mammal, including but not limited to human or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at kazusa.or.jp/codon/ and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell, such as Gene Forge (Aptagen; Jacobus, PA), are also available. In some embodiments, one or more codons (e.g. 1, 2, 3, 4, 5, 10, 15, 20, 25, 50, or more, or all codons) in a sequence encoding a Cas correspond to the most frequently used codon for a particular amino acid.

In certain embodiments, the methods as described herein may comprise providing a Cas transgenic cell in which one or more nucleic acids encoding one or more guide RNAs are provided or introduced operably connected in the cell with a regulatory element comprising a promoter of one or more gene of interest. As used herein, the term "Cas transgenic cell" refers to a cell, such as a eukaryotic cell, in which a Cas gene has been genomically integrated. The nature, type, or origin of the cell are not particularly limiting according to the present invention. Also the way the Cas transgene is introduced in the cell may vary and can be any method as is known in the art. In certain embodiments, the Cas transgenic cell is obtained by introducing the Cas transgene in an isolated cell. In certain other embodiments, the Cas transgenic cell is obtained by isolating cells from a Cas transgenic organism. By means of example, and without limitation, the Cas transgenic cell as referred to herein may be derived from a Cas transgenic eukaryote, such as a Cas knock-in eukaryote. Reference is made to WO 2014/093622 (PCT/US13/74667), incorporated herein by reference. Methods of US Patent Publication Nos. 20120017290 and 20110265198 assigned to Sangamo BioSciences, Inc. directed to targeting the Rosa locus may be modified to utilize the CRISPR Cas system of the present invention. Methods of US Patent Publication No. 20130236946 assigned to Cellectis directed to targeting the Rosa locus may also be modified to utilize the CRISPR Cas system of the present invention. By means of further example, reference is made to Platt et. al. (Cell; 159(2):440-455 (2014)), describing a Cas9 knock-in mouse, which is incorporated herein by reference. The Cas transgene can further comprise a Lox-Stop-polyA-Lox(LSL) cassette thereby rendering Cas expression inducible by Cre recombinase. Alternatively, the Cas transgenic cell may be obtained by introducing the Cas transgene in an isolated cell. Delivery systems for transgenes are well known in the art. By means of example, the Cas transgene may be delivered in, for instance, eukaryotic cell by means of vector (e.g., AAV, adenovirus, lentivirus) and/or particle and/or nanoparticle delivery, as also described herein elsewhere.

It will be understood by the skilled person that the cell, such as the Cas transgenic cell, as referred to herein may comprise further genomic alterations besides having an integrated Cas gene or the mutations arising from the sequence specific action of Cas when complexed with RNA capable of guiding Cas to a target locus.

In certain aspects the invention involves vectors, e.g. for delivering or introducing in a cell Cas and/or RNA capable of guiding Cas to a target locus (i.e. guide RNA), but also for propagating these components (e.g. in prokaryotic cells). As used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with the proper control elements. In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell). With regard to recombination and cloning methods, mention is made of U.S. patent application Ser. No. 10/815,730, published Sep. 2, 2004 as US 2004-0171156 A1, the contents of which are herein incorporated by reference in their entirety. Thus, the embodiments disclosed herein may also comprise transgenic cells comprising the CRISPR effector system. In certain example embodiments, the transgenic cell may function as an individual discrete volume. In other words, samples comprising a masking construct may be delivered to a cell, for example in a suitable delivery vesicle and if the target is present in the delivery vesicle the CRISPR effector is activated and a detectable signal generated.

The vector(s) can include the regulatory element(s), e.g., promoter(s). The vector(s) can comprise Cas encoding sequences, and/or a single, but possibly also can comprise at least 3 or 8 or 16 or 32 or 48 or 50 guide RNA(s) (e.g., sgRNAs) encoding sequences, such as 1-2, 1-3, 1-4 1-5, 3-6, 3-7, 3-8, 3-9, 3-10, 3-16, 3-30, 3-32, 3-48, 3-50 RNA(s) (e.g., sgRNAs). In a single vector there can be a promoter for each RNA (e.g., sgRNA), advantageously when there are up to about 16 RNA(s); and, when a single vector provides for more than 16 RNA(s), one or more promoter(s) can drive expression of more than one of the RNA(s), e.g., when there are 32 RNA(s), each promoter can drive expression of two RNA(s), and when there are 48 RNA(s), each promoter can drive expression of three RNA(s). By simple arithmetic and well-established cloning protocols and the teachings in this disclosure one skilled in the art can readily practice the invention as to the RNA(s) for a suitable exemplary vector such as AAV, and a suitable promoter such as the U6 promoter. For example, the packaging limit of AAV is ~4.7 kb. The length of a single U6-gRNA (plus restriction sites for cloning) is 361 bp. Therefore, the skilled person can readily fit about 12-16, e.g., 13 U6-gRNA cassettes in a single vector. This can be assembled by any suitable means, such as a golden gate strategy used for TALE assembly (genome-engineering.org/taleffectors/). The skilled person can also use a tandem guide strategy to increase the number of U6-gRNAs by approximately 1.5 times, e.g., to increase from 12-16, e.g., 13 to approximately 18-24, e.g., about 19 U6-gRNAs. Therefore, one skilled in the art can readily reach approximately 18-24, e.g., about 19 promoter-RNAs, e.g., U6-gRNAs in a single vector, e.g., an AAV vector. A further means for increasing the number of promoters and RNAs in a vector is to use a single promoter (e.g., U6) to express an array of RNAs separated by cleavable sequences. And an even further means for increasing the number of promoter-RNAs in a vector, is to express an array of promoter-RNAs separated by cleavable sequences in the intron of a coding sequence or gene; and, in this instance it is advantageous to use a polymerase II promoter, which can have increased expression and enable the transcription of long RNA in a tissue specific manner (see, e.g., nar.oxfordjournals.org/content/34/7/e53.short and nature.com/mt/journal/v16/n9/abs/mt2008144a.html). In an advantageous embodiment, AAV may package U6 tandem gRNA targeting up to about 50 genes. Accordingly, from the knowledge in the art and the teachings in this disclosure the skilled person can readily make and use vector(s), e.g., a single vector, expressing multiple RNAs or guides under the control or operatively or functionally linked to one or more promoters-especially as to the numbers of RNAs or guides discussed herein, without any undue experimentation.

The guide RNA(s) encoding sequences and/or Cas encoding sequences, can be functionally or operatively linked to regulatory element(s) and hence the regulatory element(s) drive expression. The promoter(s) can be constitutive promoter(s) and/or conditional promoter(s) and/or inducible promoter(s) and/or tissue specific promoter(s). The promoter can be selected from the group consisting of RNA polymerases, pol I, pol II, pol III, T7, U6, H1, retroviral Rous sarcoma virus (RSV) LTR promoter, the cytomegalovirus (CMV) promoter, the SV40 promoter, the dihydrofolate reductase promoter, the β-actin promoter, the phosphoglycerol kinase (PGK) promoter, and the EF1α promoter. An advantageous promoter is the U6 promoter.

Additional effectors for use according to the invention can be identified by their proximity to cas1 genes, for example, though not limited to, within the region 20 kb from the start of the cas1 gene and 20 kb from the end of the cas1 gene. In certain embodiments, the effector protein comprises at least one HEPN domain and at least 500 amino acids, and wherein the C2c2 effector protein is naturally present in a prokaryotic genome within 20 kb upstream or downstream of a Cas gene or a CRISPR array. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified versions thereof. In certain example embodiments, the C2c2 effector protein is naturally present in a prokaryotic genome within 20 kb upstream or downstream of a Cas 1 gene. The terms "orthologue" (also referred to as "ortholog" herein) and "homologue" (also referred to as "homolog" herein) are well known in the art. By means of further guidance, a "homologue" of a protein as used herein is a protein of the same species which performs the same or a similar function as the protein it is a homologue of. Homologous proteins may but need not be structurally related, or are only partially structurally related. An "orthologue" of a protein as used herein is a protein of a different species which performs the same or a similar function as the protein it is an orthologue of. Orthologous proteins may but need not be structurally related, or are only partially structurally related.

Guide Molecules

The modulating agents may comprise one or more guide molecules in CRISPR-Cas systems. As used herein, the term "guide sequence" and "guide molecule" in the context of a CRISPR-Cas system, comprises any polynucleotide sequence having sufficient complementarity with a target nucleic acid sequence to hybridize with the target nucleic acid sequence and direct sequence-specific binding of a nucleic acid-targeting complex to the target nucleic acid sequence. The guide sequences made using the methods disclosed herein may be a full-length guide sequence, a truncated guide sequence, a full-length sgRNA sequence, a truncated sgRNA sequence, or an E+F sgRNA sequence. In some embodiments, the degree of complementarity of the guide sequence to a given target sequence, when optimally aligned using a suitable alignment algorithm, is about or more than about 50%, 60%, 75%, 80%, 85%, 90%, 95%, 97.5%, 99%, or more. In certain example embodiments, the guide molecule comprises a guide sequence that may be designed to have at least one mismatch with the target sequence, such that a RNA duplex is formed between the guide sequence and the target sequence. Accordingly, the degree of complementarity is preferably less than 99%. For instance, where the guide sequence consists of 24 nucleotides, the degree of complementarity is more particularly about 96% or less. In particular embodiments, the guide sequence is designed to have a stretch of two or more adjacent mismatching nucleotides, such that the degree of complementarity over the entire guide sequence is further reduced. For instance, where the guide sequence consists of 24 nucleotides, the degree of complementarity is more particularly about 96% or less, more particularly, about 92% or less, more particularly about 88% or less, more particularly about 84% or less, more particularly about 80% or less, more particularly about 76% or less, more particularly about 72% or less, depending on whether the stretch of two or more mismatching nucleotides encompasses 2, 3, 4, 5, 6 or 7 nucleotides, etc. In some embodiments, aside from the stretch of one or more mismatching nucleotides, the degree of complementarity, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting examples of which include the Smith-Waterman algorithm, the Needleman-Wunsch algorithm, algorithms based on the Burrows-Wheeler Transform (e.g., the Burrows Wheeler Aligner), Clustal W, Clustal X, BLAT, Novoalign (Novocraft Technologies; available at www.novocraft.com), ELAND (Illumina, San Diego, CA), SOAP (available at soap.genomics.org.cn), and Maq (available at maq.sourceforge.net). The ability of a guide sequence (within a nucleic acid-targeting guide RNA) to direct sequence-specific binding of a nucleic acid-targeting complex to a target nucleic acid sequence may be assessed by any suitable assay. For example, the components of a nucleic acid-targeting CRISPR system sufficient to form a nucleic acid-targeting complex, including the guide sequence to be tested, may be provided to a host cell having the corresponding target nucleic acid sequence, such as by transfection with vectors encoding the components of the nucleic acid-targeting complex, followed by an assessment of preferential targeting (e.g., cleavage) within the target nucleic acid sequence, such as by Surveyor assay as described herein. Similarly, cleavage of a target nucleic acid sequence (or a sequence in the vicinity thereof) may be evaluated in a test tube by providing the target nucleic acid sequence, components of a nucleic acid-targeting complex, including the guide sequence to be tested and a control guide sequence different from the test guide sequence, and comparing binding or rate of cleavage at or in the vicinity of the target sequence between the test and control guide sequence reactions. Other assays are possible, and will occur to those skilled in the art. A guide sequence and, hence, a nucleic acid-targeting guide RNA may be selected to target any target nucleic acid sequence.

In certain embodiments, the guide sequence or spacer length of the guide molecules is from 15 to 50 nt. In certain embodiments, the spacer length of the guide RNA is at least 15 nucleotides. In certain embodiments, the spacer length is from 15 to 17 nt, e.g., 15, 16, or 17 nt, from 17 to 20 nt, e.g., 17, 18, 19, or 20 nt, from 20 to 24 nt, e.g., 20, 21, 22, 23, or 24 nt, from 23 to 25 nt, e.g., 23, 24, or 25 nt, from 24 to 27 nt, e.g., 24, 25, 26, or 27 nt, from 27 to 30 nt, e.g., 27, 28, 29, or 30 nt, from 30 to 35 nt, e.g., 30, 31, 32, 33, 34, or 35 nt, or 35 nt or longer. In certain example embodiment, the guide sequence is 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nt.

In some embodiments, the guide sequence is an RNA sequence of between 10 to 50 nt in length, but more particularly of about 20 to 30 nt advantageously about 20 nt, 23 to 25 nt or 24 nt. The guide sequence is selected so as to ensure that it hybridizes to the target sequence. This is described more in detail below. Selection can encompass further steps which increase efficacy and specificity.

In some embodiments, the guide sequence has a canonical length (e.g., about 15 to 30 nt) is used to hybridize with the target RNA or DNA. In some embodiments, a guide molecule is longer than the canonical length (e.g., >30 nt) is used to hybridize with the target RNA or DNA, such that a region of the guide sequence hybridizes with a region of the RNA or DNA strand outside of the Cas-guide target complex. This can be of interest where additional modifications, such as deamination of nucleotides, is of interest. In alternative embodiments, it is of interest to maintain the limitation of the canonical guide sequence length.

In some embodiments, the sequence of the guide molecule (direct repeat and/or spacer) is selected to reduce the degree of secondary structure within the guide molecule. In some embodiments, about or less than about 75%, 50%, 40%, 30%, 25%, 20%, 15%, 10%, 5%, 1%, or fewer of the nucleotides of the nucleic acid-targeting guide RNA participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example of folding algorithm is the online webserver RNAfold, developed at the Institute for Theoretical Chemistry at the University of Vienna, using the centroid structure prediction algorithm (see e.g., A. R. Gruber et al., 2008, Cell 106(1): 23-24; and PA Carr and GM Church, 2009, Nature Biotechnology 27(12): 1151-62).

In some embodiments, it is of interest to reduce the susceptibility of the guide molecule to RNA cleavage, such as to cleavage by Cas13. Accordingly, in particular embodiments, the guide molecule is adjusted to avoid cleavage by Cas13 or other RNA-cleaving enzymes.

In certain embodiments, the guide molecule comprises non-naturally occurring nucleic acids and/or non-naturally occurring nucleotides and/or nucleotide analogs, and/or chemical modifications. Preferably, these non-naturally occurring nucleic acids and non-naturally occurring nucleotides are located outside the guide sequence. Non-naturally occurring nucleic acids can include, for example, mixtures of naturally and non-naturally occurring nucleotides. Non-naturally occurring nucleotides and/or nucleotide analogs may be modified at the ribose, phosphate, and/or base moiety. In an embodiment of the invention, a guide nucleic acid comprises ribonucleotides and non-ribonucleotides. In one such embodiment, a guide comprises one or more ribonucleotides and one or more deoxyribonucleotides. In an embodiment of the invention, the guide comprises one or more non-naturally occurring nucleotide or nucleotide analog such as a nucleotide with phosphorothioate linkage, a locked nucleic acid (LNA) nucleotides comprising a methylene bridge between the 2' and 4' carbons of the ribose ring, or bridged nucleic acids (BNA). Other examples of modified nucleotides include 2'-O-methyl analogs, 2'-deoxy analogs, or 2'-fluoro analogs. Further examples of modified bases include, but are not limited to, 2-aminopurine, 5-bromo-uridine, pseudouridine, inosine, and 7-methylguanosine. Examples of guide RNA chemical modifications include, without limitation, incorporation of 2'-O-methyl (M), 2'-O-methyl 3' phosphorothioate (MS), S-constrained ethyl(cEt), or 2'-O-methyl 3' thioPACE (MSP) at one or more terminal nucleotides. Such chemically modified guides can comprise increased stability and increased activity as compared to unmodified guides, though on-target vs. off-target specificity is not predictable. (See, Hendel, 2015, Nat Biotechnol. 33(9):985-9, doi: 10.1038/nbt.3290, published online 29 Jun. 2015; Ragdarm et al., 2015, PNAS, E7110-E7111; Allerson et al., J. Med. Chem. 2005, 48:901-904; Bramsen et al., Front. Genet., 2012, 3:154; Deng et al., PNAS, 2015, 112:11870-11875; Sharma et al., MedChemComm., 2014, 5:1454-1471; Hendel et al., Nat. Biotechnol. 2015, 33(9): 985-989; Li et al., Nature Biomedical Engineering, 2017, 1, 0066 DOI:10.1038/s41551-017-0066). In some embodiments, the 5' and/or 3' end of a guide RNA is modified by a variety of functional moieties including fluorescent dyes, polyethylene glycol, cholesterol, proteins, or detection tags. (See Kelly et al., 2016, J. Biotech. 233:74-83). In certain embodiments, a guide comprises ribonucleotides in a region that binds to a target RNA and one or more deoxyribonucleotides and/or nucleotide analogs in a region that binds to Cas13. In an embodiment of the invention, deoxyribonucleotides and/or nucleotide analogs are incorporated in engineered guide structures, such as, without limitation, stem-loop regions, and the seed region. For Cas13 guide, in certain embodiments, the modification is not in the 5'-handle of the stem-loop regions. Chemical modification in the 5'-handle of the stem-loop region of a guide may abolish its function (see Li, et al., Nature Biomedical Engineering, 2017, 1:0066). In certain embodiments, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or 75 nucleotides of a guide is chemically modified. In some embodiments, 3-5 nucleotides at either the 3' or the 5' end of a guide is chemically modified. In some embodiments, only minor modifications are introduced in the seed region, such as 2'-F modifications. In some embodiments, a 2'-F modification is introduced at the 3' end of a guide. In certain embodiments, three to five nucleotides at the 5' and/or the 3' end of the guide are chemically modified with 2'-O-methyl (M), 2'-O-methyl 3' phosphorothioate (MS), S-constrained ethyl(cEt), or 2'-O-methyl 3' thioPACE (MSP). Such modification can enhance genome editing efficiency (see Hendel et al., Nat. Biotechnol. 2015, 33(9): 985-989). In certain embodiments, all of the phosphodiester bonds of a guide are substituted with phosphorothioates (PS) for enhancing levels of gene disruption. In certain embodiments, more than five nucleotides at the 5' and/or the 3' end of the guide are chemically modified with 2'-O-Me, 2'-F or S-constrained ethyl(cEt). Such chemically modified guide can mediate enhanced levels of gene disruption (see Ragdarm et al., 2015, PNAS, E7110-E7111). In an embodiment of the invention, a guide is modified to comprise a chemical moiety at its 3' and/or 5' end. Such moieties include, but are not limited to, amine, azide, alkyne, thio, dibenzocyclooctyne (DBCO), or Rhodamine. In certain embodiments, the chemical moiety is conjugated to the guide by a linker, such as an alkyl chain. In certain embodiments, the chemical moiety of the modified guide can be used to attach the guide to another molecule, such as DNA, RNA, protein, or nanoparticles. Such chemically modified guide can be used to identify or enrich cells generically edited by a CRISPR system (see Lee et al., eLife, 2017, 6:e25312, DOI:10.7554).

In some embodiments, the modification to the guide is a chemical modification, an insertion, a deletion or a split. In some embodiments, the chemical modification includes, but is not limited to, incorporation of 2'-O-methyl (M) analogs, 2'-deoxy analogs, 2-thiouridine analogs, N6-methyladenosine analogs, 2'-fluoro analogs, 2-aminopurine, 5-bromo-uridine, pseudouridine ($\Psi$), N1-methylpseudouridine (mel$\Psi$), 5-methoxyuridine(5moU), inosine, 7-methylguanosine, 2'-O-methyl 3'phosphorothioate (MS), S-constrained ethyl(cEt), phosphorothioate (PS), or 2'-O-methyl 3'thioPACE (MSP). In some embodiments, the guide comprises one or more of phosphorothioate modifications. In certain embodiments, at least 1, 2, 3, 4, 5, 6, 7, 8, 9, 10, 11, 12, 13, 14, 15, 16, 17, 18, 19, 20, or 25 nucleotides of the guide are chemically modified. In certain embodiments, one or more nucleotides in the seed region are chemically modified. In certain embodiments, one or more nucleotides in the 3'-terminus are chemically modified. In certain embodiments, none of the nucleotides in the 5'-handle are chemically modified. In some embodiments, the chemical modification in the seed region is a minor modification, such as incorporation of a 2'-fluoro analog. In a specific embodiment, one nucleotide of the seed region is replaced with a 2'-fluoro analog. In some embodiments, 5 to 10 nucleotides in the 3'-terminus are chemically modified. Such chemical modifications at the 3'-terminus of the Cas13 CrRNA may improve Cas13 activity. In a specific embodiment, 1, 2, 3, 4, 5, 6, 7, 8, 9 or 10 nucleotides in the 3'-terminus are replaced with 2'-fluoro analogues. In a specific embodiment, 1, 2, 3, 4, 5, 6, 7, 8, 9 or 10 nucleotides in the 3'-terminus are replaced with 2'-O-methyl (M) analogs.

In some embodiments, the loop of the 5'-handle of the guide is modified. In some embodiments, the loop of the 5'-handle of the guide is modified to have a deletion, an insertion, a split, or chemical modifications. In certain embodiments, the modified loop comprises 3, 4, or 5 nucleotides. In certain embodiments, the loop comprises the sequence of UCUU, UUUU, UAUU, or UGUU.

In some embodiments, the guide molecule forms a stem-loop with a separate non-covalently linked sequence, which can be DNA or RNA. In particular embodiments, the sequences forming the guide are first synthesized using the standard phosphoramidite synthetic protocol (Herdewijn, P., ed., Methods in Molecular Biology Col 288, Oligonucleotide Synthesis: Methods and Applications, Humana Press, New Jersey (2012)). In some embodiments, these sequences can be functionalized to contain an appropriate functional group for ligation using the standard protocol known in the art (Hermanson, G. T., Bioconjugate Techniques, Academic Press (2013)). Examples of functional groups include, but are not limited to, hydroxyl, amine, carboxylic acid, carboxylic acid halide, carboxylic acid active ester, aldehyde, carbonyl, chlorocarbonyl, imidazolylcarbonyl, hydrozide, semicarbazide, thio semicarbazide, thiol, maleimide, haloalkyl, sulfonyl, ally, propargyl, diene, alkyne, and azide. Once this sequence is functionalized, a covalent chemical bond or linkage can be formed between this sequence and the direct repeat sequence. Examples of chemical bonds include, but are not limited to, those based on carbamates, ethers, esters, amides, imines, amidines, aminotriazines, hydrozone, disulfides, thioethers, thioesters, phosphorothioates, phosphorodithioates, sulfonamides, sulfonates, sulfones, sulfoxides, ureas, thioureas, hydrazide, oxime, triazole, photolabile linkages, C—C bond forming groups such as Diels-Alder cyclo-addition pairs or ring-closing metathesis pairs, and Michael reaction pairs.

In some embodiments, these stem-loop forming sequences can be chemically synthesized. In some embodiments, the chemical synthesis uses automated, solid-phase oligonucleotide synthesis machines with 2'-acetoxyethyl orthoester (2'-ACE) (Scaringe et al., J. Am. Chem. Soc. (1998) 120: 11820-11821; Scaringe, Methods Enzymol. (2000) 317: 3-18) or 2'-thionocarbamate (2'-TC) chemistry (Dellinger et al., J. Am. Chem. Soc. (2011) 133: 11540-11546; Hendel et al., Nat. Biotechnol. (2015) 33:985-989).

In certain embodiments, the guide molecule comprises (1) a guide sequence capable of hybridizing to a target locus and (2) a tracr mate or direct repeat sequence whereby the direct repeat sequence is located upstream (i.e., 5') from the guide sequence. In a particular embodiment, the seed sequence (i.e. the sequence critical for recognition and/or hybridization to the sequence at the target locus) of the guide sequence is approximately within the first 10 nucleotides of the guide sequence.

In a particular embodiment, the guide molecule comprises a guide sequence linked to a direct repeat sequence, wherein the direct repeat sequence comprises one or more stem loops or optimized secondary structures. In particular embodiments, the direct repeat has a minimum length of 16 nts and a single stem loop. In further embodiments, the direct repeat has a length longer than 16 nts, preferably more than 17 nts, and has more than one stem loop or optimized secondary structures. In particular embodiments, the guide molecule comprises or consists of the guide sequence linked to all or part of the natural direct repeat sequence. A typical Type V or Type VI CRISPR-Cas guide molecule comprises (in 3' to 5' direction or in 5' to 3' direction): a guide sequence with a first complimentary stretch (the "repeat"), a loop (which is typically 4 or 5 nucleotides long), a second complimentary stretch (the "anti-repeat" being complimentary to the repeat), and a poly A (often poly U in RNA) tail (terminator). In certain embodiments, the direct repeat sequence retains its natural architecture and forms a single stem loop. In particular embodiments, certain aspects of the guide architecture can be modified, for example by addition, subtraction, or substitution of features, whereas certain other aspects of guide architecture are maintained. Preferred locations for engineered guide molecule modifications including, but not limited to, insertions, deletions, and substitutions include guide termini and regions of the guide molecule that are exposed when complexed with the CRISPR-Cas protein and/or target, for example the stemloop of the direct repeat sequence.

In particular embodiments, the stem comprises at least about 4 base pairs comprising complementary X and Y sequences, although stems of more, e.g., 5, 6, 7, 8, 9, 10, 11 or 12 or fewer, e.g., 3, 2, base pairs are also contemplated. Thus, for example X2-10 and Y2-10 (wherein X and Y represent any complementary set of nucleotides) may be contemplated. In one aspect, the stem made of the X and Y nucleotides, together with the loop, will form a complete hairpin in the overall secondary structure; and, this may be advantageous and the amount of base pairs can be any amount that forms a complete hairpin. In one aspect, any complementary X:Y base pairing sequence (e.g., as to length) is tolerated, so long as the secondary structure of the entire guide molecule is preserved. In one aspect, the loop that connects the stem made of X:Y base pairs can be any sequence of the same length (e.g., 4 or 5 nucleotides) or longer that does not interrupt the overall secondary structure of the guide molecule. In one aspect, the stemloop can further comprise, e.g. an MS2 aptamer. In one aspect, the stem comprises about 5-7 base pairs comprising complementary X and Y sequences, although stems of more or fewer base pairs are also contemplated. In one aspect, non-Watson Crick base pairing is contemplated, where such pairing otherwise generally preserves the architecture of the stemloop at that position.

In particular embodiments, the natural hairpin or stemloop structure of the guide molecule is extended or replaced by an extended stemloop. It has been demonstrated that extension of the stem can enhance the assembly of the guide molecule with the CRISPR-Cas protein (Chen et al. Cell. (2013) 155(7): 1479-1491). In particular embodiments, the stem of the stemloop is extended by at least 1, 2, 3, 4, 5 or more complementary base pairs (i.e. corresponding to the addition of 2, 4, 6, 8, 10 or more nucleotides in the guide molecule). In particular embodiments, these are located at the end of the stem adjacent to the loop of the stemloop.

In particular embodiments, the susceptibility of the guide molecule to RNases or to decreased expression can be reduced by slight modifications of the sequence of the guide molecule which do not affect its function. For instance, in particular embodiments, premature termination of transcription, such as premature transcription of U6 Pol-III, can be removed by modifying a putative Pol-III terminator (4 consecutive U's) in the guide molecule's sequence. Where such sequence modification is required in the stemloop of the guide molecule, it is preferably ensured by a base pair flip.

In a particular embodiment, the direct repeat may be modified to comprise one or more protein-binding RNA aptamers. In a particular embodiment, one or more aptamers may be included such as part of optimized secondary structure. Such aptamers may be capable of binding a bacteriophage coat protein as detailed further herein.

In some embodiments, the guide molecule forms a duplex with a target RNA comprising at least one target cytosine residue to be edited. Upon hybridization of the guide RNA molecule to the target RNA, the cytidine deaminase binds to the single strand RNA in the duplex made accessible by the mismatch in the guide sequence and catalyzes deamination of one or more target cytosine residues comprised within the stretch of mismatching nucleotides.

A guide sequence and, hence, a nucleic acid-targeting guide RNA may be selected to target any target nucleic acid sequence. The target sequence may be mRNA.

In certain embodiments, the target sequence should be associated with a PAM (protospacer adjacent motif) or PFS (protospacer flanking sequence or site); that is, a short sequence recognized by the CRISPR complex. Depending on the nature of the CRISPR-Cas protein, the target sequence should be selected such that its complementary sequence in the DNA duplex (also referred to herein as the non-target sequence) is upstream or downstream of the PAM. In the embodiments of the present invention where the CRISPR-Cas protein is a Cas13 protein, the complementary sequence of the target sequence is downstream or 3' of the PAM or upstream or 5' of the PAM. The precise sequence and length requirements for the PAM differ depending on the Cas13 protein used, but PAMs are typically 2-5 base pair sequences adjacent the protospacer (that is, the target sequence). Examples of the natural PAM sequences for different Cas13 orthologues are provided herein below and the skilled person will be able to identify further PAM sequences for use with a given Cas13 protein.

Further, engineering of the PAM Interacting (PI) domain may allow programing of PAM specificity, improve target site recognition fidelity, and increase the versatility of the CRISPR-Cas protein, for example as described for Cas9 in Kleinstiver B P et al. Engineered CRISPR-Cas9 nucleases with altered PAM specificities. Nature. 2015 Jul. 23; 523 (7561):481-5. doi: 10.1038/nature14592. As further detailed herein, the skilled person will understand that Cas13 proteins may be modified analogously.

In particular embodiments, the guide is an escorted guide. By "escorted" is meant that the CRISPR-Cas system or complex or guide is delivered to a selected time or place within a cell, so that activity of the CRISPR-Cas system or complex or guide is spatially or temporally controlled. For example, the activity and destination of the 3 CRISPR-Cas system or complex or guide may be controlled by an escort RNA aptamer sequence that has binding affinity for an aptamer ligand, such as a cell surface protein or other localized cellular component. Alternatively, the escort aptamer may, for example, be responsive to an aptamer effector on or in the cell, such as a transient effector, such as an external energy source that is applied to the cell at a particular time.

The escorted CRISPR-Cas systems or complexes have a guide molecule with a functional structure designed to improve guide molecule structure, architecture, stability, genetic expression, or any combination thereof. Such a structure can include an aptamer.

Aptamers are biomolecules that can be designed or selected to bind tightly to other ligands, for example, using a technique called systematic evolution of ligands by exponential enrichment (SELEX; Tuerk C, Gold L: "Systematic evolution of ligands by exponential enrichment: RNA ligands to bacteriophage T4 DNA polymerase." Science 1990, 249:505-510). Nucleic acid aptamers can, for example, be selected from pools of random-sequence oligonucleotides, with high binding affinities and specificities for a wide range of biomedically relevant targets, suggesting a wide range of therapeutic utilities for aptamers (Keefe, Anthony D., Supriya Pai, and Andrew Ellington. "Aptamers as therapeutics." Nature Reviews Drug Discovery 9.7 (2010): 537-550). These characteristics also suggest a wide range of uses for aptamers as drug delivery vehicles (Levy-Nissenbaum, Etgar, et al. "Nanotechnology and aptamers: applications in drug delivery." Trends in Biotechnology 26.8 (2008): 442-449; and, Hicke B J, Stephens A W. "Escort aptamers: a delivery service for diagnosis and therapy." J Clin Invest 2000, 106:923-928.). Aptamers may also be constructed that function as molecular switches, responding to a que by changing properties, such as RNA aptamers that bind fluorophores to mimic the activity of green fluorescent protein (Paige, Jeremy S., Karen Y. Wu, and Samie R. Jaffrey. "RNA mimics of green fluorescent protein." Science 333.6042 (2011): 642-646). It has also been suggested that aptamers may be used as components of targeted siRNA therapeutic delivery systems, for example targeting cell surface proteins (Zhou, Jiehua, and John J. Rossi. "Aptamer-targeted cell-specific RNA interference." Silence 1.1 (2010): 4).

Accordingly, in particular embodiments, the guide molecule is modified, e.g., by one or more aptamer(s) designed to improve guide molecule delivery, including delivery across the cellular membrane, to intracellular compartments, or into the nucleus. Such a structure can include, either in addition to the one or more aptamer(s) or without such one or more aptamer(s), moiety(ies) so as to render the guide molecule deliverable, inducible or responsive to a selected effector. The invention accordingly comprehends a guide molecule that responds to normal or pathological physiological conditions, including without limitation pH, hypoxia, $O_2$ concentration, temperature, protein concentration, enzymatic concentration, lipid structure, light exposure, mechanical disruption (e.g. ultrasound waves), magnetic fields, electric fields, or electromagnetic radiation.

Light responsiveness of an inducible system may be achieved via the activation and binding of cryptochrome-2 and CIB1. Blue light stimulation induces an activating conformational change in cryptochrome-2, resulting in recruitment of its binding partner CIB1. This binding is fast and reversible, achieving saturation in <15 sec following pulsed stimulation and returning to baseline <15 min after the end of stimulation. These rapid binding kinetics result in a system temporally bound only by the speed of transcription/translation and transcript/protein degradation, rather than uptake and clearance of inducing agents. Cryptochrome-2 activation is also highly sensitive, allowing for the use of low light intensity stimulation and mitigating the risks of phototoxicity. Further, in a context such as the intact mammalian brain, variable light intensity may be used to control the size of a stimulated region, allowing for greater precision than vector delivery alone may offer.

The invention contemplates energy sources such as electromagnetic radiation, sound energy or thermal energy to induce the guide. Advantageously, the electromagnetic radiation is a component of visible light. In a preferred embodiment, the light is a blue light with a wavelength of about 450 to about 495 nm. In an especially preferred embodiment, the wavelength is about 488 nm. In another preferred embodiment, the light stimulation is via pulses. The light power may range from about 0-9 $mW/cm^2$. In a preferred embodiment, a stimulation paradigm of as low as 0.25 sec every 15 sec should result in maximal activation.

The chemical or energy sensitive guide may undergo a conformational change upon induction by the binding of a chemical source or by the energy allowing it to act as a guide and have the Cas13 CRISPR-Cas system or complex function. The invention can involve applying the chemical source or energy so as to have the guide function and the Cas13 CRISPR-Cas system or complex function; and optionally further determining that the expression of the genomic locus is altered.

There are several different designs of this chemical inducible system: 1. ABI-PYL based system inducible by Abscisic Acid (ABA) (see, e.g., stke.sciencemag.org/cgi/content/abstract/sigtrans; 4/164/rs2), 2. FKBP-FRB based system inducible by rapamycin (or related chemicals based on rapamycin) (see, e.g., www.nature.com/nmeth/journal/v2/n6/full/nmeth763.html), 3. GID1-GAI based system inducible by Gibberellin (GA) (see, e.g., www.nature.com/nchembio/journal/v8/n5/full/nchembio.922.html).

A chemical inducible system can be an estrogen receptor (ER) based system inducible by 4-hydroxytamoxifen (4OHT) (see, e.g., www.pnas.org/content/104/3/1027.abstract). A mutated ligand-binding domain of the estrogen receptor called ERT2 translocates into the nucleus of cells upon binding of 4-hydroxytamoxifen. In further embodiments of the invention, any naturally occurring or engineered derivative of any nuclear receptor, thyroid hormone receptor, retinoic acid receptor, estrogren receptor, estrogen-related receptor, glucocorticoid receptor, progesterone receptor, or androgen receptor may be used in inducible systems analogous to the ER based inducible system.

Another inducible system is based on the design using Transient receptor potential (TRP) ion channel based system inducible by energy, heat or radio-wave (see, e.g., www.sciencemag.org/content/336/6081/604). These TRP family proteins respond to different stimuli, including light and heat. When this protein is activated by light or heat, the ion channel will open and allow the entering of ions such as calcium into the plasma membrane. This influx of ions will bind to intracellular ion interacting partners linked to a polypeptide including the guide and the other components of the Cas13 CRISPR-Cas complex or system, and the binding will induce the change of sub-cellular localization of the polypeptide, leading to the entire polypeptide entering the nucleus of cells. Once inside the nucleus, the guide protein and the other components of the Cas13 CRISPR-Cas complex will be active and modulating target gene expression in cells.

While light activation may be an advantageous embodiment, sometimes it may be disadvantageous especially for in vivo applications in which the light may not penetrate the skin or other organs. In this instance, other methods of energy activation are contemplated, in particular, electric field energy and/or ultrasound which have a similar effect.

Electric field energy is preferably administered substantially as described in the art, using one or more electric pulses of from about 1 Volt/cm to about 10 kVolts/cm under in vivo conditions. Instead of or in addition to the pulses, the electric field may be delivered in a continuous manner. The electric pulse may be applied for between 1 µs and 500 milliseconds, preferably between 1 µs and 100 milliseconds. The electric field may be applied continuously or in a pulsed manner for 5 about minutes.

As used herein, "electric field energy" is the electrical energy to which a cell is exposed. Preferably, the electric field has a strength of from about 1 Volt/cm to about 10 kVolts/cm or more under in vivo conditions (see WO97/49450).

As used herein, the term "electric field" includes one or more pulses at variable capacitance and voltage and including exponential and/or square wave and/or modulated wave and/or modulated square wave forms. References to electric fields and electricity should be taken to include reference to the presence of an electric potential difference in the environment of a cell. Such an environment may be set up by way of static electricity, alternating current (AC), direct current (DC), etc., as known in the art. The electric field may be uniform, non-uniform or otherwise, and may vary in strength and/or direction in a time dependent manner.

Single or multiple applications of electric field, as well as single or multiple applications of ultrasound are also possible, in any order and in any combination. The ultrasound and/or the electric field may be delivered as single or multiple continuous applications, or as pulses (pulsatile delivery).

Electroporation has been used in both in vitro and in vivo procedures to introduce foreign material into living cells. With in vitro applications, a sample of live cells is first mixed with the agent of interest and placed between electrodes such as parallel plates. Then, the electrodes apply an electrical field to the cell/implant mixture. Examples of systems that perform in vitro electroporation include the Electro Cell Manipulator ECM600 product, and the Electro Square Porator T820, both made by the BTX Division of Genetronics, Inc. (see U.S. Pat. No. 5,869,326).

The known electroporation techniques (both in vitro and in vivo) function by applying a brief high voltage pulse to electrodes positioned around the treatment region. The electric field generated between the electrodes causes the cell membranes to temporarily become porous, whereupon molecules of the agent of interest enter the cells. In known electroporation applications, this electric field comprises a single square wave pulse on the order of 1000 V/cm, of about 100 .mu.s duration. Such a pulse may be generated, for example, in known applications of the Electro Square Porator T820.

Preferably, the electric field has a strength of from about 1 V/cm to about 10 kV/cm under in vitro conditions. Thus, the electric field may have a strength of 1 V/cm, 2 V/cm, 3 V/cm, 4 V/cm, 5 V/cm, 6 V/cm, 7 V/cm, 8 V/cm, 9 V/cm, 10 V/cm, 20 V/cm, 50 V/cm, 100 V/cm, 200 V/cm, 300 V/cm, 400 V/cm, 500 V/cm, 600 V/cm, 700 V/cm, 800 V/cm, 900 V/cm, 1 kV/cm, 2 kV/cm, 5 kV/cm, 10 kV/cm, 20 kV/cm, 50 kV/cm or more. More preferably, from about 0.5 kV/cm to about 4.0 kV/cm under in vitro conditions. Preferably, the electric field has a strength of from about 1 V/cm to about 10 kV/cm under in vivo conditions. However, the electric field strengths may be lowered where the number of pulses delivered to the target site are increased. Thus, pulsatile delivery of electric fields at lower field strengths is envisaged.

Preferably, the application of the electric field is in the form of multiple pulses such as double pulses of the same strength and capacitance or sequential pulses of varying strength and/or capacitance. As used herein, the term "pulse" includes one or more electric pulses at variable capacitance and voltage and including exponential and/or square wave and/or modulated wave/square wave forms.

Preferably, the electric pulse is delivered as a waveform selected from an exponential wave form, a square wave form, a modulated wave form and a modulated square wave form.

A preferred embodiment employs direct current at low voltage. Thus, Applicants disclose the use of an electric field which is applied to the cell, tissue or tissue mass at a field strength of between 1 V/cm and 20 V/cm, for a period of 100 milliseconds or more, preferably 15 minutes or more.

Ultrasound is advantageously administered at a power level of from about 0.05 W/cm2 to about 100 W/cm2. Diagnostic or therapeutic ultrasound may be used, or combinations thereof.

As used herein, the term "ultrasound" refers to a form of energy which consists of mechanical vibrations, the frequencies of which are so high they are above the range of human hearing. Lower frequency limit of the ultrasonic spectrum may generally be taken as about 20 kHz. Most diagnostic applications of ultrasound employ frequencies in the range 1 and 15 MHz (From Ultrasonics in Clinical Diagnosis, P. N. T. Wells, ed., 2nd. Edition, Publ. Churchill Livingstone [Edinburgh, London & NY, 1977]).

Ultrasound has been used in both diagnostic and therapeutic applications. When used as a diagnostic tool ("diagnostic ultrasound"), ultrasound is typically used in an energy density range of up to about 100 mW/cm2 (FDA recommendation), although energy densities of up to 750 mW/cm2 have been used. In physiotherapy, ultrasound is typically used as an energy source in a range up to about 3 to 4 W/cm2 (WHO recommendation). In other therapeutic applications, higher intensities of ultrasound may be employed, for example, HIFU at 100 W/cm up to 1 kW/cm2 (or even higher) for short periods of time. The term "ultrasound" as used in this specification is intended to encompass diagnostic, therapeutic and focused ultrasound.

Focused ultrasound (FUS) allows thermal energy to be delivered without an invasive probe (see Morocz et al. 1998 Journal of Magnetic Resonance Imaging Vol. 8, No. 1, pp. 136-142). Another form of focused ultrasound is high intensity focused ultrasound (HIFU) which is reviewed by Moussatov et al. in Ultrasonics (1998) Vol. 36, No. 8, pp. 893-900 and TranHuuHue et al. in Acustica (1997) Vol.83, No.6, pp.1103-1106.

Preferably, a combination of diagnostic ultrasound and a therapeutic ultrasound is employed. This combination is not intended to be limiting, however, and the skilled reader will appreciate that any variety of combinations of ultrasound may be used. Additionally, the energy density, frequency of ultrasound, and period of exposure may be varied.

Preferably, the exposure to an ultrasound energy source is at a power density of from about 0.05 to about 100 W/cm-2. Even more preferably, the exposure to an ultrasound energy source is at a power density of from about 1 to about 15 W/cm-2.

Preferably, the exposure to an ultrasound energy source is at a frequency of from about 0.015 to about 10.0 MHz. More preferably, the exposure to an ultrasound energy source is at a frequency of from about 0.02 to about 5.0 MHz or about 6.0 MHz. Most preferably, the ultrasound is applied at a frequency of 3 MHz.

Preferably, the exposure is for periods of from about 10 milliseconds to about 60 minutes. Preferably, the exposure is for periods of from about 1 second to about 5 minutes. More preferably, the ultrasound is applied for about 2 minutes. Depending on the particular target cell to be disrupted, however, the exposure may be for a longer duration, for example, for 15 minutes.

Advantageously, the target tissue is exposed to an ultrasound energy source at an acoustic power density of from about 0.05 W/cm-2 to about 10 W/cm-2 with a frequency ranging from about 0.015 to about 10 MHz (see WO 98/52609). However, alternatives are also possible, for example, exposure to an ultrasound energy source at an acoustic power density of above 100 W/cm-2, but for reduced periods of time, for example, 1000 W/cm-2 for periods in the millisecond range or less.

Preferably, the application of the ultrasound is in the form of multiple pulses; thus, both continuous wave and pulsed wave (pulsatile delivery of ultrasound) may be employed in any combination. For example, continuous wave ultrasound may be applied, followed by pulsed wave ultrasound, or vice versa. This may be repeated any number of times, in any order and combination. The pulsed wave ultrasound may be applied against a background of continuous wave ultrasound, and any number of pulses may be used in any number of groups.

Preferably, the ultrasound may comprise pulsed wave ultrasound. In a highly preferred embodiment, the ultrasound is applied at a power density of 0.7 W/cm-2 or 1.25 W/cm-2 as a continuous wave. Higher power densities may be employed if pulsed wave ultrasound is used.

Use of ultrasound is advantageous as, like light, it may be focused accurately on a target. Moreover, ultrasound is advantageous as it may be focused more deeply into tissues unlike light. It is, therefore, better suited to whole-tissue penetration (such as but not limited to a lobe of the liver) or whole organ (such as but not limited to the entire liver or an entire muscle, such as the heart) therapy. Another important advantage is that ultrasound is a non-invasive stimulus which is used in a wide variety of diagnostic and therapeutic applications. By way of example, ultrasound is well known in medical imaging techniques and, additionally, in orthopedic therapy. Furthermore, instruments suitable for the application of ultrasound to a subject vertebrate are widely available and their use is well known in the art.

In particular embodiments, the guide molecule is modified by a secondary structure to increase the specificity of the CRISPR-Cas system and the secondary structure can protect against exonuclease activity and allow for 5' additions to the guide sequence also referred to herein as a protected guide molecule.

In one aspect, the invention provides for hybridizing a "protector RNA" to a sequence of the guide molecule, wherein the "protector RNA" is an RNA strand complementary to the 3' end of the guide molecule to thereby generate a partially double-stranded guide RNA. In an embodiment of the invention, protecting mismatched bases (i.e. the bases of the guide molecule which do not form part of the guide sequence) with a perfectly complementary protector sequence decreases the likelihood of target RNA binding to the mismatched base pairs at the 3' end. In particular embodiments of the invention, additional sequences comprising an extended length may also be present within the guide molecule such that the guide comprises a protector sequence within the guide molecule. This "protector sequence" ensures that the guide molecule comprises a "protected sequence" in addition to an "exposed sequence" (comprising the part of the guide sequence hybridizing to the target sequence). In particular embodiments, the guide molecule is modified by the presence of the protector guide to comprise a secondary structure such as a hairpin. Advantageously, there are three or four to thirty or more, e.g., about 10 or more, contiguous base pairs having complementarity to the protected sequence, the guide sequence or both. It is advantageous that the protected portion does not impede thermodynamics of the CRISPR-Cas system interacting with its target. By providing such an extension, including a partially double stranded guide molecule, the guide molecule is considered protected and results in improved specific binding of the CRISPR-Cas complex, while maintaining specific activity.

In particular embodiments, use is made of a truncated guide (tru-guide), i.e. a guide molecule which comprises a guide sequence which is truncated in length with respect to the canonical guide sequence length. As described by Nowak et al. (Nucleic Acids Res (2016) 44 (20): 9555-9564), such guides may allow catalytically active CRISPR-Cas enzyme to bind its target without cleaving the target RNA. In particular embodiments, a truncated guide is used which allows the binding of the target but retains only nickase activity of the CRISPR-Cas enzyme.

CRISPR RNA-Targeting Effector Proteins

The modulating agents may comprise one or more Cas proteins or nucleic acids encoding thereof. The Cas proteins may be CRISPR RNA-Targeting Effector Proteins. In one example embodiment, the CRISPR system effector protein is an RNA-targeting effector protein. In certain embodiments, the CRISPR system effector protein is a Type VI CRISPR system targeting RNA (e.g., Cas13a, Cas13b, Cas13c or Cas13d). Example RNA-targeting effector proteins include Cas13b and C2c2 (now known as Cas13a). It will be understood that the term "C2c2" herein is used interchangeably with "Cas13a". "C2c2" is now referred to as "Cas13a", and the terms are used interchangeably herein unless indicated otherwise. As used herein, the term "Cas13" refers to any Type VI CRISPR system targeting RNA (e.g., Cas13a, Cas13b, Cas13c or Cas13d). When the CRISPR protein is a C2c2 protein, a tracrRNA is not required. C2c2 has been described in Abudayyeh et al. (2016) "C2c2 is a single-component programmable RNA-guided RNA-targeting CRISPR effector"; Science; DOI: 10.1 126/science.aaf5573; and Shmakov et al. (2015) "Discovery and Functional Characterization of Diverse Class 2 CRISPR-Cas Systems", Molecular Cell, DOI: dx.doi.org/10.1016/j.molcel.2015.10.008; which are incorporated herein in their entirety by reference. Cas13b has been described in Smargon et al. (2017) "Cas13b Is a Type VI-B CRISPR-Associated RNA-Guided RNases Differentially Regulated by Accessory Proteins Csx27 and Csx28," Molecular Cell. 65, 1-13; dx.doi.org/10.1016/j.molcel.2016.12.023., which is incorporated herein in its entirety by reference.

In some embodiments, one or more elements of a nucleic acid-targeting system is derived from a particular organism comprising an endogenous CRISPR RNA-targeting system. In certain example embodiments, the effector protein CRISPR RNA-targeting system comprises at least one HEPN domain, including but not limited to the HEPN domains described herein, HEPN domains known in the art, and domains recognized to be HEPN domains by comparison to consensus sequence motifs. Several such domains are provided herein. In one non-limiting example, a consensus sequence can be derived from the sequences of C2c2 or Cas13b orthologs provided herein. In certain example embodiments, the effector protein comprises a single HEPN domain. In certain other example embodiments, the effector protein comprises two HEPN domains.

In one example embodiment, the effector protein comprises one or more HEPN domains comprising a RxxxxH motif sequence. The RxxxxH motif sequence can be, without limitation, from a HEPN domain described herein or a HEPN domain known in the art. RxxxxH motif sequences further include motif sequences created by combining portions of two or more HEPN domains. As noted, consensus sequences can be derived from the sequences of the orthologs disclosed in U.S. Provisional Application 62/432, 240 entitled "Novel CRISPR Enzymes and Systems," U.S. Provisional Application 62/471,710 entitled "Novel Type VI CRISPR Orthologs and Systems" filed on Mar. 15, 2017, and U.S. Provisional Application entitled "Novel Type VI CRISPR Orthologs and Systems," and filed on Apr. 12, 2017.

In certain other example embodiments, the CRISPR system effector protein is a C2c2 nuclease. The activity of C2c2 may depend on the presence of two HEPN domains. These have been shown to be RNase domains, i.e. nuclease (in particular an endonuclease) cutting RNA. C2c2 HEPN may also target DNA, or potentially DNA and/or RNA. On the basis that the HEPN domains of C2c2 are at least capable of binding to and, in their wild-type form, cutting RNA, then it is preferred that the C2c2 effector protein has RNase function. Regarding C2c2 CRISPR systems, reference is made to U.S. Provisional Application No. 62/351,662 filed on Jun. 17, 2016 and U.S. Provisional Application No. 62/376,377 filed on Aug. 17, 2016. Reference is also made to U.S. Provisional Application No. 62/351,803 filed on Jun. 17, 2016. Reference is also made to U.S. Provisional Application entitled "Novel Crispr Enzymes and Systems" filed Dec. 8, 2016 bearing Broad Institute No. 10035. PA4. Reference is further made to East-Seletsky et al. "Two distinct RNase activities of CRISPR-C2c2 enable guide-RNA processing and RNA detection" Nature doi:10/1038/nature19802 and Abudayyeh et al. "C2c2 is a single-component programmable RNA-guided RNA targeting CRISPR effector", bioRxiv doi:10.1101/054742.

In certain embodiments, the C2c2 effector protein is from an organism of a genus selected from the group consisting of: *Leptotrichia, Listeria, Corynebacterium, Sutterella, Legionella, Treponema, Filifactor, Eubacterium, Streptococcus, Lactobacillus, Mycoplasma, Bacteroides, Fluviicola, Flavobacterium, Sphaerochaeta, Azospirillum, Gluconacetobacter, Neisseria, Roseburia, Parvibaculum, Staphylococcus, Nitratifractor, Mycoplasma, Campylobacter*, and *Lachnospira*, or the C2c2 effector protein is an organism selected from the group consisting of *Leptotrichia shahii, Leptotrichia. wadei, Listeria seeligeri, Clostridium aminophilum, Carnobacterium gallinarum, Paludibacter propionicigenes, Listeria* weihenstephanensis, or the C2c2 effector protein is a *L. wadei* F0279 or *L. wadei* F0279 (Lw2) C2C2 effector protein. In another embodiment, the one or more guide RNAs are designed to detect a single nucleotide polymorphism, splice variant of a transcript, or a frameshift mutation in a target RNA or DNA.

In certain example embodiments, the RNA-targeting effector protein is a Type VI-B effector protein, such as Cas13b and Group 29 or Group 30 proteins. In certain example embodiments, the RNA-targeting effector protein comprises one or more HEPN domains. In certain example embodiments, the RNA-targeting effector protein comprises a C-terminal HEPN domain, a N-terminal HEPN domain, or both. Regarding example Type VI-B effector proteins that may be used in the context of this invention, reference is made to U.S. application Ser. No. 15/331,792 entitled "Novel CRISPR Enzymes and Systems" and filed Oct. 21, 2016, International Patent Application No. PCT/US2016/058302 entitled "Novel CRISPR Enzymes and Systems", and filed Oct. 21, 2016, and Smargon et al. "Cas13b is a Type VI-B CRISPR-associated RNA-Guided RNase differentially regulated by accessory proteins Csx27 and Csx28" Molecular Cell, 65, 1-13 (2017); dx.doi.org/10.1016/j.molcel.2016.12.023, and U.S. Provisional Application No. to be assigned, entitled "Novel Cas13b Orthologues CRISPR Enzymes and System" filed Mar. 15, 2017. In particular embodiments, the Cas13b enzyme is derived from *Bergeyella zoohelcum*.

In certain example embodiments, the RNA-targeting effector protein is a Cas13c effector protein as disclosed in U.S. Provisional Application No. 62/525,165 filed Jun. 26, 2017, and International Application No. PCT/US2017/047193 filed Aug. 16, 2017.

In some embodiments, one or more elements of a nucleic acid-targeting system is derived from a particular organism comprising an endogenous CRISPR RNA-targeting system. In certain embodiments, the CRISPR RNA-targeting system is found in *Eubacterium* and *Ruminococcus*. In certain embodiments, the effector protein comprises targeted and collateral ssRNA cleavage activity. In certain embodiments, the effector protein comprises dual HEPN domains. In certain embodiments, the effector protein lacks a counterpart to the Helical-1 domain of Cas13a. In certain embodiments, the effector protein is smaller than previously characterized class 2 CRISPR effectors, with a median size of 928 aa. This median size is 190 aa (17%) less than that of Cas13c, more than 200 aa (18%) less than that of Cas13b, and more than 300 aa (26%) less than that of Cas13a. In certain embodiments, the effector protein has no requirement for a flanking sequence (e.g., PFS, PAM).

In certain embodiments, the effector protein locus structures include a WYL domain containing accessory protein (so denoted after three amino acids that were conserved in the originally identified group of these domains; see, e.g., WYL domain IPR026881). In certain embodiments, the WYL domain accessory protein comprises at least one helix-turn-helix (HTH) or ribbon-helix-helix (RHH) DNA-binding domain. In certain embodiments, the WYL domain containing accessory protein increases both the targeted and the collateral ssRNA cleavage activity of the RNA-targeting effector protein. In certain embodiments, the WYL domain containing accessory protein comprises an N-terminal RHH domain, as well as a pattern of primarily hydrophobic conserved residues, including an invariant tyrosine-leucine doublet corresponding to the original WYL motif. In certain embodiments, the WYL domain containing accessory protein is WYL1. WYL1 is a single WYL-domain protein associated primarily with *Ruminococcus*.

In other example embodiments, the Type VI RNA-targeting Cas enzyme is Cas13d. In certain embodiments, Cas13d is *Eubacterium* siraeum DSM 15702 (EsCas13d) or *Ruminococcus* sp. N15. MGS-57 (RspCas13d) (see, e.g., Yan et al., Cas13d Is a Compact RNA-Targeting Type VI CRISPR Effector Positively Modulated by a WYL-Domain-Containing Accessory Protein, Molecular Cell (2018), doi.org/10.1016/j.molcel.2018.02.028). RspCas13d and EsCas13d have no flanking sequence requirements (e.g., PFS, PAM).

Cas13 RNA Editing

In one aspect, the invention provides a method of modifying or editing a target transcript in a eukaryotic cell. In some embodiments, the method comprises allowing a CRISPR-Cas effector module complex to bind to the target polynucleotide to effect RNA base editing, wherein the CRISPR-Cas effector module complex comprises a Cas effector module complexed with a guide sequence hybridized to a target sequence within said target polynucleotide, wherein said guide sequence is linked to a direct repeat sequence. In some embodiments, the Cas effector module comprises a catalytically inactive CRISPR-Cas protein. In some embodiments, the guide sequence is designed to introduce one or more mismatches to the RNA/RNA duplex formed between the target sequence and the guide sequence. In particular embodiments, the mismatch is an A-C mismatch. In some embodiments, the Cas effector may associate with one or more functional domains (e.g. via fusion protein or suitable linkers). In some embodiments, the effector domain comprises one or more cytidine or adenosine deaminases that mediate endogenous editing of via hydrolytic deamination. In particular embodiments, the effector domain comprises the adenosine deaminase acting on RNA (ADAR) family of enzymes. In particular embodiments, the adenosine deaminase protein or catalytic domain thereof capable of deaminating adenosine or cytidine in RNA or is an RNA specific adenosine deaminase and/or is a bacterial, human, cephalopod, or *Drosophila* adenosine deaminase protein or catalytic domain thereof, preferably TadA, more preferably ADAR, optionally huADAR, optionally (hu)ADAR1 or (hu)ADAR2, preferably huADAR2 or catalytic domain thereof.

The present application relates to modifying a target RNA sequence of interest (see, e.g, Cox et al., Science. 2017 Nov. 24; 358(6366):1019-1027). Using RNA-targeting rather than DNA targeting offers several advantages relevant for therapeutic development. First, there are substantial safety benefits to targeting RNA: there will be fewer off-target events because the available sequence space in the transcriptome is significantly smaller than the genome, and if an off-target event does occur, it will be transient and less likely to induce negative side effects. Second, RNA-targeting therapeutics will be more efficient because they are cell-type independent and do not have to enter the nucleus, making them easier to deliver.

A further aspect of the invention relates to the method and composition as envisaged herein for use in prophylactic or therapeutic treatment, preferably wherein said target locus of interest is within a human or animal and to methods of modifying an Adenine or Cytidine in a target RNA sequence of interest, comprising delivering to said target RNA, the composition as described herein. In particular embodiments, the CRISPR system and the adenosine deaminase, or catalytic domain thereof, are delivered as one or more polynucleotide molecules, as a ribonucleoprotein complex, optionally via particles, vesicles, or one or more viral vectors. In particular embodiments, the invention thus comprises compositions for use in therapy. This implies that the methods can be performed in vivo, ex vivo or in vitro. In particular embodiments, when the target is a human or animal target, the method is carried out ex vivo or in vitro.

A further aspect of the invention relates to the method as envisaged herein for use in prophylactic or therapeutic treatment, preferably wherein said target of interest is within a human or animal and to methods of modifying an adenine or cytidine in a target RNA sequence of interest, comprising delivering to said target RNA the composition as described herein. In particular embodiments, the CRISPR system and the adenosine deaminase, or catalytic domain thereof, are delivered as one or more polynucleotide molecules, as a ribonucleoprotein complex, optionally via particles, vesicles, or one or more viral vectors.

In one aspect, the invention provides a method of generating a eukaryotic cell comprising a modified or edited gene. In some embodiments, the method comprises (a) introducing one or more vectors into a eukaryotic cell, wherein the one or more vectors drive expression of one or more of a Cas effector module, and a guide sequence linked to a direct repeat sequence, wherein the Cas effector module associates one or more effector domains that mediate base editing, and (b) allowing a CRISPR-Cas effector module complex to bind to a target polynucleotide to effect base editing of the target polynucleotide within said disease gene, wherein the CRISPR-Cas effector module complex comprises a Cas effector module complexed with the guide sequence that is hybridized to the target sequence within the target polynucleotide, wherein the guide sequence may be designed to introduce one or more mismatches between the RNA/RNA duplex formed between the guide sequence and the target sequence. In particular embodiments, the mismatch is an A-C mismatch. In some embodiments, the Cas effector may associate with one or more functional domains (e.g. via fusion protein or suitable linkers). In some embodiments, the effector domain comprises one or more cytidine or adenosine deaminases that mediate endogenous editing of via hydrolytic deamination. In particular embodiments, the effector domain comprises the adenosine deaminase acting on RNA (ADAR) family of enzymes. In particular embodiments, the adenosine deaminase protein or catalytic domain thereof capable of deaminating adenosine or cytidine in RNA is an RNA specific adenosine deaminase and/or is a bacterial, human, cephalopod, or *Drosophila* adenosine deaminase protein or catalytic domain thereof, preferably TadA, more preferably ADAR, optionally huADAR, optionally (hu)ADAR1 or (hu)ADAR2, preferably huADAR2 or catalytic domain thereof.

A further aspect relates to an isolated cell obtained or obtainable from the methods described herein comprising the composition described herein or progeny of said modified cell, preferably wherein said cell comprises a hypoxanthine or a guanine in replacement of said adenine in said target RNA of interest compared to a corresponding cell not subjected to the method. In particular embodiments, the cell is a eukaryotic cell, preferably a human or non-human animal cell, optionally a therapeutic T cell or an antibody-producing B-cell.

In some embodiments, the modified cell is a therapeutic T cell, such as a T cell suitable for adoptive cell transfer therapies (e.g., CAR-T therapies). The modification may result in one or more desirable traits in the therapeutic T cell, as described further herein.

The invention further relates to a method for cell therapy, comprising administering to a patient in need thereof the modified cell described herein, wherein the presence of the modified cell remedies a disease in the patient.

The present invention may be further illustrated and extended based on aspects of CRISPR-Cas development and use as set forth in the following articles and particularly as relates to delivery of a CRISPR protein complex and uses of an RNA guided endonuclease in cells and organisms:

Multiplex genome engineering using CRISPR-Cas systems. Cong, L., Ran, F. A., Cox, D., Lin, S., Barretto, R., Habib, N., Hsu, P. D., Wu, X., Jiang, W., Marraffini, L. A., & Zhang, F. Science February 15; 339(6121): 819-23 (2013);

RNA-guided editing of bacterial genomes using CRISPR-Cas systems. Jiang W., Bikard D., Cox D., Zhang F, Marraffini L A. Nat Biotechnol March; 31(3):233-9 (2013);

One-Step Generation of Mice Carrying Mutations in Multiple Genes by CRISPR-Cas-Mediated Genome Engineering. Wang H., Yang H., Shivalila C S., Dawlaty M M., Cheng A W., Zhang F., Jaenisch R. Cell May 9; 153(4):910-8 (2013);

Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. August 22; 500(7463):472-6. doi: 10.1038/Nature12466. Epub 2013 Aug. 23 (2013);

Double Nicking by RNA-Guided CRISPR Cas9 for Enhanced Genome Editing Specificity. Ran, FA., Hsu, PD., Lin, CY., Gootenberg, J S., Konermann, S., Trevino, AE., Scott, DA., Inoue, A., Matoba, S., Zhang, Y., & Zhang, F. Cell August 28. pii: S0092-8674(13) 01015-5 (2013-A);

DNA targeting specificity of RNA-guided Cas9 nucleases. Hsu, P., Scott, D., Weinstein, J., Ran, FA., Konermann, S., Agarwala, V., Li, Y., Fine, E., Wu, X., Shalem, O., Cradick, TJ., Marraffini, LA., Bao, G., & Zhang, F. Nat Biotechnol doi:10.1038/nbt.2647 (2013);

Genome engineering using the CRISPR-Cas9 system. Ran, FA., Hsu, PD., Wright, J., Agarwala, V., Scott, DA., Zhang, F. Nature Protocols November; 8(11): 2281-308 (2013-B);

Genome-Scale CRISPR-Cas9 Knockout Screening in Human Cells. Shalem, O., Sanjana, NE., Hartenian, E., Shi, X., Scott, DA., Mikkelson, T., Heckl, D., Ebert, BL., Root, DE., Doench, JG., Zhang, F. Science December 12. (2013);

Crystal structure of cas9 in complex with guide RNA and target DNA. Nishimasu, H., Ran, FA., Hsu, PD., Konermann, S., Shehata, SI., Dohmae, N., Ishitani, R., Zhang, F., Nureki, O. Cell February 27, 156(5):935-49 (2014);

Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp P A. Nat Biotechnol. April 20. doi: 10.1038/nbt.2889 (2014);

CRISPR-Cas9 Knockin Mice for Genome Editing and Cancer Modeling. Platt R J, Chen S, Zhou Y, Yim M J, Swiech L, Kempton H R, Dahlman J E, Parnas O, Eisenhaure T M, Jovanovic M, Graham D B, Jhunjhunwala S, Heidenreich M, Xavier R J, Langer R, Anderson D G, Hacohen N, Regev A, Feng G, Sharp P A, Zhang F. Cell 159(2): 440-455 DOI: 10.1016/j.cell.2014.09.014(2014);

Development and Applications of CRISPR-Cas9 for Genome Engineering, Hsu P D, Lander E S, Zhang F., Cell. June 5; 157(6):1262-78 (2014).

Genetic screens in human cells using the CRISPR-Cas9 system, Wang T, Wei J J, Sabatini D M, Lander E S., Science. January 3; 343(6166): 80-84. doi:10.1126/science.1246981 (2014);

Rational design of highly active sgRNAs for CRISPR-Cas9-mediated gene inactivation, Doench J G, Hartenian E, Graham D B, Tothova Z, Hegde M, Smith I, Sullender M, Ebert B L, Xavier R J, Root D E., (published online 3 Sep. 2014) Nat Biotechnol. December; 32(12):1262-7 (2014);

In vivo interrogation of gene function in the mammalian brain using CRISPR-Cas9, Swiech L, Heidenreich M, Banerjee A, Habib N, Li Y, Trombetta J, Sur M, Zhang F., (published online 19 Oct. 2014) Nat Biotechnol. January; 33(1):102-6 (2015);

Genome-scale transcriptional activation by an engineered CRISPR-Cas9 complex, Konermann S, Brigham M D, Trevino A E, Joung J, Abudayyeh O O, Barcena C, Hsu P D, Habib N, Gootenberg J S, Nishimasu H, Nureki O, Zhang F., Nature. January 29; 517(7536):583-8 (2015).

A split-Cas9 architecture for inducible genome editing and transcription modulation, Zetsche B, Volz S E, Zhang F., (published online 2 Feb. 2015) Nat Biotechnol. February; 33(2):139-42 (2015);

Genome-wide CRISPR Screen in a Mouse Model of Tumor Growth and Metastasis, Chen S, Sanjana N E, Zheng K, Shalem O, Lee K, Shi X, Scott D A, Song J, Pan J Q, Weissleder R, Lee H, Zhang F, Sharp P A. Cell 160, 1246-1260, Mar. 12, 2015 (multiplex screen in mouse), and In vivo genome editing using *Staphylococcus aureus* Cas9, Ran F A, Cong L, Yan W X, Scott D A, Gootenberg J S, Kriz A J, Zetsche B, Shalem O, Wu X, Makarova K S, Koonin E V, Sharp P A, Zhang F., (published online 1 Apr. 2015), Nature. April 9; 520 (7546):186-91(2015).

Shalem et al., "High-throughput functional genomics using CRISPR-Cas9," Nature Reviews Genetics 16, 299-311 (May 2015).

Xu et al., "Sequence determinants of improved CRISPR sgRNA design," Genome Research 25, 1147-1157 (August 2015).

Parnas et al., "A Genome-wide CRISPR Screen in Primary Immune Cells to Dissect Regulatory Networks," Cell 162, 675-686 (Jul. 30, 2015).

Ramanan et al., "CRISPR-Cas9 cleavage of viral DNA efficiently suppresses hepatitis B virus," Scientific Reports 5:10833. doi: 10.1038/srep10833 (Jun. 2, 2015)

Nishimasu et al., "Crystal Structure of *Staphylococcus aureus* Cas9," Cell 162, 1113-1126 (Aug. 27, 2015)

BCL11A enhancer dissection by Cas9-mediated in situ saturating mutagenesis, Canver et al., Nature 527

(7577):192-7 (Nov. 12, 2015) doi: 10.1038/nature15521. Epub 2015 Sep. 16.

Cpf1 Is a Single RNA-Guided Endonuclease of a Class 2 CRISPR-Cas System, Zetsche et al., Cell 163, 759-71 (Sep. 25, 2015).

Discovery and Functional Characterization of Diverse Class 2 CRISPR-Cas Systems, Shmakov et al., Molecular Cell, 60(3), 385-397 doi: 10.1016/j.molcel.2015.10.008 Epub Oct. 22, 2015.

Rationally engineered Cas9 nucleases with improved specificity, Slaymaker et al., Science 2016 Jan. 1 351 (6268): 84-88 doi: 10.1126/science.aad5227. Epub 2015 Dec. 1.

Gao et al, "Engineered Cpf1 Enzymes with Altered PAM Specificities," bioRxiv 091611; doi: http://dx.doi.org/10.1101/091611 (Dec. 4, 2016).

Cox et al., "RNA editing with CRISPR-Cas13," Science. 2017 Nov. 24; 358(6366):1019-1027. doi: 10.1126/science.aaq0180. Epub 2017 Oct. 25.

each of which is incorporated herein by reference, may be considered in the practice of the instant invention, and discussed briefly below:

Cong et al. engineered type II CRISPR-Cas systems for use in eukaryotic cells based on both *Streptococcus thermophilus* Cas9 and also *Streptococcus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR-Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of *Streptococcus pneumoniae* and *Escherichia coli*. The approach relied on dual-RNA:Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multinucleotide changes carried on editing templates. The study showed that simultaneous use of two crRNAs enabled multiplex mutagenesis. Furthermore, when the approach was used in combination with recombineering, in *S. pneumoniae*, nearly 100% of cells that were recovered using the described approach contained the desired mutation, and in *E. coli*, 65% that were recovered contained the mutation.

Wang et al. (2013) used the CRISPR-Cas system for the one-step generation of mice carrying mutations in multiple genes which were traditionally generated in multiple steps by sequential recombination in embryonic stem cells and/or time-consuming intercrossing of mice with a single mutation. The CRISPR-Cas system will greatly accelerate the in vivo study of functionally redundant genes and of epistatic gene interactions.

Konermann et al. (2013) addressed the need in the art for versatile and robust technologies that enable optical and chemical modulation of DNA-binding domains based CRISPR Cas9 enzyme and also Transcriptional Activator Like Effectors.

Ran et al. (2013-A) described an approach that combined a Cas9 nickase mutant with paired guide RNAs to introduce targeted double-strand breaks. This addresses the issue of the Cas9 nuclease from the microbial CRISPR-Cas system being targeted to specific genomic loci by a guide sequence, which can tolerate certain mismatches to the DNA target and thereby promote undesired off-target mutagenesis. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. (2013) characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors showed that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and guide RNA can be titrated to minimize off-target modification. Additionally, to facilitate mammalian genome engineering applications, the authors reported providing a web-based software tool to guide the selection and validation of target sequences as well as off-target analyses.

Ran et al. (2013-B) described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knockout (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of *Streptococcus pyogenes* Cas9 in complex with sgRNA and its target DNA at 2.5 A° resolution. The structure revealed a bilobed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from *Streptococcus pyogenes* loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Platt et al. established a Cre-dependent Cas9 knockin mouse. The authors demonstrated in vivo as well as ex vivo genome editing using adeno-associated virus (AAV)-, lentivirus-, or particle-mediated delivery of guide RNA in neurons, immune cells, and endothelial cells.

Hsu et al. (2014) is a review article that discusses generally CRISPR-Cas9 history from yogurt to genome editing, including genetic screening of cells.

Wang et al. (2014) relates to a pooled, loss-of-function genetic screening approach suitable for both positive and negative selection that uses a genome-scale lentiviral single guide RNA (sgRNA) library.

Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

Swiech et al. demonstrate that AAV-mediated SpCas9 genome editing can enable reverse genetic studies of gene function in the brain.

Konermann et al. (2015) discusses the ability to attach multiple effector domains, e.g., transcriptional activator, functional and epigenomic regulators at appropriate positions on the guide such as stem or tetraloop with and without linkers.

Zetsche et al. demonstrates that the Cas9 enzyme can be split into two and hence the assembly of Cas9 for activation can be controlled.

Chen et al. relates to multiplex screening by demonstrating that a genome-wide in vivo CRISPR-Cas9 screen in mice reveals genes regulating lung metastasis.

Ran et al. (2015) relates to SaCas9 and its ability to edit genomes and demonstrates that one cannot extrapolate from biochemical assays.

Shalem et al. (2015) described ways in which catalytically inactive Cas9 (dCas9) fusions are used to synthetically repress (CRISPRi) or activate (CRISPRa) expression, showing advances using Cas9 for genome-scale screens, including arrayed and pooled screens, knockout approaches that inactivate genomic loci and strategies that modulate transcriptional activity.

Xu et al. (2015) assessed the DNA sequence features that contribute to single guide RNA (sgRNA) efficiency in CRISPR-based screens. The authors explored efficiency of CRISPR-Cas9 knockout and nucleotide preference at the cleavage site. The authors also found that the sequence preference for CRISPRi/a is substantially different from that for CRISPR-Cas9 knockout.

Parnas et al. (2015) introduced genome-wide pooled CRISPR-Cas9 libraries into dendritic cells (DCs) to identify genes that control the induction of tumor necrosis factor (Tnf) by bacterial lipopolysaccharide (LPS). Known regulators of Tlr4 signaling and previously unknown candidates were identified and classified into three functional modules with distinct effects on the canonical responses to LPS.

Ramanan et al. (2015) demonstrated cleavage of viral episomal DNA (cccDNA) in infected cells. The HBV genome exists in the nuclei of infected hepatocytes as a 3.2 kb double-stranded episomal DNA species called covalently closed circular DNA (cccDNA), which is a key component in the HBV life cycle whose replication is not inhibited by current therapies. The authors showed that sgRNAs specifically targeting highly conserved regions of HBV robustly suppresses viral replication and depleted cccDNA.

Nishimasu et al. (2015) reported the crystal structures of SaCas9 in complex with a single guide RNA (sgRNA) and its double-stranded DNA targets, containing the 5'-TTGAAT-3' PAM and the 5'-TTGGGT-3' PAM. A structural comparison of SaCas9 with SpCas9 highlighted both structural conservation and divergence, explaining their distinct PAM specificities and orthologous sgRNA recognition.

Canver et al. (2015) demonstrated a CRISPR-Cas9-based functional investigation of non-coding genomic elements. The authors developed pooled CRISPR-Cas9 guide RNA libraries to perform in situ saturating mutagenesis of the human and mouse BCL11A enhancers which revealed critical features of the enhancers.

Zetsche et al. (2015) reported characterization of Cpf1, a class 2 CRISPR nuclease from *Francisella novicida* U112 having features distinct from Cas9. Cpf1 is a single RNA-guided endonuclease lacking tracrRNA, utilizes a T-rich protospacer-adjacent motif, and cleaves DNA via a staggered DNA double-stranded break.

Shmakov et al. (2015) reported three distinct Class 2 CRISPR-Cas systems. Two system CRISPR enzymes (C2c1 and C2c3) contain RuvC-like endonuclease domains distantly related to Cpf1. Unlike Cpf1, C2c1 depends on both crRNA and tracrRNA for DNA cleavage. The third enzyme (C2c2) contains two predicted HEPN RNase domains and is tracrRNA independent.

Slaymaker et al. (2016) reported the use of structure-guided protein engineering to improve the specificity of *Streptococcus pyogenes* Cas9 (SpCas9). The authors developed "enhanced specificity" SpCas9 (eSpCas9) variants which maintained robust on-target cleavage with reduced off-target effects.

Cox et al. (2017) reported the use of catalytically inactive Cas13 (dCas13) to direct adenosine-to-inosine deaminase activity by ADAR2 (adenosine deaminase acting on RNA type 2) to transcripts in mammalian cells. The system, referred to as RNA Editing for Programmable A to I Replacement (REPAIR), has no strict sequence constraints and can be used to edit full-length transcripts. The authors further engineered the system to create a high-specificity variant and minimized the system to facilitate viral delivery.

The methods and tools provided herein may be designed for use with Cas13, a type II nuclease that does not make use of tracrRNA. Orthologs of Cas13 have been identified in different bacterial species as described herein. Further type II nucleases with similar properties can be identified using methods described in the art (Shmakov et al. 2015, 60:385-397; Abudayeh et al. 2016, Science, 5; 353(6299)). In particular embodiments, such methods for identifying novel CRISPR effector proteins may comprise the steps of selecting sequences from the database, encoding a seed which identifies the presence of a CRISPR Cas locus, identifying loci located within 10 kb of the seed comprising Open Reading Frames (ORFs) in the selected sequences, selecting therefrom loci comprising ORFs of which only a single ORF encodes a novel CRISPR effector having greater than 700 amino acids and no more than 90% homology to a known CRISPR effector. In particular embodiments, the seed is a protein that is common to the CRISPR-Cas system, such as Cas1. In further embodiments, the CRISPR array is used as a seed to identify new effector proteins.

Also, "Dimeric CRISPR RNA-guided FokI nucleases for highly specific genome editing", Shengdar Q. Tsai, Nicolas Wyvekens, Cyd Khayter, Jennifer A. Foden, Vishal Thapar, Deepak Reyon, Mathew J. Goodwin, Martin J. Aryee, J. Keith Joung, Nature Biotechnology 32(6): 569-77 (2014), relates to dimeric RNA-guided FokI nucleases that recognize extended sequences and can edit endogenous genes with high efficiencies in human cells.

With respect to general information on CRISPR/Cas Systems, components thereof, and delivery of such components, including methods, materials, delivery vehicles, vectors, particles, and making and using thereof, including as to amounts and formulations, as well as CRISPR-Cas-expressing eukaryotic cells, CRISPR-Cas expressing eukaryotes, such as a mouse, reference is made to: U.S. Pat. Nos. 8,999,641, 8,993,233, 8,697,359, 8,771,945, 8,795,965, 8,865,406, 8,871,445, 8,889,356, 8,889,418, 8,895,308, 8,906,616, 8,932,814, and 8,945,839; US Patent Publications US 2014-0310830 A1 (U.S. application Ser. No. 14/105,031), US 2014-0287938 A1 (U.S. application Ser. No. 14/213,991), US 2014-0273234 A1 (U.S. application Ser. No. 14/293,674), US 2014-0273232 A1 (U.S. application Ser. No. 14/290,575), US 2014-0273231 A1 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256,912), US 2014-0189896 A1 (U.S. application Ser. No. 14/105,035), US 2014-0186958 A1 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 A1 (U.S. application Ser. No. 14/183,429); US 2015-0184139 A1 (U.S. application Ser. No. 14/324,960); Ser. No. 14/054,414 European Patent Applications EP 2 771 468 (EP13818570.7), EP 2 764 103 (EP13824232.6), and EP 2 784 162 (EP14170383.5); and PCT Patent Publications WO2014/093661 (PCT/US2013/074743), WO2014/093694 (PCT/US2013/074790), WO2014/093595 (PCT/US2013/074611), WO2014/093718 (PCT/US2013/074825), WO2014/093709 (PCT/US2013/074812), WO2014/093622 (PCT/US2013/074667), WO2014/093635 (PCT/US2013/074691), WO2014/093655 (PCT/US2013/074736), WO2014/093712 (PCT/US2013/074819), WO2014/093701 (PCT/US2013/074800), WO2014/018423 (PCT/US2013/051418), WO2014/204723 (PCT/US2014/041790), WO2014/204724 (PCT/US2014/041800), WO2014/204725 (PCT/US2014/041803), WO2014/204726 (PCT/US2014/041804), WO2014/204727 (PCT/US2014/041806), WO2014/204728 (PCT/US2014/041808), WO2014/204729 (PCT/US2014/041809), WO2015/089351 (PCT/US2014/069897), WO2015/089354 (PCT/US2014/069902), WO2015/089364 (PCT/US2014/069925), WO2015/089427 (PCT/US2014/070068), WO2015/089462 (PCT/US2014/070127), WO2015/089419 (PCT/US2014/070057), WO2015/089465 (PCT/US2014/070135), WO2015/089486 (PCT/US2014/070175), WO2015/058052 (PCT/US2014/061077), WO2015/070083 (PCT/US2014/064663), WO2015/089354 (PCT/US2014/069902), WO2015/089351 (PCT/US2014/069897), WO2015/089364 (PCT/US2014/069925), WO2015/089427 (PCT/US2014/070068), WO2015/089473 (PCT/US2014/070152), WO2015/089486 (PCT/US2014/070175), WO2016/049258 (PCT/US2015/051830), WO2016/094867 (PCT/US2015/065385), WO2016/094872 (PCT/US2015/065393), WO2016/094874 (PCT/US2015/065396), WO2016/106244 (PCT/US2015/067177).

Mention is also made of U.S. application 62/180,709, 17 Jun. 2015, PROTECTED GUIDE RNAS (PGRNAS); U.S. application 62/091,455, filed, 12 Dec. 2014, PROTECTED GUIDE RNAS (PGRNAS); U.S. application 62/096,708, 24 Dec. 2014, PROTECTED GUIDE RNAS (PGRNAS); U.S. applications 62/091,462, 12 Dec. 2014, 62/096,324, 23 Dec. 2014, 62/180,681, 17 Jun. 2015, and 62/237,496, 5 Oct. 2015, DEAD GUIDES FOR CRISPR TRANSCRIPTION FACTORS; U.S. application 62/091,456, 12 Dec. 2014 and 62/180,692, 17 Jun. 2015, ESCORTED AND FUNCTIONALIZED GUIDES FOR CRISPR-CAS SYSTEMS; U.S. application 62/091,461, 12 Dec. 2014, DELIVERY, USE AND THERAPEUTIC APPLICATIONS OF THE CRISPR-CAS SYSTEMS AND COMPOSITIONS FOR GENOME EDITING AS TO HEMATOPOIETIC STEM CELLS (HSCs); U.S. application 62/094,903, 19 Dec. 2014, UNBIASED IDENTIFICATION OF DOUBLE-STRAND BREAKS AND GENOMIC REARRANGEMENT BY GENOME-WISE INSERT CAPTURE SEQUENCING; U.S. application 62/096,761, 24 Dec. 2014, ENGINEERING OF SYSTEMS, METHODS AND OPTIMIZED ENZYME AND GUIDE SCAFFOLDS FOR SEQUENCE MANIPULATION; U.S. application 62/098,059, 30 Dec. 2014, 62/181,641, 18 Jun. 2015, and 62/181,667, 18 Jun. 2015, RNA-TARGETING SYSTEM; U.S. application 62/096,656, 24 Dec. 2014 and 62/181,151, 17 Jun. 2015, CRISPR HAVING OR ASSOCIATED WITH DESTABILIZATION DOMAINS; U.S. application 62/096,697, 24 Dec. 2014, CRISPR HAVING OR ASSOCIATED WITH AAV; U.S. application 62/098,158, 30 Dec. 2014, ENGINEERED CRISPR COMPLEX INSERTIONAL TARGETING SYSTEMS; U.S. application 62/151,052, 22 Apr. 2015, CELLULAR TARGETING FOR EXTRACELLULAR EXOSOMAL REPORTING; U.S. application 62/054,490, 24 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS; U.S. application 61/939,154, 12 Feb. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/055,484, 25 Sep. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/087,537, 4 Dec. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/054,651, 24 Sep. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/067,886, 23 Oct. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. applications 62/054,675, 24 Sep. 2014 and 62/181,002, 17 Jun. 2015, DELIVERY, USE AND THERAPEUTIC APPLICATIONS OF THE CRISPR-CAS SYSTEMS AND COMPOSITIONS IN NEURONAL CELLS/TISSUES; U.S. application 62/054,528, 24 Sep. 2014, DELIVERY, USE AND THERAPEUTIC APPLICATIONS OF THE CRISPR-CAS SYSTEMS AND COMPOSITIONS IN IMMUNE DISEASES OR DISORDERS; U.S. application 62/055,454, 25 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING CELL PENETRATION PEPTIDES (CPP); U.S. application 62/055,460, 25 Sep. 2014, MULTIFUNCTIONAL-CRISPR COMPLEXES AND/OR OPTIMIZED ENZYME LINKED FUNCTIONAL-CRISPR COMPLEXES; U.S. application 62/087,475, 4 Dec. 2014 and 62/181,690, 18 Jun. 2015, FUNCTIONAL SCREENING WITH OPTIMIZED FUNCTIONAL CRISPR-CAS SYSTEMS; U.S. application 62/055,487, 25 Sep. 2014, FUNCTIONAL SCREENING WITH OPTIMIZED FUNCTIONAL CRISPR-CAS SYSTEMS; U.S. application 62/087,546, 4 Dec. 2014 and 62/181,687, 18 Jun. 2015, MULTIFUNCTIONAL CRISPR COMPLEXES AND/OR OPTIMIZED ENZYME LINKED FUNCTIONAL-CRISPR COMPLEXES; and U.S. application 62/098,285, 30 Dec. 2014, CRISPR MEDIATED IN VIVO MODELING AND GENETIC SCREENING OF TUMOR GROWTH AND METASTASIS.

Mention is made of U.S. applications 62/181,659, 18 Jun. 2015 and 62/207,318, 19 Aug. 2015, ENGINEERING AND OPTIMIZATION OF SYSTEMS, METHODS, ENZYME AND GUIDE SCAFFOLDS OF CAS9 ORTHOLOGS AND VARIANTS FOR SEQUENCE MANIPULATION. Mention is made of U.S. applications 62/181,663, 18 Jun. 2015 and 62/245,264, 22 Oct. 2015, NOVEL CRISPR ENZYMES AND SYSTEMS, U.S. applications 62/181,675, 18 Jun. 2015, 62/285,349, 22 Oct. 2015, 62/296,522, 17 Feb. 2016, and 62/320,231, 8 Apr. 2016, NOVEL CRISPR ENZYMES AND SYSTEMS, U.S. application 62/232,067, 24 Sep. 2015, U.S. application Ser. No. 14/975,085, 18 Dec. 2015, European application No. 16150428.7, U.S. application 62/205,733, 16 Aug. 2015, U.S. application 62/201,542, 5 Aug. 2015, U.S. application 62/193,507, 16 Jul. 2015, and U.S. application 62/181,739, 18 Jun. 2015, each entitled NOVEL CRISPR ENZYMES AND SYSTEMS and of U.S. application 62/245,270, 22 Oct. 2015, NOVEL CRISPR ENZYMES AND SYSTEMS. Mention is also made of U.S. application 61/939,256, 12 Feb. 2014, and WO 2015/089473 (PCT/US2014/070152), 12 Dec. 2014, each entitled ENGINEERING OF SYSTEMS, METHODS AND OPTIMIZED GUIDE COMPOSITIONS WITH NEW ARCHITECTURES FOR SEQUENCE MANIPULATION. Mention is also made of PCT/US2015/045504, 15 Aug. 2015, U.S. application 62/180,699, 17 Jun. 2015, and U.S. application 62/038,358, 17 Aug. 2014, each entitled GENOME EDITING USING CAS9 NICKASES.

Each of these patents, patent publications, and applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appln cited documents) are incorporated herein by reference to the same extent as if each individual document was specifically and individually indicated to be incorporated by reference.

In particular embodiments, pre-complexed guide RNA and CRISPR effector protein, (optionally, adenosine deaminase fused to a CRISPR protein or an adaptor) are delivered as a ribonucleoprotein (RNP). RNPs have the advantage that they lead to rapid editing effects even more so than the RNA method because this process avoids the need for transcription. An important advantage is that both RNP delivery is transient, reducing off-target effects and toxicity issues. Efficient genome editing in different cell types has been observed by Kim et al. (2014, Genome Res. 24(6):1012-9), Paix et al. (2015, Genetics 204(1):47-54), Chu et al. (2016, BMC Biotechnol. 16:4), and Wang et al. (2013, Cell. 9; 153(4):910-8).

In particular embodiments, the ribonucleoprotein is delivered by way of a polypeptide-based shuttle agent as described in WO 2016/161516. WO 2016/161516 describes efficient transduction of polypeptide cargos using synthetic peptides comprising an endosome leakage domain (ELD) operably linked to a cell penetrating domain (CPD), to a histidine-rich domain and a CPD. Similarly, these polypeptides can be used for the delivery of CRISPR-effector based RNPs in eukaryotic cells.

The Cas proteins may include homologues and orthologues of the Cas proteins described herein. The terms "orthologue" (also referred to as "ortholog" herein) and "homologue" (also referred to as "homolog" herein) are well known in the art. By means of further guidance, a "homologue" of a protein as used herein is a protein of the same species which performs the same or a similar function as the protein it is a homologue of. Homologous proteins may but need not be structurally related, or are only partially structurally related. An "orthologue" of a protein as used herein is a protein of a different species which performs the same or a similar function as the protein it is an orthologue of. Orthologous proteins may but need not be structurally related, or are only partially structurally related. Thus, when reference is made to mouse genes and proteins, it is understood that the same is believed to apply to the corresponding ortholog in humans or other species.

Likewise, when referencing Cas9 and other proteins, it is understood to likewise apply to orthologs and homologs.

The CRISPR-CRISPR associated (Cas) systems of bacterial and archaeal adaptive immunity are some such systems that show extreme diversity of protein composition and genomic loci architecture. The CRISPR-Cas system loci has more than 50 gene families and there is no strictly universal genes indicating fast evolution and extreme diversity of loci architecture. So far, adopting a multi-pronged approach, there is comprehensive cas gene identification of about 395 profiles for 93 Cas proteins. Classification includes signature gene profiles plus signatures of locus architecture. A new classification of CRISPR-Cas systems is proposed in which these systems are broadly divided into two classes, Class 1 with multisubunit effector complexes and Class 2 with single-subunit effector modules exemplified by the Cas9 protein. Novel effector proteins associated with Class 2 CRISPR-Cas systems may be developed as powerful genome engineering tools and the prediction of putative novel effector proteins and their engineering and optimization is important.

The effector protein may comprise a chimeric effector protein comprising a first fragment from a first effector protein ortholog and a second fragment from a second effector protein ortholog, and wherein the first and second effector protein orthologs are different. At least one of the first and second effector protein orthologs may comprise an effector protein from an organism comprising *Bergeyella, Prevotella, Porphyromonas, Bacteroides, Alistipes, Riemerella, Myroides, Flavobacterium, Capnocytophaga, Chryseobacterium, Paludibacter, Phaeodactylibacter* or *Psychroflexus*.

In certain embodiments, the effector protein, particularly a Group 29 or Group 30 effector protein may be at least 700 amino acids long. In preferred embodiments, the effector protein may be about 1100 to about 1500 amino acids long, e.g., about 1100 to about 1200 amino acids long, or about 1200 to about 1300 amino acids long, or about 1300 to about 1400 amino acids long, or about 1400 to about 1500 amino acids long, e.g., about 900, about 1000, about 1100, about 1200, about 1300, about 1400, about 1500, about 1600, about 1700, or about 1800 amino acids long.

In certain embodiments, the Group 29 or Group 30 effector proteins as intended herein may be associated with a locus comprising short CRISPR repeats between 30 and 40 bp long, more typically between 34 and 38 bp long, even more typically between 36 and 37 bp long, e.g., 30, 31, 32, 33, 34, 35, 36, 37, 38, 39, or 40 bp long. In certain embodiments, the CRISPR repeats are long or dual repeats between 80 and 350 bp long such as between 80 and 200 bp long, even more typically between 86 and 88 bp long, e.g., 80, 81, 82, 83, 84, 85, 86, 87, 88, 89, or 90 bp long.

Orthologous proteins may but need not be structurally related, or are only partially structurally related. In particular embodiments, the homologue or orthologue of a Group 29 or Group 30 protein as referred to herein has a sequence homology or identity of at least 80%, more preferably at least 85%, even more preferably at least 90%, such as for instance at least 95% with the Group 29 or Group 30 effector protein. In a preferred embodiment, the Group 29 or Group 30 effector protein may be an ortholog of an organism of a genus which includes, but is not limited to, *Bergeyella, Prevotella, Porphyromonas, Bacteroides, Alistipes, Riemerella, Myroides, Flavobacterium, Capnocytophaga, Chryseobacterium, Phaeodactylibacter, Paludibacter* or *Psychroflexus*. Some methods of identifying orthologs of CRISPR system enzymes may involve identifying tracr sequences in genomes of interest. Identification of tracr sequences may relate to the following steps: Search for the direct repeats or tracr mate sequences in a database to identify a CRISPR region comprising a CRISPR enzyme. Search for homologous sequences in the CRISPR region flanking the CRISPR enzyme in both the sense and antisense directions. Look for transcriptional terminators and secondary structures. Identify any sequence that is not a direct repeat or a tracr mate sequence but has more than 50% identity to the direct repeat or tracr mate sequence as a potential tracr sequence. Take the potential tracr sequence and analyze for transcriptional terminator sequences associated therewith.

It will be appreciated that any of the functionalities described herein may be engineered into CRISPR enzymes from other orthologs, including chimeric enzymes comprising fragments from multiple orthologs. Examples of such orthologs are described elsewhere herein. Thus, chimeric enzymes may comprise fragments of CRISPR enzyme orthologs of an organism which includes, but is not limited to, *Bergeyella, Prevotella, Porphyromonas, Bacteroides, Alistipes, Riemerella, Myroides, Flavobacterium, Capnocytophaga, Chryseobacterium, Phaeodactylibacter, Paludibacter* or *Psychroflexus*. A chimeric enzyme can comprise a first fragment and a second fragment, and the fragments can be of CRISPR enzyme orthologs of organisms of genuses herein mentioned or of species herein mentioned; advantageously the fragments are from CRISPR enzyme orthologs of different species.

TALE Systems

The modulating agents may be one or more components of a TALE system, or nucleic acids encoding thereof. As disclosed herein, editing can be made by way of the transcription activator-like effector nucleases (TALENs) system. Transcription activator-like effectors (TALEs) can be engineered to bind practically any desired DNA sequence. Exemplary methods of genome editing using the TALEN system can be found, for example, in Cermak T. Doyle E L. Christian M. Wang L. Zhang Y. Schmidt C, et al. Efficient design and assembly of custom TALEN and other TAL effector-based constructs for DNA targeting. Nucleic Acids Res. 2011; 39:e82; Zhang F. Cong L. Lodato S. Kosuri S. Church G M. Arlotta P Efficient construction of sequence-specific TAL effectors for modulating mammalian transcription. Nat Biotechnol. 2011; 29:149-153 and U.S. Pat. Nos. 8,450,471, 8,440,431 and 8,440,432, all of which are specifically incorporated by reference.

In some embodiments, the methods provided herein use isolated, non-naturally occurring, recombinant or engineered DNA binding proteins that comprise TALE monomers as a part of their organizational structure that enable the targeting of nucleic acid sequences with improved efficiency and expanded specificity.

Naturally occurring TALEs or "wild type TALEs" are nucleic acid binding proteins secreted by numerous species of proteobacteria. TALE polypeptides contain a nucleic acid binding domain composed of tandem repeats of highly conserved monomer polypeptides that are predominantly 33, 34 or 35 amino acids in length and that differ from each other mainly in amino acid positions 12 and 13. In advantageous embodiments, the nucleic acid is DNA. As used herein, the term "polypeptide monomers", or "TALE monomers" will be used to refer to the highly conserved repetitive polypeptide sequences within the TALE nucleic acid binding domain and the term "repeat variable di-residues" or "RVD" will be used to refer to the highly variable amino acids at positions 12 and 13 of the polypeptide monomers. As provided throughout the disclosure, the amino acid residues of the RVD are depicted using the IUPAC single letter code for amino acids. A general representation of a TALE monomer which is comprised within the DNA binding domain is $X_{1-11}$—$(X_{12}X_{13})$—$X_{14-33}$ or 34 or 35, where the subscript indicates the amino acid position and X represents any amino acid. $X_{12}X_{13}$ indicate the RVDs. In some polypeptide monomers, the variable amino acid at position 13 is missing or absent and in such polypeptide monomers, the RVD consists of a single amino acid. In such cases, the RVD may be alternatively represented as X*, where X represents $X_{12}$ and (*) indicates that $X_{13}$ is absent. The DNA binding domain comprises several repeats of TALE monomers and this may be represented as $(X_{11}$—$(X_{12}X_{13})$—$X_{14-33}$ or 34 or 35)z, where in an advantageous embodiment z is at least 5 to 40. In a further advantageous embodiment, z is at least 10 to 26.

The TALE monomers have a nucleotide binding affinity that is determined by the identity of the amino acids in its RVD. For example, polypeptide monomers with an RVD of NI preferentially bind to adenine (A), polypeptide monomers with an RVD of NG preferentially bind to thymine (T), polypeptide monomers with an RVD of HD preferentially bind to cytosine (C) and polypeptide monomers with an RVD of NN preferentially bind to both adenine (A) and guanine (G). In yet another embodiment of the invention, polypeptide monomers with an RVD of IG preferentially bind to T. Thus, the number and order of the polypeptide monomer repeats in the nucleic acid binding domain of a TALE determines its nucleic acid target specificity. In still further embodiments of the invention, polypeptide monomers with an RVD of NS recognize all four base pairs and may bind to A, T, G or C. The structure and function of TALEs is further described in, for example, Moscou et al., Science 326:1501 (2009); Boch et al., Science 326:1509-1512 (2009); and Zhang et al., Nature Biotechnology 29:149-153 (2011), each of which is incorporated by reference in its entirety.

The TALE polypeptides used in methods of the invention are isolated, non-naturally occurring, recombinant or engineered nucleic acid-binding proteins that have nucleic acid or DNA binding regions containing polypeptide monomer repeats that are designed to target specific nucleic acid sequences.

As described herein, polypeptide monomers having an RVD of HN or NH preferentially bind to guanine and thereby allow the generation of TALE polypeptides with high binding specificity for guanine containing target nucleic acid sequences. In a preferred embodiment of the invention, polypeptide monomers having RVDs RN, NN, NK, SN, NH, KN, HN, NQ, HH, RG, KH, RH and SS preferentially bind to guanine. In a much more advantageous embodiment of the invention, polypeptide monomers having RVDs RN, NK, NQ, HH, KH, RH, SS and SN preferentially bind to guanine and thereby allow the generation of TALE polypeptides with high binding specificity for guanine containing target nucleic acid sequences. In an even more advantageous embodiment of the invention, polypeptide monomers having RVDs HH, KH, NH, NK, NQ, RH, RN and SS preferentially bind to guanine and thereby allow the generation of TALE polypeptides with high binding specificity for guanine containing target nucleic acid sequences. In a further advantageous embodiment, the RVDs that have high binding specificity for guanine are RN, NH RH and KH. Furthermore, polypeptide monomers having an RVD of NV preferentially bind to adenine and guanine. In more preferred embodiments of the invention, polypeptide monomers having RVDs of H*, HA, KA, N*, NA, NC, NS, RA, and S* bind to adenine, guanine, cytosine and thymine with comparable affinity.

Figure 8:
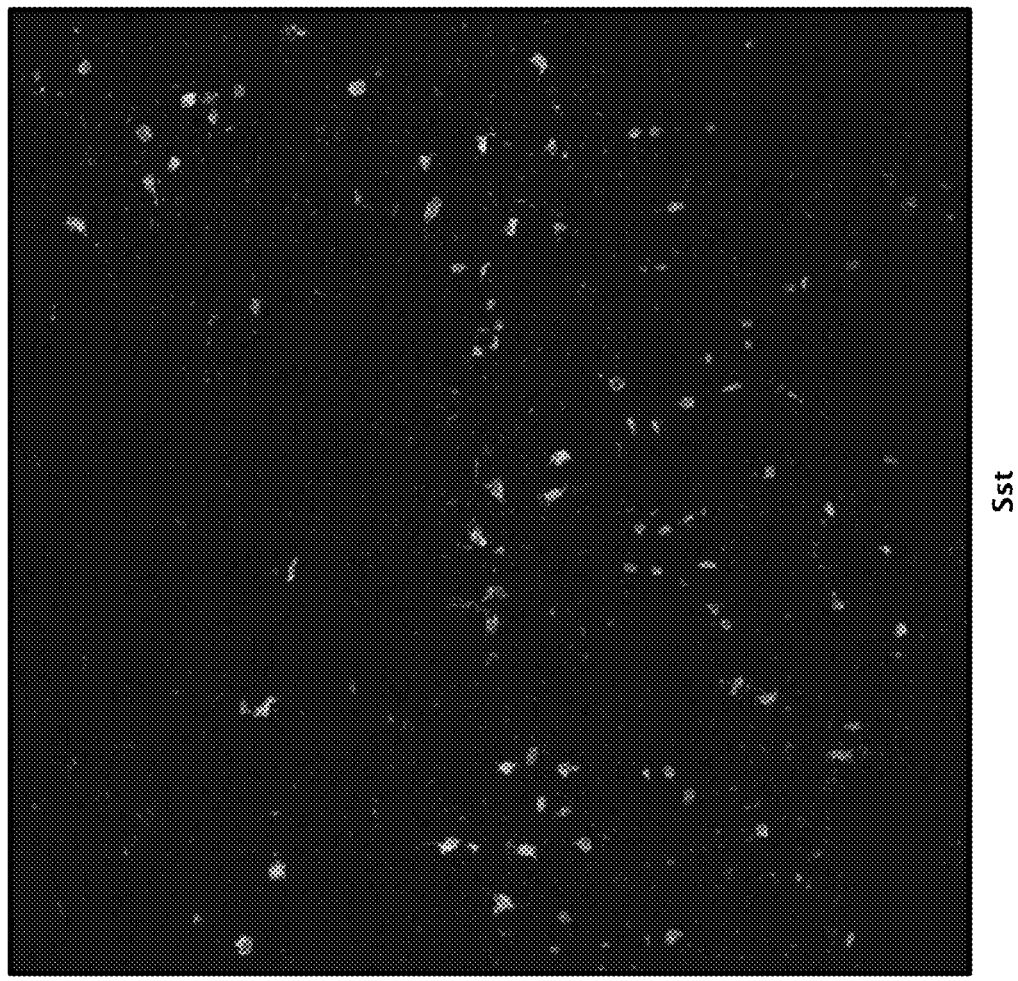
FIG. 8 shows a validation of experiments analyzing the Sst gene by making direct and composite measurements in the same tissue.

The predetermined N-terminal to C-terminal order of the one or more polypeptide monomers of the nucleic acid or DNA binding domain determines the corresponding predetermined target nucleic acid sequence to which the TALE polypeptides will bind. As used herein, the polypeptide monomers and at least one or more half polypeptide monomers are "specifically ordered to target" the genomic locus or gene of interest. In plant genomes, the natural TALE-binding sites always begin with a thymine (T), which may be specified by a cryptic signal within the non-repetitive N-terminus of the TALE polypeptide; in some cases, this region may be referred to as repeat 0. In animal genomes, TALE binding sites do not necessarily have to begin with a thymine (T) and TALE polypeptides may target DNA sequences that begin with T, A, G or C. The tandem repeat of TALE monomers always ends with a half-length repeat or a stretch of sequence that may share identity with only the first 20 amino acids of a repetitive full length TALE monomer and this half repeat may be referred to as a half-monomer (FIG. 8), which is included in the term "TALE monomer". Therefore, it follows that the length of the nucleic acid or DNA being targeted is equal to the number of full polypeptide monomers plus two.

As described in Zhang et al., Nature Biotechnology 29:149-153 (2011), TALE polypeptide binding efficiency may be increased by including amino acid sequences from the "capping regions" that are directly N-terminal or C-terminal of the DNA binding region of naturally occurring TALEs into the engineered TALEs at positions N-terminal or C-terminal of the engineered TALE DNA binding region. Thus, in certain embodiments, the TALE polypeptides described herein further comprise an N-terminal capping region and/or a C-terminal capping region.

An exemplary amino acid sequence of a N-terminal capping region is:

(SEQ. I.D. No. 4)
M D P I R S R T P S P A R E L L S G P Q P D G V Q P

T A D R G V S P P A G G P L D G L P A R R T M S R T

R L P S P P A P S P A F S A D S F S D L L R Q F D P

-continued

```
S L F N T S L F D S L P P F G A H H T E A A T G E W

D E V Q S G L R A A D A P P P T M R V A V T A A R P

P R A K P A P R R R A A Q P S D A S P A A Q V D L R

T L G Y S Q Q Q Q E K I K P K V R S T V A Q H H E A

L V G H G F T H A H I V A L S Q H P A A L G T V A V

K Y Q D M I A A L P E A T H E A I V G V K Q W S G

A R A L E A L L T V A G E L R G P P L Q L D T G Q L

L K I A K R G G V T A V E A V H A W R N A L T G A P

L N
```

An exemplary amino acid sequence of a C-terminal capping region is:

```
                                          (SEQ. I.D. No. 5)
R P A L E S I V A Q L S R P D P A L A A L T N D H L

V A L A C L G G R P A L D A V K K G L P H A P A L I

K R T N R R I P E R T S H R V A D H A Q V V R V L G

F F Q C H S H P A Q A F D D A M T Q F G M S R H G L

L Q L F R R V G V T E L E A R S G T L P P A S Q R W

D R I L Q A S G M K R A K P S P T S T Q T P D Q A S

L H A F A D S L E R D L D A P S P M H E G D Q T R A

S
```

As used herein, the predetermined "N-terminus" to "C terminus" orientation of the N-terminal capping region, the DNA binding domain comprising the repeat TALE monomers and the C-terminal capping region provide structural basis for the organization of different domains in the d-TALEs or polypeptides of the invention.

The entire N-terminal and/or C-terminal capping regions are not necessary to enhance the binding activity of the DNA binding region. Therefore, in certain embodiments, fragments of the N-terminal and/or C-terminal capping regions are included in the TALE polypeptides described herein.

In certain embodiments, the TALE polypeptides described herein contain a N-terminal capping region fragment that included at least 10, 20, 30, 40, 50, 54, 60, 70, 80, 87, 90, 94, 100, 102, 110, 117, 120, 130, 140, 147, 150, 160, 170, 180, 190, 200, 210, 220, 230, 240, 250, 260 or 270 amino acids of an N-terminal capping region. In certain embodiments, the N-terminal capping region fragment amino acids are of the C-terminus (the DNA-binding region proximal end) of an N-terminal capping region. As described in Zhang et al., Nature Biotechnology 29:149-153 (2011), N-terminal capping region fragments that include the C-terminal 240 amino acids enhance binding activity equal to the full length capping region, while fragments that include the C-terminal 147 amino acids retain greater than 80% of the efficacy of the full length capping region, and fragments that include the C-terminal 117 amino acids retain greater than 50% of the activity of the full-length capping region.

In some embodiments, the TALE polypeptides described herein contain a C-terminal capping region fragment that included at least 6, 10, 20, 30, 37, 40, 50, 60, 68, 70, 80, 90, 100, 110, 120, 127, 130, 140, 150, 155, 160, 170, 180 amino acids of a C-terminal capping region. In certain embodiments, the C-terminal capping region fragment amino acids are of the N-terminus (the DNA-binding region proximal end) of a C-terminal capping region. As described in Zhang et al., Nature Biotechnology 29:149-153 (2011), C-terminal capping region fragments that include the C-terminal 68 amino acids enhance binding activity equal to the full length capping region, while fragments that include the C-terminal 20 amino acids retain greater than 50% of the efficacy of the full length capping region.

In certain embodiments, the capping regions of the TALE polypeptides described herein do not need to have identical sequences to the capping region sequences provided herein. Thus, in some embodiments, the capping region of the TALE polypeptides described herein have sequences that are at least 50%, 60%, 70%, 80%, 85%, 90%, 91%, 92%, 93%, 94%, 95%, 96%, 97%, 98% or 99% identical or share identity to the capping region amino acid sequences provided herein. Sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences. In some preferred embodiments, the capping region of the TALE polypeptides described herein have sequences that are at least 95% identical or share identity to the capping region amino acid sequences provided herein.

Sequence homologies may be generated by any of a number of computer programs known in the art, which include, but are not limited to, BLAST or FASTA. Suitable computer programs for carrying out alignments, like the GCG Wisconsin Bestfit package, may also be used. Once the software has produced an optimal alignment, it is possible to calculate % homology, preferably % sequence identity. The software typically does this as part of the sequence comparison and generates a numerical result.

In some embodiments described herein, the TALE polypeptides of the invention include a nucleic acid binding domain linked to the one or more effector domains. The terms "effector domain" or "regulatory and functional domain" refer to a polypeptide sequence that has an activity other than binding to the nucleic acid sequence recognized by the nucleic acid binding domain. By combining a nucleic acid binding domain with one or more effector domains, the polypeptides of the invention may be used to target the one or more functions or activities mediated by the effector domain to a particular target DNA sequence to which the nucleic acid binding domain specifically binds.

In some embodiments of the TALE polypeptides described herein, the activity mediated by the effector domain is a biological activity. For example, in some embodiments the effector domain is a transcriptional inhibitor (i.e., a repressor domain), such as an mSin interaction domain (SID), SID4X domain or a Kruppel-associated box (KRAB), or fragments of the KRAB domain. In some embodiments, the effector domain is an enhancer of transcription (i.e. an activation domain), such as the VP16, VP64 or p65 activation domain. In some embodiments, the nucleic acid binding is linked, for example, with an effector domain that includes, but is not limited to, a transposase, integrase, recombinase, resolvase, invertase, protease, DNA methyltransferase, DNA demethylase, histone acetylase, histone deacetylase, nuclease, transcriptional repressor, transcriptional activator, transcription factor recruiting, protein nuclear-localization signal or cellular uptake signal.

In some embodiments, the effector domain is a protein domain which exhibits activities which include, but are not limited to, transposase activity, integrase activity, recombinase activity, resolvase activity, invertase activity, protease activity, DNA methyltransferase activity, DNA demethylase activity, histone acetylase activity, histone deacetylase activity, nuclease activity, nuclear-localization signaling activity, transcriptional repressor activity, transcriptional activator activity, transcription factor recruiting activity, or cellular uptake signaling activity. Other preferred embodiments of the invention may include any combination of the activities described herein.

Zn-Finger Nucleases

The one or more agents may comprise Zn-finger nucleases or nucleic acids encoding thereof. Other preferred tools for genome editing for use in the context of this invention include zinc finger systems and TALE systems. One type of programmable DNA-binding domain is provided by artificial zinc-finger (ZF) technology, which involves arrays of ZF modules to target new DNA-binding sites in the genome. Each finger module in a ZF array targets three DNA bases. A customized array of individual zinc finger domains is assembled into a ZF protein (ZFP).

ZFPs can comprise a functional domain. The first synthetic zinc finger nucleases (ZFNs) were developed by fusing a ZF protein to the catalytic domain of the Type IIS restriction enzyme FokI. (Kim, Y. G. et al., 1994, Chimeric restriction endonuclease, Proc. Natl. Acad. Sci. U.S.A. 91, 883-887; Kim, Y. G. et al., 1996, Hybrid restriction enzymes: zinc finger fusions to Fok I cleavage domain. Proc. Natl. Acad. Sci. U.S.A. 93, 1156-1160). Increased cleavage specificity can be attained with decreased off target activity by use of paired ZFN heterodimers, each targeting different nucleotide sequences separated by a short spacer. (Doyon, Y. et al., 2011, Enhancing zinc-finger-nuclease activity with improved obligate heterodimeric architectures. Nat. Methods 8, 74-79). ZFPs can also be designed as transcription activators and repressors and have been used to target many genes in a wide variety of organisms. Exemplary methods of genome editing using ZFNs can be found, for example, in U.S. Pat. Nos. 6,534,261, 6,607,882, 6,746,838, 6,794,136, 6,824,978, 6,866,997, 6,933,113, 6,979,539, 7,013,219, 7,030,215, 7,220,719, 7,241,573, 7,241,574, 7,585,849, 7,595,376, 6,903,185, and 6,479,626, all of which are specifically incorporated by reference.

Meganucleases

As disclosed herein editing can be made by way of meganucleases, which are endodeoxyribonucleases characterized by a large recognition site (double-stranded DNA sequences of 12 to 40 base pairs). Exemplary methods for using meganucleases can be found in U.S. Pat. Nos. 8,163, 514, 8,133,697, 8,021,867, 8,119,361, 8,119,381; 8,124,369, and 8,129,134, which are specifically incorporated by reference.

In certain embodiments, any of the nucleases, including the modified nucleases as described herein, may be used in the methods, compositions, and kits according to the invention. In particular embodiments, nuclease activity of an unmodified nuclease may be compared with nuclease activity of any of the modified nucleases as described herein, e.g. to compare for instance off-target or on-target effects. Alternatively, nuclease activity (or a modified activity as described herein) of different modified nucleases may be compared, e.g. to compare for instance off-target or on-target effects.

Other Example Types of Modulating Agents

Also provided herein are compositions for use in carrying out the methods of the invention. More particularly, non-naturally occurring or engineered compositions are provided which comprise one or more of the elements required to ensure genomic perturbation. In particular embodiments, the compositions comprise one or more of the (modified) DNA binding protein, and/or a guide RNA. In particular embodiments, the composition comprises a vector. In further particular embodiments, the vector comprises a polynucleotide encoding a gRNA. In particular embodiments, the vector comprises two or more guide RNAs. The two or more guide RNAs may target a different target (so as to ensure multiplex targeting) or the same target, in which case the different guide RNAs will target different sequences within the same target sequence. Where provided in a vector, the different guide RNAs may be under common control of the same promotor, or each may be under control of the same or different promoters.

In certain embodiments, a modulating agent may comprise silencing one or more endogenous genes. As used herein, "gene silencing" or "gene silenced" in reference to an activity of an RNAi molecule, for example a siRNA or miRNA refers to a decrease in the mRNA level in a cell for a target gene by at least about 5%, about 10%, about 20%, about 30%, about 40%, about 50%, about 60%, about 70%, about 80%, about 90%, about 95%, about 99%, about 100% of the mRNA level found in the cell without the presence of the miRNA or RNA interference molecule. In one preferred embodiment, the mRNA levels are decreased by at least about 70%, about 80%, about 90%, about 95%, about 99%, about 100%.

As used herein, the term "RNAi" refers to any type of interfering RNA including, but not limited to, siRNAi, shRNAi, endogenous microRNA and artificial microRNA. For instance, it includes sequences previously identified as siRNA, regardless of the mechanism of down-stream processing of the RNA (i.e. although siRNAs are believed to have a specific method of in vivo processing resulting in the cleavage of mRNA, such sequences can be incorporated into the vectors in the context of the flanking sequences described herein). The term "RNAi" can include both gene silencing RNAi molecules, and also RNAi effector molecules which activate the expression of a gene.

As used herein, a "siRNA" refers to a nucleic acid that forms a double stranded RNA, which double stranded RNA has the ability to reduce or inhibit expression of a gene or target gene when the siRNA is present or expressed in the same cell as the target gene. The double stranded RNA siRNA can be formed by the complementary strands. In one embodiment, a siRNA refers to a nucleic acid that can form a double stranded siRNA. The sequence of the siRNA can correspond to the full-length target gene, or a subsequence thereof. Typically, the siRNA is at least about 15-50 nucleotides in length (e.g., each complementary sequence of the double stranded siRNA is about 15-50 nucleotides in length, and the double stranded siRNA is about 15-50 base pairs in length, preferably about 19-30 base nucleotides, preferably about 20-25 nucleotides in length, e.g., 20, 21, 22, 23, 24, 25, 26, 27, 28, 29, or 30 nucleotides in length).

As used herein "shRNA" or "small hairpin RNA" (also called stem loop) is a type of siRNA. In one embodiment, these shRNAs are composed of a short, e.g. about 19 to about 25 nucleotide, antisense strand, followed by a nucleotide loop of about 5 to about 9 nucleotides, and the analogous sense strand. Alternatively, the sense strand can precede the nucleotide loop structure and the antisense strand can follow.

The terms "microRNA" or "miRNA" are used interchangeably herein and are endogenous RNAs, some of which are known to regulate the expression of protein-coding genes at the posttranscriptional level. Endogenous microRNAs are small RNAs naturally present in the genome that are capable of modulating the productive utilization of mRNA. The term artificial microRNA includes any type of RNA sequence, other than endogenous microRNA, which is capable of modulating the productive utilization of mRNA. MicroRNA sequences have been described in publications such as Lim et al. Genes & Development, 17, p. 991-1008 (2003), Lim et al Science 299, 1540 (2003), Lee and Ambros Science, 294, 862 (2001), Lau et al., Science 294, 858-861 (2001), Lagos-Quintana et al, Current Biology, 12, 735-739 (2002), Lagos Quintana et al. Science 294, 853-857 (2001), and Lagos-Quintana et al. RNA, 9, 175-179 (2003), which are incorporated by reference. Multiple microRNAs can also be incorporated into a precursor molecule. Furthermore, miRNA-like stem-loops can be expressed in cells as a vehicle to deliver artificial miRNAs and short interfering RNAs (siRNAs) for the purpose of modulating the expression of endogenous genes through the miRNA and/or RNAi pathways.

As used herein, "double stranded RNA" or "dsRNA" refers to RNA molecules that are comprised of two strands. Double-stranded molecules include those comprised of a single RNA molecule that doubles back on itself to form a two-stranded structure. For example, the stem loop structure of the progenitor molecules from which the single-stranded miRNA is derived, called the pre-miRNA (Bartel et al. 2004. Cell 1 16:281-297), comprises a dsRNA molecule.

In certain embodiments, a modulant may comprise (i) a DNA-binding portion configured to specifically bind to the endogenous gene and (ii) an effector domain mediating a biological activity.

In certain embodiments, the DNA-binding portion may comprise a zinc finger protein or DNA-binding domain thereof, a transcription activator-like effector (TALE) protein or DNA-binding domain thereof, or an RNA-guided protein or DNA-binding domain thereof.

In certain embodiments, the DNA-binding portion may comprise (i) Cas9 or Cpf1 or any Cas protein described herein modified to eliminate its nuclease activity, or (ii) DNA-binding domain of Cas9 or Cpf1 or any Cas protein described herein.

In some embodiments, the effector domain may be a transcriptional inhibitor (i.e., a repressor domain), such as an mSin interaction domain (SID), SID4X domain or a Kruppel-associated box (KRAB), or fragments of the KRAB domain. In some embodiments, the effector domain may be an enhancer of transcription (i.e. an activation domain), such as the VP16, VP64 or p65 activation domain. In some embodiments, the nucleic acid binding portion may be linked, for example, with an effector domain that includes, but is not limited to, a transposase, integrase, recombinase, resolvase, invertase, protease, DNA methyltransferase, DNA demethylase, histone acetylase, histone deacetylase, nuclease, transcriptional repressor, transcriptional activator, transcription factor recruiting, protein nuclear-localization signal or cellular uptake signal. In some embodiments, the effector domain may be a protein domain which exhibits activities which include, but are not limited to, transposase activity, integrase activity, recombinase activity, resolvase activity, invertase activity, protease activity, DNA methyl- transferase activity, DNA demethylase activity, histone acetylase activity, histone deacetylase activity, nuclease activity, nuclear-localization signaling activity, transcriptional repressor activity, transcriptional activator activity, transcription factor recruiting activity, or cellular uptake signaling activity.

Pharmaceutical Compositions

The present disclosure also provides for pharmaceutical compositions comprising the one or more modulating agents. A "pharmaceutical composition" refers to a composition that usually contains an excipient, such as a pharmaceutically acceptable carrier that is conventional in the art and that is suitable for administration to cells or to a subject.

In yet other embodiments, the methods of the disclosure include administering to a subject in need thereof an effective amount (e.g., therapeutically effective amount or prophylactically effective amount) of the treatments provided herein. Such treatment may be supplemented with other known treatments, such as surgery on the subject. In certain embodiments, the surgery is strictureplasty, resection (e.g., bowel resection, colon resection), colectomy, surgery for abscesses and fistulas, proctocolectomy, restorative proctocolectomy, vaginal surgery, cataract surgery, or a combination thereof.

The term "pharmaceutically acceptable" as used throughout this specification is consistent with the art and means compatible with the other ingredients of a pharmaceutical composition and not deleterious to the recipient thereof.

As used herein, "carrier" or "excipient" includes any and all solvents, diluents, buffers (such as, e.g., neutral buffered saline or phosphate buffered saline), solubilisers, colloids, dispersion media, vehicles, fillers, chelating agents (such as, e.g., EDTA or glutathione), amino acids (such as, e.g., glycine), proteins, disintegrants, binders, lubricants, wetting agents, emulsifiers, sweeteners, colorants, flavorings, aromatizers, thickeners, agents for achieving a depot effect, coatings, antifungal agents, preservatives, stabilizers, antioxidants, tonicity controlling agents, absorption delaying agents, and the like. The use of such media and agents for pharmaceutically active components is well known in the art. Such materials should be non-toxic and should not interfere with the activity of the cells or active components.

The precise nature of the carrier or excipient or other material will depend on the route of administration. For example, the composition may be in the form of a parenterally acceptable aqueous solution, which is pyrogen-free and has suitable pH, isotonicity and stability. For general principles in medicinal formulation, the reader is referred to Cell Therapy: Stem Cell Transplantation, Gene Therapy, and Cellular Immunotherapy, by G. Morstyn & W. Sheridan eds., Cambridge University Press, 1996; and Hematopoietic Stem Cell Therapy, E. D. Ball, J. Lister & P. Law, Churchill Livingstone, 2000.

The pharmaceutical composition can be applied parenterally, rectally, orally or topically. Preferably, the pharmaceutical composition may be used for intravenous, intramuscular, subcutaneous, peritoneal, peridural, rectal, nasal, pulmonary, mucosal, or oral application. In a preferred embodiment, the pharmaceutical composition according to the invention is intended to be used as an infuse. The skilled person will understand that compositions which are to be administered orally or topically will usually not comprise cells, although it may be envisioned for oral compositions to also comprise cells, for example when gastro-intestinal tract indications are treated. Each of the cells or active components (e.g., modulants, immunomodulants, antigens) as discussed herein may be administered by the same route or may be administered by a different route. By means of example, and without limitation, cells may be administered parenterally and other active components may be administered orally.

Liquid pharmaceutical compositions may generally include a liquid carrier such as water or a pharmaceutically acceptable aqueous solution. For example, physiological saline solution, tissue or cell culture media, dextrose or other saccharide solution or glycols such as ethylene glycol, propylene glycol or polyethylene glycol may be included.

The composition may include one or more cell protective molecules, cell regenerative molecules, growth factors, anti-apoptotic factors or factors that regulate gene expression in the cells. Such substances may render the cells independent of their environment.

Such pharmaceutical compositions may contain further components ensuring the viability of the cells therein. For example, the compositions may comprise a suitable buffer system (e.g., phosphate or carbonate buffer system) to achieve desirable pH, more usually near neutral pH, and may comprise sufficient salt to ensure isoosmotic conditions for the cells to prevent osmotic stress. For example, suitable solution for these purposes may be phosphate-buffered saline (PBS), sodium chloride solution, Ringer's Injection or Lactated Ringer's Injection, as known in the art. Further, the composition may comprise a carrier protein, e.g., albumin (e.g., bovine or human albumin), which may increase the viability of the cells.

Further suitably pharmaceutically acceptable carriers or additives are well known to those skilled in the art and, for instance, may be selected from proteins such as collagen or gelatine, carbohydrates such as starch, polysaccharides, sugars (dextrose, glucose and sucrose), cellulose derivatives like sodium or calcium carboxymethylcellulose, hydroxypropyl cellulose or hydroxypropylmethyl cellulose, pregelatinized starches, pectin agar, carrageenan, clays, hydrophilic gums (acacia gum, guar gum, arabic gum and xanthan gum), alginic acid, alginates, hyaluronic acid, polyglycolic and polylactic acid, dextran, pectins, synthetic polymers such as water-soluble acrylic polymer or polyvinylpyrrolidone, proteoglycans, calcium phosphate and the like.

If desired, cell preparation can be administered on a support, scaffold, matrix or material to provide improved tissue regeneration. For example, the material can be a granular ceramic, or a biopolymer such as gelatine, collagen, or fibrinogen. Porous matrices can be synthesized according to standard techniques (e.g., Mikos et al., Biomaterials 14: 323, 1993; Mikos et al., Polymer 35:1068, 1994; Cook et al., J. Biomed. Mater. Res. 35:513, 1997). Such support, scaffold, matrix or material may be biodegradable or non-biodegradable. Hence, the cells may be transferred to and/or cultured on suitable substrate, such as porous or non-porous substrate, to provide for implants.

The pharmaceutical compositions may comprise one or more pharmaceutically acceptable salts. The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. The term "pharmaceutically acceptable salt" further includes all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, pamoate, valerate, and the like which can be used as a dosage form for modifying the solubility or hydrolysis characteristics or can be used in sustained release or pro-drug formulations. It will be understood that, as used herein, references to specific agents (e.g., neuromedin U receptor agonists or antagonists), also include the pharmaceutically acceptable salts thereof.

Methods of administrating the pharmacological compositions, including agents, cells, agonists, antagonists, antibodies or fragments thereof, to an individual include, but are not limited to, intradermal, intrathecal, intramuscular, intraperitoneal, intravenous, subcutaneous, intranasal, epidural, by inhalation, and oral routes. The compositions can be administered by any convenient route, for example by infusion or bolus injection, by absorption through epithelial or mucocutaneous linings (for example, oral mucosa, rectal and intestinal mucosa, and the like), ocular, and the like and can be administered together with other biologically-active agents. Administration can be systemic or local. In addition, it may be advantageous to administer the composition into the central nervous system by any suitable route, including intraventricular and intrathecal injection. Pulmonary administration may also be employed by use of an inhaler or nebulizer, and formulation with an aerosolizing agent. It may also be desirable to administer the agent locally to the area in need of treatment; this may be achieved by, for example, and not by way of limitation, local infusion during surgery, topical application, by injection, by means of a catheter, by means of a suppository, or by means of an implant.

Therapy or treatment according to the invention may be performed alone or in conjunction with another therapy, and may be provided at home, the doctor's office, a clinic, a hospital's outpatient department, or a hospital. Treatment generally begins at a hospital so that the doctor can observe the therapy's effects closely and make any adjustments that are needed. The duration of the therapy depends on the age and condition of the patient, the stage of the cancer, and how the patient responds to the treatment. Additionally, a person having a greater risk of developing an inflammatory response (e.g., a person who is genetically predisposed or predisposed to allergies or a person having a disease characterized by episodes of inflammation) may receive prophylactic treatment to inhibit or delay symptoms of the disease.

Delivery of Modulating Agents and Pharmaceutical Compositions

Various delivery systems are known and can be used to administer the agents and pharmacological compositions including, but not limited to, encapsulation in liposomes, microparticles, microcapsules, minicells, polymers, capsules, tablets, and the like. In one embodiment, the agent may be delivered in a vesicle, in particular a liposome. In a liposome, the agent is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,837,028 and 4,737,323. In yet another embodiment, the pharmacological compositions can be delivered in a controlled release system including, but not limited to, a delivery pump (see, for example, Saudek, et al., New Engl. J. Med. 321: 574 (1989) and a semi-permeable polymeric material (see, for example, Howard, et al., J. Neurosurg. 71: 105 (1989)). Additionally, the controlled release system can be placed in proximity of the therapeutic target (e.g., a tumor), thus requiring only a fraction of the systemic dose. See, for example, Goodson, In: Medical Applications of Controlled Release, 1984. (CRC Press, Boca Raton, Fla.).

Delivery of Modulating Agents that are Polynucleotides

In cases the modulating agents are polynucleotides, they may be delivered to cell using suitable methods. In some embodiments, the polynucleotides may be packaged in viruses or particles, or conjugated to a vehicle for delivering into cells.

In some embodiments, the methods include packaging the polynucleotides in viruses and transducing cell with the viruses. Transduction or transducing herein refers to the delivery of a polynucleotide molecule to a recipient cell either in vivo or in vitro, by infecting the cells with a virus carrying that polynucleotide molecule. The virus may be a replication-defective viral vector. In some examples, the viruses may be e.g. retroviruses, replication defective retroviruses, adenoviruses, replication defective adenoviruses, and adeno-associated viruses (AAVs)).

In some examples, the viruses are lentiviruses. Lentiviruses are complex retroviruses that have the ability to infect and express their genes in both mitotic and post-mitotic cells. Examples of lentiviruses include human immunodeficiency virus (HIV) (e.g., strain 1 and strain 2), simian immunodeficiency virus (SIV), feline immunodeficiency virus (FIV), BLV, EIAV, CEV, and visna virus. Lentiviruses may be used for nondividing or terminally differentiated cells such as neurons, macrophages, hematopoietic stem cells, retinal photoreceptors, and muscle and liver cells, cell types for which previous gene therapy methods could not be used. A vector containing such a lentivirus core (e.g. gag gene) can transduce both dividing and non-dividing cells.

In certain embodiments, the viruses are adeno-associated viruses (AAVs). AAVs are naturally occurring defective viruses that require helper viruses to produce infectious particles (Muzyczka, N., Curr. Topics in Microbiol. Immunol. 158:97 (1992)). It is also one of the few viruses that can integrate its DNA into nondividing cells. Vectors containing as little as 300 base pairs of AAV can be packaged and can integrate, but space for exogenous DNA is limited to about 4.5 kb. In some cases, an AAV vector may include all the sequences necessary for DNA replication, encapsidation, and host-cell integration. The recombinant AAV vector can be transfected into packaging cells which are infected with a helper virus, using any standard technique, including lipofection, electroporation, calcium phosphate precipitation, etc. Appropriate helper viruses include adenoviruses, cytomegaloviruses, vaccinia viruses, or herpes viruses. Once the packaging cells are transfected and infected, they will produce infectious AAV viral particles which contain the polynucleotide construct. These viral particles are then used to transduce eukaryotic cells.

Methods of non-viral delivery of nucleic acids include lipofection, nucleofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386, 4,946,787, and 4,897,355, and lipofection reagents are sold commercially (e.g., Transfectam™ and Lipofectin™). Cationic and neutral lipids that are suitable for efficient receptor-recognition lipofection of polynucleotides include those of Felgner, WO 91/17424; WO 91/16024. Delivery can be to cells (e.g. in vitro or ex vivo administration) or target tissues (e.g. in vivo administration). Physical methods of introducing polynucleotides may also used. Examples of such methods include injection of a solution containing the polynucleotides, bombardment by particles covered by the polynucleotides, soaking a cell, tissue sample or organism in a solution of the polynucleotides, or electroporation of cell membranes in the presence of the polynucleotides.

Examples of delivery methods and vehicles include viruses, nanoparticles, exosomes, nanoclews, liposomes, lipids (e.g., LNPs), supercharged proteins, cell permeabilizing peptides, and implantable devices. The nucleic acids, proteins and other molecules, as well as cells described herein may be delivered to cells, tissues, organs, or subjects using methods described in paragraphs [00117] to [00278] of Feng Zhang et al., (WO 2016/106236 A1), which is incorporated by reference herein in its entirety.

In some cases, the methods include delivering the barcode construct and/or another element (e.g., a perturbation element) to cells. In such cases, the barcode construct and/or another element (e.g., a perturbation element) may be RNA molecules.

Diseases and Conditions

The methods and compositions herein may be used for treating various diseases and conditions. In some examples, the diseases and conditions include olfactory diseases or disorders, which include disorders, dysfunctions or diseases resulting in a diminished olfactory sensation (e.g., smell aberration). Examples of olfactory disorders, dysfunctions and/or diseases include head trauma, upper respiratory infections, tumors of the anterior cranial fossa, Kallmann syndrome, Foster Kennedy syndrome, Parkinson's disease, Alzheimer's disease, Huntington chorea, and exposure to toxic chemicals or infections. Diminished olfactory sensation is classified as anosmia-absence of smell sensation; hyposmia-decreased smell sensation; dysosmia-distortion of smell sensation; cacosmia-sensation of a bad or foul smell; and parosmia-sensation of smell in the absence of appropriate stimulus.

The invention is further described in the following examples, which do not limit the scope of the invention described in the claims.

EXAMPLES

Example 1

Multiplexed imaging of mRNA abundance in mouse motor cortex was investigated. To capture all of the genes provided in Tables 1-4 below, 37 genes, standard cyclic FISH would take 13 rounds of 3-color imaging. The goal of using exemplary methods as disclosed herein are to recover all 37 genes from 10 composite images, which would allow for 4 rounds of 3-color imaging.

TABLE 1

| Non-neuronal cell types | Gene |
| --- | --- |
| Astrocytes | Gja1 |
| Astrocytes | F3 |
| Astrocytes (F3 assoc.) | Prex2 |
| Endothelial | Flt1 |
| Endothelial | Xdh |
| Endothelial | Id1 |
| Microglia | Ctss |
| Microglia | Csf1r |
| Microglia (Csf1r assoc.) | Hmha1 |
| Oligodendrocytes | Olig1 |
| Oligodendrocytes (Olig1 assoc.) | Vcan |
| Oligodendrocytes (Olig2) | Olig2 |
| Oligodendrocytes precursor | Pdgfra |
| Oligodendrocytes precursor | Mog |
| SMC | Vtn |
| SMC (Vtn assoc.) | Colec12 |

TABLE 2

| Neuronal subtypes | Gene |
| --- | --- |
| Gabaergic | Gad1 |
| Glutamatergic | Slc17a7 |
| Vip interneurons | Vip |
| Vip interneurons | Parm1 |
| Sst interneurons | Sst |
| Sst interneurons (Sst assoc.) | Grin3a |
| Pvalb interneurons | Pvalb |
| Ndnf interneurons | Ndnf |
| Ndnf interneurons (assoc.) | Fgf13 |

TABLE 3

| Layer-specific Glutamatergic | Gene |
| --- | --- |
| Layer 4 | Rorb |
| Layer 4 (Rorb assoc.) | Paqr8 |
| Layer 5 | Deptor |
| Layer 6a | Foxp2 |
| Layer 6a/b | Tle4 |
| Layer 6b | Rgs12 |

TABLE 4

| Additional genes | Gene |
| --- | --- |
| Layer 2/3 excitatory | Stard8 |
| Non-neural-Glia | Pdgfd |
| Broad excitatory | Cux2 |
| Specific excitatory | Sulf1 |
| Specific glia | Id3 |
| Specific glia | Ly86 |

Figure 4:
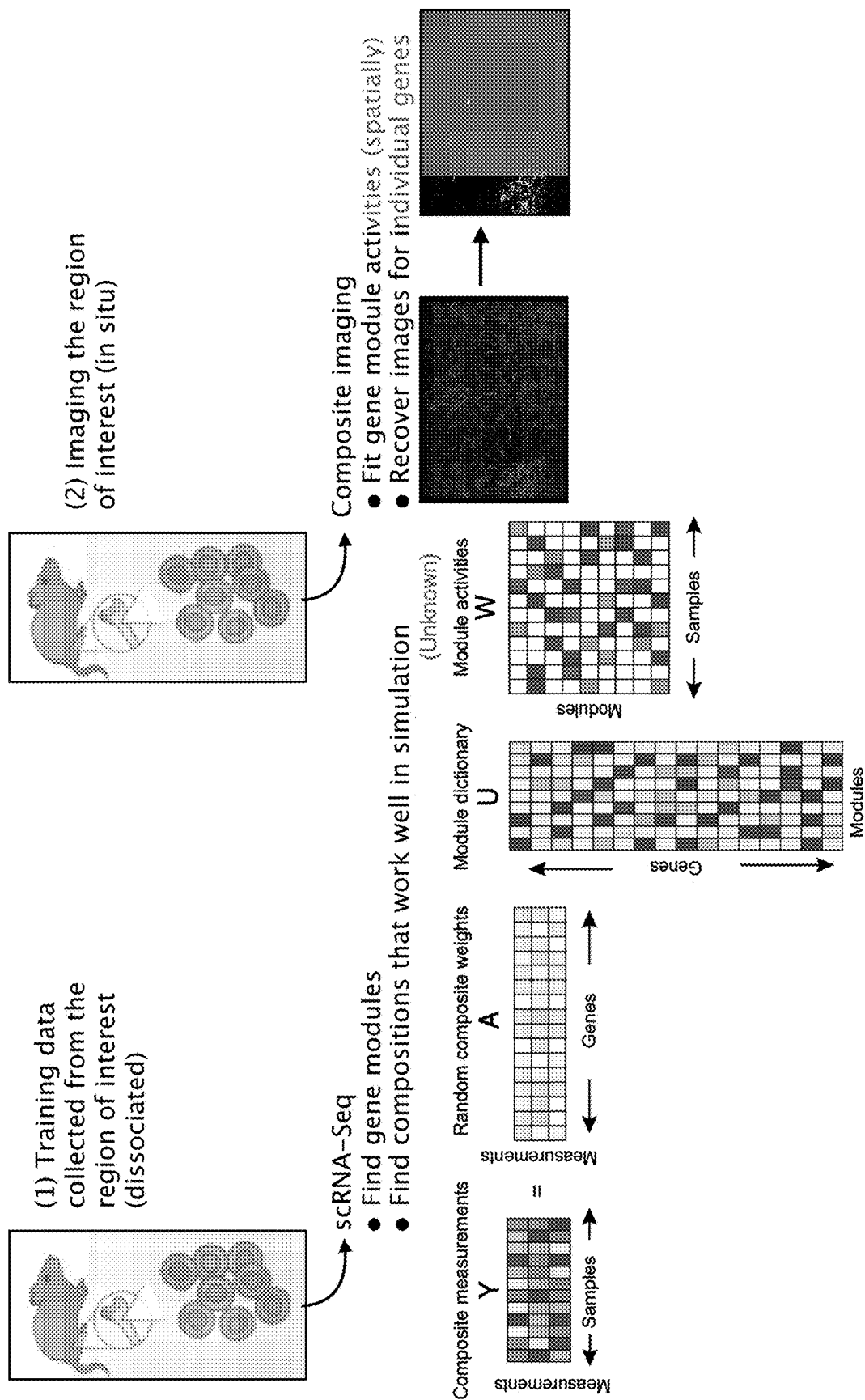
FIG. 4 shows an exemplary workflow using scRNA-Seq paired with composite imaging according to the methods disclosed herein.
Figures 5A, 5B, 5C:
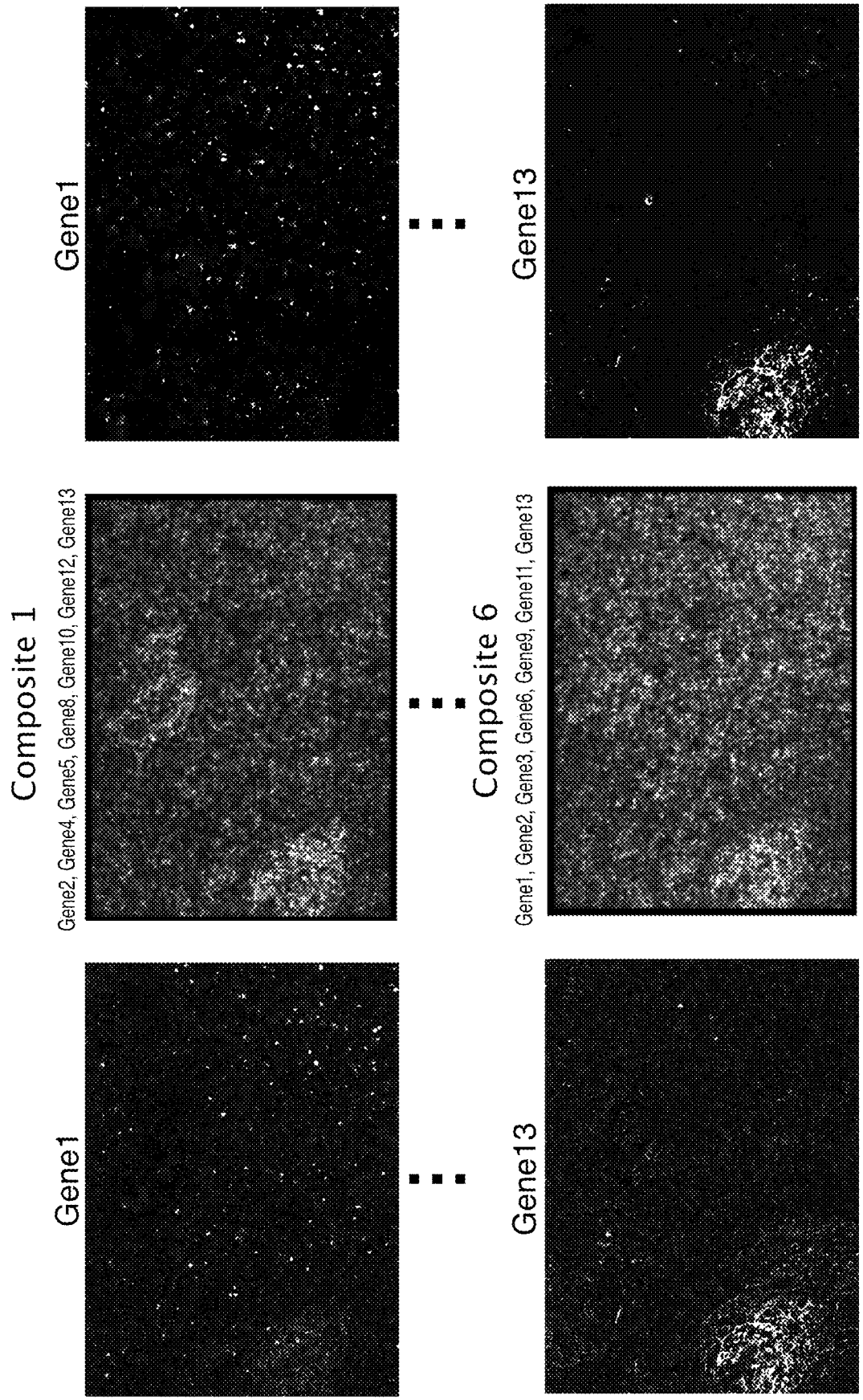
FIG. 5A-5C illustrate the ability to recover individual genes from simulated composite images.
Figure 6:
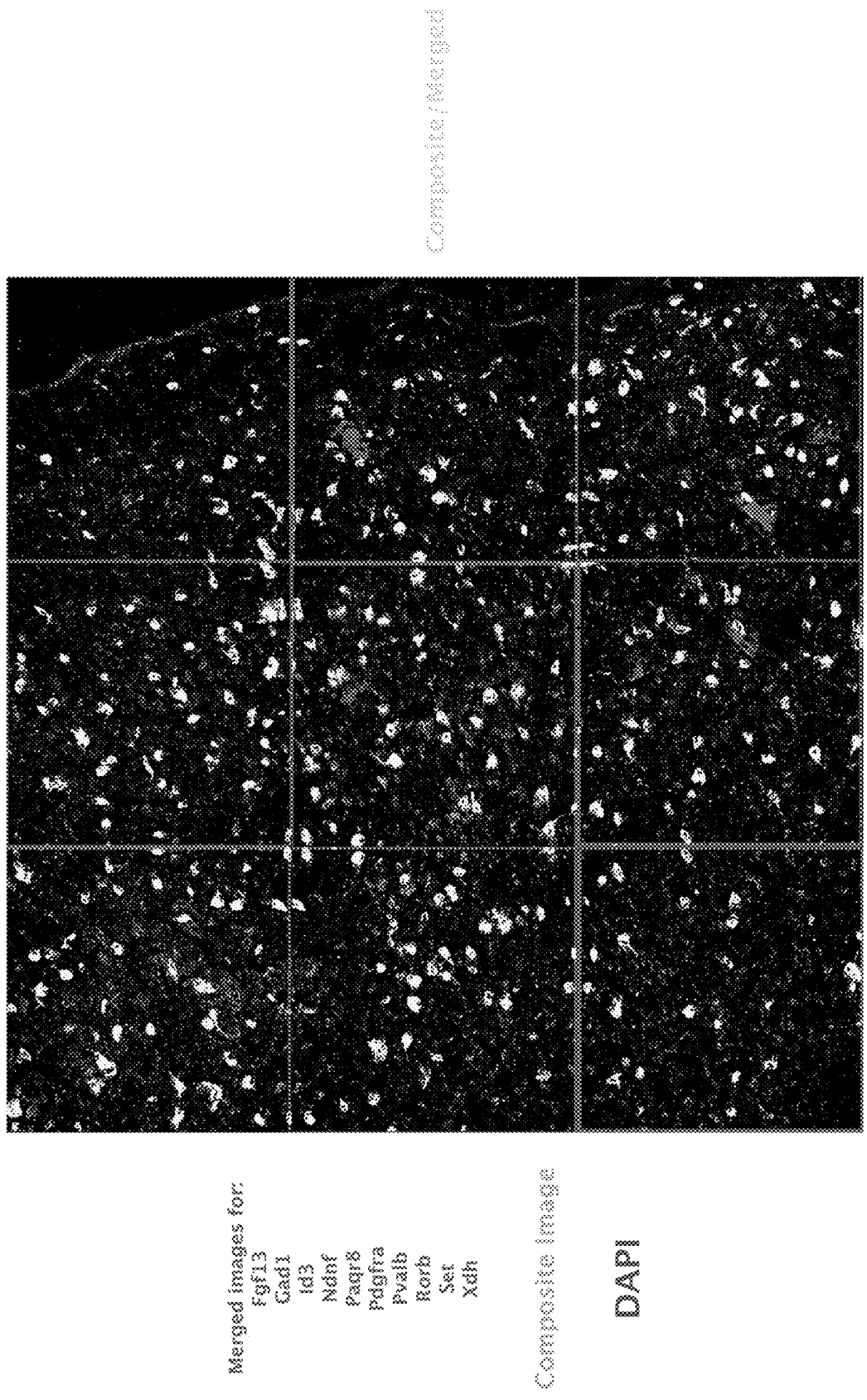
FIG. 6 shows merged fluorescence images for Fgf13, Gad1, Id3, Ndnf, Pagr8, Pdgfra, Pvalb, Rorb, Set, and Xdh genes.
Figure 7B:
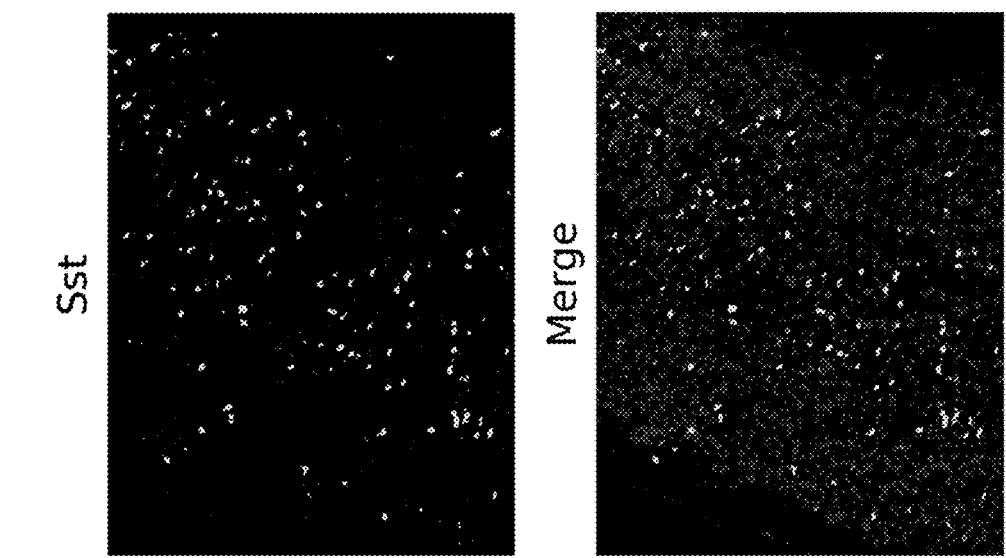
FIG. 7A, 7B illustrate results of an experiment in which the accuracy of gene expression of genes with stereotypical expression patterns was assessed.
Figure 7B:
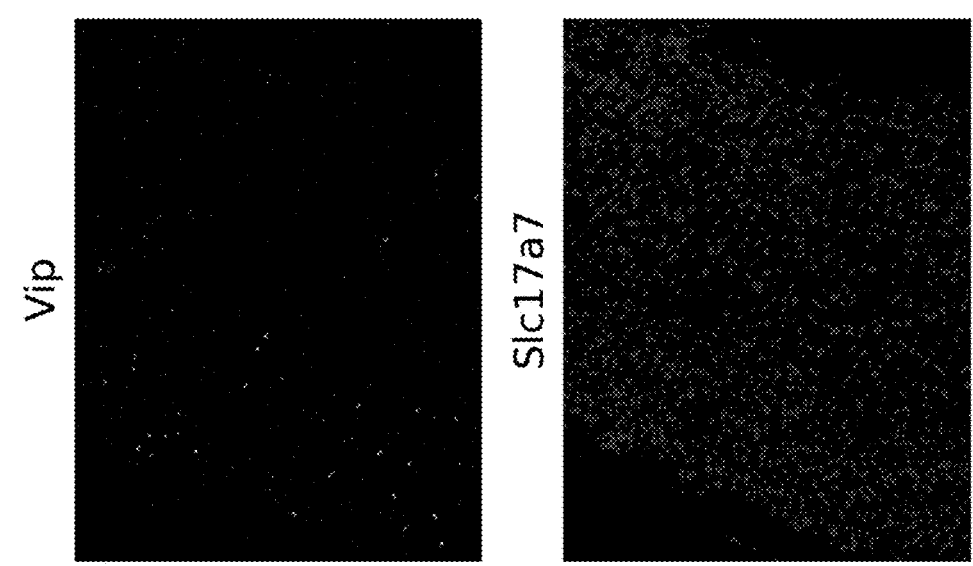
Figure 7A:
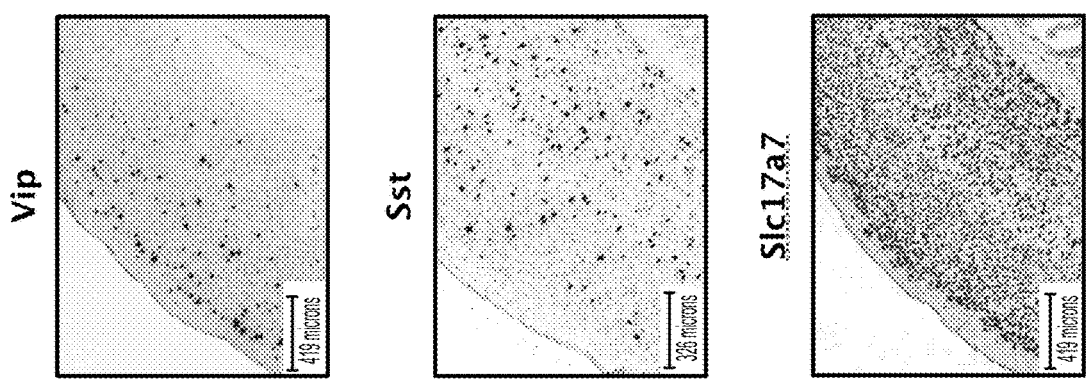
Figure 9:
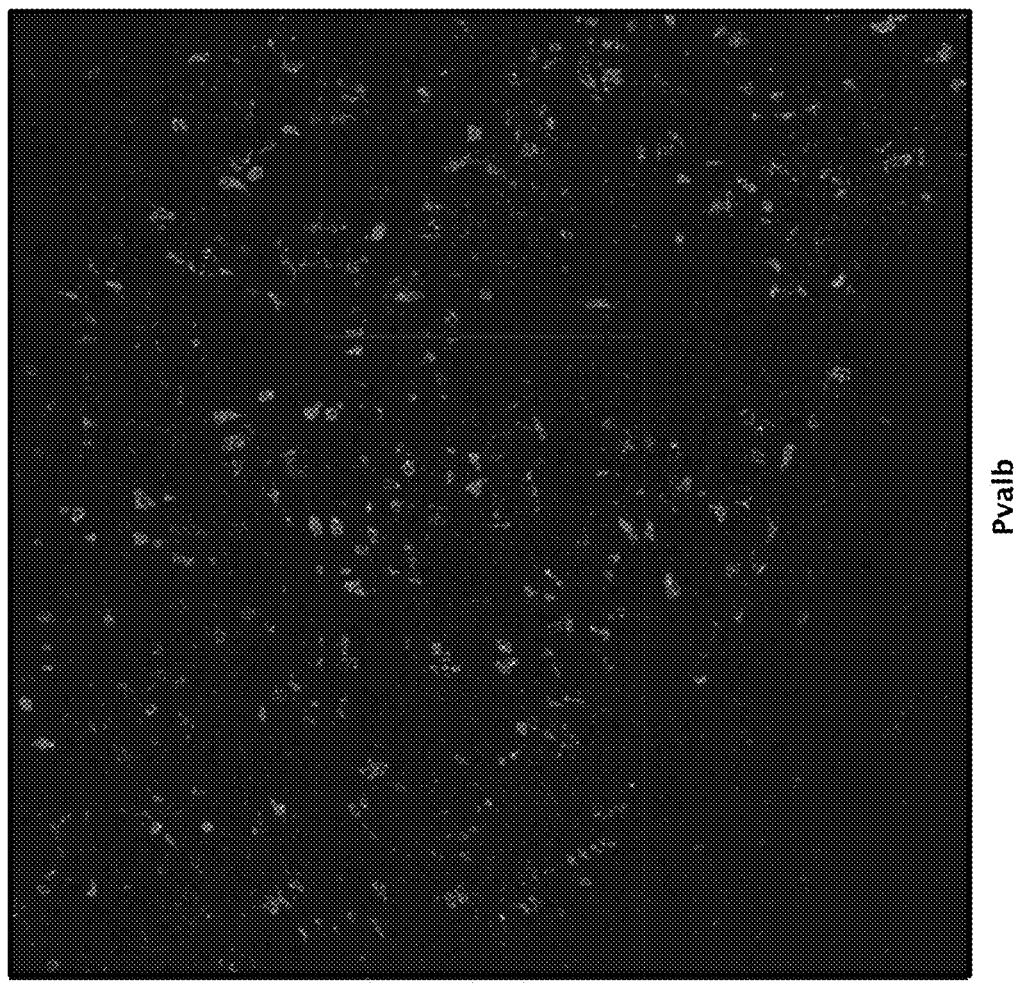
FIG. 9 shows a validation of experiments analyzing the Pvalb gene by making direct and composite measurements in the same tissue.

Utilizing the workflow shown in FIG. 4, composite imaging can be performed, with alignment of directly measured genes and recovered from composites, see, e.g. FIG. 9, validating direct and composite measurements in the same tissue.

Example 2

The molecular mechanisms of how food molecules are sensed is important for understanding how components of food trigger allergic reactions. A class of receptors emerging as an candidate for food sensing are olfactory receptors, which constitute nearly half of all GPCRs, with 400 functional olfactory receptors encoded by the human genome and 1000 by the mouse genome. In the nose, these receptors detect small, volatile chemicals in a combinatorial manner, allowing 400 or 1000 unique receptors to encode more than a million unique mixtures. Specific sets of olfactory receptors are expressed abundantly in other organs including the heart, immune system, and gut, and often in a cell-type specific manner, suggesting functionally important transcriptional regulation of these genes outside of the nose. These so-called "ectopic" olfactory receptors may serve as general chemosensors that detect the vast library of small molecules in gut and the blood. Combined with importance of smell in the recognition of food, olfactory receptors are attractive food sensing candidates.

This example demonstrates an exemplary in vivo screening method to uncover combinatorial activation of olfactory receptors by ligands.

Figure 13:
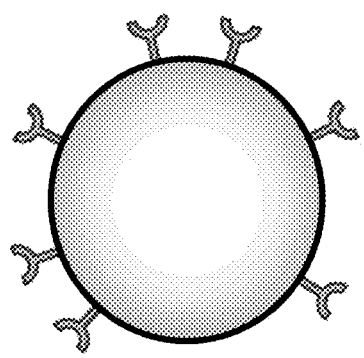
FIG. 13 shows each olfactory sensory neuron expresses only one olfactory receptor.
Figure 13:
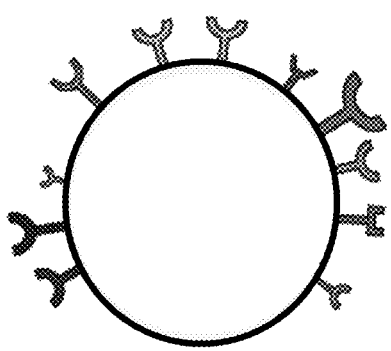
Figure 14:
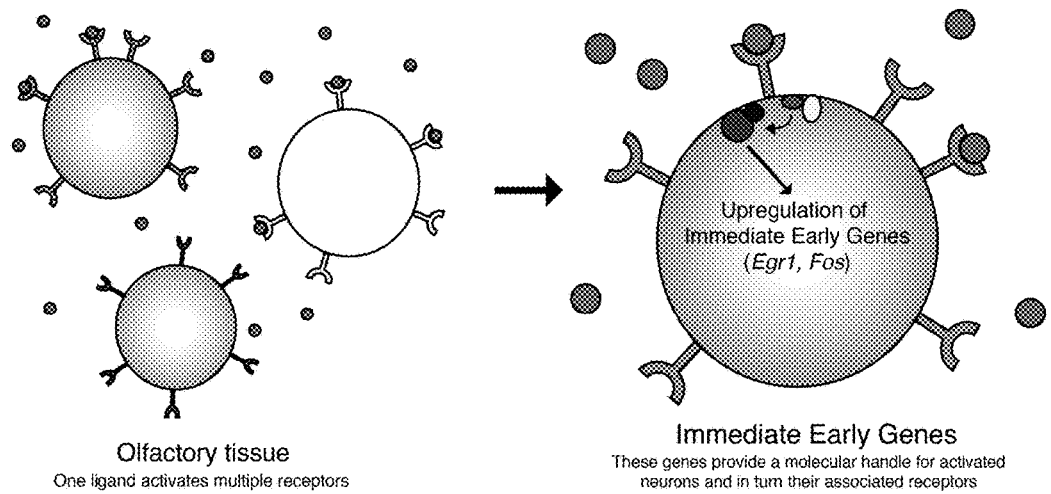
FIG. 14 shows an example receptors/ligands system used in some embodiments.
Figure 14:
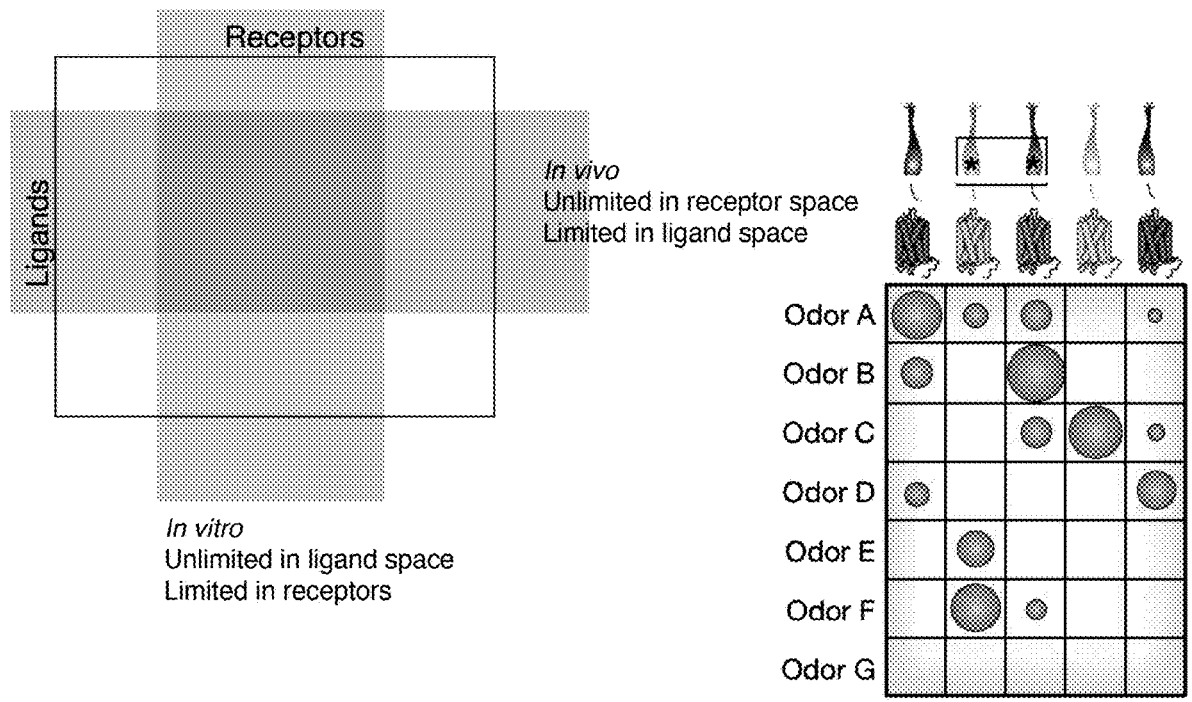

Leveraging natural organization of olfactory epithelium for in vivo assay. Several works using in vitro cell-based screens for discovering olfactory receptor ligands (Jones et al. 2018, Saito et al. 2009) have generated numerous exciting candidates. However, scaling up these platforms to express all 400 human or 1000 mouse receptors remains challenging. Here, Applicant leveraged the natural organization of the olfactory epithelium where almost the entire olfactory receptor repertoire is expressed across the >10 million sensory neurons, This tissue is specially organized such that each neuron expresses only one olfactory receptor (FIG. 13). Coupled with activity markers that neurons express upon firing, Applicant related neuronal activity to its receptor identity. Furthermore, this system allowed simultaneous combinatorial measurements of activated receptors, which may better reflect actual biological processes (FIG. 14).

Figure 15:
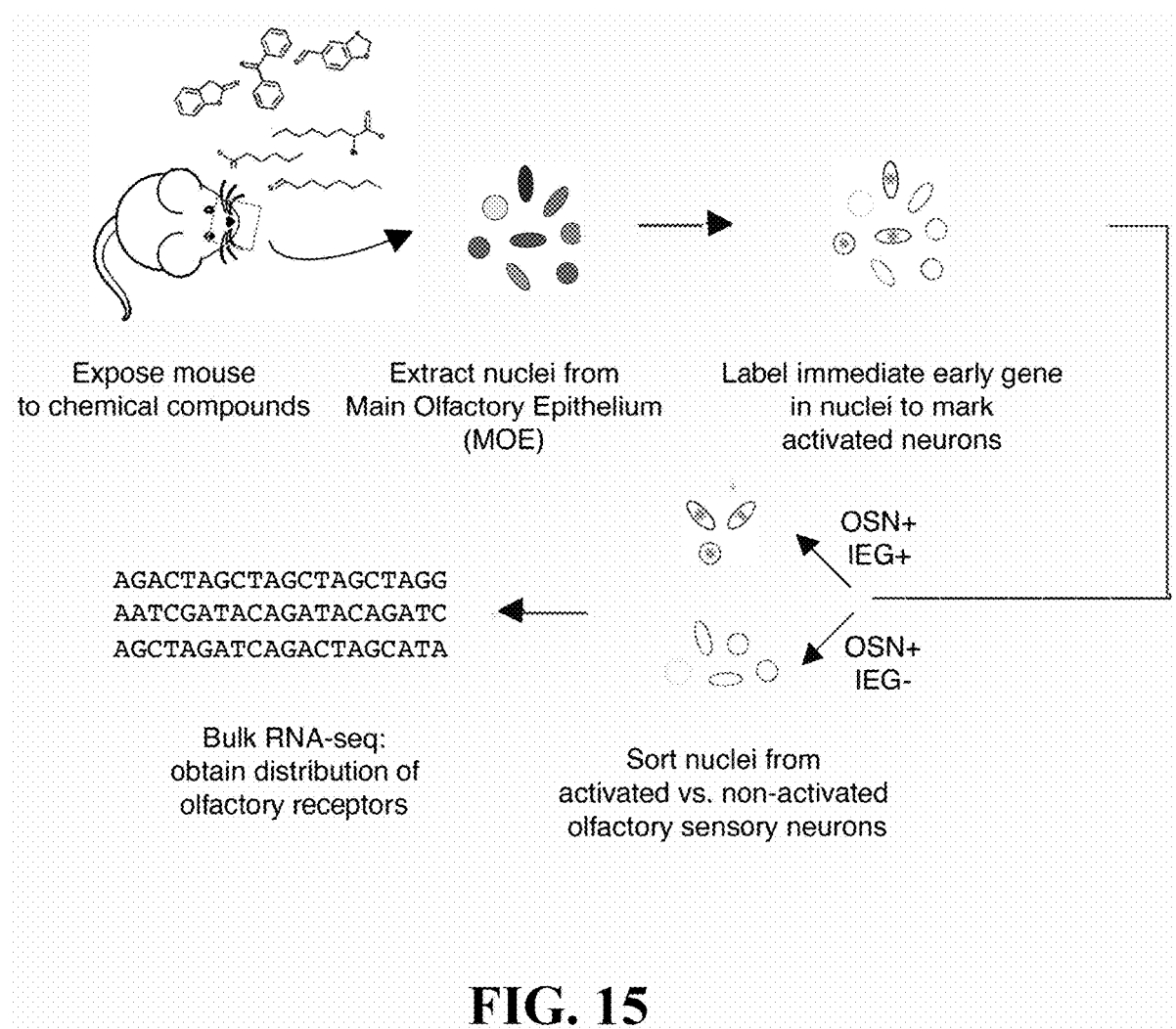
FIG. 15 shows an example method for screening receptors in response to stimuli (SEQ ID NOs:1-3).

Enriching for nuclei of activated neurons. FIG. 15 shows an example method for screening receptors in response to stimuli. In brief, mice were exposed to one or more chemical compounds. Main olfactory epithelia (MOE) were harvest from the mice and nuclei were isolated from the MOE tissues. One or more immediate early genes (e.g., nuclei-specific olfactory sensory neuron markers such as Snap25) or their gene products were labeled to mark nuclei from activated olfactory sensory neurons. Nuclei from activated and non-activated neurons were sorted. Bulk RNA-seq was performed to determine distributions of olfactory receptors.

A key advantage of working with nuclei was preserving meaningful immediate early genes (IEG) expression, in contrast to cells where the dissociation process leads to spurious IEG expression. However, as nuclei contains <10% of the total RNA in a cell, Applicant first validated that the specific transcripts of interest were captured and observed via FISH and sequencing.

Figure 16:
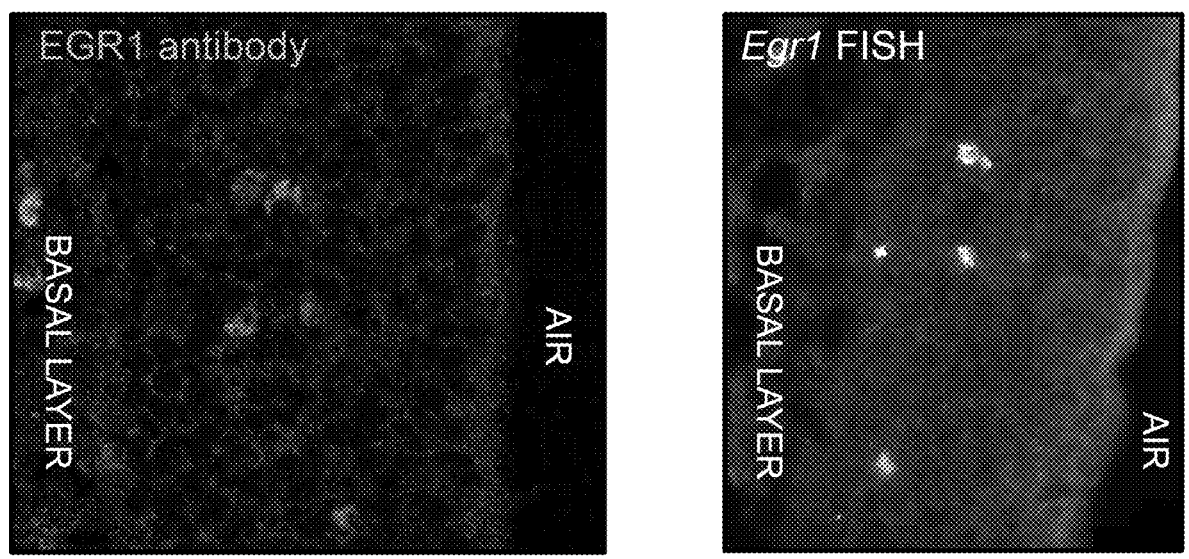
FIG. 16 shows antibody staining of EGR1 protein and FISH test of Egr1 gene.

IEG expression in response to chemical stimuli. Applicant confirmed that immediate early genes were upregulated in olfactory sensory neurons (OSNs) after chemical stimulation. Mice were administered with acetophenone and their olfactory epithelium were harvested. The tissue was stained with an antibody against EGR1 and FISH probes against Egr1 (FIG. 16).

Figure 17:
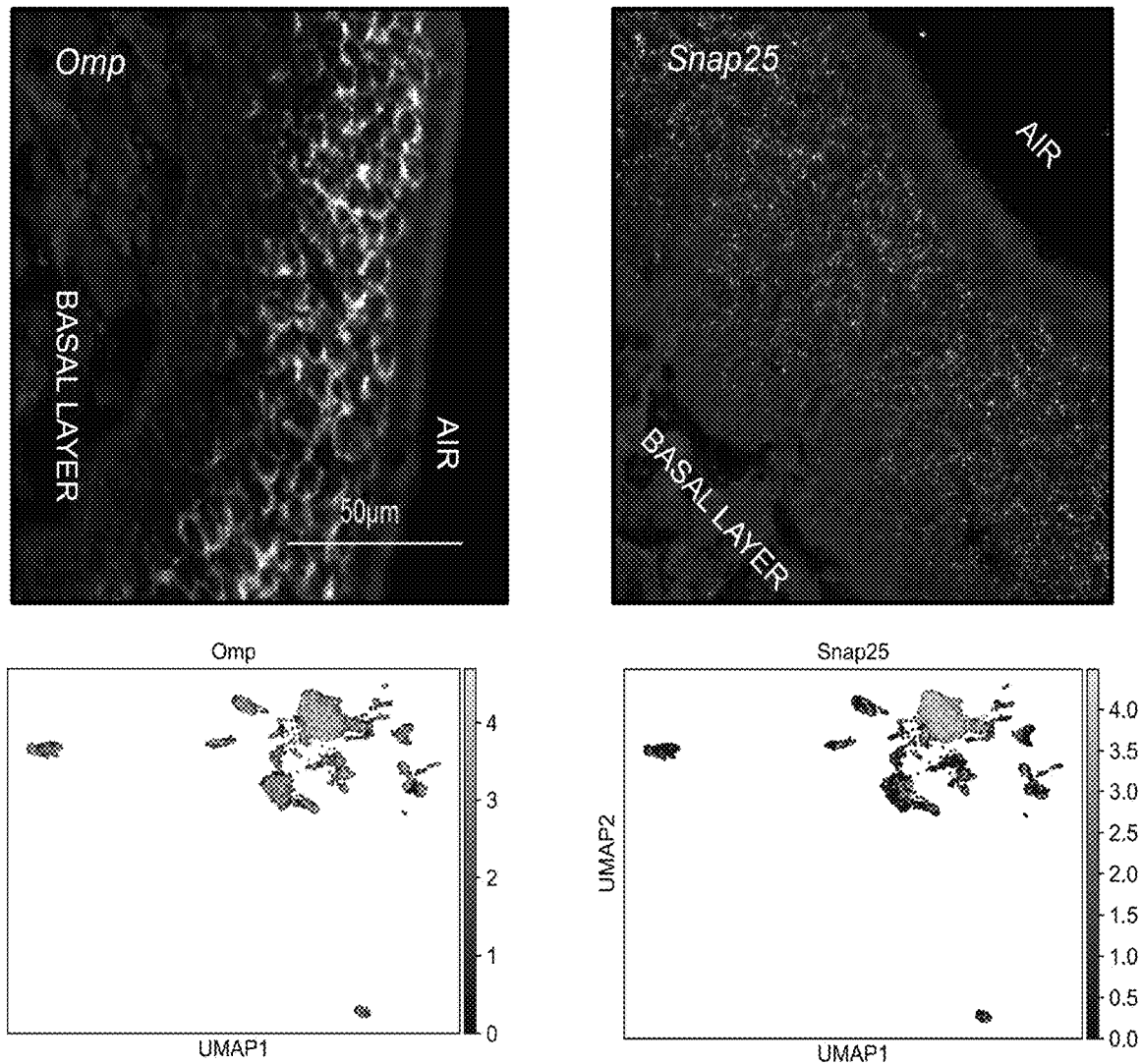
FIG. 17 shows discovery of Snap25 as a OSN marker at the nuclei level.

Finding nuclei-specific OSN marker. While Omp (olfactory marker protein) is the canonical marker for olfactory sensory neurons (OSNs) as verified by FISH, it is found mostly in the cytoplasm. At the level of nuclei, it is found in almost all cell types of the olfactory epithelium, not just the OSNs. Therefore, it is not an ideal target for nuclei-based enrichment of OSNs. Applicant used 10× data and found an OSN marker at the nuclei level, Snap25 (FIG. 17).

Figure 18:
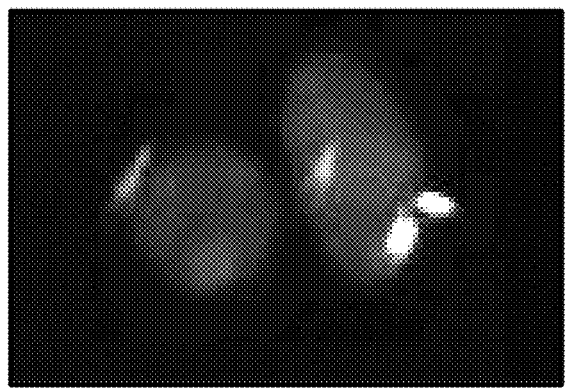
FIG. 18 shows optimization of FISH conditions.
Figure 18:
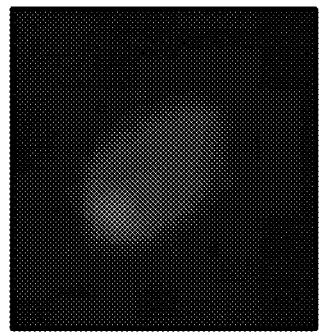

The FISH test conditions were optimized (FIG. 18).

Figure 19:
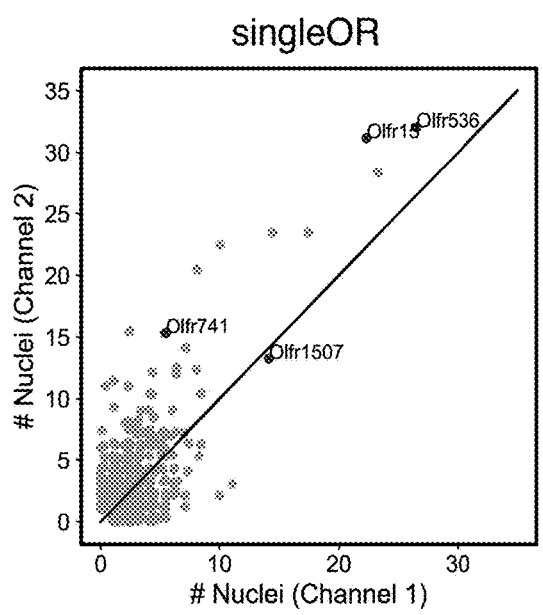
FIG. 19 shows detection of olfactory receptors in nuclei with 10× sequencing.
Figure 19:
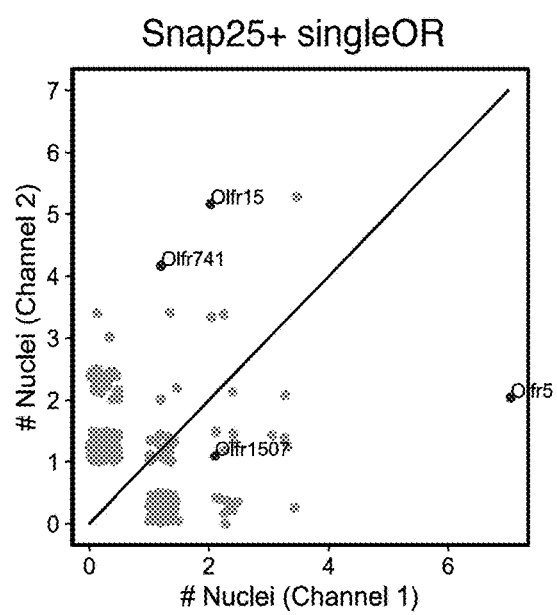

Olfactory receptors in nuclei were detected with 10× sequencing (FIG. 19).

Figure 20:
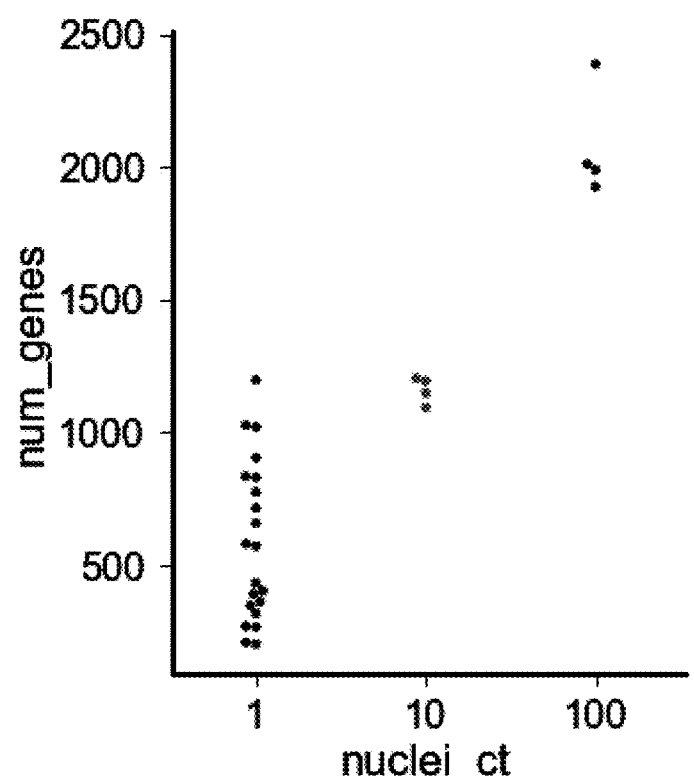
FIG. 20 shows sorting results of 1, 10, or 100 Omp+ nuclei and conducted SS2.

Sequencing RNA from PFA fixed nuclei. Applicant sequenced PFA fixed nuclei after sorting to validate that decrosslinking followed by Smart-Seq2 works (Thomsen et al. 2016). Applicant sorted 1, 10, or 100 Omp+ nuclei and conducted SS2 (FIG. 20).

Figure 21:
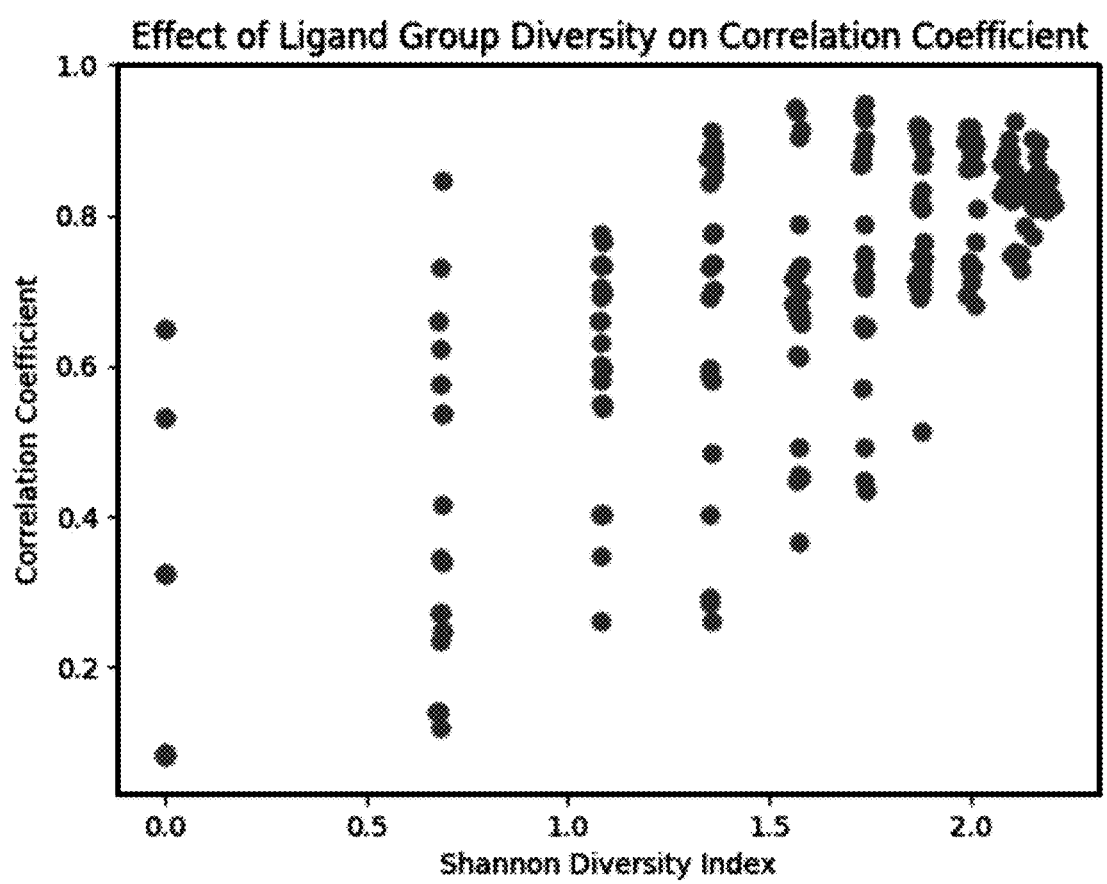
FIG. 21 shows test results in exemplary methods of designing composite ligands.

Designing composite ligands. Applicant designed composite ligands (FIG. 21). Applicant identified chemical properties of each ligand that prevents them from being in the same composite. Applicant used variational autoencoder to embed ligands in a continuous, quantitative space. Applicant simultaneously encoded the ligand's ability to activate a specific receptor.

Figure 22:
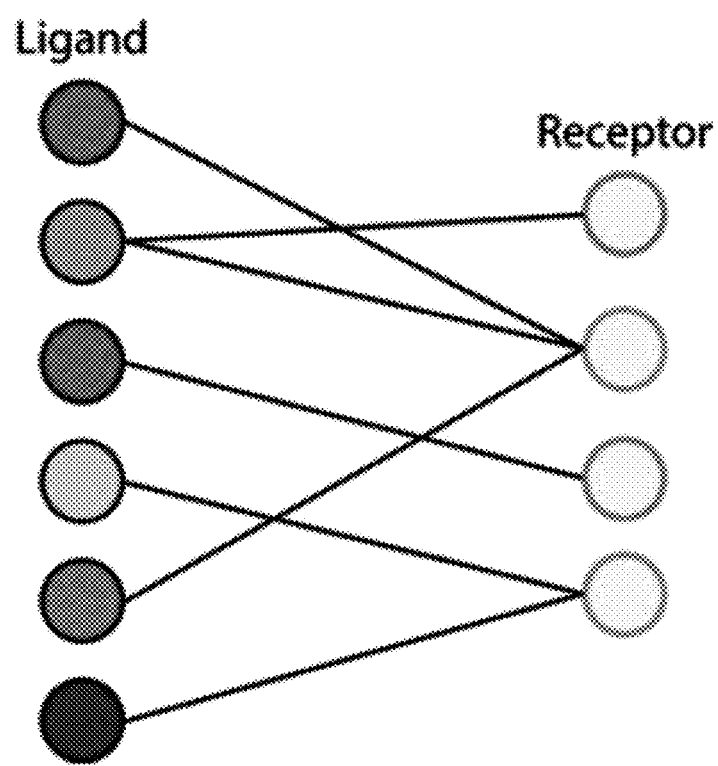
FIG. 22 is a schematic showing ligand-receptor combinations that can be revealed by methods in some embodiments.

An in vivo receptor-ligand screen enables collecting data to elucidate how chemicals are represented in a combinatorial receptor space (FIG. 22). This platform is useful in numerous different applications, including finding ligands for "orphan" receptors, e.g., those without a known ligand. A particular class of ligands of interest are food molecules. Olfactory receptors are expressed in many other tissues such as the gut, and pose as attractive candidates for sensing food and microbiome-derived molecules. Ultimately, an in vivo method that enables uncovering receptor-ligand interactions of olfactory receptors is established.

Example 3

Gaining a systematic molecular understanding of tissue physiology in health and disease will require the ability to rapidly profile the abundances of many genes at high resolution over large tissue volumes. Many current methods of imaging transcriptomics are based on single-molecule fluorescent in situ hybridization, with barcodes to allow multiplexing across genes. These approaches have serious limitations with respect to (i) the number of genes that can be studied and (ii) imaging time, due to the need for high-resolution to resolve individual signals. Here, Applicants show that both challenges can be overcome by introducing an approach that leverages the biological fact that gene expression is often structured across both cells and tissue organization. Applicants develop Composite In situ Imaging (CISI), that combines this biological insight with algorithmic advances in compressed sensing to achieve greater efficiency. Applicants demonstrate that CISI accurately recovers the spatial abundance of each of 37 individual genes in the mouse primary motor cortex (MOp) from 10 composite measurements and without the need for spot-level resolution. CISI achieves the current scale of multiplexing with an order of magnitude greater efficiency, and can be leveraged in combination with existing methods to multiplex far beyond current scales.

Limitations on Current Technologies

Multiplex methods have provided an unprecedented tool for tissue biology and histopathology, but they typically measure fewer than 1% of genes, necessitate choosing a gene-expression signature, and can require a week or more to collect these data in a single tissue section. Ideally, it would be possible to quickly generate data on thousands of gene abundance levels in large tissue volumes, perhaps even entire organs.

Notably, existing barcoding methods ignore prior knowledge or biological principles: each spot is decoded independently, without using any 'local' information (such as gene-expression information at nearby spots). This choice leads to two fundamental limitations on scalability. First, both linear and combinatorial quantification requires imaging at high magnification (up to 100×) so that individual RNA molecules appear as bright, well-separated spots, so that their individual identities can be decoded from the hybridization images. High-resolution image acquisition over large volumes is a major time bottleneck. Second, there are limitations on the number of genes. In linear barcoding, it is not feasible to substantially increase the number G of genes assayed, because the number of rounds of imaging scales with G (100-fold more genes requires 100-fold more rounds) and with combinatorial barcoding, increases are limited by optical crowding (spatial overlap between fluorescent spots), because the number of spots scales with G. Recent efforts to ameliorate this latter issue with sparser combinatorial barcodes increase the number of rounds of hybridization and, so far, result in a relatively high rate of false positives (Eng et al., 2019).

Applicants reasoned that a biology-informed strategy could be more efficient, by incorporating knowledge about the principles of gene expression patterns. Because many genes are co-regulated, measurements of one gene give information about the likely abundances of others. In such cases, one might infer the expression of many individual genes from a much smaller number of composite measurements of gene abundance—mathematically defined as linear combinations of gene abundance levels—consisting of combined signal from multiple genes on the same channel. That is, instead of measuring the level of multiple genes but each of them separately (i.e., in one channel), Applicants should use each channel to measure the composite (sum) abundances of multiple genes in each channel, and later be able to decompress and determine individual gene levels by leveraging the biological insights that genes are co-regulated in modules. Applicants have previously published the theoretical foundations of this strategy, based on the mathematics of compressed sensing (Cleary et al., 2017), which describes how under-sampled composite data can be decompressed to recover structured, high-dimensional expression signals for individual genes.

Figure 23A:
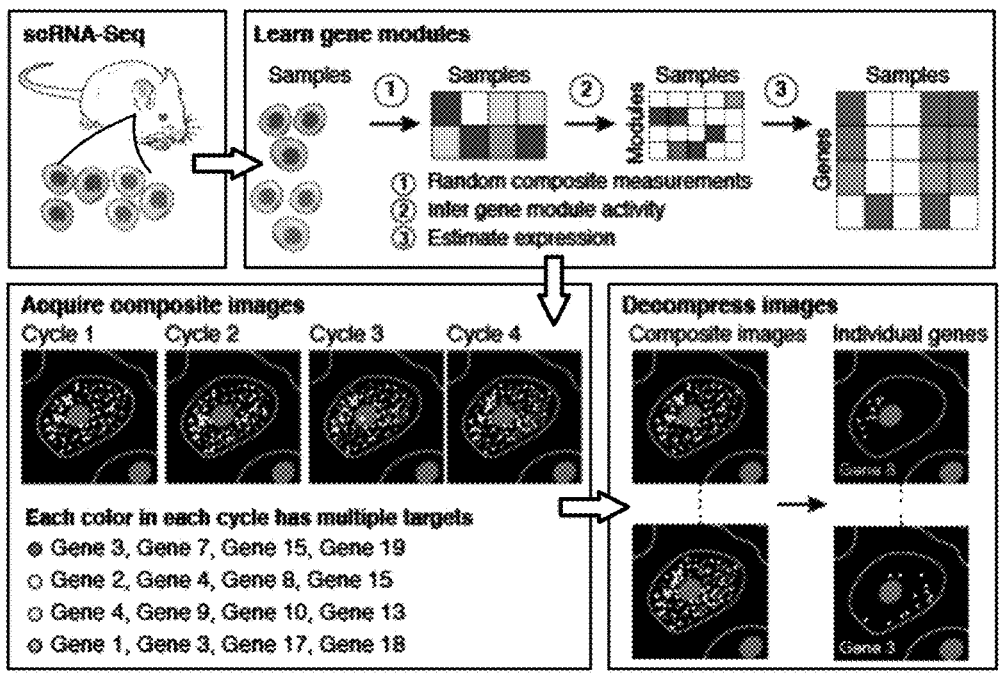
FIG. 23A-23B Composite In situ Imaging (CISI) (FIG. 23A) Method overview. snRNA-Seq data (top left) is first analyzed (top right) to learn a dictionary of gene modules, simulate compressed sensing, and select measurement compositions to be used in CISI experiments (bottom left). In a CISI experiment, in each color in each round of imaging, probes for every gene in a given composite measurement are hybridized simultaneously. The process is repeated for different compositions over several cycles of stripping and hybridization (bottom left). Finally, composite images are then decompressed computationally (bottom right) to recover individual images for each gene.

Here, Applicants develop such a scheme, Composite In situ Imaging (CISI), implement it in a lab method and computational algorithm, and show that it improves the current throughput of convenient linear barcoding methods by at least an order of magnitude. The implementation of CISI consists of four steps (FIG. 23a), and described in the enumerated steps below.

(1) Create a dictionary of gene-expression modules. To study the spatial expression pattern of G genes in tissue samples, Applicants first obtain single-cell profiles (e.g., from single cell RNA-Seq (scRNA-Seq)) from comparable samples to identify co-expression patterns among the selected genes and to compute a dictionary consisting of M sparse gene-expression modules (i.e., each module is a sparse vector of nonnegative coefficients for the genes) such that the single-cell profiles can be well approximated by D-sparse linear combinations of the modules (i.e., involving at most D non-zero weights) (Cleary et al., 2017). Below, Applicants use D=3 and explain how it was chosen empirically.

(2) Select composite measurements. Applicants next select K composite measurements that enable accurate recovery of the chosen genes. Each composite measurement consists of probes for a subset of genes, corresponding to a linear combination of gene abundance. To select the compositions and numbers of measurements needed for accurate recovery, Applicants simulate compressed sensing in the single-cell data: Applicants first generate a random assignment of genes to measurements, simulate composite measurements as the sum of those genes' abundances, and compute the recovered (decompressed) profiles. Applicants use simulations to test parameters for (1) the total number of measurements K, (2) the maximum number of measurements in which each gene was included, (3) the individual genes for each measurement, and (4) the size M of the module dictionary and sparsity D of the linear combinations. To simplify laboratory implementation, Applicants considered only measurement compositions consisting of binary weights, where each gene was either not included, or included in equal proportion. For each combination of design parameters (1) and (2), Applicants generate many simulated compositions and compute the recovered profiles from each, and then select compositions that most accurately recover the original expression levels (Methods).

(3) Generate image data. Applicants then synthesize probes for each gene, and create composite probes for each composite measurement by mixing the probes according to the coefficients in the composite design. (Since the weights are binary, the probes for each gene included in a composition are mixed in equal proportions.) Applicants hybridize the composite probes using the linear barcoding approach: in each round, Applicants label c composite probes with distinct colors. (For validation, Applicants can include one or more additional cycles to directly measure a subset of individual genes.)

(4) Computational inference of gene-expression in each cell. Finally, Applicants infer the gene expression patterns in the image, using one of two approaches. In the first, the image is segmented into cells. In each segmented cell, Applicants add up the intensity of each color in each round to get a vector y, corresponding to the composite measurements. Applicants then solve a sparse optimization problem to estimate the gene module activities, w, and individual gene abundances, x=Uw, given the composite designs, A, and a gene module dictionary, U. (That is, Applicants solve for w in y=AUw and then calculate x; this is the core optimization problem of compressed sensing).

Figure 23B:
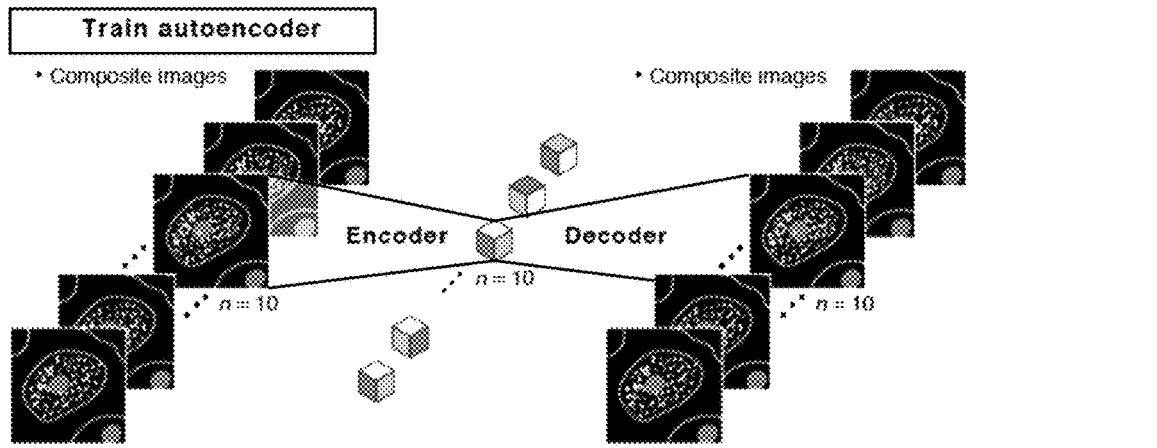
Figure 23B:
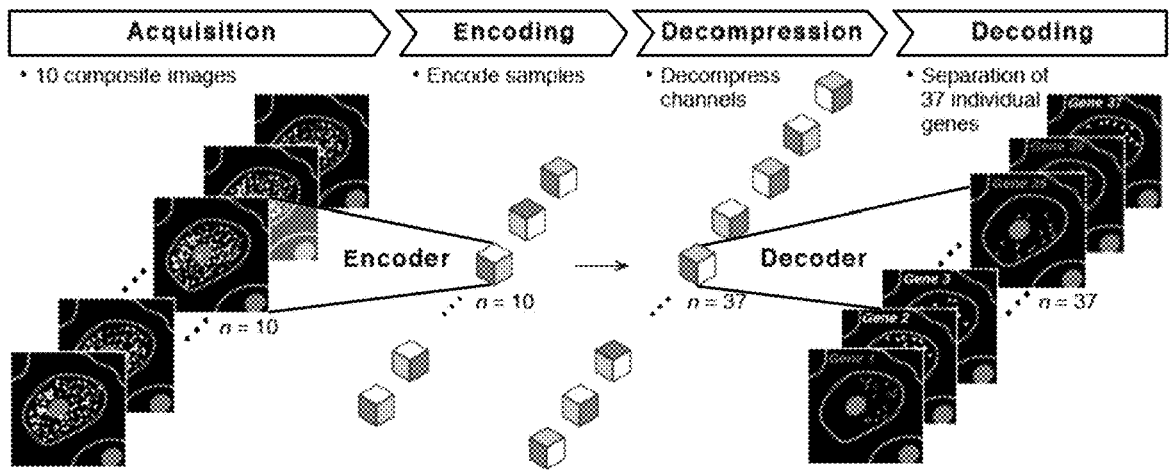

In a second, alternative approach, Applicants analyze the image without cell segmentation or explicit spot detection by using a convolutional autoencoder to infer individual gene abundances at each pixel in the image. Specifically, Applicants use a convolutional autoencoder to compute a low-dimensional, encoded representation of each image, and perform decompression in the encoded latent space (FIG. 23b, Methods). In the segmentation-free algorithm Applicants developed for this purpose, Applicants first train a convolutional encoder to represent each of the composite images in a lower-dimensional space. This effectively aggregates local pixel intensities according to data-driven features. At the same time, Applicants train a decoder that can take these encoded representations as input, and then output images that match the originals. Next, for decompression, Applicants take the K-channel encoded representation of each tissue section as input (each channel corresponding to one of the K composite images). For each node in the encoded representation of a given tissue section, Applicants then solve a sparse optimization problem to estimate gene module activities, and compute the encoded representation of the (unobserved) image for each individual gene (i.e., Applicants decompress the encoded representation from K to G channels). Applicants then decode the encoded representation of each unobserved gene, outputting G individual images. During this optimization Applicants include in the loss function the error between the re-composed individual genes and the original composites at both the encoded and decoded layers (among other constraints and regularizations; Methods).

CISI offers two important advantages. Like combinatorial barcoding, CISI requires exponentially fewer rounds r of hybridization than linear barcoding ($r_{CISI}$=O(D ln(M)/c), $r_{combinatorial}$=ln(G)/ln(c), and $r_{linear}$=G/c; Applicants estimate that, in practice, that the number of rounds with either method will be comparable, with $r_{CISI}/r_{combinatorial}$ typically between ⅓ and 3; Methods). But unlike combinatorial barcoding, CISI does not require spot-level resolution, and thus allows for faster imaging over large areas: whereas individual spots are often imaged between 60-100× magnification, CISI can be imaged from 10-40×, allowing for imaging that is 2.25-100 fold faster in two dimensional scanning.

Figure 25:
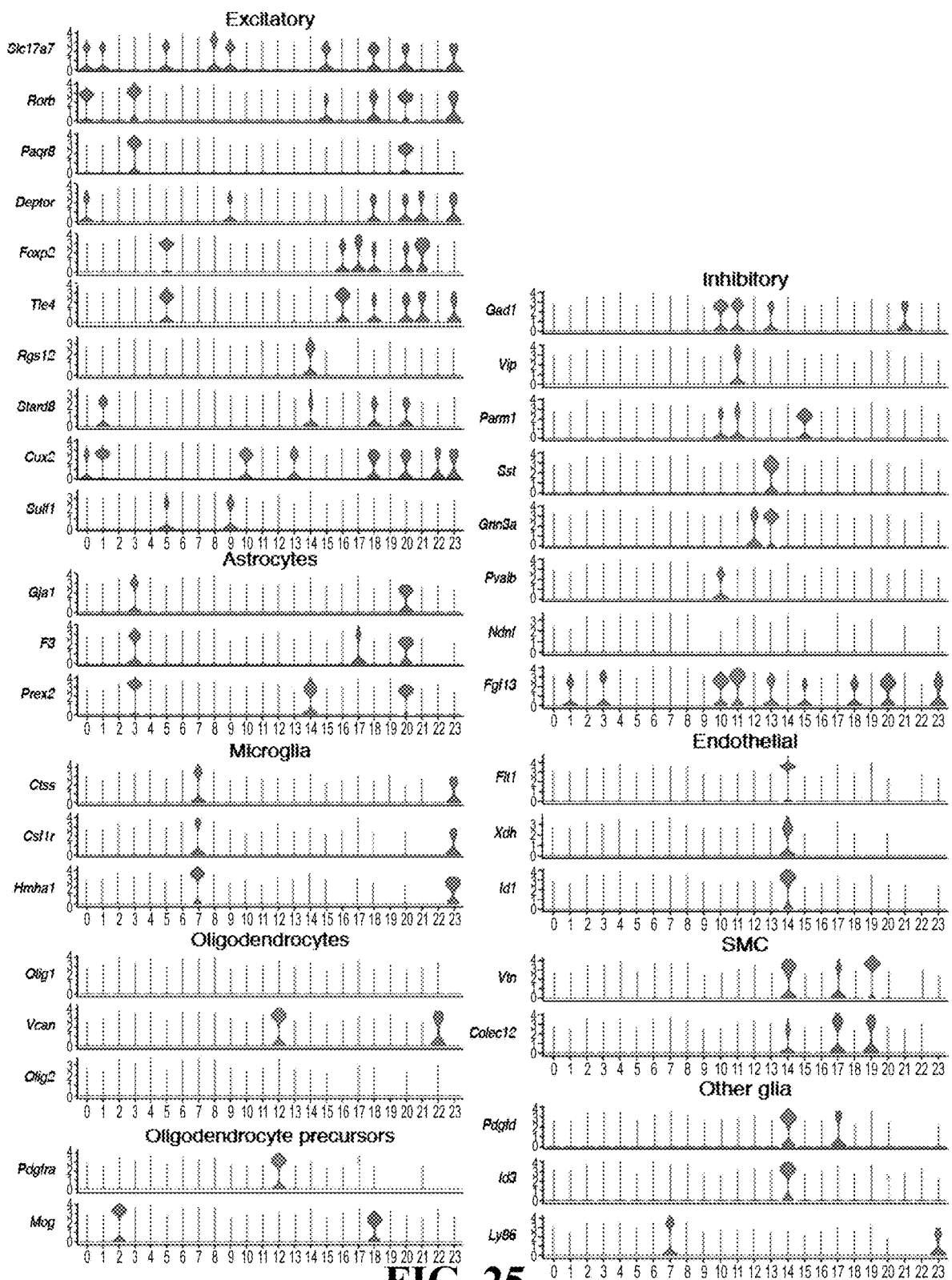
FIG. 25 Marker gene expression in snRNA-seq clusters. For each of 37 genes, shown is the distribution of expression (individual violin plots; y-axis) in each of 23 snRNA-Seq clusters (x axis). Marker genes for similar cell types are grouped together with the cell type labeled on top.

To demonstrate CISI in practice, Applicants applied it in the mouse primary motor cortex (MOp). Applicants analyzed a set of 31,516 previously published single-nucleus RNA-Seq (snRNA-Seq) profiles from MOp (biccn.org/data). Applicants chose to study G=37 genes, consisting of 30 genes that are markers of either broader (excitatory and inhibitory neurons, and various glial cells) or narrower (e.g., layer specific inhibitory neurons) subtypes (FIG. 25), and 7 additional genes that were co-expressed with these markers. In the 27,491 cells in which at least 1 of the 37 genes was detected, the effective number of genes expressed (out of 37, using Shannon Diversity) per cell was 2.87. Given dropouts in snRNA-seq, this is likely an underestimate of true expression.

Figure 26A:
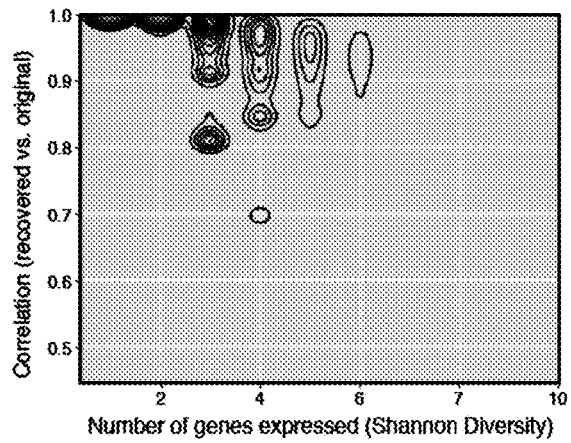
FIG. 26A-26B Analysis of modular factorization based on gene and module diversity Pearson correlation (y-axis) between the original expression levels of 37 genes in each cell and those approximated in those cells by Sparse Module Activity Factorization (SMAF). Contour plots depict the density of cells at each level of correlation with either a given number of genes expressed (FIG. 26A; x-axis) or a given number of gene modules by SMAF decomposition (FIG. 26B; x-axis).
Figure 26B:
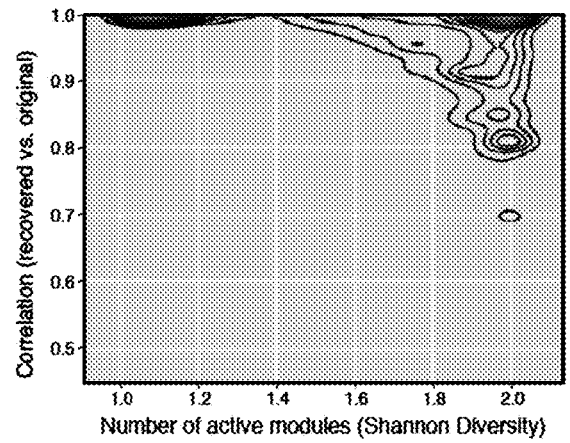

Applicants then learned a sparse modular representation of the expression of the 37 genes in the 27,491 cells. For cells with only 1 or 2 of the genes expressed, Applicants could trivially represent their expression with 1 or 2 parameters (corresponding to singleton gene modules). For cells with more genes expressed, it is more efficient to represent expression in terms of modules of co-expressed genes. Applicants used the previously published method, Sparse Module Activity Factorization (SMAF (Cleary et al., 2017)), to identify a dictionary of M=80 modules. The modules effectively consist of 1 to 6 genes (2.66 on average;), such that the expression of each of the 37 genes in each of 27,491 cells can be represented with a linear combination of 3 or fewer modules with 94.3% correlation. This representation was good (88% correlation), even in cells with greater than 5 of 37 genes expressed (FIG. 26a). On average, each cell was described by the activity of 1.72 modules, and most cells were very accurately described (correlation >95%) by just 1 or 2 modules (FIG. 26b).

Figure 27A:
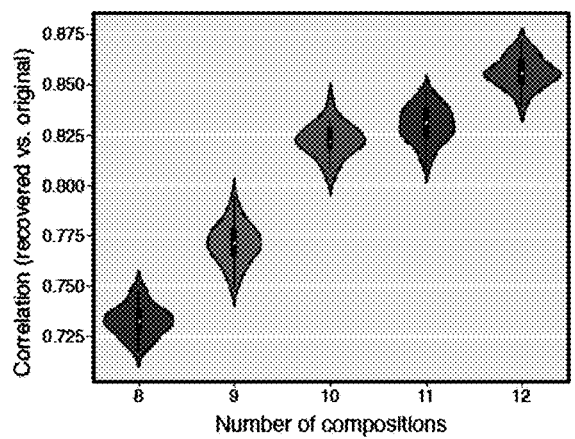
FIG. 27A-27B Evaluation of performance of simulated compositions. Distribution of Pearson correlation between the original and recovered expression levels of 37 genes in each cell (y axis) across simulation trials for different numbers of composite measurements (FIG. 27A), or for different measurement densities, set by the maximum number of measurements in which each gene was included (FIG. 27B). In (FIG. 27A) the maximum compositions per gene is 3, and in (FIG. 27B) the number of compositions is 10. Mini boxplots depict median (dots), inner quartiles (box), and 1.5× quartile range (whiskers).
Figure 27B:
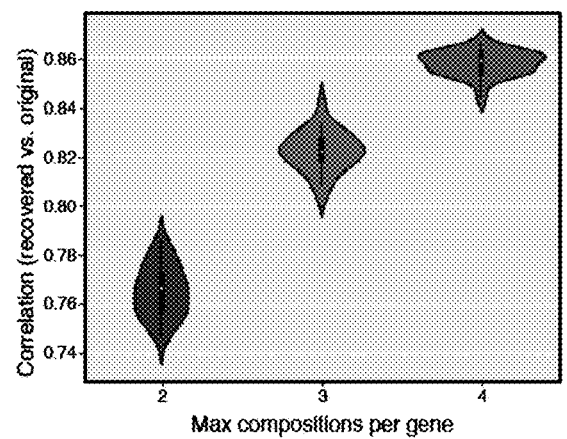

Applicants then used the simulation procedure described above to develop barcodes and composite measurements that would allow us to learn the modules in each cell (or small region of a tissue section), and subsequently approximate the 37 genes. As expected, performance improved with increasing numbers of measurements (criterion (1)), leveling off around 10 measurements (FIG. 27a). The best compositions using each gene in a maximum of 2, 3, or 4 measurements (criterion (2)) resulted in recovered profiles that were 78%, 84%, and 87% correlated with the original profiles (FIG. 27b). Applicants also considered scalability of probe synthesis. In particular, the number of gene-composition combinations that Applicants would need to synthesize when each gene was included in 2, 3, or 4 measurements was 74, 97, and 120, respectively. Balancing the performance of the different designs and the estimated costs, Applicants selected the best performing set of 10 composite measurements, with each gene included in up to 3 compositions. Using these parameters, Applicants found that simulation refined performance from a median correlation of 76% to 84% with the best performing selection, with these compositions including between 6 and 13 genes.

Applicants synthesized, pooled, and successfully tested the 10 selected compositions. Applicants designed probe pairs targeting multiple regions of each gene for fluorescent in situ hybridization with HCR amplification (HCR-FISH (Choi et al., 2018), Methods), where each oligonucleotide contains a gene targeting sequence and a barcode that determines the channel (color) of the HCR amplified signal. Applicants assigned each of the 10 compositions to one of three colors, to be imaged during 3⅓ rounds, pooling the assignment barcoded probes into the 10 compositions. For each of the 10 compositions, Applicants tested these pools by imaging each gene individually, along with the pool of probes for the composition. Applicants simulated composite images by merging into a composition the images acquired individually for each gene. The real and simulated composite images agreed well visually (FIG. 24a), and had 90.1% correlation between integrated intensity values in segmented cells (on average, across the 10 compositions).

Next, Applicants generated a large imaging dataset, using the validated composite probe libraries, together with probes for individual genes measured and used only for later confirmation. In each tissue section comprising ~2,500-3,000 cells, Applicants first imaged the 10 composite measurements over 3⅓ rounds. Using the remaining two colors in the fourth round, and all three colors in a fifth round of imaging, Applicants also directly measured each of up to five individual genes, for subsequent validation purposes. Applicants repeated this in 8 tissue sections, picking different individual genes each time, such that in total Applicants directly measured each of the 37 genes individually along with the compressed measurements.

Applicants decompressed the experimental data with the segmentation-based and segmentation-free algorithms, and evaluated the accuracy of the results in several ways. First, the decompressed images for several genes corresponded well to their known distinct and readily identifiable spatial expression patterns, available as reference images from the Allen Brain Atlas (FIG. 24c). For example, these included: Slc17a7, which is broadly expressed in excitatory neurons throughout MOp; Vip, a marker of a subtype of inhibitory neurons, which is expressed more frequently in layer 2/3; and Sst, a marker of another inhibitory neuron subtype, which is expressed more frequently in layer 5.

Figure 28:
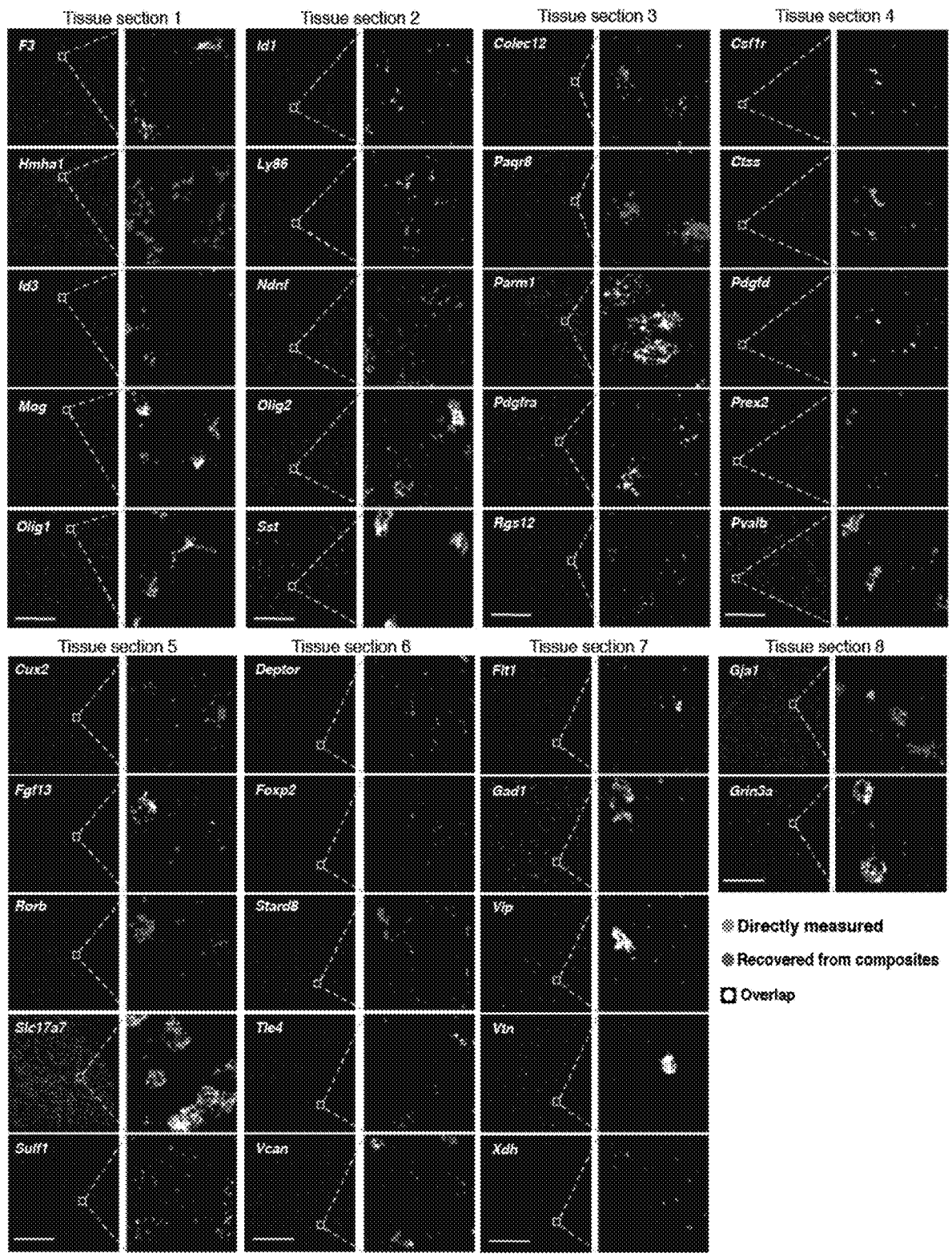
FIG. 28. Autoencoder based decompression successfully recovers accurate spatial patterns of individual genes compared to direct measurement on the same section. RNA images recovered by decompression with the segmentation free algorithm (magenta) and directly measured (green) in the same tissue section. White: images overlap exactly. Genes are grouped based on the section in which their direct measurements were made. Insets for all genes in a section show the same region, or an adjacent region if no cells for a given gene were present. Scale bar: 500 um.

Second, the decompressed images agreed well with the direct measurements of each gene made in the same section, for genes expressed in both rare and common cell types, and in cells of varying morphologies (FIG. 24c and FIG. 28). The correlation between direct and recovered (decompressed) measurements based on integrated signal intensity in segmented cells was high, either when using recovered values from the segmentation-free autoencoding algorithm (83.6%) or when using decompression from segmented cells (88.4%). (Applicants expected the autoencoding algorithm to perform slightly worse by this metric, since it is not optimized for the segmentation masks.) Both are in line with the simulations used to design the measurements, which predicted a correlation of 84%.

Figure 29:
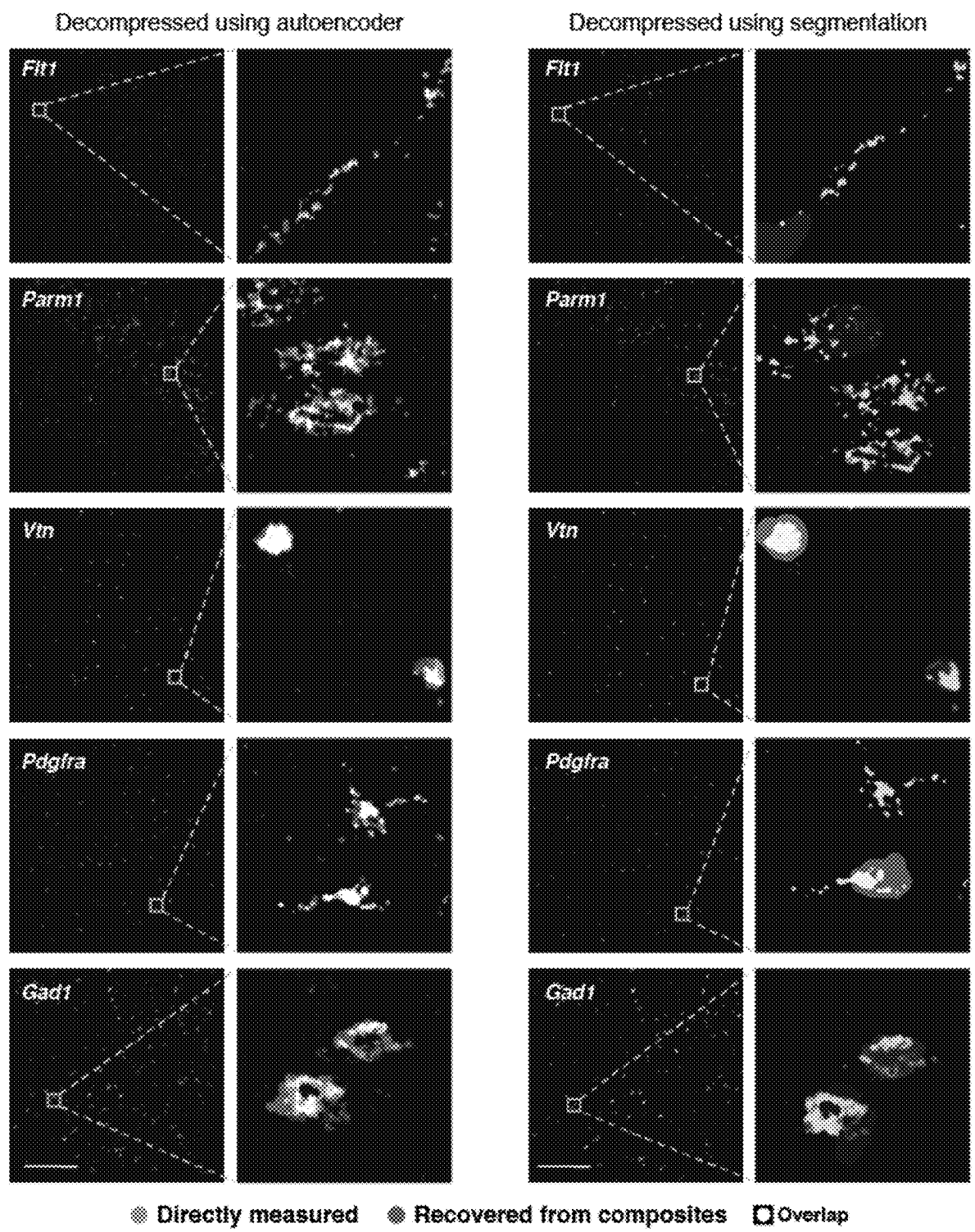
FIG. 29. Comparison of autoencoding and segmentation-based decompression. Individual gene images recovered (darker gray) using the autoencoding algorithm (left) or the segmentation-based algorithm (right) are overlaid with direct measurement (lighter gray) of the genes in the same tissue sections (white: direct overlap). For segmentation-based decompression, the decompressed signal for each gene is projected uniformly over each segmentation mask. Scale bar: 500 um.

Notably, the segmentation-free autoencoder out-performs the segmentation-based algorithm for genes whose expression does not necessarily follow simple patterns (FIG. 29). The segmentation-based approach omits regions of the image outside of successfully segmented cells, and can result in loss of morphological information, since the output typically consists of filled polygons with uniform intensity. Conversely, the autoencoding algorithm does not omit any regions, and retains morphology by data-driven convolutional features. As a result, while genes like Vtn have expression patterns easily captured by the filled polygons of segmented cells, others such as Flt1 and Parm1 are well-described by autoencoding, but not by segmentation (FIG. 24d, FIG. 29).

Applicants analyzed cell-type composition of the autoencoding results, by segmenting cells post hoc (on decompressed images) and clustering the segmented cells based on the integrated intensity values across genes (Methods). Based on the markers in each cluster, neurons comprised about half of all (successfully segmented) cells: 33.3% of cells in 9 excitatory clusters, and 16.9% of cells in 6 inhibitory clusters. In addition, Applicants find 4 clusters of oligodendrocytes and oligodendrocyte precursor cells (16.8%), 3 clusters of astrocytes (12.8%), 3 clusters of microglia (9.1%), 2 clusters of smooth muscle cells (6.5%) and 2 clusters of endothelial cells (4.4%). These in situ results are comparable with the representation of these cell subsets in snRNA-seq, albeit somewhat enriched in glial and depleted in endothelial cells: 44.5% excitatory, 14.5% inhibitory, 8.9% oligodendrocyte/OPC, 10.4% astrocyte, 4.6% microglia, 1.9% smooth muscle cells, and 15% endothelial.

Figure 30A:
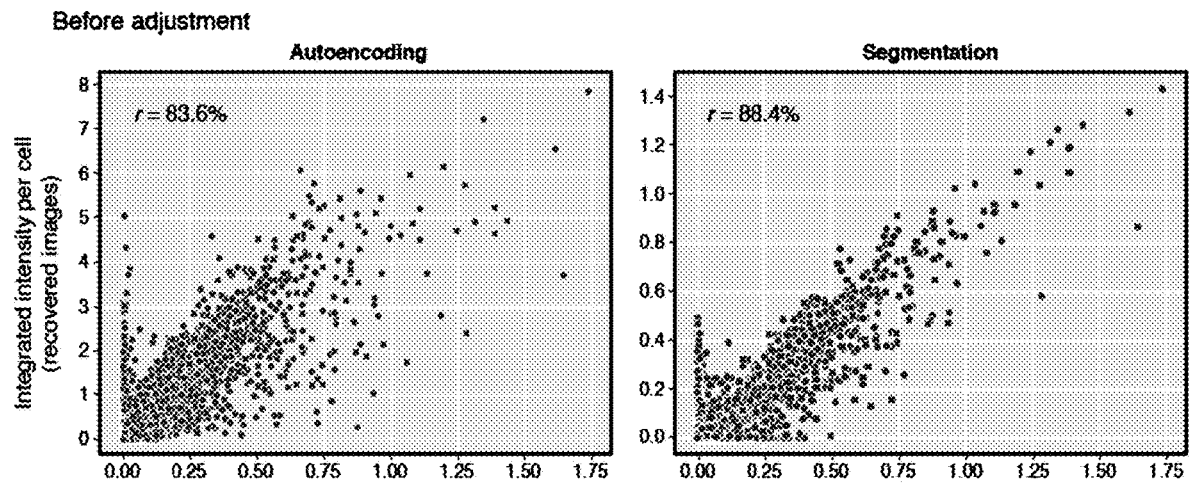
FIG. 30A-30C Evaluation of recovered signals before and after co-measurement adjustment.
Figure 30B:
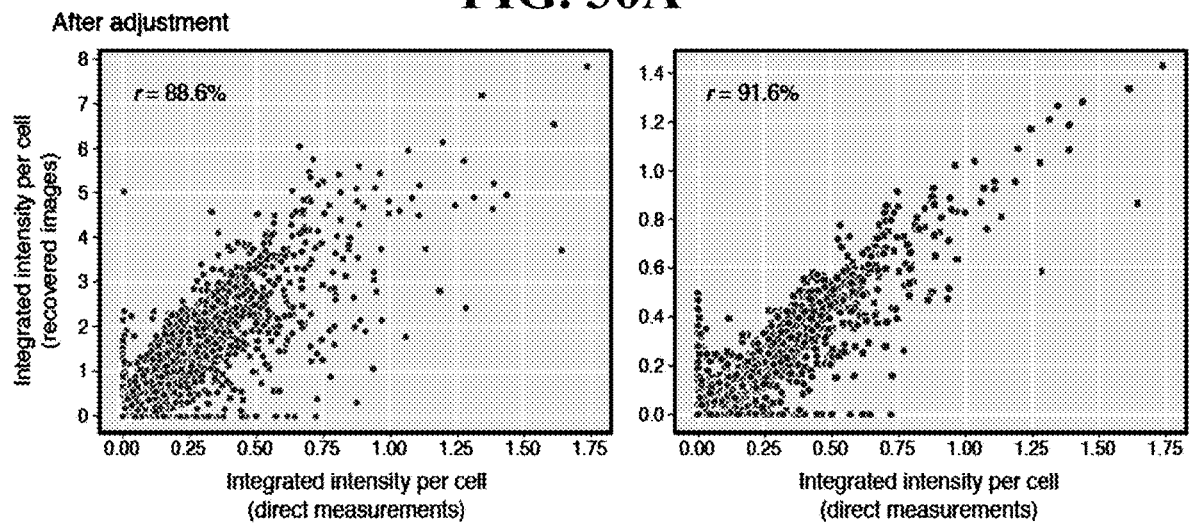
Figure 30C:
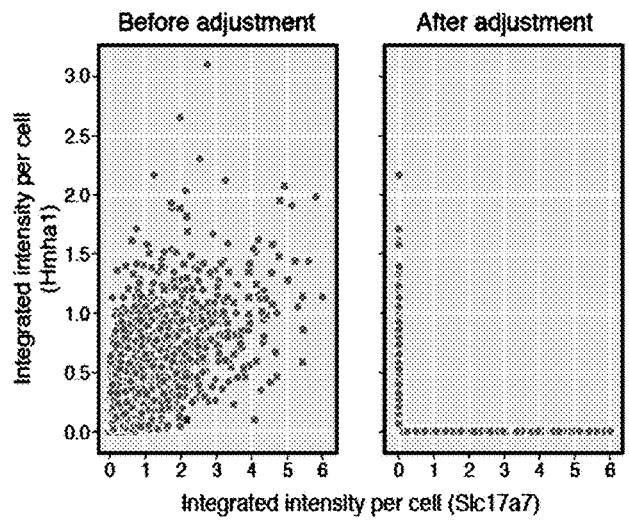

The points of inaccurate recovery were relatively predictable and consistent between the two algorithms, with some false positives for several genes, but few false negatives (FIG. 30a). Eight genes had some false positive expression patterns in the recovered images that were absent from the direct measurements. In each case, the false positive signals co-occurred with a gene that had probes included in overlapping measurements. For instance, false positives for Hmha1 are found in cells that express Slc17a7 (FIG. 30c, left). Hmha1 is a member of two compositions, both of which also included Slc17a7, which is additionally included in a third composition.

Applicants developed a simple heuristic to address this, by reducing false positives at the expense of some false negatives. For the 104 pairs of co-measured genes (i.e., that co-occur in more than one composition) that were not correlated (<10%) in snRNA-Seq, Applicants set the expression of one of the two genes to zero whenever they were co-expressed in recovered images (Methods). To select which gene to adjust, Applicants calculate the correlation between the 10 composite measurements in a cell, and the pattern of measurements for each of the two genes (e.g., the binary vector indicating which measurements included the gene), and then adjust to zero the gene with the lower correlation. Applying this simple rule reduced false positives and improved the overall correlation from 83.6% to 88.6% with autoencoding, and from 88.4% to 91.6% with segmentation (FIG. 30a, 30b).

Finally, using these adjusted values, Applicants found that decompressed measurements are substantially less sparse than snRNA-Seq, while preserving the co-expression programs observed in snRNA-Seq. As previously observed with osm-FISH (Codeluppi et al., 2018), the degree of sparsity is much greater in snRNA-Seq than in the decompressed measurements, with 2.87 genes detected on average in each cell in snRNA-Seq vs. 5.96 based on decompressed images (6.49 with segmentation) (FIG. 31a). To compare co-expression patterns, Applicants clustered cells in the (post hoc segmented) decompressed data (as discussed above) and in snRNA-Seq (using only the 37 genes), finding 29 and 28 clusters, respectively. Most clusters had expression signatures that were highly correlated with a counterpart in snRNA-Seq, and had identical sets of marker genes (i.e., the gene with the highest normalized expression in each cluster) (FIG. 31b).

Discussion

CISI addresses the two key bottlenecks in imaging transcriptomics: increasing the number of genes studied per round of hybridization and decreasing the time needed to scan large tissue volumes per round. In the results here, Applicants improved the multiplexing efficiency by 3.7-fold (by assaying 37 individual genes with 10 composite measurements) and reduced the imaging time by 6.25-fold (by using 40× vs. 100× magnification) compared to state-of-the-art methods that achieve a similar scale of multiplexing with osmFISH (Codeluppi et al., 2018). In principle, CISI could also be used to increase multiplexing with combinatorial labeling (with each combinatorial barcode corresponding to one composite), although high-magnification imaging would be needed to resolve (and decode) each individual spot, and fluorescence crowding would still pose a challenge.

The results here point towards the possibility of greatly increased throughput in imaging transcriptomics. More broadly, CISI is in a class of methods that leverage algorithmic insights and biological structure to be more efficient in generating and interpreting data. Further applications in this class could increase multiplexed protein detection with antibodies, make single cell and single nucleus RNA-seq more efficient by sequencing small pools of cells, or efficiently study genetic perturbations by leveraging common outcomes across experiments.

Methods

Mice

All mouse work was done with an adult C57B/L6 mouse according to IACUC procedures specified on protocol 0211-06-18.

Analysis of Single-Nucleus RNA-Seq Data

Applicants selected 37 cell type/layer-specific markers by analyzing snRNA-seq data sets released by BICCN (U19 Huang generated by Regev lab; http://data.nemoarchive.org/biccn/lab/regev/transcriptome/sncell/) for mouse primary motor cortex (M1 or MOp) and generated using the 10× single-cell 3' protocol (V2). To align the reads, a custom reference was created by 10× Cell Ranger (v.2.0.1, 10× Genomics) using mouse genome and pre-mRNA annotation (Mus_musculus.GRCm38, release 84) according to the instructions provided on the 10× Genomics website (https://support.10× genomics.com/single-cell-gene-expression/software/release-notes/build #mm10_1.2.0). The default parameters were used to align reads, perform UMI counting, filter high quality nuclei and generate gene by nucleus count matrices. In total, ~30,000 nuclei passed QC metrics including (i) the number of unique genes detected in each cell (>200) and (ii) the percentage of reads that map to the mitochondrial genome (<10%), and featured in the further downstream analyses using the Seurat package (version 2.2.1).

Compressed Sensing Simulations

Applicants use compressed sensing to recover sparse signals from composite measurements. In the basic formulation, Applicants seek to recover sparse gene module activities, $W \in \mathbb{R}^{d \times n}$, and estimate unobserved gene abundances, $UW = \hat{X} \in \mathbb{R}^{g \times n}$ given observations $AUW = Y \in \mathbb{R}^{m \times n}$, a gene module dictionary $U \in \mathbb{R}^{g \times d}$, and measurement compositions $A \in \mathbb{R}^{m \times g}$ where there are m composite measurements of g genes in each of n cells, and the dictionary consists of d gene modules.

Using the snRNA-Seq data above, and the 37 selected genes, Applicants evaluated different composite designs by simulating composite measurements and recovering individual expression levels by sparse optimization (as previously described(Cleary et al., 2017); see also https://github.com/cleary-lab/CISI). Briefly, Applicants first randomly selected training, validation and testing subsets, using 60%, 20%, and 20% of all cells for each respective group. In the training set, Applicants calculated a dictionary, $U \in \mathbb{R}^{g \times d}$, with d=80 modules of g=37 genes (and default SMAF parameters found on https://github.com/cleary-lab/CISI). A given simulation trial with m measurements consists of (i) randomly assigning genes to compositions, A; (ii) simulating noisy composite measurements in validation data, $Y = A(X+\epsilon)$ (with a signal-to-noise ratio of 5); (iii) decoding sparse module activity levels, $\min_W \|W\|_1$;

$$\text{s.t.} \ \frac{\|Y - AUW\|}{\|Y\|} < \lambda;$$

(iv) estimating individual expression levels, $\hat{X} = UW$; and (v) calculating the correlation between the original and estimated levels, corr=Pearson(X,$\hat{X}$). When evaluating different measurement designs in step (i), Applicants varied the total number of measurements (from 8 to 12), and the maximum number of measurements in which each gene appeared (either 2, 3, or 4). Each gene was then randomly assigned to a randomly chosen number of measurements (up to the maximum). Final assignments resulting in either two or more genes being perfectly co-assigned or in large measurement imbalance (any gene appearing more than 4 times more frequently than any other gene) were excluded. Applicants then iterated steps (i)-(v) 2,000 times, selected the 50 composition matrices resulting in the top correlations, and evaluated (steps (ii)-(v)) in testing data. The correlations in testing data were then used to compare different numbers of measurements, and maximum assignments per gene (FIG. 27).

Selection of the Final Library

Based on these comparisons (FIG. 27), and considering the number of probes that would need to be synthesized in each scenario, Applicants selected the composition with the highest performance in testing data among those with 10 measurements and a maximum of 3 assignments per gene. Each of the 10 compositions was assigned to one of three colors, to be imaged during 3⅓ rounds.

Probe Design and Validation

For each target mRNA, HCRv3.0 DNA probe sets of ~20 probe pairs each were ordered from Molecular Technologies. All HCR v3.0 reagents are now only available from Molecular Instruments, Inc. (molecularinstruments.com).

Tissue Preparation and Brain Extraction

An adult C57B/L6 mouse was perfused with ice-cold PBS (10010023, Thermo Fisher Scientific) prior to dissection of the brain. The brain was then extracted and flash frozen in liquid nitrogen. After OCT embedding, the brain was sectioned directly into an APTES coated 24-well glass bottom plate (82050-898, VWR). For coating, plates were coated with a 1:50 solution of APTES (440140, Sigma) in 100% Ethanol (V1016, DeconLabs) for 5 minutes followed by 3× washes with 100% ethanol before drying. Tissues were fixed in 10% Formalin (100503-120, VWR) for 15 minutes and washed with PBS before overnight permeabilization with 70% ethanol. Tissues were re-hydrated with PBS prior to hybridization.

In Situ Hybridization

In situ HCR version 3.0 with split-initiator probe sets was performed using the protocol detailed in(Choi et al., 2018) with some slight adaptations. Probe sets for each individual target mRNA were diluted to the concentration specified in the protocol and organized into composite channels. A composite channel is comprised of a mix of probe sets for approximately 10 different target mRNAs, each with the same initiator. In total, 10 composite channels were created. Three composite channels can be hybridized per round of imaging. Thus, for the first round of hybridization, probe sets for three composite channels with distinct initiator sequences were added at once to each tissue.

Probes were hybridized for approximately 8 hours in hybridization buffer and then tissues were washed 4 times with 30% wash buffer for 15 minutes each and 3 times with 5×SSCT for 5 minutes each (buffer compositions available from Molecular Instruments). Snap-cooled hairpins were added at a 1:500 diluted concentration and amplification was allowed to proceed for 8 hours. Excess hairpins were then washed off with 5×SSCT (15557044, Thermo Fisher Scientific), with 0.2% Tween-20 for three washes of 15 minutes each. Tissues were stained with DAPI (1:5,000 TCA2412-5MG, VWR) immediately prior to imaging. After imaging, probes were stripped from tissues using 80% formamide at 37° C. for 30 minutes. This entire process (hybridization, amplification, imaging, stripping) was repeated for up to five rounds of imaging. All DNA HCR amplifiers (hairpins), hybridization buffers, wash buffers, and amplification buffers were ordered from Molecular Technologies. All HCR v3.0 reagents are now only available from Molecular Instruments, Inc. (molecularinstruments.com).

Imaging

Imaging was performed on a spinning disk confocal microscope (Yokogawa W1 on Nikon Eclipse Ti) equipped with a Nikon CFI APO LWD 40×/1.15 water immersion objective operating NIS-elements AR software with Andor Zyla 4.2 sCMOS detector. DAPI fluorophores were excited with a 405 nm laser, Alexa 488 HCR amplifiers were excited with a 488 nm laser with 525/36 emission filter (Semrock, 77074803), Alexa 546 HCR amplifiers were excited with a 561 nm laser with a 582/15 emission filter (Semorck, FF01-582/15-25), and Alexa 647 HCR amplifiers were excited with a 640 nm laser with a 705/72 emission filter (Semorck, 77074329).

Image Processing

Before downstream analysis, Applicants ran a series of image processing steps to normalize, stitch, align, and segment the images in each color, field of view, round, and tissue. Applicants first took a maximum projection across the z-axis, and then used the DAPI channel to stitch the fields of view within each round of imaging (using ImageJ software(Abramoff et al., 2004)). Applicants applied the stitching coordinates from the DAPI channel to each of the other channels. Applicants then smoothed the image for each channel using a median filter (with a width of 8 pixels). (If spot-level resolution is needed, this step may not be advised.

Since Applicants do not need this resolution, Applicants use this step to make autoencoder reconstruction an easier task.) From each smoothed image, Applicants aligned and subtracted background signal, obtained by imaging after stripping the final round of fluorescent probes. Applicants then adjusted brightness and contrast by rescaling according to upper and lower thresholds determined using auto-adjust in ImageJ. The same rescaling parameters for each channel (determined from the maximum upper threshold and minimum lower threshold) were applied to all tissues and rounds. After rescaling, Applicants applied a flat field correction to each field of view, by normalizing (dividing) each pixel by the median smoothed pixel intensity across all images (with smoothing by a Gaussian filter with a width ⅛ of the image dimension). Each round of the flat field-corrected images in a given tissue was then aligned using ImageJ. These images were used in the remainder of downstream analysis.

For segmentation, Applicants used CellProfiler(McQuin et al., 2018), and calculated one image mask per nucleus in each tissue using DAPI in the first round. Each mask was then expanded by up to 10 pixels (without overlapping a neighboring cell). Comparisons and decompression with segmented cells were done using the integrated image intensity in each expanded nucleus mask.

Decompression of Composite Signals

Applicants developed two methods to decompress composite signal intensities into signals for individual genes.

The first method, which Applicants used primarily as a point of reference for validation statistics, is based on cell segmentation. Given the intensities of each composite measurement in each segmented cell, $Y \in \mathbb{R}^{m \times n}$, Applicants solved a sparse optimization problem to decode sparse module activity levels, $\min_{W \in \mathbb{R}^{d \times n}} \|W\|_1$;

$$\text{s.t.} \frac{\|Y - AUW\|}{\|Y\|} < \lambda,$$

before estimating individual expression levels, $\hat{X} = UW$, with the same method as in the simulations (above).

The second method Applicants developed decompresses entire images using a convolutional autoencoder. In this approach, for a given set of 10-channel composite images, Applicants first train a model to identify a reduced (encoded) representation of each image, which can then be decoded to recapitulate the original. During this training, Applicants optimize the following loss function:

$$\|\log(Y+\varepsilon) - \log(\hat{Y}+\varepsilon)\|_1 + \lambda_{pixel} L_{pixel} + \lambda_{TV} L_{TV},$$

where Y is the original image, $\hat{Y}$ is the decoded image, $L_{pixel}$ is a loss on pixel density, $L_{TV}$ is the total variation of $\hat{Y}$, $\lambda_{pixel}$ and $\lambda_{TV}$ are hyperparameters, and $\varepsilon$ is a small constant. $L_{pixel}$ is calculated as the Poisson log-likelihood of the pixel density, which is computed as the Shannon Diversity across pixels, divided by the number of pixels, with prior density set by a parameter $\delta_{pixels}$. Convolutions in each layer of the network are computed across filters (or kernels), but not across the 10 composite channels. Hence, each of the 10 channels remains separated from the other channels throughout each layer of the network. However, only one set of convolutional weights is learned; these are shared across all channels. The number of parameters in the model is, thus, relatively small, and the autoencoder trained quickly on the data. As discussed below, hyperparameters, including the number of encoding and decoding layers, the number and size of filters, and pooling sizes are chosen by hyperparameter tuning on a small set of validation images.

Using the trained autoencoder, Applicants decompress composite images as follows. First, Applicants encode each 10-channel image to a reduced representation, $\tilde{Y} \in \mathbb{R}^{10 \times \tilde{w} \times \tilde{h} \times f}$, where $\tilde{w}$ and $\tilde{h}$ are the reduced width and height (after pooling at each encoding layer), and $f$ is the number of convolutional filters. Applicants then solve for sparse module activities, $\tilde{W} \in \mathbb{R}^{d \times \tilde{w} \times \tilde{h} \times f}$, where d is the number of modules in the dictionary (here, 80), and then estimate the encoded representation of each individual (unobserved) gene, $\tilde{X} \in \mathbb{R}^{37 \times \tilde{w} \times \tilde{h} \times f}$. These representations are then run through the pre-trained decoder to produce an image for each gene, $\hat{X} \in \mathbb{R}^{37 \times w \times h}$.

The loss function has components at both the encoding and decoding layers:

$$L = \|\tilde{Y} - AU\tilde{W}\|_2^2 + \|\log(Y+\varepsilon) - \log(A\hat{X}+\varepsilon)\|_1 + \lambda_{pixel} L_{pixel} + \lambda_{TV} L_{TV} + \lambda_{W} L_{W},$$

where $L_W$ is a loss on the density of $\tilde{W}$, calculated as the Poisson log-likelihood of the Shannon diversity, with prior density set by parameter $\delta_W$. Applicants implemented the model in tensorflow, using the Adam optimizer.

Hyperparameters and model architectures were chosen by hyperparameter tuning on a small set of validation images. The validation images consist of 4 of 36 patches from each of 3 images (i.e., from 3 tissue sections, each with 36 patches), for a total of 12 patches (equivalent in size to ⅓ of one image). Each patch includes signal from the 10 composite measurements, along with up to 5 directly measured genes. In each validation trial, Applicants select hyperparameters, train the autoencoder on the composite data, decompress all genes, and then calculate the trial score as the correlation between the subset of directly measured and recovered genes (this is done in post hoc segmented cells, when using the autoencoder). Applicants selected the hyperparameters from the best performing trial, and used these to run the analysis on the full dataset. More details can be found at https://github.com/cleary-lab/CISI.

Applicants applied a heuristic correction to co-measured genes. Applicants first identified 104 pairs of co-measured genes (i.e., that co-occur in more than one composition) that were not correlated (<10%) in snRNA-Seq. For each pair, Applicants set the expression of one of the two genes to zero whenever they were co-expressed in recovered images. To select which gene to adjust, Applicants calculate the correlation between the 10 composite measurements in a cell, and the pattern of measurements for each of the two genes (e.g., the binary vector indicating which measurements included the gene), and then adjust to zero the gene with the lower correlation.

Plotting Decompressed Images

The decompressed results for each gene vary in their relative signal intensities (as do direct measurements for each gene). When plotting merged validation images (as in FIG. 24d and FIG. 28), Applicants normalize the signal for each gene to automatically adjust contrast and brightness. The specific parameters of this normalization can be found in the code demo of the online repository (github.com/cleary-lab/CISI/blob/master/getting_started/plot_decompressed_images.py). The signal plotted for direct measurements have been pre-processed according to the methods described above.

Comparison of CISI and Combinatorial Barcoding

Applicants can approximate the number of imaging rounds in CISI, $r_{CISI}$, relative to that in combinatorial barcoding methods, $r_{combinatorial}$, defined as $r_{CISI}/r_{combinatorial}$, based on the results here, using simulation to extrapolate to larger scales, and by comparing with existing combinatorial methods. Here, Applicants used 3 and a ⅓ rounds to measure 37 genes; the same could be achieved using 3-color combinatorial barcoding without error correction. More commonly, 4 or 5 rounds would be used to measure 37 genes and allow for error correction. At larger scales, simulations in the earlier work (Cleary et al., 2017) suggest that ~100 composite measurements would suffice to approximate the expression of 10,000 genes. This could be done in 33 and a ⅓ rounds of CISI. To date, the only combinatorial method to scale to this level did so with 80 rounds of imaging(Eng et al., 2019). Applicants therefore very roughly approximate that the required rounds of imaging with either approach will be comparable, and that $r_{CISI}/r_{combinatorial}$ will be in the range ⅓ to 3, allowing for improvements in combinatorial methods and the possibility of needing more rounds than anticipated with CISI.

The following references related to Example 2

Abramoff, M. D., Magalhães, P. J., and Ram, S. J. (2004). Image processing with imageJ. Biophotonics Int.

Angelo, M., Bendall, S. C., Finck, R., Hale, M. B., Hitzman, C., Borowsky, A. D., Levenson, R. M., Lowe, J. B., Liu, S. D., Zhao, S., et al. (2014). Multiplexed ion beam imaging of human breast tumors. Nat. Med. 20, 436-442.

Chen, K. H., Boettiger, A. N., Moffitt, J. R., Wang, S., and Zhuang, X. (2015). Spatially resolved, highly multiplexed RNA profiling in single cells. Science (80-.). 348, aaa6090-aaa6090.

Choi, H. M. T., Schwarzkopf, M., Fornace, M. E., Acharya, A., Artavanis, G., Stegmaier, J., Cunha, A., and Pierce, N. A. (2018). Third-generation in situ hybridization chain reaction: multiplexed, quantitative, sensitive, versatile, robust. Development 145, dev165753.

Cleary, B., Cong, L., Cheung, A., Lander, E. S., and Regev, A. (2017). Efficient Generation of Transcriptomic Profiles by Random Composite Measurements. Cell 171, 1424-1436.e18.

Codeluppi, S., La Manno, G., van Lunteren, J. A., Linnarsson, S., Zeisel, A., Borm, L. E., Svensson, C. I., Zeisel, A., La Manno, G., van Lunteren, J. A., et al. (2018). Spatial organization of the somatosensory cortex revealed by osmFISH. Nat. Methods 15, 932-935.

Eng, C. H. L., Lawson, M., Zhu, Q., Dries, R., Koulena, N., Takei, Y., Yun, J., Cronin, C., Karp, C., Yuan, G. C., et al. (2019). Transcriptome-scale super-resolved imaging in tissues by RNA seqFISH+. Nature.

Goltsev, Y., Samusik, N., Kennedy-Darling, J., Bhate, S., Hale, M., Vazquez, G., Black, S., and Nolan, G. P. (2018). Deep Profiling of Mouse Splenic Architecture with CODEX Multiplexed Imaging. Cell 203166.

Keren, L., Bosse, M., Marquez, D., Angoshtari, R., Jain, S., Varma, S., Yang, S.-R., Kurian, A., Van Valen, D., West, R., et al. (2018). A Structured Tumor-Immune Microenvironment in Triple Negative Breast Cancer Revealed by Multiplexed Ion Beam Imaging. Cell 174, 1373-1387.e19.

McQuin, C., Goodman, A., Chernyshev, V., Kamentsky, L., Cimini, B. A., Karhohs, K. W., Doan, M., Ding, L., Rafelski, S. M., Thirstrup, D., et al. (2018). CellProfiler 3.0: Next-generation image processing for biology. PLoS Biol.

Raj, A., van den Bogaard, P., Rifkin, S. A., van Oudenaarden, A., and Tyagi, S. (2008). Imaging individual mRNA molecules using multiple singly labeled probes. Nat. Methods.

Shah, S., Lubeck, E., Zhou, W., and Cai, L. (2016). In situ Transcription Profiling of Single Cells Reveals Spatial Organization of Cells in the Mouse Hippocampus. Neuron.

Shah, S., Lubeck, E., Zhou, W., and Cai, L. (2017). seqFISH Accurately Detects Transcripts in Single Cells and Reveals Robust Spatial Organization in the Hippocampus. Neuron.

Wang, G., Moffitt, J. R., and Zhuang, X. (2018a). Multiplexed imaging of high-density libraries of RNAs with MERFISH and expansion microscopy. Sci. Rep.

Wang, X., Allen, W. E., Wright, M. A., Sylwestrak, E. L., Samusik, N., Vesuna, S., Evans, K., Liu, C., Ramakrishnan, C., Liu, J., et al. (2018b). Three-dimensional intact-tissue sequencing of single-cell transcriptional states. Science (80-.).

Example 4

As described herein, the current approach does not require resolving individual spots, a current fundamental limitation to scaling existing IT, or on cell segmentation. To scale up the workflow, computational methods for identifying co-expression pattern; novel experimental techniques for generating composite images at scale; and a scalable composite image processing and decompression pipeline are investigated.

Figure 32:
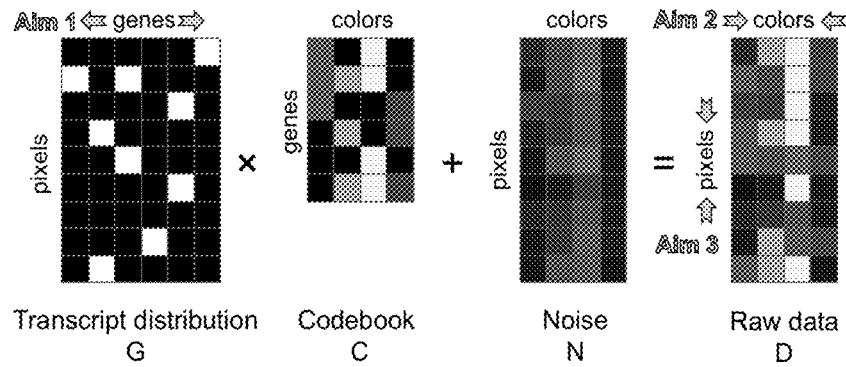
FIG. 32—Approach to improve resolution while simultaneously decreasing imaging time by leveraging co-expression to increase multiplexing ~100-fold; leveraging sparsity in the color coding of each spot to increase the space of available colors 10-fold; and super-resolving individual spots from low-resolution images to decrease imaging time 32-fold, he gains resulting in a greater than 10,0000-fold improvement in throughput over existing techniques.

To address challenges in IT to drastically scale up both throughput and information content by integrating compressed sensing and optimization methods with advanced optics, building on the interdisciplinary team of compressed sensing, optimization, optics, and biological experts. By taking advantage of underlying structure in the data and the measurement methods, Applicants will increase the number of genes about which IT methods can return information while simultaneously decreasing the imaging time (FIG. 32). Applicants will dramatically increase the throughput of IT measurements (~25,000-fold) by inferring information about 70x more genes, to reach genome-wide scale (Aim 1), requiring fewer rounds of imaging and imaging colors 10× faster (Aim 2) and requiring lower magnification, allowing 36-fold demagnified imaging (Aim 3). Combining these advances (Aim 4) Applicants will generate a spatially resolved, full transcriptome-deep atlas of the mouse primary motor and somatosensory cortices from six mice in one week at a cost of 0.11 cents/cell. Applicants will demonstrate these approaches with MERFISH (demonstrated in multiple labs) and collaborate to demonstrate in other protocols.

Test system. All work will be performed in C57B16/J mouse coronal brain slices of the primary motor and somatosensory cortex, chosen as a large, contiguous part of the mouse brain, of substantial focus and data in BICCN and other efforts[18,19]. The barrels of S1 are a helpful anatomical marker for integration to other coordinate frameworks. These regions are used in the SpaceTx project to test >15 IT techniques. 8 week old mice of either gender will be used to match to existing atlas data. To avoid activating stress-dependent transcription, mice will be housed individually for 5 days before euthanization by isoflurane delivery directly into the cage. 10 µm coronal sections of S1 and M1 will be prepared, fixed, mounted, and stained following robust protocols[20]. For technical optimization (Aims 1-3) one animal and 4-6 slices per comparison will be used. For data generation (Aim 4), Applicants will use 3 males and 3 females, with procedures for scaling and ensuring reproducibility (Aim 4.1).

Aim 1. Scale up transcriptome recovery from low numbers of genes to genome-wide: To increase the multiplexing capability of existing IT methods, Applicants have described the collection composite images[17], where instead of measuring the expression level of individual genes in each channel, composites are measured: sums of expression levels of multiple genes together, without revealing any individual one. As previously shown[17], since expression levels can be described by the activity of a small number of co-expression modules, Applicants can use a small n of composite data to reconstruct module activities, and, from them, individual gene expression. Here, this will be leveraged to increase IT multiplexing to genome-wide scale.

Figure 33:
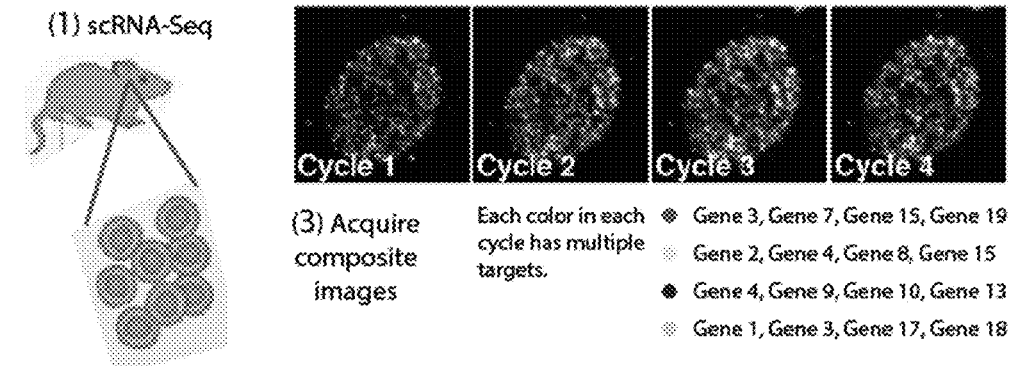
FIG. 33—Overview of approach to use composite data to increase multiplexing, to (1) obtain scRNA-Seq in the tissue to be imaged; (2) train models to represent each single cell profile by the activity of a small number of modules; (3) collect composite images of the sample, where each probe/channel combines information about multiple genes; (4) use the composite intensities to infer the latent co-expression module activities across space; and, (5) reconstruct the individual gene intensities in the tissue.
Figure 33:
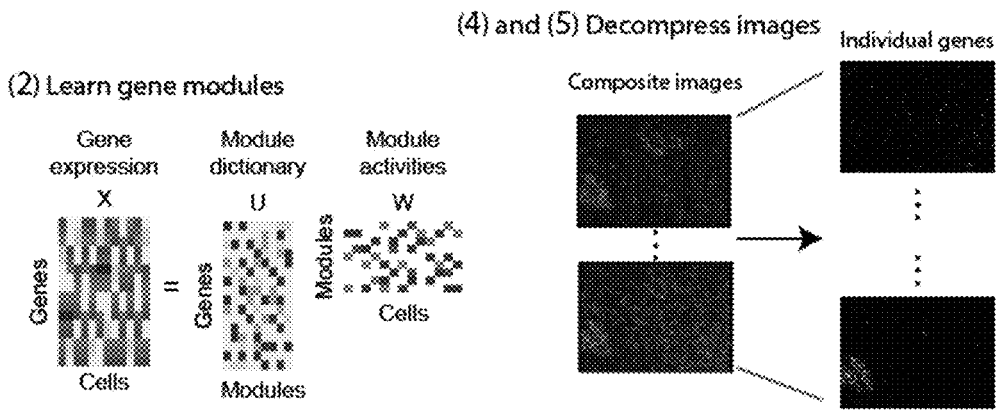

To use composite data to increase multiplexing (FIG. 33), Applicants will (1) obtain scRNA-Seq in the tissue to be imaged; (2) train models to represent each single cell profile by the activity of a small number of modules; (3) collect composite images of the sample, where each probe/channel combines information about multiple genes; (4) use the composite intensities to infer the latent co-expression module activities across space; and, (5) reconstruct the individual gene intensities in the tissue. The preliminary results show the power and accuracy of this approach in the brain, as discussed and shown regarding FIG. 24A-24D. Specifically, Applicants: (1) used BICCN scRNA-Seq from motor cortex to learn co-expression patterns and latent gene modules (Aim 1.1); (2) collected 10 composite images, each combining (with a single label) probes for 8-13 out of 37 genes (Aim 1.2); (3) decompressed the images by estimating latent module activities and using convolutional networks to determine the encoded representation of the unobserved image of each gene, then a convolutional decoder to reconstruct individual gene abundances (Aim 1.3); and (4) validated the reconstructions by direct validations of the target genes measured individually in the same tissue sections (FIG. 24A-24D). Importantly, the approach does not require resolving individual spots, a current fundamental limitation to scaling existing IT, or on cell segmentation.

Aim 1.1: Develop computational methods to find efficient representations of gene expression patterns The approach depends on reconstructing sparse (low-dimensional) latent parameters corresponding to the activity of co-regulated gene modules which are then used in decompression. Applicants will train computational models to generate such parameters from scRNA-seq data. In preliminary results, it has been shown that combining this approach for finding structure in RNA-Seq data with compressed sensing can increase the efficiency of expression profiling ~100-fold[17].

Modeling co-expression with matrix factorization. In preliminary results[17], Applicants have developed an algorithm, Sparse Module Activity Factorization (SMAF), that finds a sparse factorization of a gene expression matrix, $X=UW$, consisting of gene modules, U, and the sparse module activity levels, W, in each sample (or single cell). During decompression, the task is to solve for the module activity levels in new samples using composite data, Y, together with the design of composite measurements, A, and the gene module dictionary, U, learned during training: $Y=AUW$ (solve for W; return $X=UW$). Here, the training data consists of scRNA-Seq profiles generated by BICCN (Zeng, Arlotta, Lein LoS). Applicants will first apply the existing method SMAF to data from brain regions accrued by BICCN.

Figure 34:
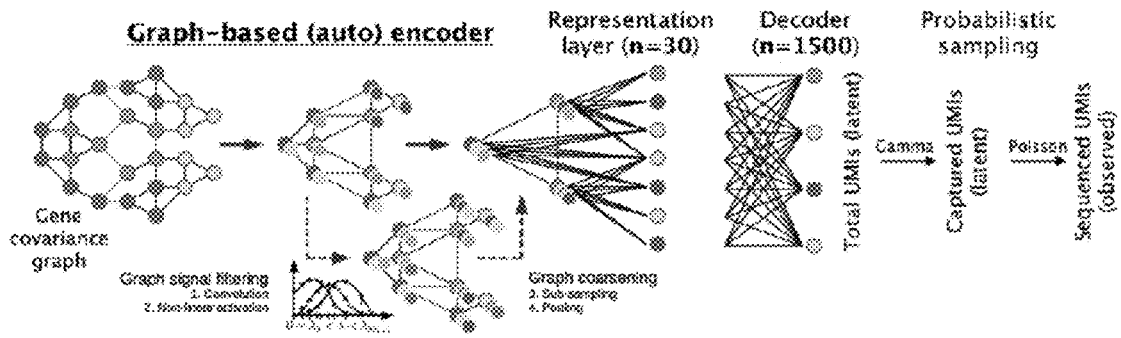
FIG. 34—Probabilistic graph-based model of scRNA-Seq expression patterns.

More efficient representations of expression patterns. Applicants will further enhance the ability to handle limited data by developing methods that use graph convolutions[21] applied to expression (FIG. 34). Here, a series of filters are trained to recognize co-expression patterns, with filters at deeper layers of the network learning to recognize complex patterns composed from the patterns recognized at the shallower layers. These filters are evaluated on a nearest neighbor graph of genes, built from co-expression data. Applicants assume that the patterns recognized by each filter are meaningful, regardless of their "location" (i.e., patterns of neighborhood expression are meaningful whether looking at neighbors of gene A or gene B). This assumption of invariance and the hierarchical composition of filters enable such models to efficiently represent complex patterns. In preliminary results, Applicants have implemented a probabilistic graph-based autoencoder that efficiently captures expression patterns in an internal "representation layer" (FIG. 34). When trained on large amounts of data, these models should allow us to recover expression from less data. Modeling power will be improved with advances in interpretable deep learning methods based on graphs[22].

Aim 1.2 Develop molecular methods to generate composite images at scale. Applicants will modify IT experimental techniques to sample according to gene compositions (defined in the matrix A), by generating composite images that combine measurements of many individual targets (e.g., 10 genes) into a single result (e.g., the sum of their abundances). In the context of any current IT method, Applicants can generate such images by combining oligonucleotide probes for multiple targets on a single channel-effectively replacing the "gene" label on the codebook with a "composition" label. In preliminary results, this was done so for a few dozen genes (FIG. 24A-24D). Here, Applicants will scale to hundreds, thousands, and ultimately all ~20,000 genes.

Design of measurement compositions. Applicants will design each composition by several considerations. (1) Gene identities. In principle, the set of genes in the compositions can be randomly selected, as previously shown[17]. However, with scRNA-Seq training data, they will be refined by simulations to maximize the fidelity of recovered gene abundances. In preliminary results, this refinement improved recovery from a median correlation of 76% to a correlation of 84% with the chosen compositions. (2) Number of genes per composition. Each composition will include probes for a small number of genes. For instance, to measure 250 genes across 25 channels, each composition should include 15-30 genes, and each gene represented in 2-5 composites. (3) Weights. Applicants aim to design compositions with binary weights, such that probes for each gene in a given composition will be present in equal abundance (for tuning weights, see below). (4) Number of compositions. The number of compositions (and thus of collected images) is guided by theoretical limitations. By theory, Applicants need on the order of k log(g) compositions, where k is the number of active gene modules, and g is the number of probed genes. The choice will be further refined with simulations in training data[17]. Preliminary estimates suggest that 100-150 compositions should suffice to recover ~10,000 genes[17].

Figure 35:
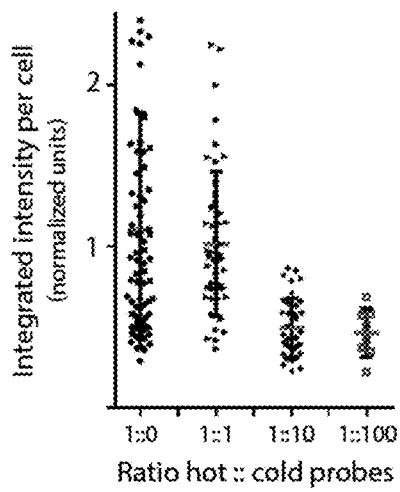
FIG. 35—Molecular normalization approach for high abundance genes.

Molecular normalization for high abundance genes. Scaling in most IT methods is prohibited by fluorescence crowding of spots, especially with high abundance genes. While the decompression methods can avoid this limitation, one might still expect signal saturation due to high abundance genes. A molecular normalization strategy will be developed to titrate in "cold" probes in inverse proportion to expected gene abundance (estimated from scRNA-Seq). Genes of similar expression levels will be assigned to expression level bins. Both the original and cold probes (same hybridization sequences but without the sequences necessary for signal amplification) will be introduced to the sample in excess, so that the ratio of original to cold probes determines the normalization without regard to target abundance in any given region of a sample. In preliminary results (FIG. 35) this approach was successfully tested.

Generation of encoding probe libraries. The conventional MERFISH hybridization scheme includes 50-100 encoding probes per transcript, each targeting a different 30-mer along the transcript. Probes for 140 genes coded with a 4 weight Hamming code can be generated using a 12,000-member oligonucleotide pool. The choice of binding sites for mouse M1 and S1 will be guided by full depth scRNA-seq data from BICCN (Zeng LoS). Applicants will identify target genes that capture transcriptional heterogeneity but are not too short or too highly expressed for MERFISH, as in the previous work in the hypothalamus[20].

Figure 36:
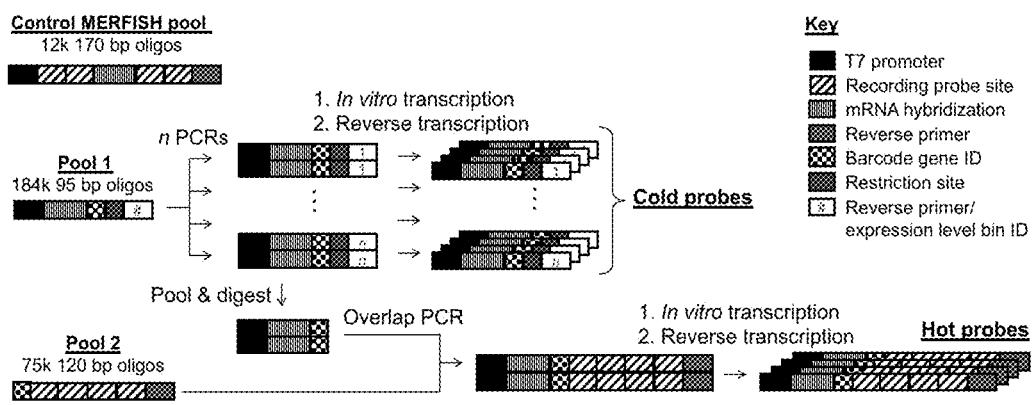
FIG. 36—Combinatorial synthesis for transcriptome scale detection.

Whole transcriptome composition measurements require ~10,000 genes to be detected with multiple sites per gene and multiple composition barcodes. Assuming 20 hybridization sites/gene, 500 genes/composition and 140 compositions, naively requiring 1.4M unique oligos. To circumvent this, combinatorial synthesis will be used (FIG. 36). Applicants will barcode 184,000 transcriptome sites with their gene identity and expression level bin, synthesize this pool cheaply (CustomArray, Inc.) and amplify with barcoded primers in separate PCR reactions to generate the cold probes for molecular normalization. The full 1.4M hot library will be generated by overlap PCR and amplification with a second oligonucleotide pool of recording probe binding sites, using the gene barcode as an overlap region. Applicants will mix hot and cold libraries by experimentally determined proportions.

Testing of probes. Applicants will evaluate probes for individual genes by: (1) consistency of distribution of expression with scRNA-Seq[1,20]; (2) co-expression with other genes; and (3) expression in morphologically or spatially distinct cells. To this end, each time composite images are collected, subset of pre-selected individual genes will also be imaged in the same tissue sections (Aim 1.3).

Testing of composites. Applicants will test that a composite image is consistent with merging the individual images from each target probed separately, by generating composite images and individual gene images in the same sample. Applicants will (1) design a panel of measurements consisting of probes for 5 genes on 1 channel; (2) in a first round of imaging, measure the composite image by probing for all genes simultaneously; and (3) in each of 5 successive rounds, measure one of the 5 genes individually. This procedure will be repeated on independent channels, using different panels of genes in each channel. To test larger gene panels, a large composite panel will be measured in the first round, then smaller composite subsets in each successive round.

Aim 1.3: Use composite imaging to infer latent module activities, and reconstruct individual gene abundances Decompression from a small number of composites to a larger number of individual genes relies on the fact that the expression of all genes in a single cell can be largely described by the activity of a small number of modules[17]. Applicants first use training scRNA-seq data to learn modules used by the different cell types in the tissue. After collecting the composite data, Applicants use the composite intensities in each cell and the model to estimate the sparse activity levels of these modules and individual gene expression. Two approaches will be used to solve this problem: cell segmentation and convolutional networks:

Cell segmentation. Applicants will determine cell boundaries according to a reference stain (e.g., with DAPI to label all nuclei), and, within each boundary, aggregate pixel intensities to achieve a net value. For each cell, Applicants will use sparse optimization to estimate latent module activities, and individual gene abundances. To generate the recovered image for each gene, Applicants will map these abundances back onto the coordinates of each cellular boundary.

Convolutional networks. While cell segmentation has been used by many, including us[20], it is a challenging problem, with difficulties in dense tissues, or when gene abundances vary across cellular compartments (e.g., cell surface, cytoplasm, nucleus), or when cells have very different shapes and sizes. As a segmentation-free alternative, Applicants will use convolutional networks that learn a series of filters than can be composed hierarchically to represent natural features of imaging data[23]. Applicants will first train a convolutional autoencoder[23] on the composite imaging data. Autoencoders first encode input images in a set of features learned by the convolutional architecture, then decode this representation to produce images that match the input. Depending on the depth of the encoding, each node in the encoded representation can be sensitive to a patch of the image that is approximately one cell in size. Using the activities of each node in the encoded representation of composite images, Applicants will estimate the latent module activities. These can be used to infer the encoded representation of the unobserved image of each gene. To produce the image for each gene, Applicants will then decode each of these representations. In preliminary results, Applicants used these methods to recover spatial profiles with greater morphological accuracy and specificity than would be expected with a coarse cell segmentation (FIG. 24A-24D).

Validations. Applicants will pursue several approaches. First, Applicants will confirm the expected patterns for genes known to correlate with morphological or gross features (e.g., genes expressed only in outer cortical layers). Second, Applicants will confirm correlation across the image for genes known to be expressed in the same cells. Third, in each experiment Applicants will generate images with probes for a subsets of individual genes as internal controls. Potential pitfalls and possible solutions include fluorescence crowding and noise and bias in scRNA-Seq training data. Fluorescence crowding. Combinatorial barcoding schemes require the resolution of individual spots, and as the number of targets increases (especially if highly expressed), current IT methods are currently critically limited by overcrowding of spots. Applicants will address this with three potential solutions: (1) Use molecular normalization to reduce signal in proportion to expected abundances (Aim 1.2); (2) Apply the mathematics of compressed sensing to super resolve individual spots from low resolution data in which spots appear merged (Aim 3); and (3) Leverage the fact that the decompression algorithm does not depend on the resolution of individual spots, but only on the net signal of composite measurements in entire cells. Applicants can therefore use alternative protocols that do not rely on combinatorial labeling (e.g., in situ HCR[7]). Noise and bias in scRNA-Seq training data. The scRNA-Seq data Applicants use in training, can be compromised by noise (including zero-inflation) and by cell composition biases introduced during tissue dissociation or nuclei preps. To address noise, Applicants will model the noise process in scRNA-Seq, as has been previously done[24]. For cell type composition biases, Applicants will first rely on the fact that the decompression methods operate cell-by-cell, and do not require assumptions on the overall abundance of any given cell type. In case that the gene modules (e.g., U in matrix factorization) are biased in favor of certain cell types, Applicants will apply methods of correcting for sampling bias[25] when training gene modules. Finally, Applicants will assess the benefit of foregoing training altogether by adapting methods of Blind Compressed Sensing (BCS), for which Applicants(Eldar) developed the theory[26], and Applicants (Cleary, Regev) have shown the application to gene expression[17]. This, however, requires a greater number of composite images to be generated.

Aim 2. Develop faster IT by decreasing the length of codewords and required sampling time. In IT measurements, multi-colored reporters are imaged over several rounds of imaging. Individual RNA molecules appear as spots in the image and are tracked across the imaging cycles. The sequence of colors constitutes a codeword for each gene which can be looked up in the pre-defined codebook (C) to recover its identity. Codewords must be long enough to both encode gene identity and detect (and even correct) errors, but this increases acquisition time. Here, Applicants will develop an improved software approach to recover codewords from raw data with greater fidelity, which will decrease the measurement error rate, and permit shorter codewords (and thus faster acquisition) (Aim 2.1). Applicants will further develop a compressed-sensing method to decrease the time needed to image a codeword by acquiring more color channels simultaneously (Aim 2.2).

Aim 2.1. Improve IT codeword recovery from raw data. IT analysis pipelines recover codewords one bit at a time by identifying individual spots in each color channel of the raw data image series ("spot calling")[6-8,27]. Because of potential chemical labeling inefficiencies and analysis errors in spot calling, successful dictionaries include an error-correction mechanism in codeword design. While hybridization errors are unavoidable, errors in spot calling can be improved. Here, Applicants will develop a general algorithm for recovering gene identity with 3-fold higher fidelity, or with 25% fewer required for error-checking. The former advance is applicable to all past and future IT experiments. The fewer bits will allow to either design libraries encoding more gene identities, encoding genes more accurately, or decreasing imaging time.

In MERFISH, error checking uses a variable Hamming distance between codewords, chosen for an acceptable error tolerance. Error detection occurs when recovered codewords do not match any in the codebook, and error correction is done by assigning those to the gene identity which is the shortest Hamming distance away. Importantly, because raw data is binarized prior to these decisions, the signal of every fluorophore labeling an individual RNA molecule must be above an empirically chosen threshold in the spot calling algorithm to avoid a "1 to 0" error at that position in the codeword. Since MERFISH depends on detection of single RNA molecules, and possibly of single fluorophores, it is possible that errors are detected in pixels where signal is present but below the chosen threshold. A pixel-by-pixel MERFISH calling algorithm has been developed which performs spot-calling after codeword assignment[13], but it is not immune from low signal levels. Though this algorithm shows higher error robustness in sparse samples, it is extremely vulnerable to misidentification if two different genes contribute signal to the same pixel[13].

An improved recovery algorithm. To improve recovery Applicants will rely on structure inherent to the data. In particular, Applicants exploit two constraints on the raw data matrix D that result from the measurement setup: (1) the rows in D correspond to known codewords and (2) the columns of D are sparse in space since they represent the fluorophore distribution. Applicants will develop an iterative algorithm to recover codeword assignments for every pixel of the image that exploits these priors via the incremental sub-gradient proximal method[28,29], which is tailored to problems with double priors. In preliminary results, this method has been used to enable fast recovery of molecular fingerprints from MRI data[15]. Similarly, Applicants will initialize here a random data matrix D and then perform iterations such that each cycle (1) takes a gradient descent step followed by (2) projection into codeword space and (3) enforces a sparsity constraint via thresholding. Applicants will develop models for initialization conditions as well as optimizing gradient descent steps and sparsity constraints to provide robust results while obtaining computationally efficient recovery-necessary given the large size of IT data sets. Efficiency will be aided by acceleration techniques as used in MRI and general imaging[15,30]. The resulting method will iterate between finding the optimal sparse images (columns of D), and then matching the rows to the closest possible code word-thus obviating the need for an additional Hamming distance calculation. This algorithm will also allow for multiple genes to overlap in space (or multiple codewords on the same molecule; Aim 1).

Aim 2.2. Incorporate knowledge of spectral properties to simultaneously increase the number of resolvable label colors and decrease sampling time. A larger number of colors available for the design of the codebook increases the number of gene identities that may be encoded in a fixed number of rounds. Since assignment of signal to a region of the color spectrum is currently done entirely by physical means (switching illumination wavelengths and optical filters), at most 4-5 fluorophores can be present in a sample before spectral crosstalk becomes a problem in assignment. Adding more colors thus requires additional rounds of hybridization or sequencing chemistry, increasing experimental time. Adding more colors also increases total imaging time as each color is typically captured on a separate camera exposure. Linear unmixing imaging techniques can recover information about larger numbers of fluorophores, leveraging the precisely known dye absorption and emission spectra. Unfortunately, these methods generally require as many measurements as resolvable fluorophores, and thus would not decrease the IT imaging time[31].

Figures 37A, 37B:
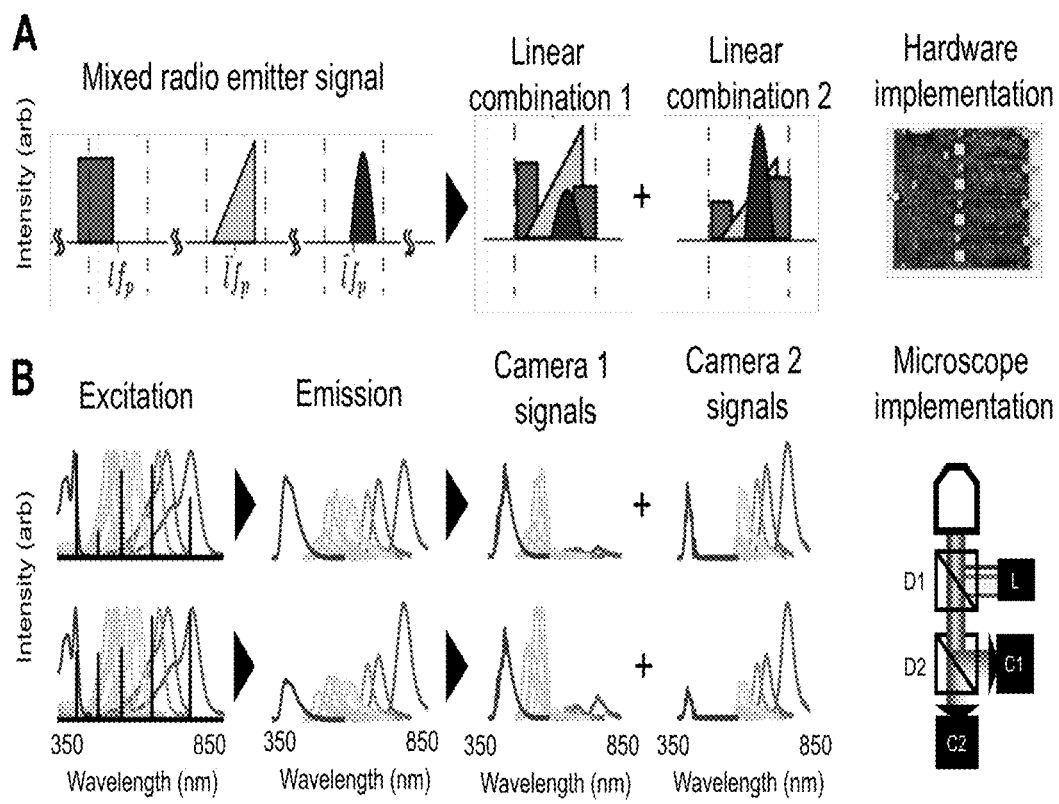
FIG. 37A-37B—Compressed sensing with FIG. 37A radio signals.

Compressed sensing approach. MERFISH and similar methods currently separately illuminate and acquire with 2-4 colors. Because each spot is typically marked with only 1 color at a time, the signal at each spot is sparse. Applicants will leverage this using compressed sensing to increase the number of fluorophores sampled, while decreasing imaging time, by illuminating with linear combinations of colors. For example, for a 1,000 gene codebook, this would reduce from 20 camera exposures to just 2, thus yielding a 10× improvement in speed. Specifically, Applicants will alter the MERFISH staining and imaging protocol to acquire measurements which are a linear combination of all fluorophore signals. Applicants will then recover the underlying labeling distribution by exploiting the sparsity of the codebook C and the expected signal correlations between different imaging rounds. In preliminary results[32], Applicants have implemented a compressed sensing method to localize radio emitters in a large frequency space using sub-Nyquist sampling rates—i.e. lower number of samples. This was achieved by processing signals by forming a small number of linear combinations of all bands, sampling a limited bandwidth of the result with at a low rate, namely, with a small number of measurements, and exploiting the sparse structure of the signal to recover the locations within the spectrum via sparse recovery techniques (FIG. 37A). With appropriate IT imaging hardware implementation to generate linear combinations (below), Applicants can use the same strategy to identify the frequencies present across a region of the spectrum, and extract color from a small number of measurements. To increase robustness, Applicants will incorporate knowledge on the absorption and emission spectra of the fluorophores introduced; the possible codewords in the sample; and the relative ratios of fluorescent recording probes binding an encoding probe.

Hardware implementation. Applicants can readily measure linear combinations of fluorophores on gray scale detectors by simultaneously illuminating with multiple excitation wavelengths at varying powers or by splitting the fluorescent signal with filters among multiple detectors. Applicants will configure a MERFISH-capable dual-view microscope from the Broad's Optical Profiling Platform (directed by Dr. Farhi) for both tasks. Linear combination measurements are most effective when they include contributions from each fluorophore. A 7W Lumencor Celesta light source with sub-millisecond switching capabilities will illuminate samples with 5 wavelengths of the Celesta (408, 473, 543, 635, and 750 nm) simultaneously. These wavelengths will excite the majority of commercially available fluorophores; different linear combinations are possible depending on the balance of excitation powers (Top and bottom row of FIG. 37B). For imaging, Applicants will form linear combinations by using a permissive dichroic to partially split each fluorophore's signal between two cameras in the dual view system in different ratios. Preliminary simulations (FIG. 37B, right) indicate that an AT600DC dichroic from Chroma can achieve this task for 10 Alexa Fluor dyes. No additional hardware is required for this aim.

Recording probe design. The approach does not require any changes to the encoding probe libraries (either standard MERFISH or those of Aim 1). The recording probes used will take the same hybridization sequences as currently used for MERFISH but will incorporate more fluorophores spanning the visible spectrum (up to 10), chosen for brightness and compatibility with the disulfide labeling chemistry necessary for MERFISH probes. These probes will be commercially synthesized by Biosynthesis Inc.

Optimization, testing, and expected results. Applicants will perform all optimizations in mouse cortex M1 and S1. For testing in Aim 2.1, Applicants will perform conventional 2 color MERFISH imaging and analyze data by both the published spot-calling methods and the improved algorithms. To assess algorithm performance, Applicants will compare the number of RNA molecules matched to codewords in vs. out of the codebook in each method. Applicants will perform all further analysis with the better performing of the two algorithms. In the estimate of throughput gains for this aim Applicants assuming the gains of Aim 2.1 will be used for more accurate gene identification.

For Aim 2.2, Applicants will perform compressed sensing imaging with recording libraries consisting of varying numbers of AlexaFluor dyes (4-10). In each round of compressed imaging, Applicants will acquire data with several excitation wavelength combinations. Applicants will benchmark compressed imaging against standard MERFISH imaging in the same cells in consecutive tissue slices. For each configuration, Applicants will extract average copy numbers per cell for each gene and calculate correlation coefficients to the corresponding values from 2-color MERFISH. This metric has been previously used to evaluate 4-color vs. 2-color MERFISH coding[13]. Applicants will optimize towards the largest set of fluorophores (and best wavelength combination) with at most a 5% drop in correlation coefficient relative to the correlation of 2-color MERFISH to itself in adjacent slides. Applicants anticipate this will be achievable with the full 10 fluorophore set. In that case, recovering 10 bits of information would require only one exposure time instead of the previous 10 exposure times, leading to 10× higher imaging speed. Thus, where 2-color MERFISH used 8 rounds of imaging to identify 140 genes (with 7 on-stage chemistry steps), this compressed approach could code >1,000 genes with 2 rounds of imaging and 1 on-stage step.

Potential pitfalls and possible solutions. The key pitfalls of compressed sensing approaches are insufficient sparsity and lack of knowledge about the structure of the underlying signal. Insufficient sparsity will require additional exposures with different illumination wavelength combinations, with a corresponding decrease in throughput. Hybridization errors are likely to be the biggest source of uncertainty about the underlying signal. To address this, Applicants will account for an expected hybridization error rate in the model and allow for recovery methods tolerant to modeling errors. Notably, the success of Aims 1 and 3 does not depend on Aim 2.

Aim 3. Develop methods that allow sampling at lower magnification.

Decreasing the number of pixels which must be sampled would allow imaging at lower magnification, an independent axis for improvement. Applicants will exploit the native sparsity of IT data to decrease the required magnification from 60× to 20×, by leveraging knowledge of codeword structure, leading to a 9-fold improvement in throughput, immediately accessible to any lab performing IT measurements (Aim 3.1). Applicants will introduce a series optics improvements and compressed sensing recovery methods for a further 4× improvement in throughput, for a total 36-fold over current technology. The work in this Aim requires no modification of wet lab protocols and is compatible with any IT methodology.

Aim 3.1. Exploit the native sparseness of MERFISH data in space to sample data at lower magnification with equal data content. Applicants will increase the throughput of MERFISH and similar methods by sampling at lower magnification and using compressed sensing recovery methods to super-resolve high magnification data. This requires no modification to biological protocols.

Figure 38:
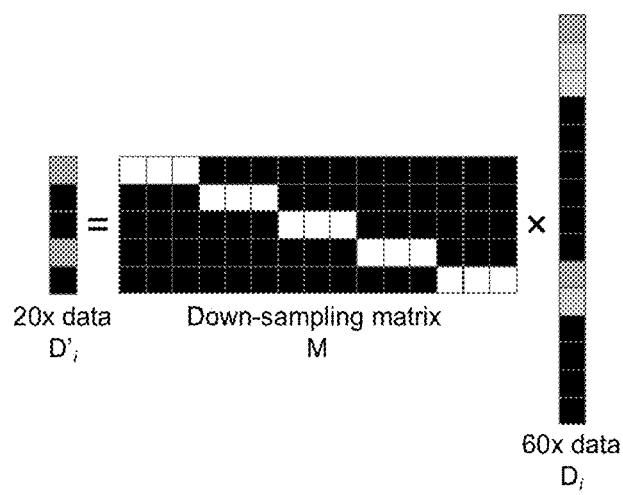
FIG. 38—High resolution recovery from low resolution data using compressed sensing (CS).

Structure of MERFISH images and data recovery. Applicants will develop a new approach to recover the columns of D ($D_i$) when sampling low magnification data D' (FIG. 38). To date, all multiplexed IT measurements require single molecule tracking throughout the experiment, with data acquired at high magnification, such that the vast majority of pixels are dark to facilitate spot calling (Aim 2.1). The acquired high magnification images (columns of D) are sparse, the common requirement for data recovery from undersampled data by compressed sensing. Furthermore, under these conditions, signal from individual RNA molecules is spread over several adjacent pixels. Mathematically, such an image (a single column of D) is "block-sparse". In preliminary results, Applicants(Eldar) have leveraged block-sparsity to recover underlying signals, achieving provably better performance than conventional compressed sensing recovery[33]. Applicants will develop a block sparsity model of $D_i$, from existing high magnification data[20] and additional data planned from BICCN and will then apply these recovery methods.

Aim 3.2. Decrease sampling magnification with hardware improvements and patterned illumination super resolution. To further gain in subsampling and increase throughput by another 3.6 fold, Applicants will make hardware adjustments of the MERFISH imaging set up, including additional demagnification and a smaller camera pixel size. To allow capturing wider FOVs, Applicants will further develop a patterned illumination super-resolution approach using a digital micromirror device (DMD) and a compressed sensing recovery method. Most required hardware items are available in the Optical Profiling Platform, and Applicants will add only shaping optics for fast beam steering. All of these approaches are applicable to any IT method or sparsely-labeled sample.

Imaging path improvements. Applicants will optimize several hardware aspects to increase throughput relative to current MERFISH implementations. Applicants will switch from the currently used 4.2 million 6.5 µm pixel cameras (e.g. Hamamatsu Orca Flash 4.0 or Andor Zyla 4.2) to the recently released Photometrics Iris 15 camera with 15 million 4.25 µm pixels (available through the Broad's Optical Profiling Platform). This change in detector, when coupled to an appropriate magnification decrease (6.5/4.25=~1.5 fold), will immediately lead to a ~3.6-fold increase in throughput (15/4.2). This throughput can still be improved upon. In-house measurements of Nikon's best performing 10× objective (CFI Plan Apo 10XC glycerol, 0.5 NA) allow a >4 mm FOV, but an Iris 15 camera would only capture 2.5 mm of this FOV. Changing the standard Nikon 200 mm tube lens tube to a 125 mm tube lens would capture the full 4 mm FOV on the camera (new magnification=6.25×). Camera pixels would then correspond to 680 nm in the sample plane. However, this pixel size would be too large for the sparsity-based reconstructions in Aim 3.1. Applicants will thus turn to patterned illumination and computation to super-resolve data in these pixels.

Patterned illumination for super-resolution. To recover the necessary resolution from demagnified data, Applicants will take an additional super-resolution approach based on acquiring several frames with patterned illumination. Structured illumination modulation (SIM) approaches[34] (now standard in commercial systems) double the lateral resolution of an objective, by acquiring several images, where the sample is illuminated with several phases and orientations of a stripe grating. SIM typically requires 9-15 images to achieve this improvement, which would decrease rather than increase the throughput of IT. Applicants will develop an alternative patterned illumination-based strategy to increase the resolution ~100× with 10 images. Applicants will modify the illumination path with a Vialux 9001 4 megapixel Digital Micromirror Device (DMD). A DMD is readily compatible with multicolor illumination (as used in Aim 2.2) and, unlike a diffuser, the patterns projected can be known precisely, which can be beneficial in subsequent reconstruction algorithms. To help in super-resolution, the DMD patterns must have a higher spatial frequency than the acquisition spatial frequency, and when magnified to fill the 4 mm FOV, DMD pixels will be twice the size of the camera pixels, 1.3 m. To achieve patterned illumination, Applicants will thus use a trick used in movie theater 4K projectors to jitter the DMD image with a voice coil activated mirror. This will enable us to increase the possible illumination spatial frequencies at the cost of losing contrast ratio between on and off pixels of the DMD. Except for this tradeoff of contrast for resolution, the spatial and spectral patterns applied can be nearly arbitrary as all hardware is driven with s temporal resolution.

Recovery of superresolved images from patterned illumination. Applicants will use SPARCOM, a sparsity-based super-resolution recovery algorithm Applicants(Eldar) developed, which depends on correlation information[35-37]. SPARCOM leverages known statistics of the illumination patterns, in particular, the ability to illuminate each (unobserved) high resolution pixel in an identically and independently distributed (iid) fashion. Together with the assumption of pixel sparsity, the covariance matrix between high resolution pixels is well-approximated by a sparse diagonal matrix, with values on the diagonal corresponding to the squared intensity of each pixel. SPARCOM takes as input the correlation between observed low resolution pixels, together with a point spread function derived from the microscope in use, and solves for the sparse diagonal of the unobserved high resolution covariance matrix. Compared with the methods of Aim 3.1, correlation-based recovery will result in similar gains in imaging time, but making weaker assumptions about the underlying signal. For example, Applicants could acquire 9 images at 6.25× magnification (as above) and super-resolve to ~60×, with a 10-fold speedup compared to directly imaging at 60×. Such resolution will be valuable as Applicants scale to thousands of genes.

Figure 39:
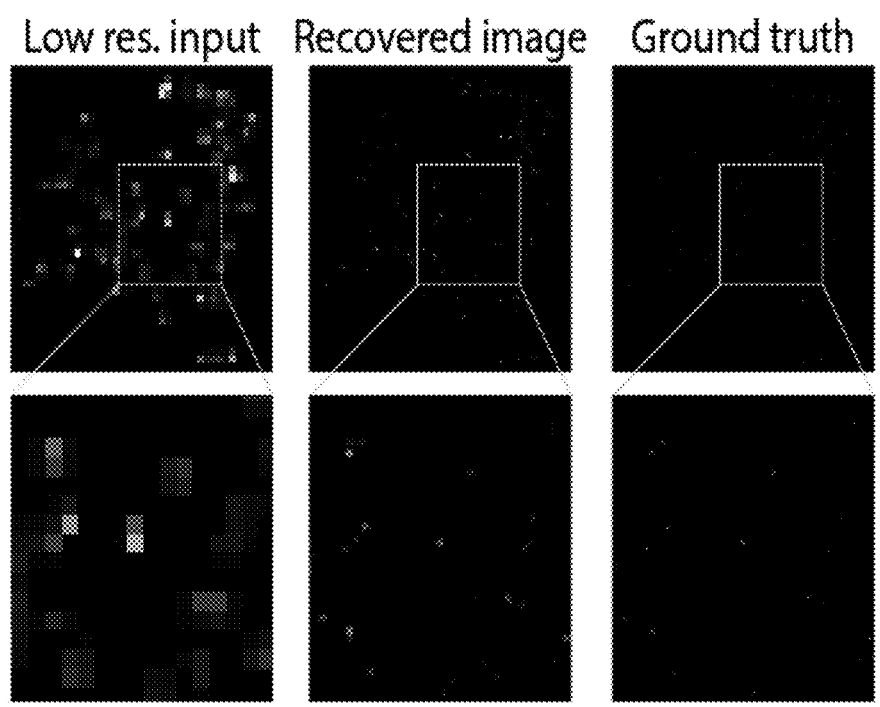
FIG. 39—Super-resolution from low magnification data in mouse brain with SPARCOM.
Figure 40:
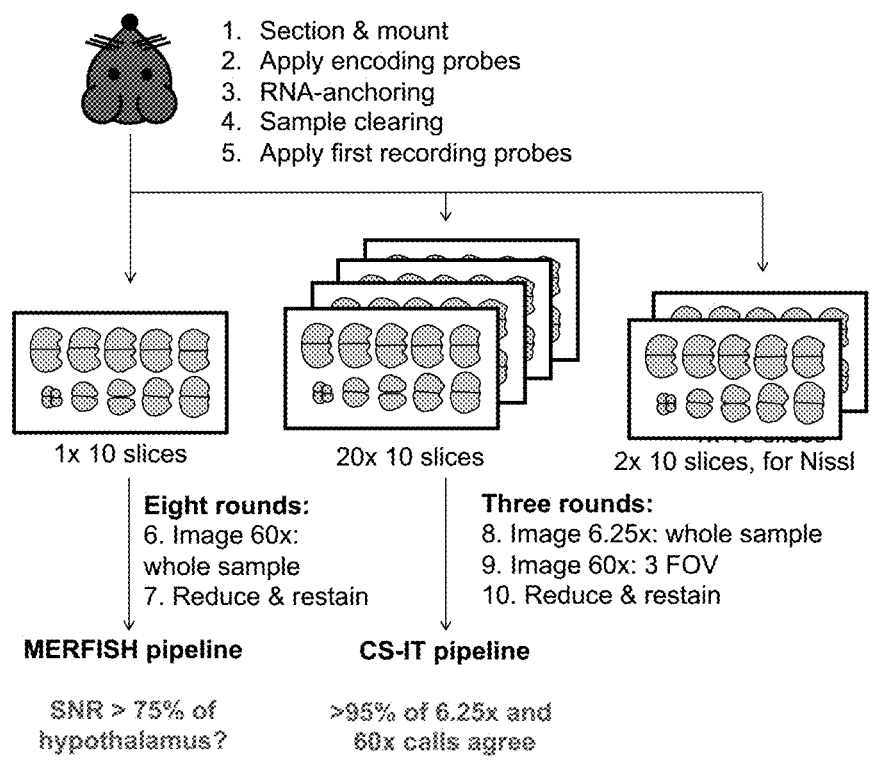
FIG. 40—Data generation pipeline for high content measurements.

In preliminary results, using these optical and computational methods on fluorescent nuclei in mouse brain slices (an equivalent optical problem, with every linear dimension of the sample and microscope scaled up by 30×), Applicants have already obtained an 8-fold throughput improvement by using 8 patterned illumination images of 64× downsampled data (FIG. 39) with a 10% false negative and 15% false positive rate. Applicants will improve this throughput while reducing error rates by optimizing the patterns applied to the sample and optimizing SPARCOM for this application.

Testing. Applicants will test these algorithms in mouse brain slices stained with 4-color MERFISH probe libraries against genes present in S1 (as designed and used in Aim 2). For Aim 3.1, the same sample will be imaged at magnifications between 10× and 60×. For Aim 3.2, samples will be imaged at high magnifications with a 6.5 µm and 4.25 µm pixel camera and on a low magnification 6.25× microscope equipped with patterned illumination. In each case, low magnification data will be computationally super-resolved to recover 60×-equivalent data, and compared to the true, gold standard 60× data. Applicants will analyze both super-resolved and gold-standard datasets with both conventional spot-calling and with the methods of Aim 2.1, and calculate false positive and false negative rates on a per transcript level to quantify super-resolution performance.

Potential pitfalls and possible solutions. There are two main optical pitfalls. First, the illumination power of the Celesta may be insufficient to illuminate such large regions of the sample simultaneously. This is readily addressable by additional investments in laser power, which would be borne by the Optical Profiling Platform. Second, fringing effects in the edges of fields of view at low magnification could lead to chromatic aberrations and loss of signal. Applicants will tackle this partially by identifying a well-matched tube lens (budgeted for here) and by preceding analysis with 3D deconvolution of each color channel's Z-stack. Notably, Aim 3.1 and 3.2 present two alternative ways to achieve the same goal of a ~36× throughput improvement.

Aim 4. Generate a whole transcriptome spatial profile of the mouse primary somatosensory and motor cortex. Work in Aims 1-3 will proceed independently, and will be integrated here: Applicants will combine the modified encoding libraries in Aim 1 with the multicolor recording probes from Aim 2 and the demagnified optics from Aim 3. Applicants will integrate the compressed sensing algorithms into a single analysis pipeline. The result will be a MERFISH workflow with up to 25,000-fold combined increase in throughput compared to the current state of the art. To demonstrate the power of these approaches Applicants will generate a large spatially resolved transcriptomic dataset from mouse M1 and S1. Applicants will compare performance to existing state of the art, present a cost model on a per-cell basis, and disseminate tools and results to beta-testers across the BICCN community (Zhang, Zeng, Lein, Arlotta, Cai LoS).

Figure 10:
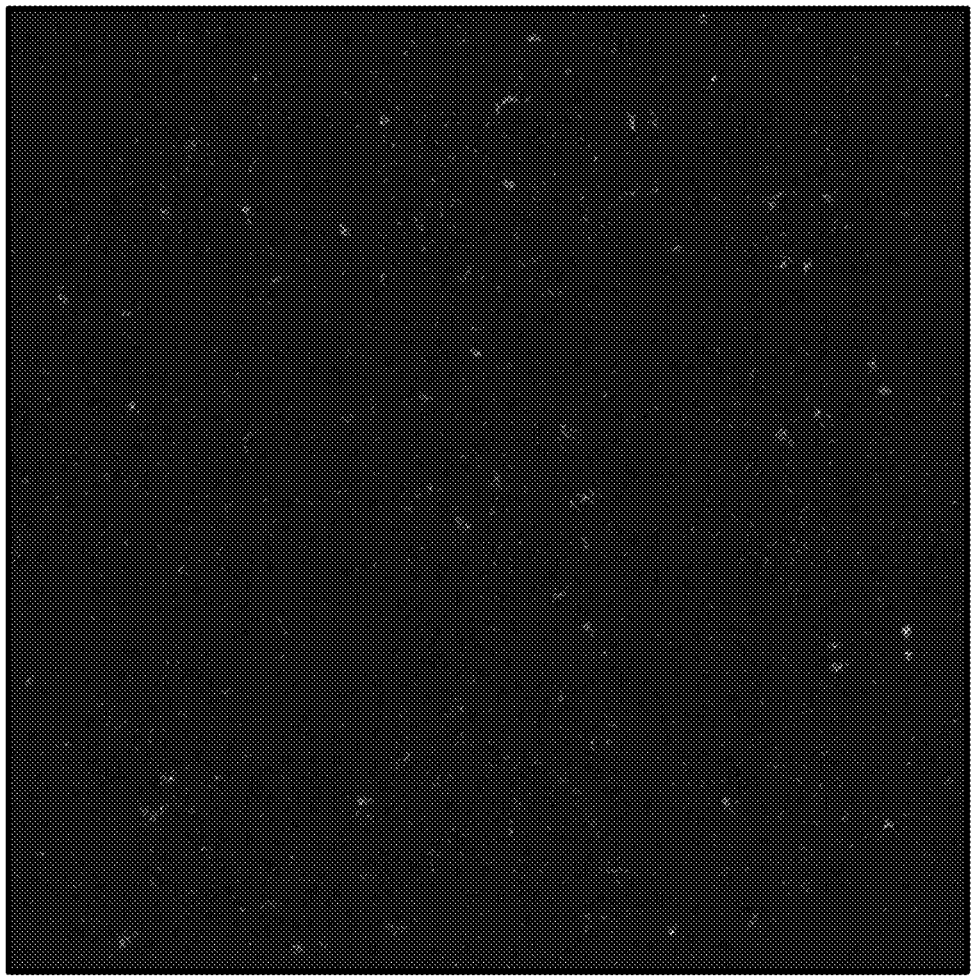
FIG. 10 shows a validation of experiments analyzing the Pdgfra gene by making direct and composite measurements in the same tissue.
Figure 12:
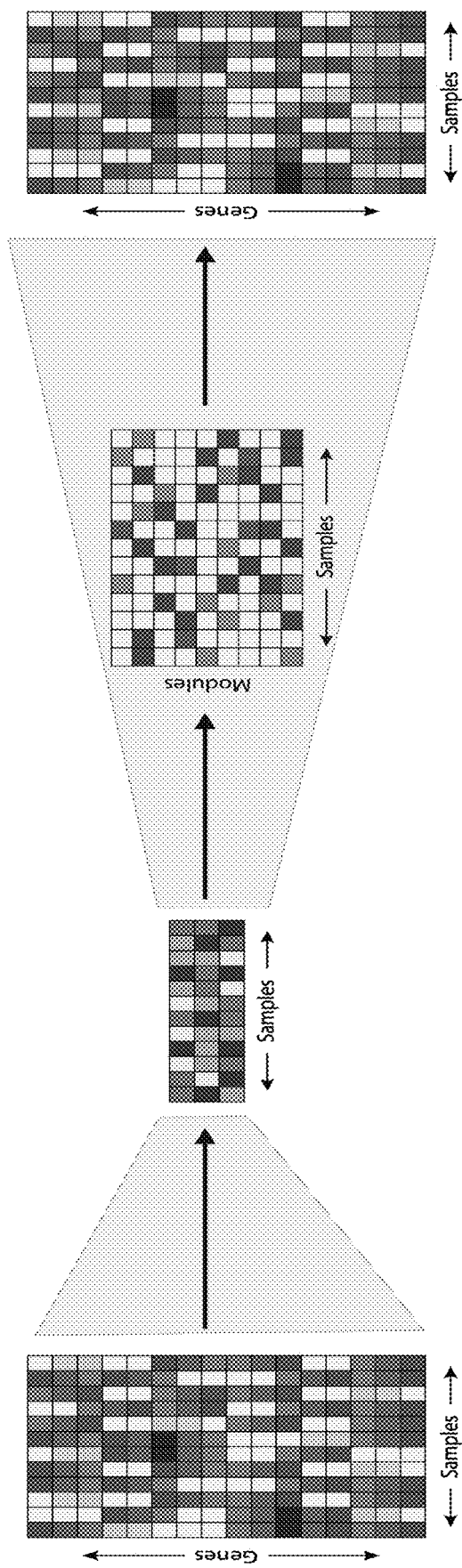
FIG. 12 depicts how composite measurements can be decompressed using compressed sensing, allowing for the identification of individual genes from composite imaging.

Workflow and quality control. Samples will be generated as described above (Test system). To profile a full M1/S1 data set, Applicants will sample a block of tissue 4 mm×4 mm×1 mm. Applicants will prepare 10 µm coronal sections (400/per brain) and image every other section (200/brain). Applicants will mount 10 sections/coverslip in a MERFISH cartridge for high content measurements (FIG. 10). In parallel, Applicants will mount 10 of the remaining 200 slices for conventional 2-color MERFISH to serve as a benchmark and sample quality step. To avoid gradient effects across the brain, slices in every cartridge will be evenly spaced across the 200 slices (i.e., every 20th). To map to a common coordinate framework, a third subset of 20 slices (every $20^{th}$) will be Nissl stained. These slices will be mapped to the CCF using established protocols from the Allen Institute[38] and cell locations in the MERFISH data sets will be interpolated between these slices.

Applicants will treat the 200-slice sample with the full transcriptome encoding probe libraries of Aim 1 and the 10-slice control sample with a control 2-color MERFISH encoding probe pool. Applicants will perform encoding probe application, RNA-anchoring, and subsequent sample clearing in parallel for both pools. For each mouse brain, Applicants will first image the 10 slice control sample with conventional 2-color readout. Applicants will quantify average ratios of spot signal vs. surrounding background noise ratios on a per-spot basis and compare values to existing data sets from hypothalamus[20]. If spot SNR values are lower than 75% of hypothalamus values, Applicants will restart the process and section and stain a fresh brain.

Applicants will perform white-light low magnification scans to identify the brain slice edges and define S1 and M1 imaging regions. Applicants will then perform 3 rounds of imaging for each slice in the 200-section sample: 2 rounds of 10-color imaging with the recording probes of Aim 2 to acquire MERFISH barcodes, followed by one round of DAPI and anti-poly-A imaging to acquire signals for cell-segmentation, registration, and normalization. Applicants will image with the low magnification protocols of Aim 3. On one slice per cartridge Applicants will also image 10 60×FOVs in addition to the low magnification data for quality control. Data will be saved directly to the Cloud (AWS or GCP) for subsequent analysis.

Since no separate fiducial marker channel is acquired, Applicants will use the sample edges and total mRNA signal to align each slices' color channels. Applicants will first reconstruct high magnification data from low magnification data using the approaches of Aim 3, followed by color channel assignment (Aim 2) and finally expansion of module signals to gene signals (Aim 1). Applicants will compare results from the 60×FOVs to the matched region in low magnification data to evaluate performance of low-magnification data, seeking at least a 95% agreement in spot assignment to module signal. If not met, Applicants will discard data from this cartridge and increase magnification to reach this threshold in subsequent cartridges. If more than 2 cartridges (20 slices) are discarded, a new brain will be sectioned. Applicants will perform cell segmentation using low magnification DAPI/poly-A signals and the approaches of Aim 1. After Applicants assign gene levels per cell, Applicants will minimize technical noise by normalizing expression by the total anti-poly-A signal detected in a slice to account for RNA degradation over time. Applicants will repeat this process until Applicants have acquired transcriptome wide maps of gene expression data across the mouse M1 and S1 from 6 brains, 3 male and 3 female.

Benchmarking. Applicants will perform three key benchmarks: (1) Applicants will benchmark technical performance to the nearest neighbor slice with 2-color MERFISH, evaluating correlation between average gene expression on a per cell basis. (2) Applicants will compare cell clusters identified from the single cell resolved data by algorithms analogous to those used for scRNA-seq[39,40] and confirm cell type assignment. (3) Applicants will provide the data set to the SpaceTx consortium for independent benchmarking (judged by the ability to classify cell types in S1) against all other IT techniques (Lein LoS).

Throughput improvements. With the throughput improvements, imaging time will be decreased to 3 minutes per cartridge per round. The number of rounds will be decreased from 8 to 3, requiring only two on-stage fluid exchanges. The first exchange will be 41 minutes but the second will be only 10 minutes as DAPI and poly-A staining are sufficiently strong to overwhelm RNA signals and will not require destaining. Thus 10 slices could be imaged in 60 minutes, with the bulk of the time dedicate to fluid exchange. All of S1 and M1 could be imaged in two 10 hour shifts. With imaging effectively removed as a barrier to data generation, the rate limiting step becomes recording probe hybridization. Designing larger cartridges capable of handling more slices would be a natural next step to further increase throughput and enable whole-brain measurements.

Cost model. When run at scale, the proposed pipeline inherits the extremely low costs of MERFISH. Both protocols involve consumable costs of 0.11 cent/cell, dominated by the enzymes necessary for library construction. Recording probes pose a significant up-front investment ($595 each) but are sufficient for staining 5,000 coronal mouse brain slices each. Encoding libraries are effectively one-time costs since they can be repeatedly PCR amplified. The up-front cost is $2,400 for MERFISH and $13,500 for the full transcriptome depth in this proposal. Applicants plan, however, to lower this cost to <$150 by distributing the prepared library to other users. Finally, MERFISH requires a roughly $200,000 investment in optics and fluidics hardware. The optics proposed here (and required only for some of the improvements) will add another $50,000 to this up-front cost. Assuming high sample availability but no additional sample handling automation, the pipeline could operate 1,500 hours/year, at 10 brain slices/hour. Assuming a conservative 5-year lifespan of the hardware yields $3 33/mouse coronal slice.

Data and tool dissemination. Applicants will deploy a robust approach to data and protocol sharing across BICCN and wider biological community (See also Resource Sharing Plan). Applicants have engaged a committed set of beta testers including Drs. Xiaowei Zhuang, Adam Cohen, Hongkui Zeng (mouse), Paola Arlotta (brain organoids and mouse), Guoping Feng (marmosets), Long Cai (seqFISH), and Ed Lein (human) (see LoS). Each of these labs has the inhouse skill sets to implement the described optical approaches, and computational experience to deploy the analysis pipeline. the computational and experimental team will actively assist with projects in these early test labs, traveling to the labs for hands on demonstrations, and further optimizing the overall workflow based on feedback. The Broad's Data Sciences Platform are part of the Brain Cell Data Center and will assist in the deposition of both raw and decompressed data from the effort. Applicants will disseminate clear, step by step instructions for implementing these tools through both the online tool protocols.io (where Applicants already disseminate protocols) and protocol papers. Applicants will make computational pipelines publicly available under an open source BSD license. As the major expenses are optics improvements and synthesized oligopools, Applicants will make a specific effort to remove these barriers, by making the enhanced optics available through the Broad's Optical Profiling Platform on a collaborative or fee for service basis and by distributing the cloning the synthesized oligo libraries into Addgene for distribution to other labs.

Discussion

Understanding of brain physiology and disease has been hampered by limited knowledge of the organ's composition. While brain cell types have been defined by morphological, electrophysiological, and molecular patterns, there remains an enormous need for a comprehensive census of the cell types of the brain, their connections, and distribution. A series of experimental advances, especially single cell and single nucleus RNA-seq (scRNA-seq, snRNA-seq)[14] and Imaging Transcriptomics (IT) methods[5-9] have opened an extraordinary opportunity that put such an atlas within reach. While scRNA-seq provides a transcriptome-scale portrait of each cell's profile, it loses key spatial information. Conversely, IT methods rely on iterated rounds of imaging and either sequencing or hybridization chemistry to detect multiple RNA species in situ in tissue sections. However, each of these demonstrated IT methods faces two substantial and inter-related challenges: generating information at much too low a throughput in both number of transcripts measured per cell and number of cells analyzed per hour. This low throughput precludes a deep survey of the 100 million cells in the mouse brain, and, ideally the 200 billion cells of the human brain. For example, at the current top data generation rate of profiling 140 genes in 100,000 cells in 24 hours, a 140-gene depth profile of whole brain would require ~3 years of instrument time in mouse and 6,000 years in human.

Here, Applicants addressed these challenges in IT to drastically scale up both throughput and information content by integrating compressed sensing and optimization methods with advanced optics, building on our interdisciplinary team of compressed sensing, optimization, optics, and biological experts. By taking advantage of underlying structure in the data and the measurement methods, the number of genes about which IT methods can return information while simultaneously decreasing the imaging time is increased. T generate a 3D common reference brain atlas requires acquiring high resolution spatial information along with multiplexed molecular information. Current Image Transcriptomics methods offer such data, though not yet at the necessary depth or scale. All existing IT methods[5-9] are similar from a data analysis point of view. The underlying transcript distribution (G) is encoded with a series of fluorescent markers according to a known codebook (C) to generate a multicolor raw data image (D). Importantly, to allow multiplexing, in many methods[5-9] the number of colors in C and D can be much larger than the number of colors resolvable by a standard microscope, requiring multiple rounds of encoding and imaging, driving up acquisition time. The analysis challenge is to perform a reverse lookup, using the known codebook, from the multicolor raw image stack to recover transcript identities. Different IT methods vary in the chemical structure of the codebook: at one extreme, fluorescent in situ sequencing uses the native gene sequence to identify transcript identity[5]. At another extreme, MERFISH, seqFISH and STARmap[6-8] depend on combinatorial fluorescent in situ hybridization. In hybrid methods probes are first hybridized and then read out by sequencing. These approaches trade off efficiency, amplification, and reagent expense. All IT methods thus face two key limitations: a limited number of genes profiled and the throughput of the technique.

Every IT approach is limited in the number of gene identities it can profile, with ~1,000 as the current upper limit[5-9]. The reasons depend on the chemistry involved. Hybridization based IT offers high detection efficiency, but suffers from limitations in the allowable gene expression levels (at high levels it is difficult to resolve individual RNA molecules for barcode readout) and transcript length (short genes are less likely to be bound by enough probes). Sequencing based approaches rely on a low efficiency reverse-transcription step (making low copy number transcripts hard to detect) and amplify the signal by rolling circle PCR (artificially crowding the optical signals together). This limitation on the number of genes is especially problematic in samples with more diverse cell types, requiring more transcripts for classification. IT methods also suffer from low imaging throughput. MERFISH profiles ~140 genes in 100,000 cells in 24 hours. If a mouse brain contains ~80M neurons and ~20M glial cells and an adult human brain contains ~100B of both neurons and glia cells, one mouse brain could be spatially profiled in 3 instrument-years with current technology, whereas a human brain would take 6 millennia of instrument time. Capturing the full transcriptome in either system would require 100-fold longer. In all IT methods, the iterated staining chemistry can be readily accelerated by treating tissue sections in parallel. Therefore, in the limit of large samples, the major bottleneck to scaling up IT technology is imaging time[13]. Imaging time includes translation of the sample, changes to the optical configuration (e.g., filter switching), and sensor exposure time, and, depending on the optical configuration, may be limited by any of these components.

To increase the throughput of current IT methods, Applicants pursuit of three independent approaches to leverage compressed sensing to tackle each of three independent axes of the IT decoding problem: genes, colors and pixels. By addressing the challenges, information about the whole transcriptome can be gathered, including difficult-to-profile genes, from ~100 measurements (Aim 1); decrease the number of colors necessary to encode gene identity and decrease the time necessary to sample multiple color channels (Aim 2); and decrease the magnification necessary to sample IT data using super-resolution compressed sensing approaches disclosed herein (Aim 3). In each aim, the acceleration is possible by knowledge of the underlying structure of the data, imposed by either available scRNA-Seq or the structure of the codebook. Advantageously, the success of any one of the aims of this example will enable full-transcriptome depth profiling with comparable throughput to that available today.

The approaches herein remove these limitations by decreasing the number of fields of view that must be imaged. The advancements disclosed herein will bring IT to the scale necessary to generate the molecular atlases needed for the success of BICCN. Innovations from the current methodologies and approaches are first demonstrated on MERFISH, one of the best-established tools, but the work is immediately extendible to all IT methods (e.g., seqFISH, Cai LoS) and will be compatible with other parallel technological improvements, such as enhanced light sources, fluorophores, or labeling techniques. Ultimately, the approaches allow for the following:

IT measurements with full transcriptome scale. All single-cell, spatially resolved transcriptomics data to date has been limited to up to 1,000 gene depth. The novel compressed sensing approach will reach full transcriptome depth on a spatially resolved single cell basis.

New, general analysis pipelines for IT data. Applicants development of new forms of gene ID extraction from raw data by eliminating the unreliable spot-calling steps with a new iterative algorithm which converges on the most likely underlying gene distribution.

IT measurements with 10× faster color sampling. Fluorescent microscopes typically resolve colors sequentially, requiring one image per channel. The disclosed implementation will resolve up to 10 colors in a single camera frame by adapting compressed sensing approaches for signal identification in frequency space to the optical domain.

36-fold increase in spatial image throughput. Rather than acquiring data at high magnification, Applicants will exploit two methods for image compression, with different underlying assumptions, to acquire data at low magnification and decrease the number of fields of view necessary to extract IT information.

Integration of optics and compressed sensing for increased IT throughput. The integrated hardware, analysis, and biological optimization, will lead to a wide array of compressed sensing approaches tailored to increasing IT data acquisition rate, with concomitant design of novel IT reagents and optics.

A large-scale full transcriptome IT dataset. We will generate a data set from mouse S1 and M1 ~60× larger than the largest currently available IT data set, with full transcriptome coverage.

References for Example 4 Citations

1. Shalek A K, Satija R, Adiconis X, Gertner R S, Gaublomme J T, Raychowdhury R, Schwartz S, Yosef N, Malboeuf C, Lu D, Trombetta J J, Gennert D, Gnirke A, Goren A, Hacohen N, Levin J Z, Park H, Regev A. Single-cell transcriptomics reveals bimodality in expression and splicing in immune cells. Nature. Nature Publishing Group; 2013 Jun. 13; 498(7453):236-40. PMCID: PMC3683364

2. Shalek A K, Satija R, Shuga J, Trombetta J J, Gennert D, Lu D, Chen P, Gertner R S, Gaublomme J T, Yosef N, Schwartz S, Fowler B, Weaver S, Wang J, Wang X, Ding R, Raychowdhury R, Friedman N, Hacohen N, Park H, May A P, Regev A. Single-cell RNA-seq reveals dynamic paracrine control of cellular variation. Nature. Nature Publishing Group; 2014 Jun. 19; 510(7505):363-9. PMCID: PMC4193940

3. Macosko E Z, Basu A, Satija R, Nemesh J, Shekhar K, Goldman M, Tirosh I, Bialas A R, Kamitaki N, Martersteck E M, Trombetta J J, Weitz D A, Sanes J R, Shalek A K, Regev A, McCarroll S A. Highly Parallel Genome-wide Expression Profiling of Individual Cells Using Nanoliter Droplets. Cell. 2015 May 21; 161(5):1202-14. PMCID: PMC4481139

4. Habib N, Avraham-Davidi I, Basu A, Burks T, Shekhar K, Hofree M, Choudhury S R, Aguet F, Gelfand E, Ardlie K, Weitz D A, Rozenblatt-Rosen O, Zhang F, Regev A. Massively parallel single-nucleus RNA-seq with DroNc-seq. Nat. Methods. Nature Publishing Group; 2017 October; 14(10):955-8. PMCID: PMC5623139
5. Lee J H, Daugharthy E R, Scheiman J, Kalhor R, Yang J L, Ferrante T C, Terry R, Jeanty S S F, Li C, Amamoto R, Peters D T, Turczyk B M, Marblestone A H, Inverso S A, Bernard A, Mali P, Rios X, Aach J, Church G M. Highly multiplexed subcellular RNA sequencing in situ. Science. 2014 Mar. 21; 343(6177):1360-3. PMCID: PMC4140943
6. Chen K H, Boettiger A N, Moffitt J R, Wang S, Zhuang X. RNA imaging. Spatially resolved, highly multiplexed RNA profiling in single cells. Science. 2015 Apr. 24; 348(6233):aaa6090-0. PMCID: PMC4662681
7. Shah S, Lubeck E, Zhou W, Cai L. In situ Transcription Profiling of Single Cells Reveals Spatial Organization of Cells in the Mouse Hippocampus. Neuron. 2016 October; 92(2):342-57.
8. Wang X, Allen W E, Wright M A, Sylwestrak E L, Samusik N, Vesuna S, Evans K, Liu C, Ramakrishnan C, Liu J, Nolan G P, Bava F-A, Deisseroth K. Three-dimensional intact-tissue sequencing of single-cell transcriptional states. Science. American Association for the Advancement of Science; 2018 Jun. 21;:eaat5691.
9. Codeluppi S, Borm L E, Zeisel A, La Manno G, van Lunteren J A, Svensson C I, Linnarsson S. Spatial organization of the somatosensory cortex revealed by osm-FISH. Nat. Methods. Nature Publishing Group; 2018 November; 15(11):932-5.
10. Saunders A, Macosko E Z, Wysoker A, Goldman M, Krienen F M, de Rivera H, Bien E, Baum M, Bortolin L, Wang S, Goeva A, Nemesh J, Kamitaki N, Brumbaugh S, Kulp D, McCarroll S A. Molecular Diversity and Specializations among the Cells of the Adult Mouse Brain. Cell. 2018 Aug. 9; 174(4):1015-6.
11. Tasic B, Yao Z, Graybuck L T, Smith K A, Nguyen T N, Bertagnolli D, Goldy J, Garren E, Economo M N, Viswanathan S, Penn O, Bakken T, Menon V, Miller J, Fong O, Hirokawa K E, Lathia K, Rimorin C, Tieu M, Larsen R, Casper T, Barkan E, Kroll M, Parry S, Shapovalova N V, Hirschstein D, Pendergraft J, Sullivan H A, Kim T K, Szafer A, Dee N, Groblewski P, Wickersham I, Cetin A, Harris J A, Levi B P, Sunkin S M, Madisen L, Daigle T L, Looger L, Bernard A, Phillips J, Lein E, Hawrylycz M, Svoboda K, Jones A R, Koch C, Zeng H. Shared and distinct transcriptomic cell types across neocortical areas. Nature. 5 ed. Nature Publishing Group; 2018 November; 563(7729):72-8.
12. Zeisel A, Hochgerner H, Lonnerberg P, Johnsson A, Memic F, van der Zwan J, Haring M, Braun E, Borm L E, La Manno G, Codeluppi S, Furlan A, Lee K, Skene N, Harris K D, Hjerling-Leffler J, Arenas E, Ernfors P, Marklund U, Linnarsson S. Molecular Architecture of the Mouse Nervous System. Cell. 2018 Aug. 9; 174(4):999-1014.e22. PMCID: PMC6086934
13. Moffitt J R, Hao J, Wang G, Chen K H, Babcock H P, Zhuang X. High-throughput single-cell gene-expression profiling with multiplexed error-robust fluorescence in situ hybridization. Proc. Natl. Acad. Sci. U.S.A. 2016 Sep. 27; 113(39):11046-51. PMCID: PMC5047202
14. Eldar Y C. Compressed Sensing. Cambridge University Press; 2012.
15. Mazor G, Weizman L, Tal A, Eldar Y C. Low-rank magnetic resonance fingerprinting. Med Phys. 2018 Jul. 4; 45(9):4066-84.
16. Bipin Mehta B, Coppo S, Frances McGivney D, Ian Hamilton J, Chen Y, Jiang Y, Ma D, Seiberlich N, Gulani V, Alan Griswold M. Magnetic resonance fingerprinting: a technical review. Magn Reson Med. 2019 January; 81(1):25-46.
17. Cleary B, Cong L, Cheung A, Lander E S, Regev A. Efficient Generation of Transcriptomic Profiles by Random Composite Measurements. Cell. 2017 Nov. 30; 171 (6):1424-1436.e18. PMCID: PMC5726792
18. Ecker J R, Geschwind D H, Kriegstein A R, Ngai J, Osten P, Polioudakis D, Regev A, Sestan N, Wickersham I R, Zeng H. The BRAIN Initiative Cell Census Consortium: Lessons Learned toward Generating a Comprehensive Brain Cell Atlas. Neuron. 2017 Nov. 1; 96(3):542-57. PMCID: PMC5689454
19. Zeng H, Sanes J R. Neuronal cell-type classification: challenges, opportunities and the path forward. Nat. Rev. Neurosci. 2017 September; 18(9):530-46.
20. Moffitt J R, Bambah-Mukku D, Eichhorn S W, Vaughn E, Shekhar K, Perez J D, Rubinstein N D, Hao J, Regev A, Dulac C, Zhuang X. Molecular, spatial, and functional single-cell profiling of the hypothalamic preoptic region. Science. 2018 Nov. 16; 362(6416):eaau5324.
21. Kipf T N, Welling M. Semi-Supervised Classification with Graph Convolutional Networks. 2016.
22. Neil D, Briody J, Lacoste A, Sim A, Creed P, Saffari A. Interpretable Graph Convolutional Neural Networks for Inference on Noisy Knowledge Graphs. 2018.
23. Masci J, Meier U, Ciregan D, Schmidhuber J. Stacked Convolutional Auto-Encoders for Hierarchical Feature Extraction. Artificial Neural Networks and Machine Learning ICANN 2011. Berlin, Heidelberg: Springer, Berlin, Heidelberg; 2011. p. 52-9.
24. Kim J K, Kolodziejczyk A A, Ilicic T, Teichmann S A, *Marioni* JC. Characterizing noise structure in single-cell RNA-seq distinguishes genuine from technical stochastic allelic expression. Nat Commun. Nature Publishing Group; 2015 Oct. 22; 6(1):8687.
25. Chen I, Johansson F D, Sontag D. Why Is My Classifier Discriminatory? 2018.
26. Gleichman S, Eldar Y C. Blind compressed sensing. IEEE Transactions on Information Theory. 2011; 57(10): 6958-75.
27. Shah S, Takei Y, Zhou W, Lubeck E, Yun J, Eng C-HL, Koulena N, Cronin C, Karp C, Liaw E J, Amin M, Cai L. Dynamics and Spatial Genomics of the Nascent Transcriptome by Intron seqFISH. Cell. 2018 Jul. 12; 174(2): 363-376.e16. PMCID: PMC6046268
28. Nedic A, Bertsekas D P. Incremental Subgradient Methods for Nondifferentiable Optimization. SIAM Journal on Optimization. Society for Industrial and Applied Mathematics; 2006 Jul. 28; 12(1):109-38.
29. Sra S, Nowozin S, Wright S J. Optimization for Machine Learning. MIT Press; 2012.
30. Palomar D P, Eldar Y C. Convex Optimization in Signal Processing and Communications. Cambridge University Press; 2010.
31. Zimmermann T, Rietdorf J, Pepperkok R. Spectral imaging and its applications in live cell microscopy. FEBS Lett. 2003 Jul. 3; 546(1):87-92.
32. Mishali M, Eldar Y C, Elron A J. Xampling: Signal Acquisition and Processing in Union of Subspaces. IEEE Transactions on Signal Processing. 2011; 59(10):4719-34.
33. Eldar Y C, Kuppinger P, Bolcskei H. Block-sparse signals: Uncertainty relations and efficient recovery. IEEE Transactions on Signal Processing. 2010; 58(6):3042-54.

34. Gustafsson M G. Surpassing the lateral resolution limit by a factor of two using structured illumination microscopy. J Microsc. 2000 May; 198(Pt 2):82-7.
35. Solomon O, Mutzafi M, Segev M, Eldar Y C. Sparsity-based super-resolution microscopy from correlation information. Opt Express. 2018 Jul. 9; 26(14):18238-69.
36. Gazit S, Szameit A, Eldar Y C, Segev M. Super-resolution and reconstruction of sparse sub-wavelength images. Opt Express. Optical Society of America; 2009; 17(26):23920-46.
37. Sidorenko P, Kfir O, Shechtman Y, Fleischer A, Eldar Y C, Segev M, Cohen O. Sparsity-based super-resolved coherent diffraction imaging of one-dimensional objects. Nat Commun. Nature Publishing Group; 2015 Sep. 8; 6(1):8209.
38. Allen Mouse Common Coordinate Framework. 2017 Oct. 16;:1-36.
39. Shekhar K, Lapan S W, Whitney I E, Tran N M, Macosko E Z, Kowalczyk M, Adiconis X, Levin J Z, Nemesh J, Goldman M, McCarroll S A, Cepko C L, Regev A, Sanes J R. Comprehensive Classification of Retinal Bipolar Neurons by Single-Cell Transcriptomics. Cell. 2016 Aug. 25; 166(5):1308-30. PMCID: PMC5003425
40. Peng Y, Shekhar K, Yan W, Herrmann D, Sappington A, Bryman G S, van TZ, Do M, Regev A, Sanes J R. Molecular Classification and Comparative Taxonomics of Foveal and Peripheral Cells in Primate Retina. bioRxiv; 2018.
41. Tanay A, Regev A. Scaling single-cell genomics from phenomenology to mechanism. Nature. Nature Publishing Group; 2017 Jan. 18; 541(7637):331-38. PMCID: PMC5438464.

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. A method of imaging genes in situ comprising:
   (a) preparing a probe set for each gene module in a set of gene modules, wherein the probe set comprises a plurality of probes to a sub-set of genes that are representative of all genes in a given gene module;
   (b) preparing composite probe sets, wherein each composite probe set comprises a different combination of probes from the plurality of probes prepared in step (a);
   (c) obtaining a set of images of a tissue sample, wherein, for each image in the set of images, a different composite probe set is used and imaged simultaneously;
   (d) encoding, using a pretrained encoder, an encoded representation of each image in the set of images;
   (e) decompressing the encoded representation of each image by solving a sparse optimization problem that estimates gene module activities and individual gene abundances given the composite probe set and the gene modules used; and
   (f) generating, using a pretrained decoder, a new set of images from the encoded representation of each image after the decompressing, the new set of images providing a spatial expression pattern for each gene represented in the composite probe set.

2. The method of claim 1, further comprising:
   identifying the set of gene modules by collecting training data from a tissue or cell by performing single cell sequencing.

3. The method of claim 2, wherein the single cell sequencing comprises whole transcriptome amplification.

4. The method of claim 2, wherein the training data is obtained across a library of cells.

5. The method of claim 2, wherein the cell comprises a eukaryotic cell.

6. The method of claim 5, wherein the eukaryotic cell is a mammalian cell.

7. The method of claim 4, wherein the library of cells comprises multiple cell types.

8. The method of claim 1, wherein the tissue sample comprises or is from a biopsy from a subject.

9. The method of claim 1, further comprising:
   identifying the set of gene modules based upon a random sampling of one or more composite genes.

10. The method of claim 2, wherein the tissue or cell is from the motor cortex.

11. The method of claim 10, wherein the motor cortex is a mouse motor cortex.

12. The method of claim 1, wherein the decompressing is by compressed sensing.

13. The method of claim 5, wherein the eukaryotic cell is a human cell.

14. The method of claim 1, wherein the tissue sample comprises neurons.

15. The method of claim 1, wherein the tissue sample is olfactory epithelium.

16. A computer-implemented method to scan in situ images and infer gene abundances, comprising:
   (a) receiving a set of images of a tissue sample obtained by simultaneously measuring expression of a composite probe set, wherein for each image in the set of images a different composite probe set is used, and wherein each composite probe set comprises a different combination of gene probes representative of different gene modules;
   (b) encoding, using a pretrained encoder, an encoded representation of each image in the set of images;
   (c) decompressing the encoded representation of each image by solving a sparse optimization problem that estimates gene module activities and individual gene abundances given the composite probe set and the gene modules used; and
   (d) generating a composite set of images that provides a spatial expression pattern for each gene represented in the composite probe set.

17. The method of claim 16, wherein the method further comprises pre-processing the set of images.

18. The method of claim 17, wherein pre-processing comprise of normalizing, stitching, aligning, and segmenting the images in each color, field of view, round, and tissue or cells.

19. The method of claim 17, wherein pre-processing comprises of smoothing and rescaling the one or more in situ image.

* * * * *

SEQUENCE LISTING

```
<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 1
agactagcta gctagctagg                                                      20

<210> SEQ ID NO 2
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 2
aatcgataca gatacagatc                                                      20

<210> SEQ ID NO 3
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 3
agctagatca gactagcata                                                      20

<210> SEQ ID NO 4
<211> LENGTH: 288
<212> TYPE: PRT
<213> ORGANISM: Artificial Sequence
<220> FEATURE:
<223> OTHER INFORMATION: Synthetic Peptide
```

-continued

```
<400> SEQUENCE: 4

Met Asp Pro Ile Arg Ser Arg Thr Pro Ser Pro Ala Arg Glu Leu Leu
1               5                   10                  15

Ser Gly Pro Gln Pro Asp Gly Val Gln Pro Thr Ala Asp Arg Gly Val
            20                  25                  30

Ser Pro Pro Ala Gly Gly Pro Leu Asp Gly Leu Pro Ala Arg Arg Thr
            35                  40                  45

Met Ser Arg Thr Arg Leu Pro Ser Pro Ala Pro Ser Pro Ala Phe
50                  55                  60

Ser Ala Asp Ser Phe Ser Asp Leu Leu Arg Gln Phe Asp Pro Ser Leu
65                  70                  75                  80

Phe Asn Thr Ser Leu Phe Asp Ser Leu Pro Pro Phe Gly Ala His His
                85                  90                  95

Thr Glu Ala Ala Thr Gly Glu Trp Asp Glu Val Gln Ser Gly Leu Arg
                100                 105                 110

Ala Ala Asp Ala Pro Pro Pro Thr Met Arg Val Ala Val Thr Ala Ala
            115                 120                 125

Arg Pro Pro Arg Ala Lys Pro Ala Pro Arg Arg Ala Ala Gln Pro
130                 135                 140

Ser Asp Ala Ser Pro Ala Ala Gln Val Asp Leu Arg Thr Leu Gly Tyr
145                 150                 155                 160

Ser Gln Gln Gln Gln Glu Lys Ile Lys Pro Lys Val Arg Ser Thr Val
                165                 170                 175

Ala Gln His His Glu Ala Leu Val Gly His Gly Phe Thr His Ala His
                180                 185                 190

Ile Val Ala Leu Ser Gln His Pro Ala Ala Leu Gly Thr Val Ala Val
                195                 200                 205

Lys Tyr Gln Asp Met Ile Ala Ala Leu Pro Glu Ala Thr His Glu Ala
210                 215                 220

Ile Val Gly Val Gly Lys Gln Trp Ser Gly Ala Arg Ala Leu Glu Ala
225                 230                 235                 240

Leu Leu Thr Val Ala Gly Glu Leu Arg Gly Pro Pro Leu Gln Leu Asp
                245                 250                 255

Thr Gly Gln Leu Leu Lys Ile Ala Lys Arg Gly Gly Val Thr Ala Val
                260                 265                 270

Glu Ala Val His Ala Trp Arg Asn Ala Leu Thr Gly Ala Pro Leu Asn
                275                 280                 285

<210> SEQ ID NO 5
<211> LENGTH: 183
<212> TYPE: PRT
<213> ORGANISM: Artificial Sequence
<220> FEATURE:
<223> OTHER INFORMATION: Synthetic Peptide

<400> SEQUENCE: 5

Arg Pro Ala Leu Glu Ser Ile Val Ala Gln Leu Ser Arg Pro Asp Pro
1               5                   10                  15

Ala Leu Ala Leu Thr Asn Asp His Leu Val Ala Leu Ala Cys Leu
            20                  25                  30

Gly Gly Arg Pro Ala Leu Asp Ala Val Lys Lys Gly Leu Pro His Ala
            35                  40                  45

Pro Ala Leu Ile Lys Arg Thr Asn Arg Arg Ile Pro Glu Arg Thr Ser
50                  55                  60
```

```
His Arg Val Ala Asp His Ala Gln Val Val Arg Val Leu Gly Phe Phe
65                  70                  75                  80

Gln Cys His Ser His Pro Ala Gln Ala Phe Asp Asp Ala Met Thr Gln
                85                  90                  95

Phe Gly Met Ser Arg His Gly Leu Leu Gln Leu Phe Arg Arg Val Gly
            100                 105                 110

Val Thr Glu Leu Glu Ala Arg Ser Gly Thr Leu Pro Pro Ala Ser Gln
        115                 120                 125

Arg Trp Asp Arg Ile Leu Gln Ala Ser Gly Met Lys Arg Ala Lys Pro
        130                 135                 140

Ser Pro Thr Ser Thr Gln Thr Pro Asp Gln Ala Ser Leu His Ala Phe
145                 150                 155                 160

Ala Asp Ser Leu Glu Arg Asp Leu Asp Ala Pro Ser Pro Met His Glu
                165                 170                 175

Gly Asp Gln Thr Arg Ala Ser
                180
```